United States Patent
Tsalik et al.

(10) Patent No.: US 10,689,701 B2
(45) Date of Patent: Jun. 23, 2020

(54) BIOMARKERS FOR THE MOLECULAR CLASSIFICATION OF BACTERIAL INFECTION

(71) Applicant: Duke University, Durham, NC (US)

(72) Inventors: Ephraim Tsalik, Durham, NC (US); Vance Fowler, Durham, NC (US); Christopher W. Woods, Durham, NC (US); Joseph E. Lucas, Chapel Hill, NC (US); Geoffrey S. Ginsburg, Durham, NC (US); Sun Hee Ahn, Gwangju (KR)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 14/214,853

(22) Filed: Mar. 15, 2014

(65) Prior Publication Data

US 2014/0323391 A1 Oct. 30, 2014

Related U.S. Application Data

(60) Provisional application No. 61/788,266, filed on Mar. 15, 2013.

(51) Int. Cl.
*C12Q 1/6883* (2018.01)
*C12Q 1/689* (2018.01)

(52) U.S. Cl.
CPC ........... *C12Q 1/6883* (2013.01); *C12Q 1/689* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2004/0083084 A1 | 4/2004 | West | |
| 2005/0170528 A1 | 8/2005 | West et al. | |
| 2007/0059720 A9 | 3/2007 | Fuqua et al. | |
| 2007/0154931 A1 | 7/2007 | Radich et al. | |
| 2009/0155180 A1 | 6/2009 | Jump et al. | |
| 2009/0319244 A1 | 12/2009 | West et al. | |
| 2014/0128277 A1* | 5/2014 | Moller et al. | 506/9 |

FOREIGN PATENT DOCUMENTS

| WO | WO 2004/037996 | 5/2004 |
|---|---|---|
| WO | WO 2004/038376 | 5/2004 |
| WO | WO 2010/096331 | 8/2010 |

OTHER PUBLICATIONS

Acharya CR, Hsu DS, Anders CK, et al. "Gene expression signatures, clinicopathological features, and individualized therapy in breast cancer." Jama 2008, 299:1574-1587.
Ahn et al., "Two genes on A/J chromosome 18 are associated with susceptibility to *Staphylococcus aureus* infection by combined microarray and QTL analyses," PLoS Pathog, 2010, 6:e1001088, 14 pages.
Ahn, S. H. et al., "Gene Expression-Based Classifiers Identify *Staphylococcus aureus* Infection in Mice and Humans," PLoS ONE 2013, 8(1): e48979, 16 pages.
Alam, et al., "Comparative evaluation of (1,3)-beta-D-glucan, mannan and anti-mannan antibodies, and *candida* species-specific snPCR in patients with candidemia" BMC Infect. Dis. 7, 103 (2007), 9 pages.
Ardura et al., "Enhanced monocyte response and decreased central memory T cells in children with invasive *Staphylococcus aureus* infections," PLoS One, 2009, 4:e5446, 17 pages.
Arruda E, Pitkaranta A, Witek TJ, Jr., et al., "Frequency and natural history of rhinovirus infections in adults during autumn." J Clin Microbial 1997, 35:2864-2868.
Aziz H, Zaas A, Ginsburg GS, "Peripheral blood gene expression profiling for cardiovascular disease assessment." Genomic Med 2007, 1: 105-112.
Barenco, et al., Correction of scaling mismatches in oligonucleotide microarray data. BMC Bioinformatics 7, 251 (2006), 13 pages.
Barrett B, Brown R, Voland R, et al., "Relations among questionnaire and laboratory measures of rhinovirus infection." Eur Respir J 2006, 28:358-363.
Bassetti M, Righi E, Tumbarello M, et al., "Candida infections in the intensive care unit: epidemiology, risk factors and therapeutic strategies" Expert Rev Anti Infect Ther 2006, 4:875-885.
Berenguer J, Buck M, Witebsky F, et at., "Lysis-centrifugation blood cultnres in the detection of tissue-proven invasive candidiasis. Disseminated versus single organ infection" Diagn Microbiol Infect Dis 1993, 17: 103-109.
Berry et al., "An interferon-inducible neutrophil-driven blood transcriptional signature in human tuberculosis," Nature, 2010, 446:973-977.
Bhoj VG, Sun Q, Bhoj EJ, et al., "MAVS and MyD88 are essential for innate immunity but not cytotoxic T lymphocyte response against respiratory syncytial virus." Proc Natl Acad Sci US A 2008, 105:14046-14051.
Boldrick JC, Alizadeh AA, Diehn M, et al., "Stereotyped and specific gene expression programs in human innate immune responses to bacteria." Proc Natl Acad Sci USA 2002, 99:972-977.
Bone et al., "Definitions for sepsis and organ failure and guidelines for the use of innovative therapies in sepsis. The ACCP/SCCM Consensus Conference Committee American College of the Chest Physicians/Society of Critical Care Medicine," Chest, 1992, 101:1644-1655.
Botterel, et al., "Real-time PCR on the first galactomannan-positive serum sample for diagnosing invasive aspergillosis in liver transplant recipients" Transpl. Infect. Dis. 10, 333-338 (2008).
Boucher, H. W. et al., "Bad bugs, no drugs: no ESKAPE! An update from the Infections Diseases Society of America," Clin Infect Dis, 2009, 48:1-12.
Breiman L, "Statistical Modeling: The Two Cultures." Statistical Science 2001, 16:199-231.
Breiman L, Friedman JH, Olshen LA, et al., "Classification and regression trees," Chapman and Hall/CRC; 1984, 5 pages.
Brocker et al., "Evolutionary divergence and functions of the human interleukin (IL) gene family," Human Genomics, 2010, 5:30-55.
Bryant PA, Venter D, Robins-Browne R, et al., "Chips with everything: DNA microarrays in infectious diseases." Lancet Infect Dis 2004, 4:100-111.

(Continued)

*Primary Examiner* — Channing S Mahatan
(74) *Attorney, Agent, or Firm* — Michael Best & Friedrich LLP

(57) ABSTRACT

Disclosed herein are biomarkers useful for identifying and/or classifying bacterial infections in a subject.

13 Claims, 47 Drawing Sheets

(56) References Cited

OTHER PUBLICATIONS

Cameron, C. M.. et al., "Gene expression analysis of host innate immune responses during lethal H5N1 infection in ferrets," J. Virol. (2008) 29 pages.

Campbell and Ghazal, "Molecular signatures for diagnosis of infection: application of microarray technology," J Appl Microbial (2004) vol. 96, 18-23.

Carvalho et al., "High dimensional sparse factor modeling: applications in gene expression genomics," Journal of American Statistical Association (2008) pp. 1-51.

Chan et al., "Integrating Transcriptomics and Proteomics," G&P magazine, 6(3): 20-26, 2006.

Chang et al., "A genomic strategy to elucidate modules of ocogenic pathway signaling networks," Mol Cell, 2009, 34:104-114.

Chang, et al., "GATHER: A systems approach to interpreting genomic signatures." Bioinformatics 22, 2926-2933 (2006).

Chaussabel et al., "A modular analysis framework for blood genomics studies: application to systemic lupus erythematosus," Immunity, 2008, 29:150-164.

Chen et al., "Detection of viruses via statistical gene expression analysis," IEEE Transactions on Biomedical Engineering, 2011, 58: 468-479.

Chen et al., "Predicting Viral Infection from High-Dimensional Biomarker Trajectories," Journal of the American Statistical Association in Press, 2011, 46 pages.

Chiarini A, Palmeri A, Amato T, et al., "Detection of bacteria and yeast species by the BACTEC 9120 automated system with the routine use of aerobic, anaerobic, and fungal media." J Clin Microbial 2008, 4029-4033.

Chin et al., "Genome wide transcriptome profiling of a murine acute melioidosis model reveals new insights into how Burkholderia pseudomallei overcomes host innate immunity," BMC Genomics, 2010, 11:672, 14 pages.

Chin KC, Cresswell P, "Viperin (cig5), an IFN-inducible antiviral protein directly induced by human cytomegalovirus." Proc Natl Acad Sci USA 2001 , 98:15125-15130.

Chipman H, George E, McCulloch RE, "Bayesian CART model search." Theory and Methods, No. 443, 1998, 93:935-960.

Cross et al., "Patterns of cytokine induction by gram-positive and gram-negative probiotic bacteria," FEMS Immunol Med Microbiol, 2004, 42:173-180.

Cyr et al., "Characterization of serum proteins associated with IL28B genotype among patients with chronic hepatitis C," PLoS One, 2011, 6:e21854.

Deitch et al., "Animal models of sepsis and shock: a review and lessons learned," Shock, 1998, 9:1-11.

Desai et al., "Chipping away at breast cancer: insights from microarray studies of human and mouse mammary cancer," Endocr Relat Cancer, 2002, 9:207-220.

Downey, T., "Analysis of a multifactor microarray study using Partek genomics solution," Methods Enzymol, 2006, 411:256-270.

Drake CL, Roehrs TA, Royer H, et al., "Effects of an experimentally induced rhinovirus cold on sleep, performance, and daytime alertness." Physiol Behav 2000, 71:75-81.

Dressman HK, Muramoto GG, Chao NJ, et al., "Gene expression signatures that predict radiation exposure in mice and humans" PLoS Med 2007, 4:e106, 12 pages.

Dyson, "Animal models of sepsis: why does preclinical efficacy fail to translate to the clinical setting?," Crit Care Med, 2009, 37:S30-37.

Dziarski et al., "MD-2 enables Toll-like receptor 2 (TLR2)-mediated responses to lipopolysaccharide and enhances TLR2-mediated responses to Gram-positive and Gram-negative bacteria and their cell wall components," J Immunol, 2001, 166:1938-1944.

Esmon, "Why do animal models (sometimes) fail to mimic human sepsis?," Crit Care Med, 2004, 34:S219-222.

Falsey AR, Hennessey PA, Fmmica MA, et al., "Respiratory syncytial virus infection in elderly and high-risk adults." N Engl J Med 2005, 352:1749-1759.

Feezor, R. J. et al., "Molecular characterization of the acute inflammatory response to infections with gram-negative versus gram-positive bacteria," Infect Immun, 2003, 71:5803-5813.

Fernandez-Arenas et al. "Integrated proteomics and genomics strategies bring new insight into Candida albicans response upon macrophage interaction" Mol Cell Proteom 2007, 6(3):460-478.

Finlay et al., "Common Themes in Microbial Pathogenicity Revisited," Microbiology and Molecular Biology Reviews, 1997, 61 (2): 136-169.

Fisher et al, "Treatment of septic shock with the tumor necrosis factor receptor: Fc fusion protein. The Soluble TNF Receptor Sepsis Study Group," N Engl J Med, 1996, 334:1697-1702.

Fjaerli, H-O. et la., "Whole blood gene expression in infants with respiratory syncytial virus bronchiolitis," BMC Infectious Diseases (2006) 6(175):7 pages.

Fradin, et al., "Granulocytes govern the transcriptional response, morphology and proliferation of Candida albicans in human blood" Mol. Microbial. 56, 397-415 (2005).

Fradin, et al., "Stage-specific gene expression of Candida albicans in human blood." Mol. Microbial. 47, 1523-1543 (2003).

Garey K W, Rege M, Pai MP, et al., "Time to initiation of fluconazole therapy impacts mortality in patients with candidemia: a multi-institutional study" Clin Infect Dis 2006, 43:25-31.

Garman KS, Acharya CR, Edelman E, et al. "A genomic approach to colon cancer risk stratification yields biologic insights into therapeutic opportunities." Proc Natl Acad Sci USA 2008, 105:19432-19437.

Glickman et al., "Disease progression in hemodynamically stable patients presenting to the emergency department with sepsis," Acad Emerg Med, 2010, 17:383-390.

Goodridge, et al., "Dectin-1 stimulation by Candida albicans yeast or zymosan triggers NF AT activation in macrophages and dendritic cells." J lmmunol. 178, 3107-3115 (2007).

Gums JG, Pelletier EM, Blumentals WA, "Oseltamivir and influenza-related complications, hospitalization and healthcare expenditure in healthy adults and children." Expert Opin Pharmacother 2008,9:151-161.

Gwaltney JM, Jr., Hendley, Hayden FG, et al., "Updated recommendations for safety-testing of viral inocula used in volunteer experiments on rhinovirus colds." Prog Med Virol 1992, 39:256-263.

Hans, et al., "Shotgun stochastic search for "Large p" regression" J Am. Stat. Assoc. 102, 507-516 (2007).

He et al., "Expression signature developed from a complex series of mouse models accurately predicts human breast cancer survival," Clin Cancer Res, 2010, 16:249-259.

Hessle et al., "Gram-positive and Gram-negative bacteria elicit different patterns of pro-inflamatory cytokines in human monocytes," Cytokine, 2005, 30:311-318.

Hong CY, Lin RT, Tan ES, et al., "Acute respiratory symptoms in adults in general practice." Fam Pract 2004, 21:317-323.

How to: Find a homolog for a gene in another organism (Retrieved on Dec. 12, 2013 from the internet: <http://www.ncbi. nl m. n i h.gov/guide/howto/find-homolog-gene/> ), 2 pages.

Jackson GG, Dowling HF, Spiesman IG, et al., "Transmission of the common cold to volunteers under controlled conditions. I. The common cold as a clinical entity." AMA Arch Intern Med 1959, 101:762-769.

Japour et al. "Standardized Peripheral Blood Mononuclear Cell Culture Assay for Determination of Drug Susceptibilities of Clinical Human Immunodeficiency Virus Type 1 Isolates" Antimicrob. Agen. Chemother. May 1993, vol. 37, No. 5, p. 1095-1101.

Jenner RG, Young RA, "Insights into host responses against pathogens from transcriptional profiling." Nat Rev Microbiol 2005, 3:281-294.

Jiang D, Guo H, Xu C, et al., "Identification of three interferon-inducible cellular enzymes that inhibit the replication of hepatitis C virus." J Virol 2008, 82:1665-1678.

Johnston SL, "Natural and experimental rhinovirus infections of the lower respiratory tract." Am J Respir Crit Care Med 1995, 152:S46-S52.

(56) References Cited

OTHER PUBLICATIONS

Johnstone J, Majumdar SR, Fox JD, et al., "Viral Infection in Adults Hospitalized with Community Acquired Pneumonia: Prevalence, Pathogens and Presentation." Chest 2008, 1141-1148.
Jonathan, "Diagnostic utility of BINAX NOW RSV—an evaluation of the diagnostic performance of BINAX NOW RSV in comparison with cell culture and direct immunofluorescence," Ann Clin Microbial Antimicrob (2006) vol. 5, 13, 5 pages.
Kawada et al., "Analysis of gene-expression profiles by oligonucleotide microarray in children with influenza," J Gen Virol, 2006, 87:1677-1683.
Kim et al. "Expression of genes encoding innate host defense molecules in normal human monocytes in response to Candida albicans." Infect lmmun 2005, 73(6):3714-3724.
Kim, J. H. et al., "Observations on spiraling empiricism: its causes, allure, and perils, with particular reference to antibiotic therapy," Am J Med, 1989, 87:201-206.
Kirchberger S, Majdic O, Stockl J, "Modulation of the immune system by human rhinoviruses." Int Arch Allergy Immunol 2007, 142:1-10.
Klein, E. et al., "Hospitalizations and deaths caused by methicillin-resistant *Staphylococcus aureus*, United States 1999-2005," Emerg Infect Dis, 2007, 13:1840-1846.
Kobayashi SD, Braughton KR, Whitney AR, et al., "Bacterial pathogens modulate an apoptosis differentiation program in human neutrophils." Proc Natl Acad Sci US A 2003, 100:10948-10953.
Kollef, M. H. et al., "Inadequate antimicrobial treatment of infections: a risk factor for hospital mortality among critically ill patients," Chest, 1999, 115:462-474.
Kooperberg C, Ruczinski I, LeBlanc ML, et al., "Sequence analysis using logic regression." Gen. Epidem. 2001, 21:626-631.
Kumar, A. et al., "Initiation of inappropiate antimicrobial therapy results in a fivefold reduction of survival in human septic shock," Chest, 2009, 136:1237-1248.
Labreche et al., "Integrating factor analysis and a transgenic mouse model to reveal a peripheral blood predictor of breast tumors," BMC Med Genomics, 2011, 4:61.
Lambert SB, Whiley DM, O'Neill NT, et al., "Comparing nose-throat swabs and nasopharyngeal aspirates collected from children with symptoms for respiratory virus identification using real-time polymerase chain reaction." Pediatrics 2008, 122:e615-620.
Landry ML, Cohen S, Ferguson D: "Real-time PCR compared to Binax NOW and cytospin-immunofluorescence for detection of influenza in hospitalized patients." J Clin Virol 2008, 43:148-151.
Larsson et al., "Kinetics of senescence-associated changes of gene expression in an epithelial, temperature-sensitive SV40 large T antigen model," Cancer Res, 2004, 64:482-489.
Lee et al. "Systems-Level Comparison of Host-Responses Elicited by Avian H5N1 and Seasonal H1N1 Influenza Viruses in Primary Human Macrophages" PLoS ONE, 2009, 4(12): e8072, 11 pages.
Lee, A. et al., "Detection of bloodstream infections in adults: how many blood cultures are needed?," J Clin Microbiol, 2007, 45:3546-3548.
Lorenz, et al., "Transcriptional response of Candida albicans upon internalization by macrophages" Eukaryot. Cell 3,1076-1087 (2004).
Lucas et al., "Sparse statistical modeling in gene expression genomics" Bayesian Inference for Gene Expression and Proteomics (Cambridge Univ. Press, New York, 2006), pp. 155-176.
Lucas et al., "A bayesian analysis strategy for cross-study translation of gene expression biomarkers," Stat Appl genet Mol Biol, 2009, 8: Article 11, 28 pages.
Lucas JE, Carvalho CM, Merl D, et al., "In-Vitro to In-Vivo factor profiling in expression genomics." Bayesian Modeling in Bioinformatics. Edited by Dey D, Ghosh S, Mallick B: Taylor-Francis; 2008, 11-35.
Luther, et al., "Characterisation of the phagocytic uptake of Aspergillusfumigatus conidia by macrophages" Microbes Infect. 10, 175-184 (2000).

Lytkin et al., "Expanding the understanding of biases in development of clinical-grade molecular signatures: a case study in acute respiratory viral infections," PLoS One, 2011, 6:e20662, 10 pages.
MacCallum, "Massive induction of innate immune response to Candida albicans in the kidney in a murine intravenous challenge model." FEMS Yeast Res 9, 1111-1122 (2009).
Martin, G. S. et al., "The epidemiology of sepsis in the United States from 1979 through 2000," N Engl J Med, 2003, 348:1546-1554.
Mashimo T, Simon-Chazottes D, Guenet JL, "Innate resistance to flavivirus infections and the functions of 2'-5' oligoadenylate synthetases." Curr Top Microbial Immunol 2008, 321:85-100.
McDunn et al., "Plasticity of the systemic inflammatory response to acute infection during critical illness: development of the riboleukogram," PLoS One, 2008, 3:e1564, 14 pages.
Meadows et al., "Diagnosis of partial body radiation exposure in mice using peripheral blood gene expression profiles," PLoS One, 2010, 5:e11535, 9 pages.
Meadows SK, Dressman HK, Muramoto GG, et al., "Gene expression signatures of radiation response are specific, durable and accurate in mice and humans." PLoS ONE 2008, 3:e1912.
Memoli MJ, Morens DM, Taubenberger JK, "Pandemic and seasonal influenza: therapeutic challenges." Drug Discov Today 2008, 13:590-595.
Merl et al., "Trans-study Projection of Genomic Biomarkers in Analysis of Oncogene Deregulation and Breast Cancer," The Oxford Handbook of Applied Bayesian Analysis (2009), 35 pages.
Mestas et al., "Of mice and not men: differences between mouse and human immunology," J Immunol, 2004, 172:2731-2738.
Miller et al., "Guanine phosphoribosyltransferase from *Escherichia coli*, specificity and properties," Biochemistry, 1972, 11:4723-4731.
Min JY, Krug RM, "The primary function of RNA binding by the influenza A virus NS1 protein in infected cells: Inhibiting the 2'-5' oligo (A) synthetase/RNase L pathway." Proc Natl Acad Sci US A 2006, 103:7100-7105.
Mohler et al., "Soluble tumor necrosis factor (TNF) receptors are effective therapeutic agents in lethal endotoxemia and function simultaneously as both TNF carriers and TNF antagonists," J Immunol, 1993, 1548-1561.
Mueller et al., "Distinct gene expression profiles characterize the histopathological stages of disease in helicobacter-induced mucosa-associated lymphoid tissue lymphoma," Proc Natl Acad Sci USA, 2003, 100:1292-1297.
Mullick et al. "Cardiac failure in C5-deficient AlJ mice after Candida albicans infection." Infect lmmun 2006, 74(8):4439-4451.
Nau et al., "Cummulative Toll-like receptor activation in human macrophages treated with whole bacteria," J Immunol, 2003, 170:5203-5209.
Netea et al., "An integrated model of the recognition of Candida albicans by the innate immune system," Nature Review: Microbiology, 2008, 6:67-78.
Netea, et al., "Immune sensing of Candida aibicans requires cooperative recognition of mannans and glucans by lectin and Toll-like receptors." J Clin. Invest. 116, 1642-1650 (2006).
Ng et al., "Gene expression profiling of mouse host response to Listeria monocytogenes infection," Genomics, 2005, 86:657-667.
Ostrosky-Zeichner L, Alexander BD, Kelt DH et al., "Multicenter clinical evaluation of the (1->3) beta-D-glucan assay as an aid to diagnosis of fungal infections in humans" Clin Infect Dis 2005, 41:654-659.
Overland, G., et al., "Cytokine responses to fungal pathogens in Kupffer cells are Toll-like receptor 4 independent and mediated by tyrosine kinases" Scand. J. Immunol 62, 148-154 (2005).
Pankla et al., "Genomic transcriptional profiling identifies a candidate blood biomarker for the diagnosis of septicemic melioidosis," Genome Biol, 2009, 10:R127, 22 pages.
Peltola V, Waris M, Osterback R, et al., "Rhinovirus transmission within families with children: incidence of symptomatic and asymptomatic infections." J Infect Dis 2008, 197:382-389.
Proud D, et al., "Gene Expression Profiles During In Vivo Human Rhinovirus Infection: Insights into the Host Response." Am J Respir Crit Care Med, Jul. 31, 2008, (pp. 1-42).
Raftery, et al., "Bayesian model averaging for linear regression models" J Am. Stat. Assoc 92, 179-191 (1997).

(56) References Cited

OTHER PUBLICATIONS

Rahman M, Vandermause MF, Kieke BA, et al., "Performance of Bin ax NOW Flu A and B and direct fluorescent assay in comparison with a composite of viral culture or reverse transcription polymerase chain reaction for detection of influenza infection during the 2006 to 2007 season." Diagn Microbial Infect Dis 2008, 62:162-166.
Rakes GP, Arruda E, Ingram JM, et al., "Rhinovirus and respiratory syncytial virus in wheezing children requiring emergency care. lgE and eosinophil analyses." Am J Respir Crit Care Med 1999, 159:785-790.
Ramilo et al., "Gene expression patterns in blood leukocytes discriminate patients with acute infections," Blood (2007) vol. 109, 2066-2077.
Rice et al., "The *Staphylococcus aureus* cidAB operon: evaluation of its role in regulation of murein hydrolase activity and penicillin tolerance," J Bacteriol, 2003, 185:2635-2643.
Rigamonti et al., Regulation of Macrophage Functions by PPAR-α, PPAR-γ and LXRs in Mice and Men, Arteriosclerosis, Thrombosis, and Vascular Biology, 2008, 28:1050-1059.
Rios JJ, Perelygin AA, Long MT, et al., "Characterization of the equine 2'-5' oligoadenylate synthetase 1 (OAS1) and ribonuclease L (RNASEL) innate immunity genes." BMC Genomics 2007, 8:313, 14 pages.
Robinson JL, Lee BE, Kothapalli S, et al., "Use of throat swab or saliva specimens for detection of respiratory viruses in children." Clin Infect Dis 2008, 46:e61-64.
Rubin-Bejerano, et al., "Phagocytosis by neutrophils induces an amino acid deprivation response in *Saccharomyces cerevisiae* and *Candida albicans*" Proc Natl. Acad. Sci. U.S.A 100, 11007-11012 (2003).
Ruczinski I, Kooperberg C, LeBlanc ML, "Logic regression." J. Comp. Graph. Statist. 2003, 475-511.
Schaller M, Hogaboam CM, Lukacs N, et al., "Respiratory viral infections drive chemokine expression and exacerbate the asthmatic response." J Allergy Clin Immunol 2006, 118:295-302.
Scheper et al. "Farnesol, a fungal quorum-sensing molecule triggers apoptosis in human oral squamous carcinoma cells" Neoplasia 2008, 10 (9):954-963.
Seo D, Ginsburg GS, Goldschmidt-Clermont PJ, "Gene expression analysis of cardiovascular diseases: novel insights into biology and clinical applications." J Am Call Cardiol 2006, 48:227-235.
Seo, et al., "Of mice and men: Sparse statistical modeling in cardiovascular genomics" Ann. Appl. Stat. 1, 152-178 (2007).
Shanley et al., "Genome-level longitudinal expression os signaling pathways and gene networks in pediatric septic shock," Mol Med, 2007, 495-508.
Simmons CP, Popper S, Dolocek C, et al., "Patterns of host genome-wide gene transcript abundance in the peripheral blood of patients with acute dengue hemorrhagic fever." J Infect Dis 2007, 195:1097-1107.
Spellberg, et al., "Mice with disseminated candidiasis die of progressive sepsis" J. Infect. Dis. 192, 336-343 (2005).
Sriskandan et al., "Gram-positive sepsis, Mechanisms and differences from gram-negative sepsis," Infect Dis Clin North Am, 1999, 13:397-412.
Steinbach, et al., "Calcineurin inhibition or mutation enhances cell wall inhibitors against Aspergillus fumigatus" Antimicrob. Agents Chemother. 51, 2979-2981 (2007).
Subauste et al., "Infection of a Human Respiratory Epithelial Cell Line with Rhinovirus—Induction of Cytokine Release and Modulation of Susceptibility to Infection by Cytokine Exposure." J. Clin. Invest. 1995. 96:549-557.
Szabo et al., "The contribution of mouse models to our understanding of systemic candidiasis," FEMS Microbial Lett, 2011, 320: 1-8.
Takeuchi et al., "Differential roles of TLR2 and TLR4 in recognition of gram-negative and gram-positive bacterial cell wall components," Immunity, 1999, 11:443-451.
Tang et al., "Gene-expression profiling of gram-posistive and gram-negative sepsis in critically ill patients," Crit Care Med, 2008, pp. 1125-1128.
Thanaraj et al., "Conservation of human alternative splice events in mouse," Nucleic Acids Research, 2003, vol. 31, No. 10, 2544-2552.
Thankker et al., "*Staphylococcus aureus* serotype 5 capsular polysaccharide is antiphagocytic and enhances bacterial virulence in a murine cateremia model," Infect Immun, 1998, 66:5183-5189.
Timofeeva et al., "Comparative transcriptome analysis of human aorta atherosclerotic lesions and peripheral blood leukocytes from essential hypertension patients," Kardiologiia, 2009, 49:27-38.
Tompkins et al., "Identification of Candidate B-Lymphoma Genes by Cross-Species Gene Expression Profiling," PLOS ONE, Oct. 2013, vol. 8, Issue 10, e76889, 15 pages.
Tsalik et al., "Multiplex PCR to diagnose bloodstream infections in patients admitted from the emergency department with sepsis," J Clin Microbiol, 2010, 48:26-33.
Turner RB, "Ineffectiveness of intranasal zinc gluconate for prevention of experimental rhinovirus colds." Clin Infect Dis 2001 , 33:1865-1870.
UC Davis' Gene Expression Resource Webpage (retrieved on Jul. 25, 2013 from the internet: <http://www.ucdmc.ucdavis.edu/ctsc/docu ments/geneexpression .pdf>; dated Jul. 12, 2007), 14 pages.
Unsinger et al., "Sepsis-induced human lymphocyte apoptosis and cytokine production in "humanized" mice," J Leukoc Biol, 2009, 86:219-227.
Von Bernuth et al., "Pyogenic bacterial infections in humans with MyD88 deficiency," Science, 2008, 321:691-696.
Von Kockritz-Blickwede et al., "Immunological mechanisms underlying the genetic predisposition to serve *Staphylococcus aureus* infection in the mouse model," Am J Pathol, 2008, 173:1657-1668.
Voora et al., "A Whole Blood RNS Signature Accurately Classifies Multiple Measures of Platelet Function on Aspirin in Healthy Volunteers and Highlights a Common Underlying Pathway," Circulation, 2010, Abstract 16293, 122:A16293, 3 pages.
Wang et al., "Bayesian factor regression modeling," Bulletin of the International Society of Bayesian Analysis, 2007, 14:4-5, 10 pages.
Wang F, Gao X, Barrett JW, et al., "RIG-I mediates the co-induction of tumor necrosis factor and type I interferon elicited by myxoma virus in primary human macrophages." PLoS Pathog 2008, 4:e1000099, 13 pages.
Wang Q, Carvalho CM, Lucas JE, et al., "BFRM: Bayesian factor regression modeling." Bulletin of the International Society of Bayesian Analysis 2007, 14:4-5, 1 page.
Wang X, Hinson ER, Cresswell P, "The interferon-inducible protein viperin inhibits influenza virus release by perturbing lipid rafts." Cell Host Microbe 2007, 2:96-105.
Wang Z, Neuburg D, Li C, et al., "Global gene expression profiling in whole-blood samples from individuals exposed to metal fumes." Environ Health Perspect 2005, 113:233-241.
Weindruch et al., "Microarray profiling of gene expression in aging and its alteration by caloric restriction in mice," J Nutr, 2001, 131:918S-923S.
Wennmalm et al., "The expression signature of in vitro senescence resembles mouse but not human aging," Genome Biol, 2005, 6:R109.
West, "Bayesian Factor Regression Models in the "Large p, Small n" Paradigm," Bayesian Statistics 7, 2003, p. 1-11.
Xu et al., "Cloning and characterization of human protease-activated receptor 4," Proceedings of the National Academy of Sciences, 1998, 95:6642-6646.
Xu M, Kao MC, Nunez-Iglesias J, et al., "An integrative approach to characterize disease-specific pathways and their coordination: a case study in cancer." BMC Genomics 2008, 9 Suppl 1:S12.
Yu et al., "Differential gene expression in gram-negative and gram-positive sepsis," Am J Respir Crit Care, 2004, 169:1135-1143.
Zaas et al. "Blood Gene Expression Signatures Predict Invasive Candidiasis" Sci Transl Med EPub Mar. 3, 2010, 2(21):1-10 and Supplemental Data Pages.
Zaas et al., "A Host-Based RT-PCR Gene Expression Signature to Identify Acute Respiratory Viral Infection," www.ScienceTranslationalMedicine.org, Sep. 18, 2013, vol. 5, Issue 203, 1-10.
Zass et al., "Gene Expression Signatures Diagnose Influenza and Other Symptomatic Respiratory Viral Infections in Humans" Cell Host & Microbe Sep. 17, 2009, 6, 207-217.

(56) References Cited

OTHER PUBLICATIONS

Zeni et al., "Anti-inflamatory therapies to treat sepsis and septic shock: a reassessment," Crit Care Med, 1997, 25:1095-1100.
Zhang, H. et al., "Signature patters revealed by microarray analyses of mice infected with influenza virus A and *Streptococcus pneumoniae*," Microbes and Infection (2006) 8:2172-2185.
United States Patent Office Action for U.S. Appl. No. 14/880,668 dated Nov. 4, 2016 (27 pages).
United States Patent Office Action for U.S. Appl. No. 14/880,668 dated Feb. 2, 2016 (25 pages).
Ramilo et al. Gene Expression Patterns in Blood Leukocyte discriminate patients with acute infections. Mar. 1, 2007. Blood. vol. 109, No. 5, pp. 2066-2077.
De Repentigny, "Animal models in the analysis of Candida host-pathogen interactions" Current Opinion in Microbiology. 2004. 7: 324-329.
Miranda et al., "Candida colonisation as a source for candidaemia" Journal of Hospital Infection. 2009. 72: 9-16.
Conti et al., "Host responses to Candida albicans: Th17 cells and mucosal Candidiasis" Microbes and Infection. 2010. 12: 518-527.
Ingersoll et al., "Comparison of gene expression profiles between human and mouse monocyte subsets" Blood. 2010. 115(3): e10-9.
Dix et al. "Biomarker-based classification of bacterial and fungal whole-blood infections in a genome-wide expression study," Frontiers in Microbiology. 2015. 8: Article 171 and Supplementary Materials.
Bailey et al., "IFITM-Family Proteins: The Cell's First Line of Antiviral Defense," Annu Rev Virol., 2014, 1:261-283.
"Human Genome U133A Annotated Chip—Broad Institute. Accessed on Mar. 1, 2017 at https://software.broadinstitute.org/cancer/software/genepattern/tutorial/1 inked Files/HG_ U 133A _ an not.chip; pp. 1-223."
Loughner et al., "Organization, evolution and functions of the human and mouse Ly6/uPAR family genes," Human Genetics. 2016. 10:10, 19 pages.
MGI. Retrieved on Sep. 14, 2017 from the internet: http://www.informatics.jax.org/marker/MGI:105983, 2 pages.
NCBI. Retrieved on Sep. 14, 2017 from the internet: https://www.ncbi.nlm.nih.gov/IEB/Research/Acembly/av.cgi?db=mouse&c=Gene&I =NGP, 2 pages.
UniProtKB—O08692, Retreived on Sep. 14, 2017 from the internet: http://www.uniprot.org/unioprot/O08692, 5 pages.
United States Patent Office Summary of Applicant Initiated Interview for U.S. Appl. No. 14/880,668 dated Mar. 7, 2017 (4 pages).
United States Patent Office Notice of Allowance for U.S. Appl. No. 14/880,668 dated Aug. 2, 2017 (10 pages).

\* cited by examiner

A

B

A

B

Human pairwise comparisons

BIOMARKERS FOR THE MOLECULAR CLASSIFICATION OF BACTERIAL INFECTION

CROSS REFERENCE TO RELATED APPLICATION

This application claims priority to U.S. Provisional Application No. 61/788,266, filed Mar. 15, 2013, which is incorporated herein by reference in its entirety.

STATEMENT OF GOVERNMENT INTEREST

This invention was made with government support under federal grant numbers R01-AI068804, K24-A1093969, 5U01AI066569-05, 3U01AI066569-05 S1 awarded by the National Institutes of Health and N66001-09-C-2082 awarded by Defense Advanced Research Projects Agency of the Department of Defense. The U.S. Government has certain rights to this invention.

TECHNICAL FIELD

The present invention relates to methods of identifying and treating subjects suffering from bacterial infection.

BACKGROUND

Septicemia causes substantial morbidity and mortality among patients in the United States, with a rising burden of Staphylococcus aureus infection. Although blood cultures are the diagnostic gold standard for blood stream infection (BSI), sensitivity is limited and results are not rapidly available. Such diagnostic delays can extend the time to administration of effective antibiotics, which is an independent risk factor for mortality. Conversely, diagnostic uncertainty also leads to high rates of empiric overtreatment, fueling the burden of antimicrobial resistance. Thus, novel approaches that are faster and more accurate are needed to differentiate between the major pathogens causing sepsis and BSI.

Whereas conventional diagnostic approaches have focused on identifying the infecting pathogen, a growing body of evidence suggests that the host's inflammatory response to the pathogen also represents a potential diagnostic tool. In vitro and In vivo experiments have revealed fundamental differences in host response to Gram-positive and Gram-negative bacterial infection, including significant differences in Toll-like receptor (TLR) signaling and cytokine production. Distinctive gene expression profiles exist for viral, bacterial, and fungal infections in both animal model systems and ex vivo stimulation of human peripheral blood leukocytes. Peripheral blood mononuclear cell (PBMC) gene expression signatures have also been evaluated in humans for a variety of conditions including severe infection, bacterial vs. viral illness, systemic lupus erythematosus, atherosclerosis, and radiation exposure. Taken together, these studies provide strong evidence that global changes in host blood gene expression patterns can be used to differentiate disease states.

Staphylococcus aureus causes a spectrum of human infection. Diagnostic delays and uncertainty lead to treatment delays and inappropriate antibiotic use. Early diagnostic strategies for S. aureus BSI could improve patient care by reducing the time required to establish the diagnosis and provide appropriate treatment while avoiding unnecessary anti-MRSA antibiotics. There is a need in the art to have alternative methods for diagnosing and treating patients with bacterial infection, such as sepsis.

SUMMARY

The present invention is directed to a method of developing a diagnostic assay for identifying and/or classifying a bacterial infection in a subject. The method comprising determining the gene expression levels of at least two biomarkers in a subject infected with bacterial infection, wherein the biomarkers are selected from one or more of Tables 3-17; comparing the gene expression levels of the biomarkers in the subject with the gene expression levels of the biomarkers in a control; identifying factors, wherein each factor comprises differentially expressed biomarkers that have the greatest ability to differentiate between gene expression in the subject and the control; providing a weighted value for the differentially expressed biomarkers within the factor; and determining a relationship between the factor and the bacterial infection using the weighted values of the differentially expressed biomarkers with an algorithm, wherein a relationship between the factor and the bacterial infection is used to develop the diagnostic assay. The method may distinguish a subject that has a Staphylococcus aureus blood stream infection from a healthy subject. The biomarkers may be selected from Table 8 and Table 10. The factor may comprise about 5 to about 250 biomarkers. The relationship may have an AUC value of 0.9898. The method may distinguish a subject that has a Staphylococcus aureus blood stream infection from a subject that has an Escherichia coli blood stream infection. The biomarkers may be selected from Table 8 and Table 10. The factor may comprise about 5 to about 250 biomarkers. The relationship may have an AUC value of 0.8372. The method may distinguish a subject that has an Escherichia coli blood stream infection from a healthy subject. The biomarkers may be selected from Table 8 and Table 10. The factor may comprise about 5 to about 250 biomarkers. The relationship may have an AUC value of 0.9229. The method may distinguish a subject that has a gram positive blood stream infection from a subject that has a gram negative blood stream infection. The biomarkers may be selected from Table 9. The factor may comprise about 5 to about 250 biomarkers. The relationship may have an AUC value of 0.8503. The method may distinguish a subject that has a Staphylococcus aureus blood stream infection from a healthy subject. The biomarkers may be selected from Table 7. The factor may comprise about 5 to about 250 biomarkers. The relationship may have an AUC value of 0.9217. The method may distinguish a subject that has a Staphylococcus aureus blood stream infection from a healthy subject. The biomarkers may be selected from Tables 3, 4, and 6. The factor may comprise about 5 to about 250 biomarkers. The relationship may have an AUC value of 0.9522. The method may distinguish a subject that has a Staphylococcus aureus blood stream infection from a healthy subject. The biomarkers may be selected from Tables 3, 4, 5 and 6. The factor may comprise about 5 to about 250 biomarkers. The relationship may have an AUC value of 0.9964. The method may distinguish a subject that has a Staphylococcus aureus blood stream infection from a subject that has an Escherichia coli blood stream infection. The biomarkers may be selected from Tables 3, 4, 5 and 6. The factor may comprise about 5 to about 250 biomarkers. The relationship may have an AUC value of 0.9935. The method may distinguish a subject that has an Escherichia coli blood stream infection from a healthy subject. The biomarkers may be selected from Tables 3, 4, 5 and 6. The factor may comprise about 5 to about 250 biomarkers. The relationship may have an AUC value of 0.9484. At least one of the differentially expressed biomarkers may have an increased expression level compared to the control. At least one of the differentially expressed biomarkers may have a decreased expression level compared to the control. At least one of the differentially expressed biomarkers may have an increased expression level compared to the control and at least one of the differentially expressed biomarkers may have a decreased expression level compared to the control. The factor may comprise about 10 biomarkers. The method of any one of the preceding claims, wherein the factor may comprise about 20 biomarkers. The factor may comprise about 50 biomarkers. The factor may comprise about 100 biomarkers. The factor may comprise about 150 biomarkers. The factor may comprise about 200 biomarkers. The factor may comprise about 250 biomarkers. The subject may be a mammal. The subject may be a human. The subject may be a mouse. The biological sample may be selected from the group consisting of tissues, cells, biopsies, blood, lymph, serum, plasma, urine, saliva, mucus, and tears. The sample may comprise plasma. The RNA gene expression levels may be determined.

The present invention is directed to method of identifying and treating a bacterial infection in a subject. The method comprises performing the diagnostic assay as developed by the methods, as described above, and administrating an antibacterial therapy to the subject diagnosed with a bacterial infection. The method further comprising quantifying the amount of at least one biomarker present in a biological sample derived from the subject, wherein the biomarker may be associated with a factor. At least one of the differentially expressed biomarkers may have an increased expression level compared to the control. At least one of the differentially expressed biomarkers may have a decreased expression level compared to the control. At least one of the differentially expressed biomarkers may have an increased expression level compared to the control and at least one of the differentially expressed biomarkers may have a decreased expression level compared to the control. The factor may comprise about 10 biomarkers. The method of any one of the preceding claims, wherein the factor may comprise about 20 biomarkers. The factor may comprise about 50 biomarkers. The factor may comprise about 100 biomarkers. The factor may comprise about 150 biomarkers. The factor may comprise about 200 biomarkers. The factor may comprise about 250 biomarkers. The subject may be a mammal. The subject may be a human. The subject may be a mouse. The biological sample may be selected from the group consisting of tissues, cells, biopsies, blood, lymph, serum, plasma, urine, saliva, mucus, and tears. The sample may comprise plasma. The RNA gene expression levels may be determined.

The present invention is also directed towards a method of identifying and treating a subject suspected of having a bacterial blood stream infection (BSI). The method comprises determining gene expression levels of at least two biomarkers in a peripheral blood cell sample of the subject, wherein the biomarkers are selected from any one of Tables 3-17; comparing the gene expression levels of the at least two biomarkers to standard gene expression levels wherein the standard gene expression levels correspond to the gene expression levels for the biomarkers in a control; identifying the subject as having a bacterial BSI if the gene expression levels of the biomarkers are different than the standard gene expression levels; and administering an effective amount of antibiotic therapy to treat the subject identified as having a bacterial BSI. The bacterial BSI may be *Staphylococcus aureus* BSI or *Escherichia coli* BSI. The bacterial blood stream infection may be *S. aureus* BSI and the biomarkers may be selected from one of Tables 3-8 or 10. At least about 2 to about 250 biomarkers may be selected from one of Tables 3-8 or 10. The bacterial blood stream infection may be *E. coli* BSI and the biomarkers may be selected from one of Tables 3-6, 8 or 10. At least about 2 to about 250 biomarkers may be selected from one of Tables 3-6, 8 or 10. The control may be a healthy subject. At least one of the biomarkers may have an increased gene expression level compared to the control. At least one of the biomarkers may have a decreased gene expression level compared to the control. At least one of the biomarkers may have an increased gene expression level compared to the control and at least one of the biomarkers has a decreased gene expression level compared to the control. The gene expression levels of about 10 biomarkers may be determined. The gene expression levels of about 20 biomarkers may be determined. The gene expression levels of about 50 biomarkers may be determined. The gene expression levels of about 100 biomarkers may be determined. The gene expression levels of about 150 biomarkers may be determined. The gene expression levels of about 200 biomarkers may be determined. The gene expression levels of about 250 biomarkers may be determined. The subject may be a mammal. The subject may be a human. The subject may be a mouse. The biological sample may be selected from the group consisting of tissues, cells, biopsies, blood, lymph, serum, plasma, urine, saliva, mucus, and tears. The sample may comprise plasma. The RNA gene expression levels may be determined.

The present invention is directed to method of distinguishing and treating *Staphylococcus aureus* blood stream infection (BSI) from *Escherichia coli* BSI in a subject suspected of having a bacterial infection. The method comprises determining gene expression levels of at least two biomarkers in a peripheral blood cell sample of the subject, wherein the biomarkers are selected from any one of Tables 8 and 10 or Tables 3-6; comparing the gene expression levels of the at least two biomarkers to standard gene expression levels wherein the standard gene expression levels correspond to the gene expression levels for the biomarkers in a control; identifying the subject as having a *S. aureus* BSI if the gene expression levels of the biomarkers are different than the standard gene expression levels and identifying the subject as having an *E. coli* BSI if the gene expression levels of the biomarkers are the same as the standard gene expression levels; and administering an effective amount of appropriate antibacterial therapy to treat the subject identified as having a *S. aureus* BSI or *E. coli*. The control may be a subject having an *E. coli* BSI. At least one of the biomarkers may have an increased gene expression level compared to the control. At least one of the biomarkers may have a decreased gene expression level compared to the control. At least one of the biomarkers may have an increased gene expression level compared to the control and at least one of the biomarkers has a decreased gene expression level compared to the control. The gene expression levels of about 10 biomarkers may be determined. The gene expression levels of about 20 biomarkers may be determined. The gene expression levels of about 50 biomarkers may be determined. The gene expression levels of about 100 biomarkers may be determined. The gene expression levels of about 150 biomarkers may be determined. The gene expression levels of about 200 biomarkers may be determined. The gene expression levels of about 250 biomarkers may be determined. The subject may be a mammal. The subject may be a human. The subject may be a mouse. The biological sample may be selected from the group consisting of tissues, cells, biopsies, blood, lymph, serum, plasma, urine, saliva, mucus, and tears. The sample may comprise plasma. The RNA gene expression levels may be determined.

The present invention is directed to method of distinguishing and treating a gram positive bacterial infection from a gram negative bacterial infection in a subject suspected of having a bacterial infection. The method comprises determining gene expression levels of at least two biomarkers in a peripheral blood cell sample of the subject, wherein the biomarkers are selected from Table 9; comparing the gene expression levels of the at least two biomarkers to standard gene expression levels wherein the standard gene expression levels correspond to the gene expression levels for the biomarkers in a control; identifying the subject as having a gram positive bacterial infection if the gene expression levels of the biomarkers are different than the standard gene expression levels in a control; and administering an effective amount of appropriate antibacterial therapy to treat the subject identified as a gram positive bacterial infection. The gram positive bacterial infection may be *Staphylococcus aureus*. The control may be a subject having a gram negative bacterial infection. The gram negative bacterial infection may be *Escherichia coli*. At least one of the biomarkers may have an increased gene expression level compared to the control. At least one of the biomarkers may have a decreased gene expression level compared to the control. At least one of the biomarkers may have an increased gene expression level compared to the control and at least one of the biomarkers has a decreased gene expression level compared to the control. The gene expression levels of about 10 biomarkers may be determined. The gene expression levels of about 20 biomarkers may be determined. The gene expression levels of about 50 biomarkers may be determined. The gene expression levels of about 100 biomarkers may be determined. The gene expression levels of about 150 biomarkers may be determined. The gene expression levels of about 200 biomarkers may be determined. The gene expression levels of about 250 biomarkers may be determined. The subject may be a mammal. The subject may be a human. The subject may be a mouse. The biological sample may be selected from the group consisting of tissues, cells, biopsies, blood, lymph, serum, plasma, urine, saliva, mucus, and tears. The sample may comprise plasma. The RNA gene expression levels may be determined.

The present invention is directed method of identifying and treating a subject suspected of having a methicillin-resistant *Staphylococcus aureus* (MRSA) infection. The method comprises determining gene expression levels of at least one biomarker in a peripheral blood cell sample of the subject wherein the biomarker is selected from Table 11; comparing the gene expression levels of the biomarker to a standard gene expression level of the biomarker, wherein the standard gene expression level corresponds to the gene expression level of the biomarker in a subject that has a methicillin-sensitive *Staphylococcus aureus* (MSSA) infection; identifying the subject as having MRSA if the gene expression levels of the biomarkers are different than the standard gene expression levels; and administering an effective amount of an antibiotic therapy to treat the subject identified as having MRSA. The antibiotic therapy may be mupirocine or vancomycin. At least one of the biomarkers may have an increased gene expression level compared to the control. At least one of the biomarkers may have a decreased gene expression level compared to the control. At least one of the biomarkers may have an increased gene expression level compared to the control and at least one of the biomarkers has a decreased gene expression level compared to the control. The gene expression levels of about 10 biomarkers may be determined. The gene expression levels of about 20 biomarkers may be determined. The gene expression levels of about 50 biomarkers may be determined. The gene expression levels of about 100 biomarkers may be determined. The gene expression levels of about 150 biomarkers may be determined. The gene expression levels of about 200 biomarkers may be determined. The gene expression levels of about 250 biomarkers may be determined. The subject may be a mammal. The subject may be a human. The subject may be a mouse. The biological sample may be selected from the group consisting of tissues, cells, biopsies, blood, lymph, serum, plasma, urine, saliva, mucus, and tears. The sample may comprise plasma. The RNA gene expression levels may be determined.

The present invention is also directed to a method for determining the efficacy of an anti-bacterial treatment regime in a subject. The method comprises determining a baseline gene expression level for at least one biomarker selected from Tables 3-17; administering to the subject a therapeutic regimen; and redetermining the gene expression level of the at least one biomarker in the subject. A difference in the gene expression level of the at least one biomarker indicates the efficacy of the therapeutic regimen. At least one of the biomarkers may have an increased gene expression level compared to the control. At least one of the biomarkers may have a decreased gene expression level compared to the control. At least one of the biomarkers may have an increased gene expression level compared to the control and at least one of the biomarkers has a decreased gene expression level compared to the control. The gene expression levels of about 10 biomarkers may be determined. The gene expression levels of about 20 biomarkers may be determined. The gene expression levels of about 50 biomarkers may be determined. The gene expression levels of about 100 biomarkers may be determined. The gene expression levels of about 150 biomarkers may be determined. The gene expression levels of about 200 biomarkers may be determined. The gene expression levels of about 250 biomarkers may be determined. The subject may be a mammal. The subject may be a human. The subject may be a mouse. The biological sample may be selected from the group consisting of tissues, cells, biopsies, blood, lymph, serum, plasma, urine, saliva, mucus, and tears. The sample may comprise plasma. The RNA gene expression levels may be determined.

The present invention is also directed to a composition of matter comprising (a) a probe array for determining a biomarker level in a sample, the array comprising of a plurality of probes that hybridizes to one or more biomarkers selected from Tables 3-17; or (b) a kit for determining a biomarker level in a sample, comprising the probe array of (a) and instructions for carrying out the determination of biomarker expression level in the sample. The composition may further comprise a solid support with the plurality of probes attached thereto.

Conditions represented include different murine hosts (A), bacterial genetic backgrounds (B), and time from inoculation (C). Animals with *S. aureus* infection are depicted by a red "x". Uninfected control mice are depicted by black circles.

Figure 3:
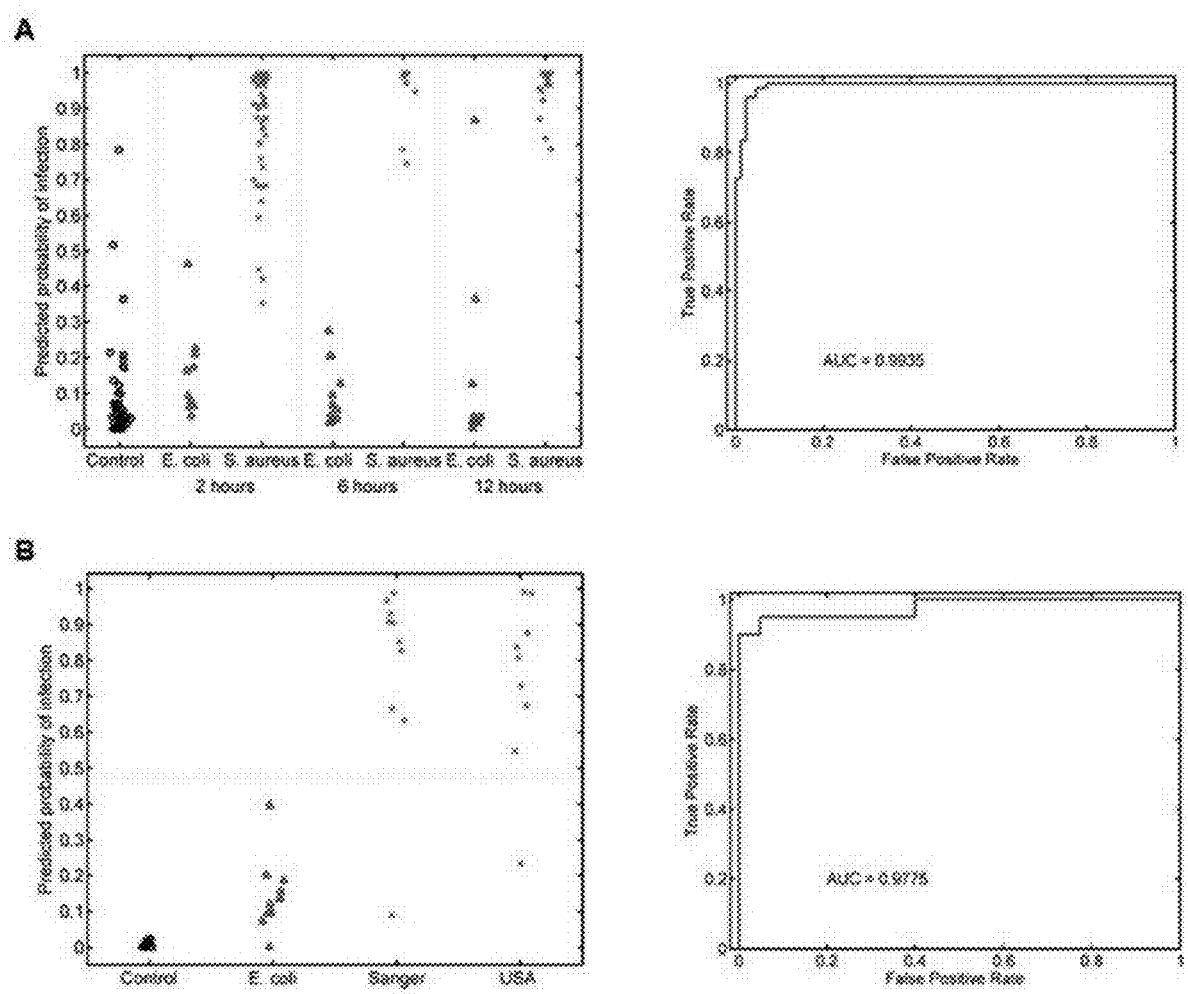

FIG. 3 shows that the murine *S. aureus* classifier differentiates *S. aureus* from *E. coli* infection. (A) Inbred mice were tested under three conditions: uninfected controls (black circles), *S. aureus* infected (red "x"), and *E. coli* infected (blue triangles). The y-axis represents the predicted probability that a given animal was infected with *S. aureus*. (B) The murine *S. aureus* classifier is validated in outbred CD-1 mice where it differentiates *S. aureus* infection from *E. coli* infection and uninfected controls.

Figure 4:
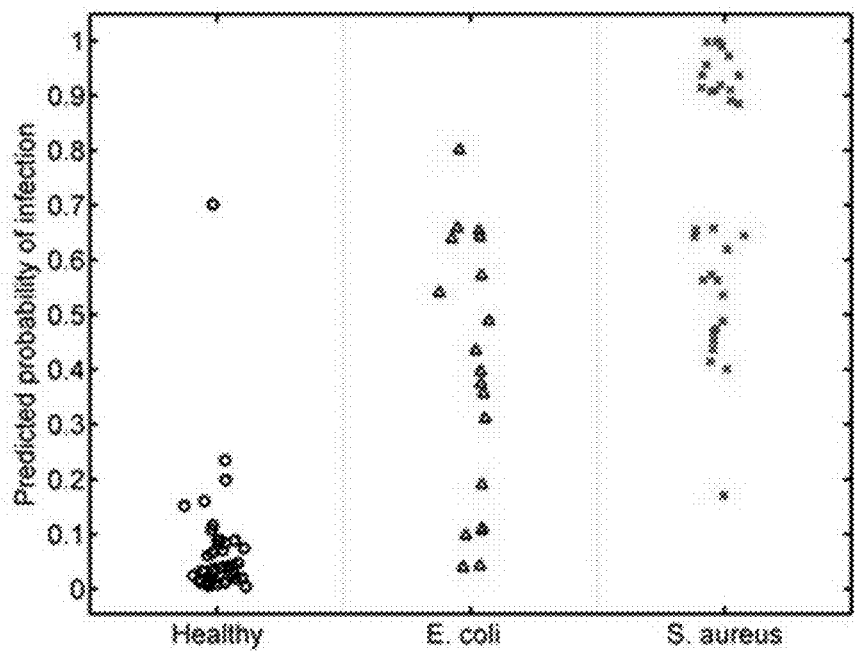
Figure 4:
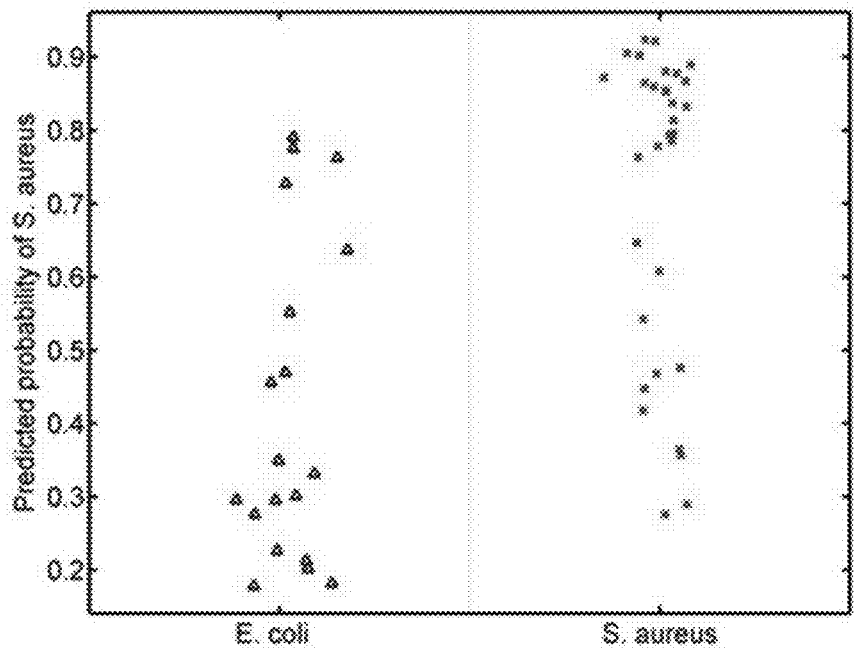

FIG. 4 shows the performance of the human *S. aureus* classifier. (A) The human *S. aureus* classifier differentiates *S. aureus* BSI from both uninfected controls and *E. coli* BSI. (B) A separate classifier was generated using only *S. aureus* and *E. coli*-infected human subjects and tested using leave-one-out cross-validation.

Figure 5:
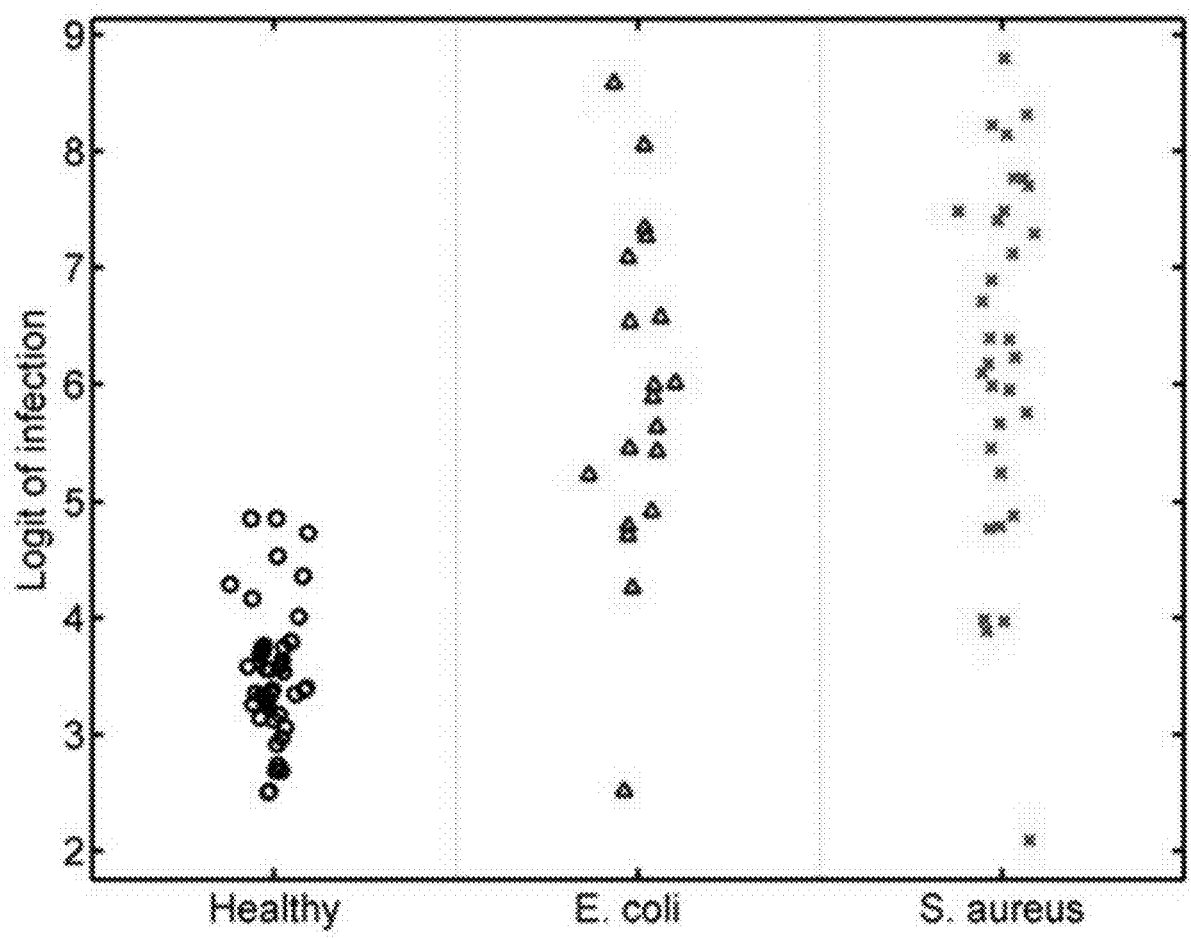

FIG. 5 shows the projection of the mouse *S. aureus* classifier onto human subjects. The murine *S. aureus* classifier identifies humans with *S. aureus* BSI, but does not differentiate *S. aureus* from *E. coli* BSI.

Figure 6:
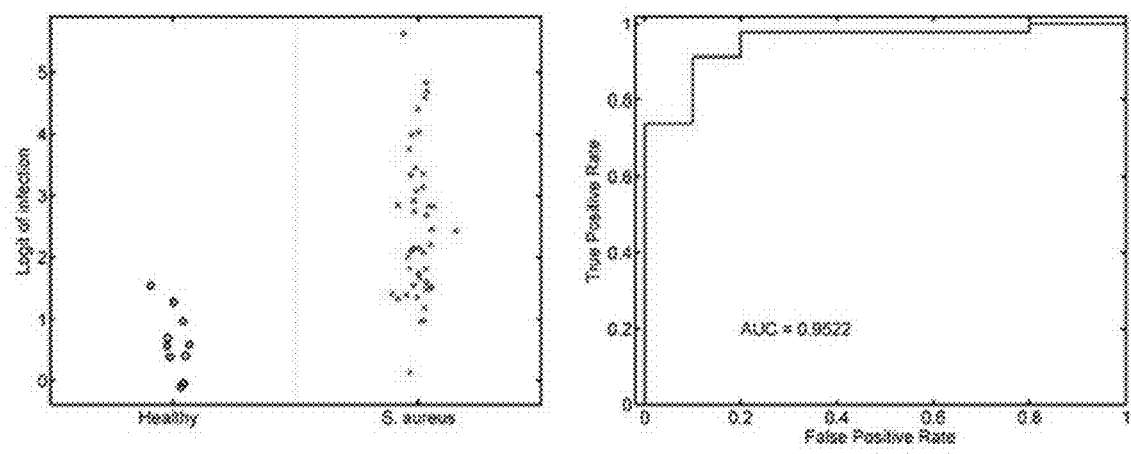
Figure 6:
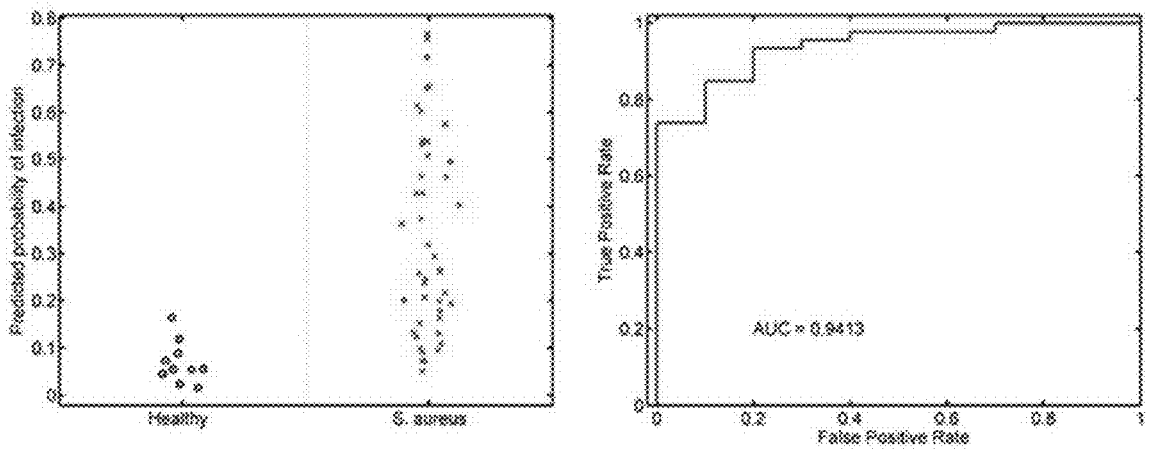

FIG. 6 shows validation in an independent human cohort. (A) The murine *S. aureus* classifier differentiates between *S. aureus* infection and healthy. (B) The human *S. aureus* classifier differentiates between *S. aureus* infection and healthy.

Figure 7:
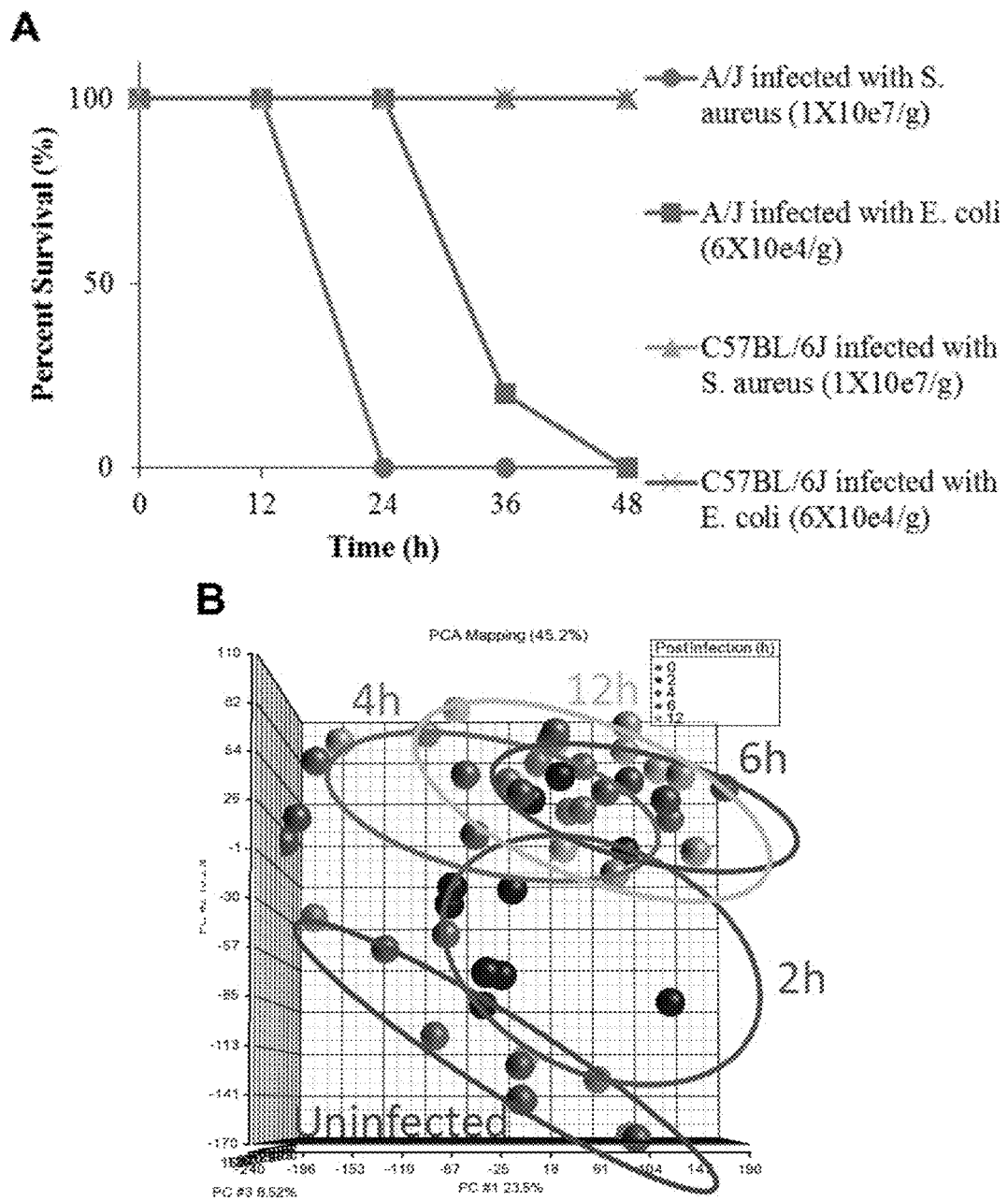
Figure 7:
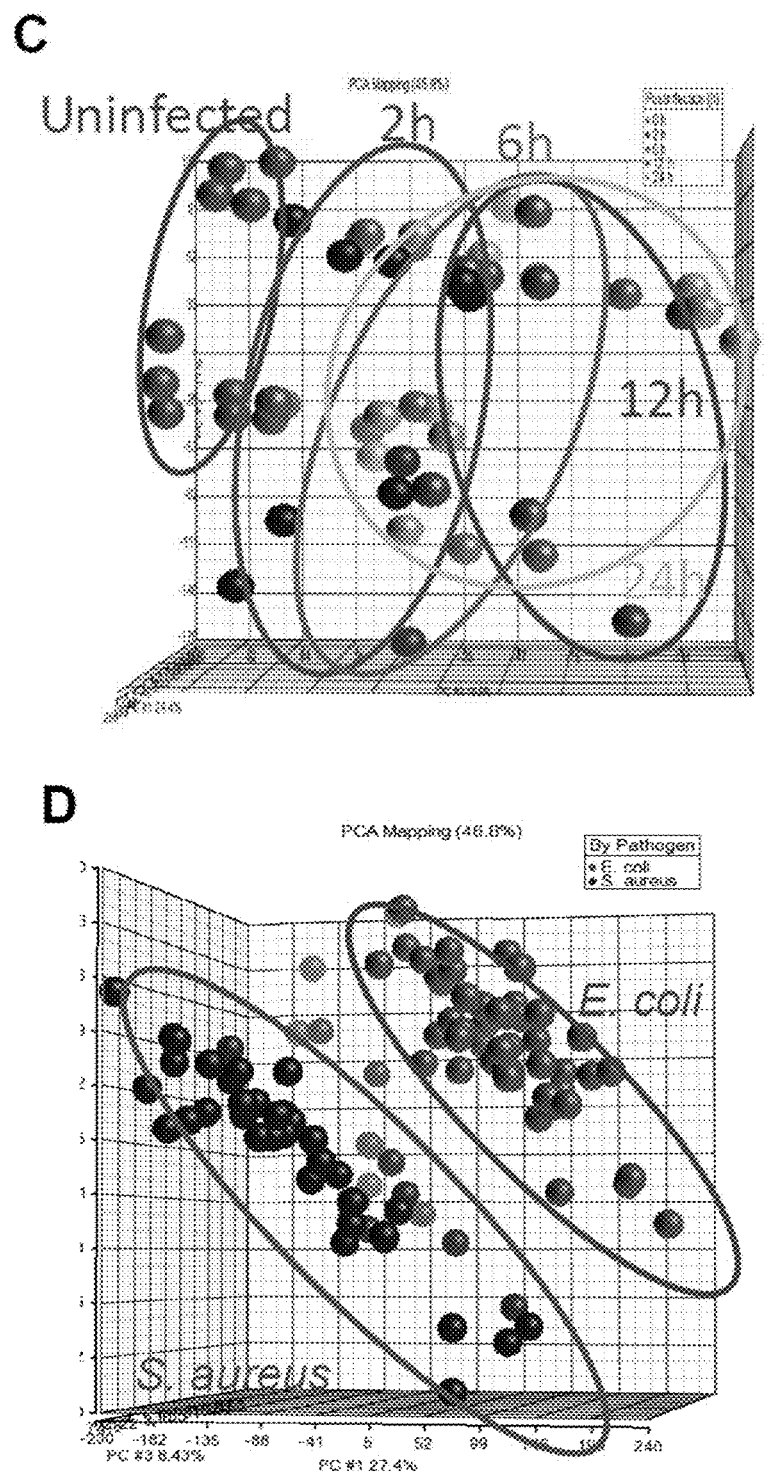

FIG. 7 shows bacterial challenge experiments. (A) Survival curves for A/J and C57BL/6J mice following an intra-peritoneal infection with *S. aureus* (16107 CFU/g) or *E. coli* (66104 CFU/g). Principal Components Analysis plots of the samples in the dataset. Samples are colored by infection status and pathogen. (B) *S. aureus* infection by time after inoculation (n=10 animals/time point). (C) *E. coli* infection by time after inoculation (n=10 animals/time point). (D) PCA differentiated by pathogen.

Figure 8:
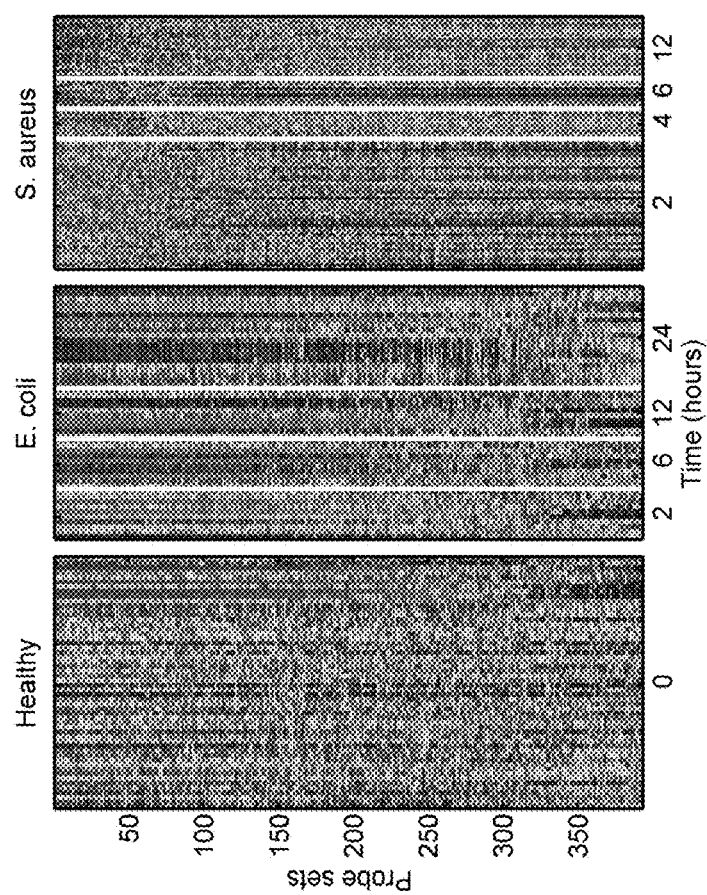
Figure 8:
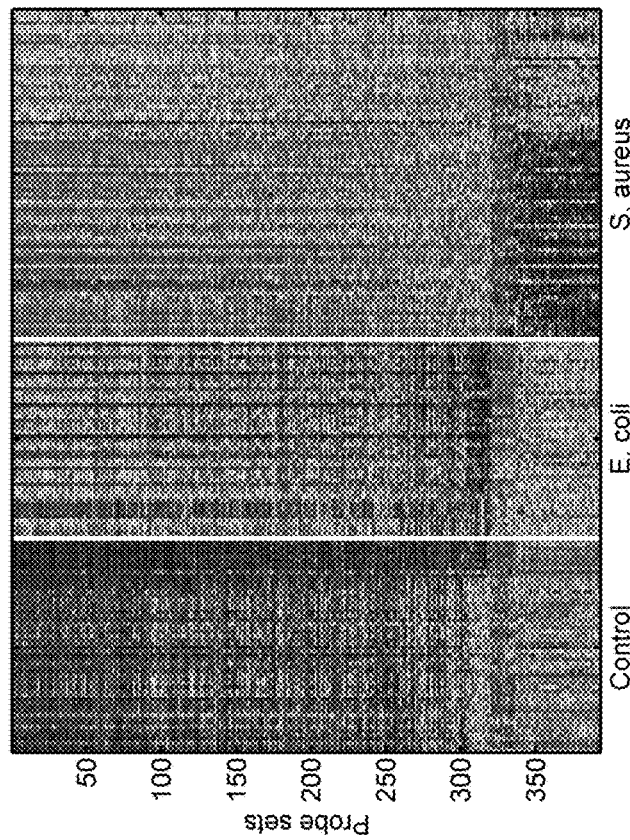

FIG. 8 shows heat maps of genes contributing to the murine *S. aureus* classifier. (A) Genes within the top five factors contributing to the murine *S. aureus* classifier were identified and ranked by p-value after Bonferroni correction. A subset of genes (393 after removing duplicates) is depicted here, stratified by pathogen. (B) The same genes depicted in part (A) are categorized first pathogen and then by time since infection.

Figure 9:
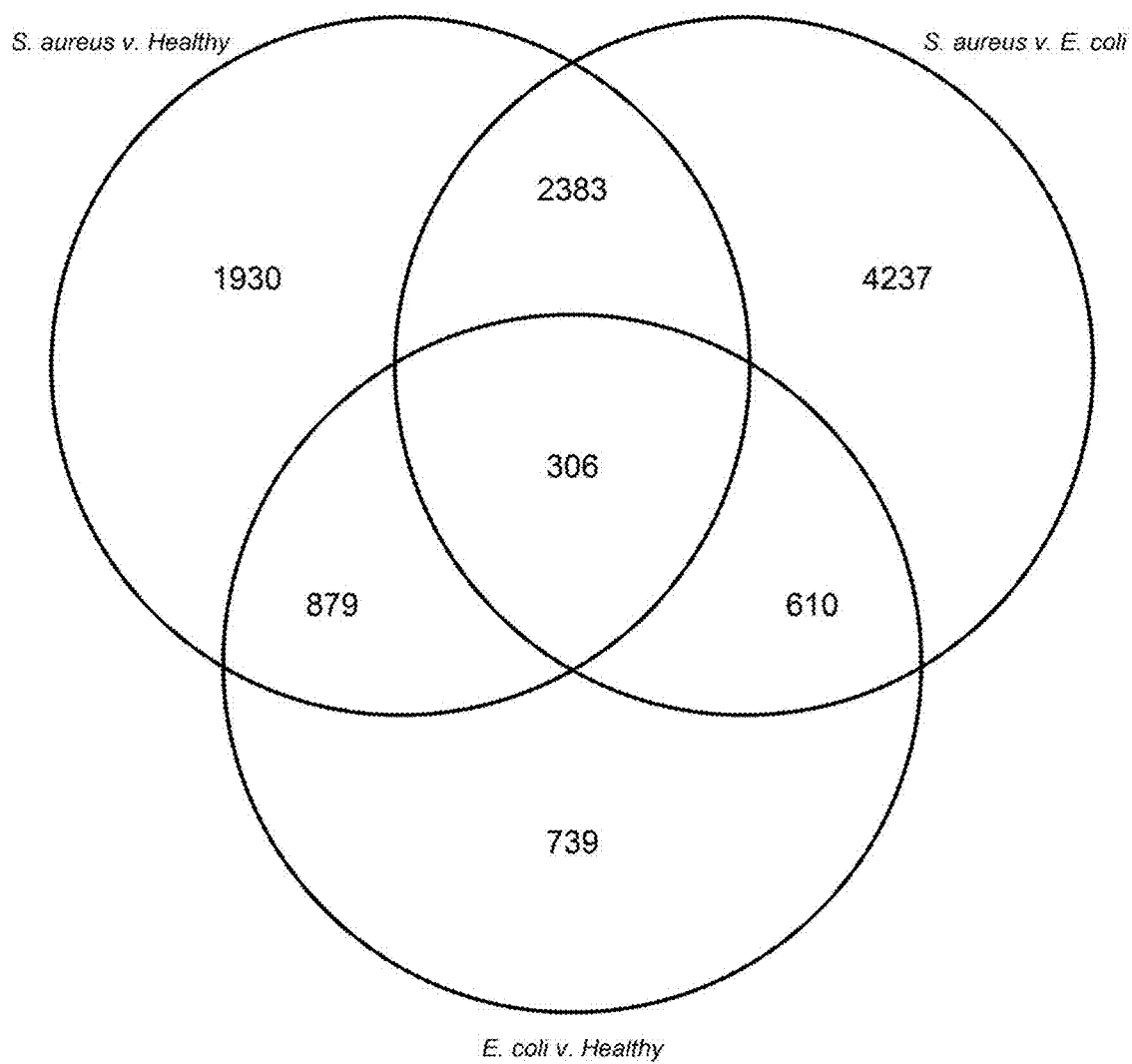

FIG. 9 shows a Venn diagram demonstrating the number of overlapping probes in each murine experimental group pairwise comparison. Probes were included that had significantly different levels of expression after Bonferroni correction.

Figure 10A:
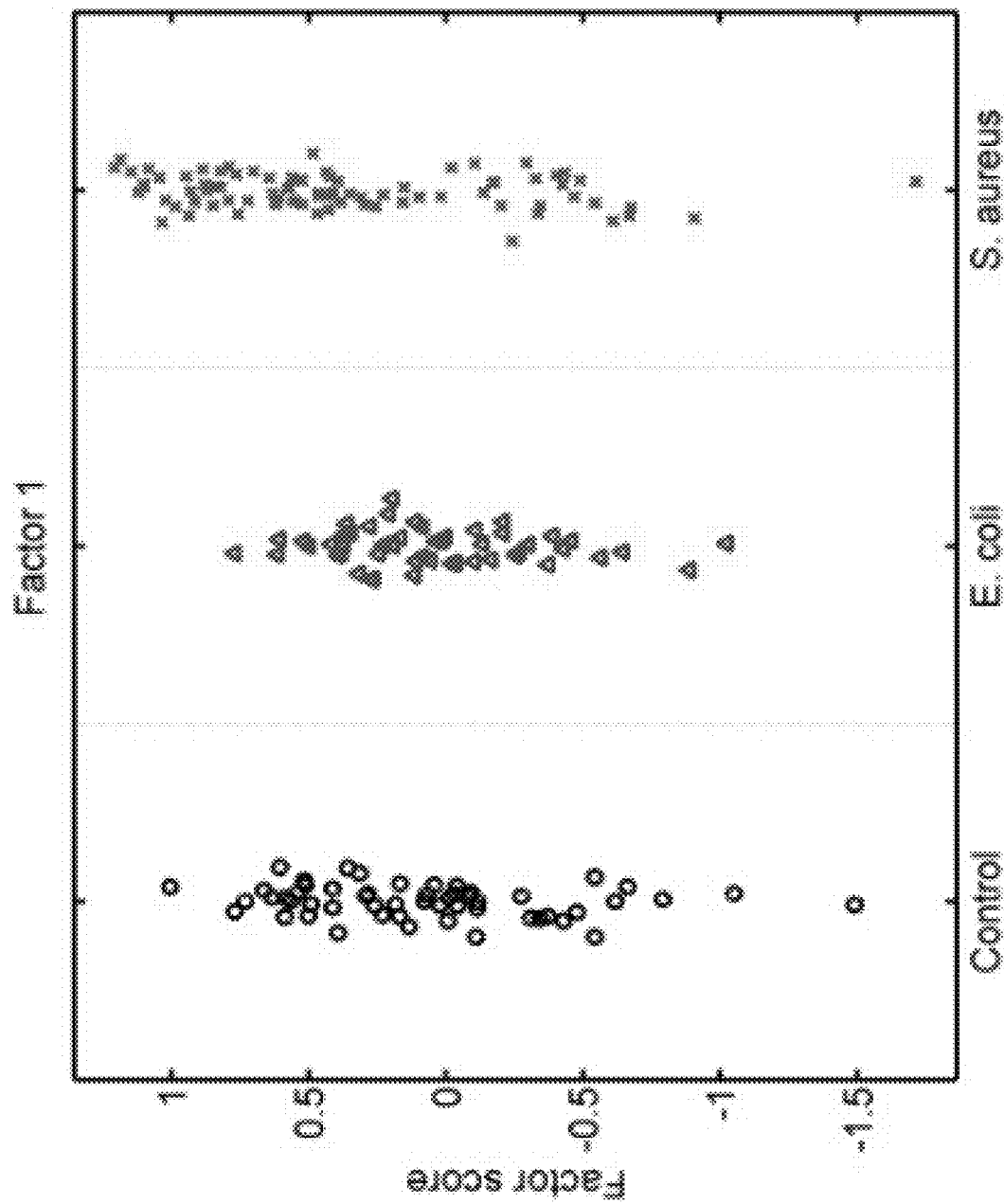
Figure 10B:
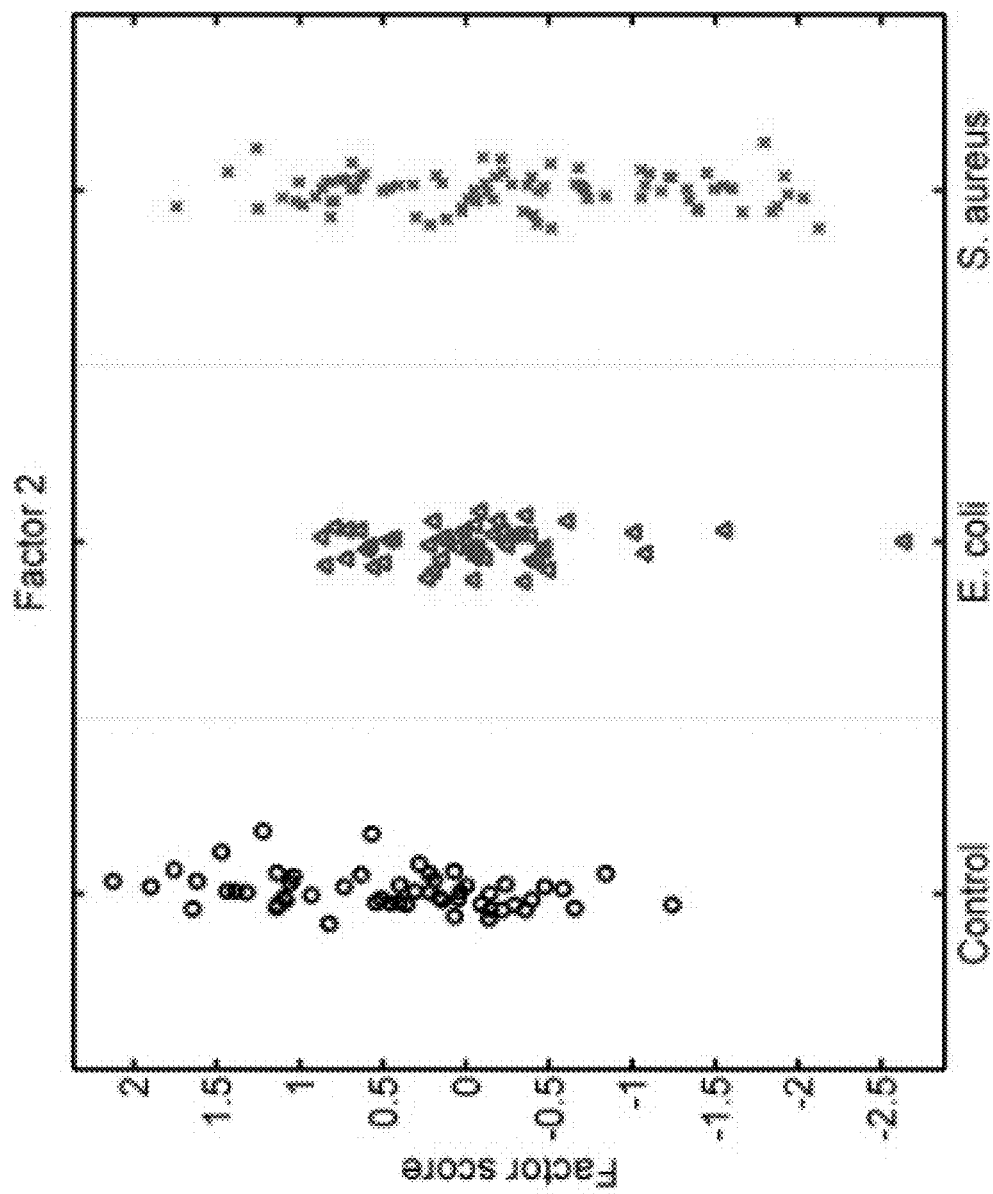
Figure 10C:
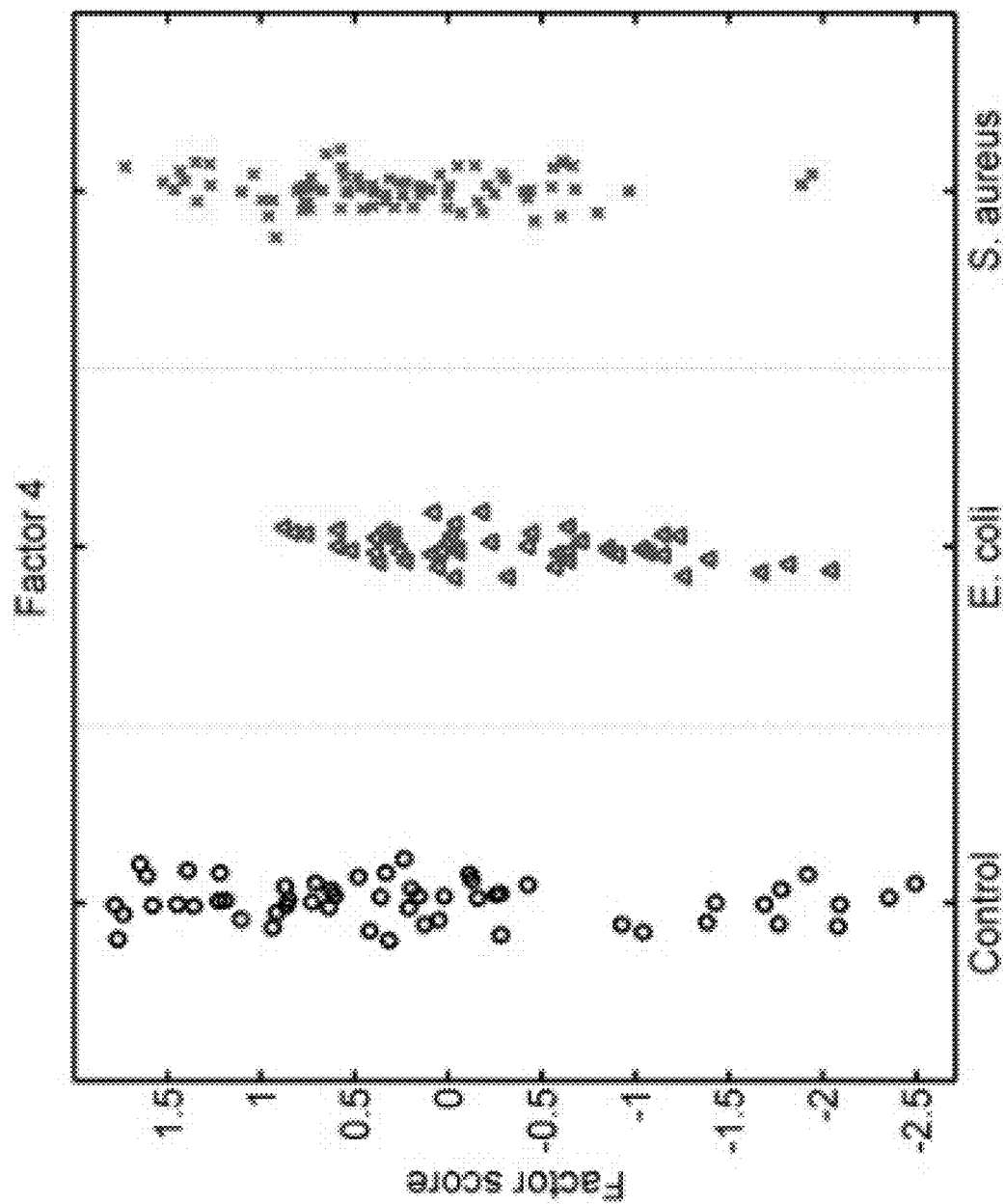
Figure 10D:
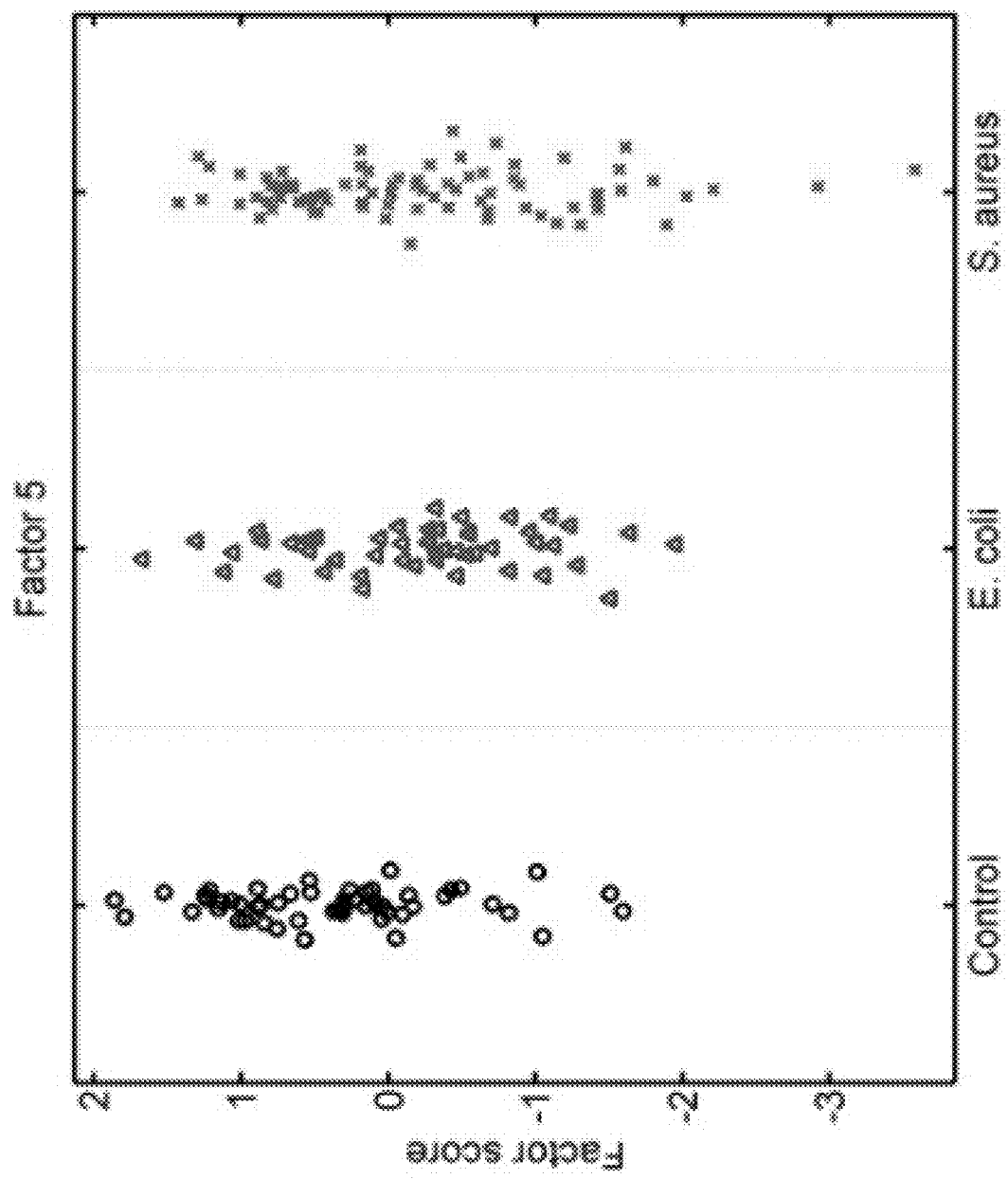
Figure 10E:
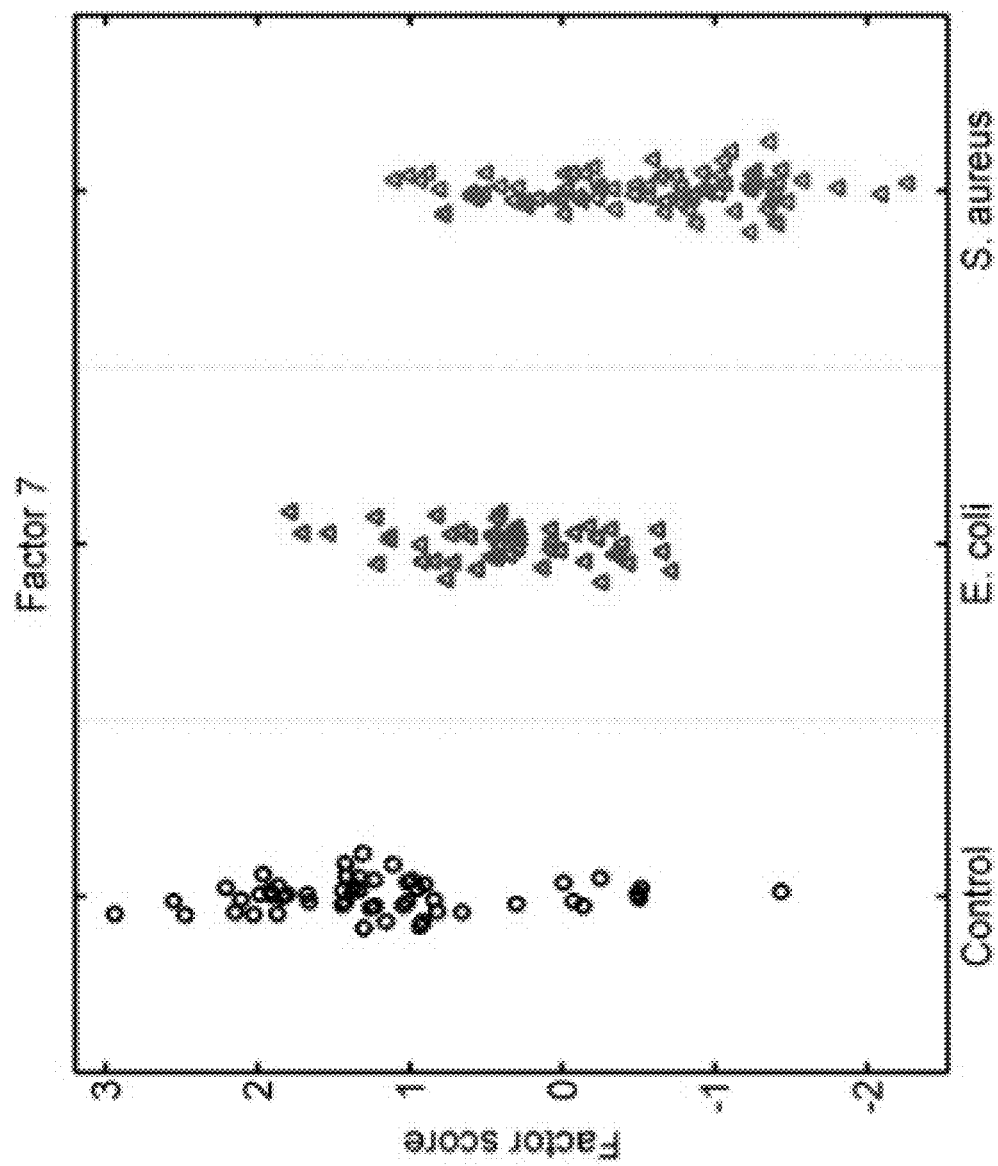
Figure 10F:
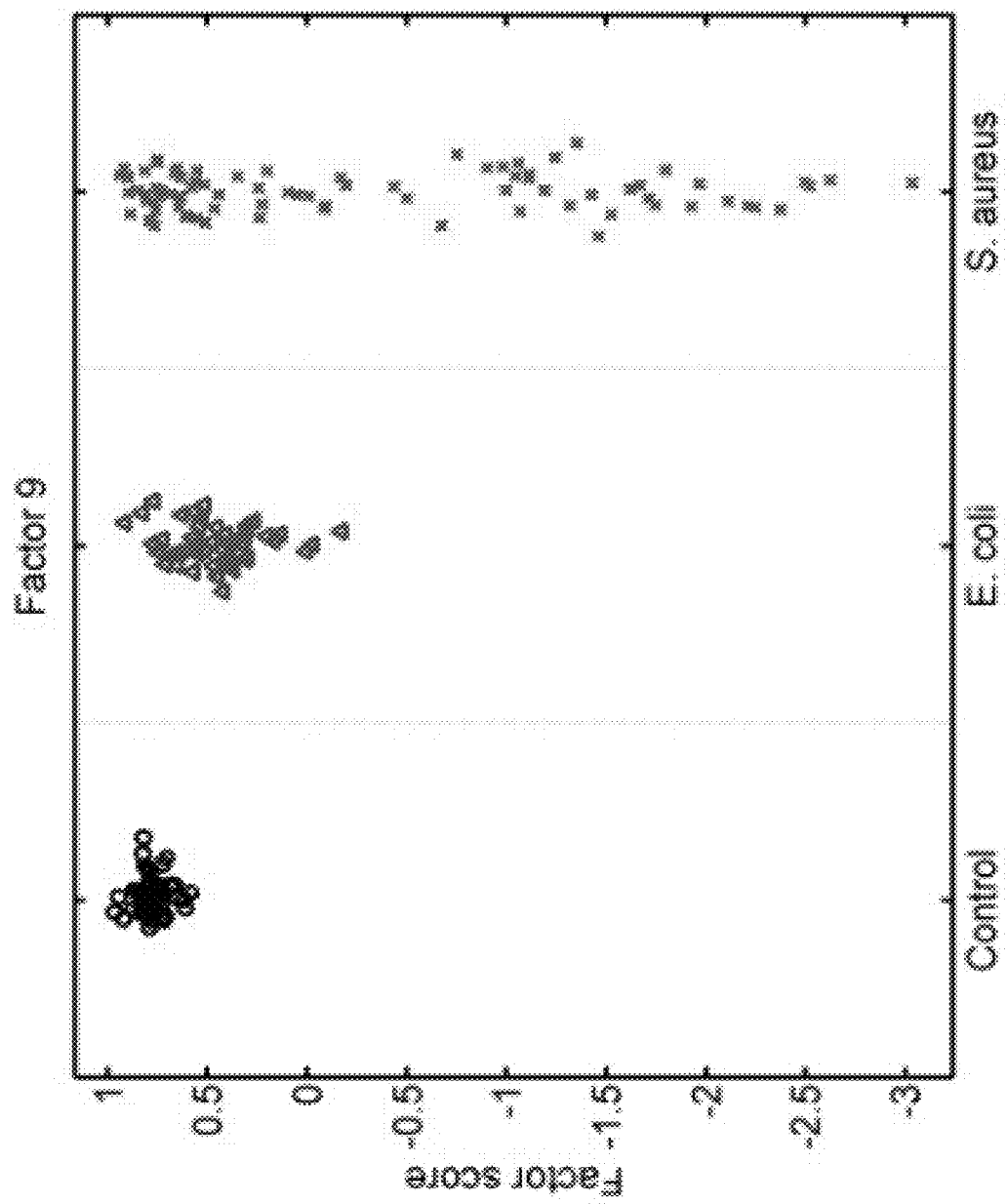
Figure 10G:
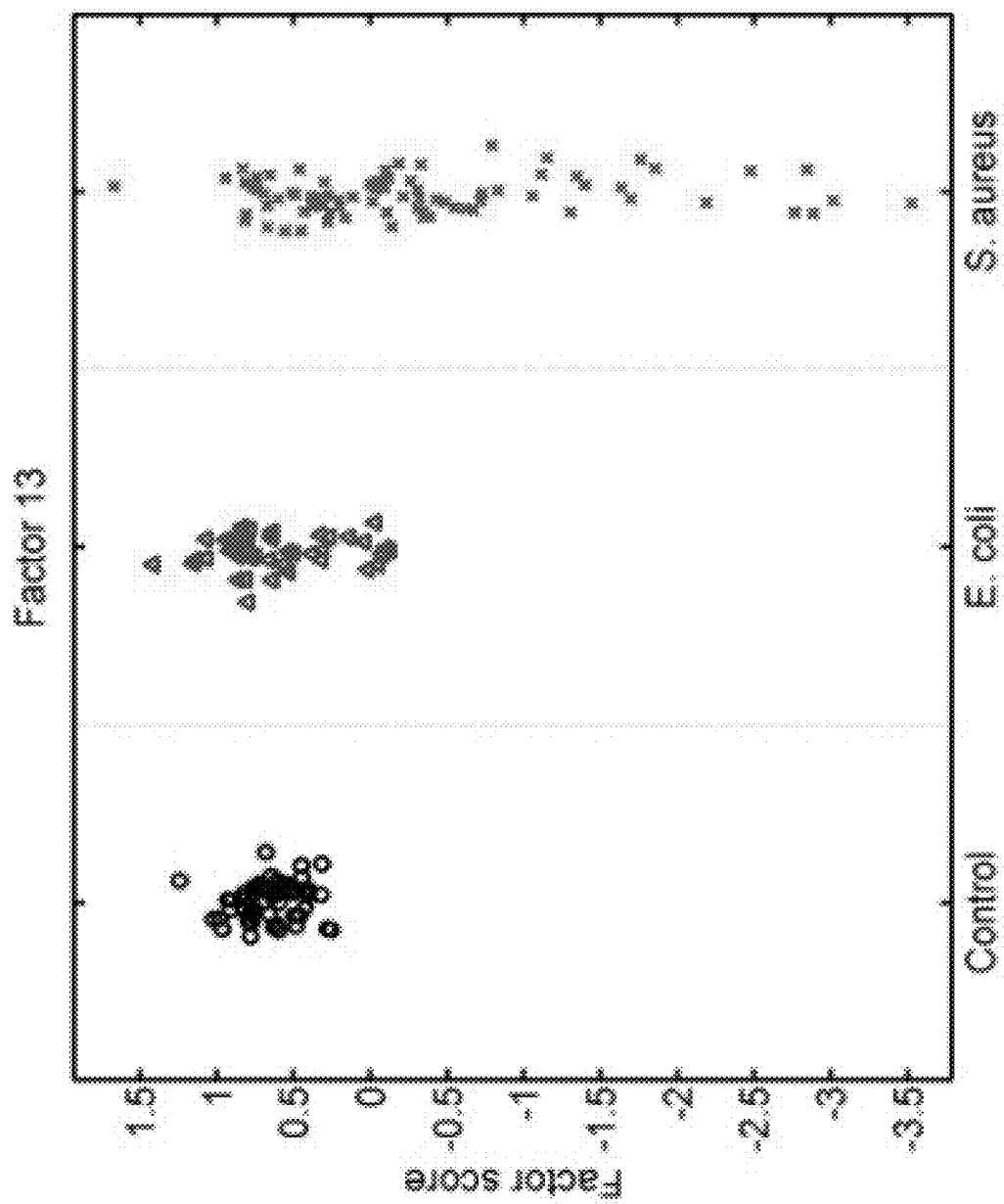
Figure 10H:
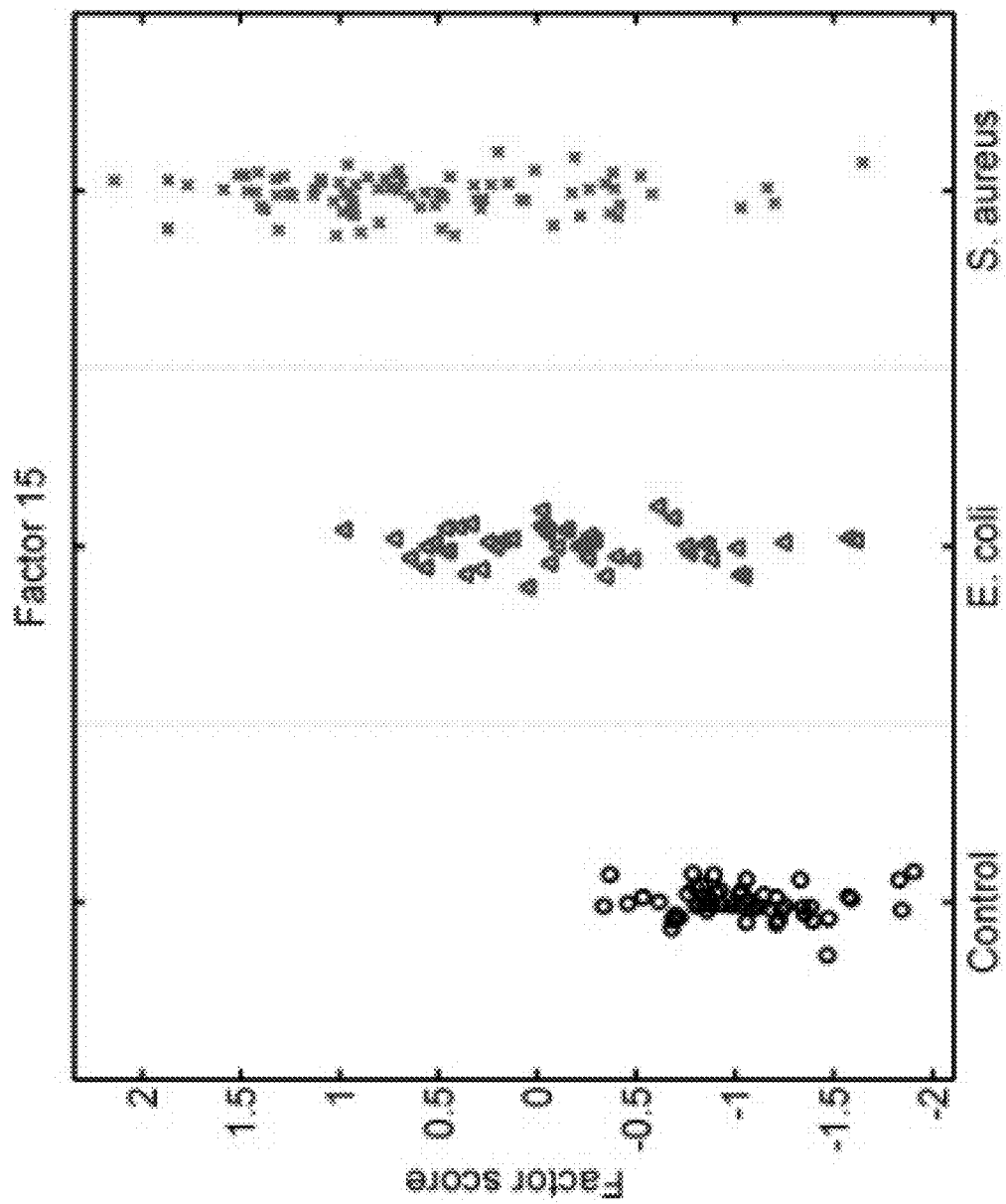
Figure 10I:
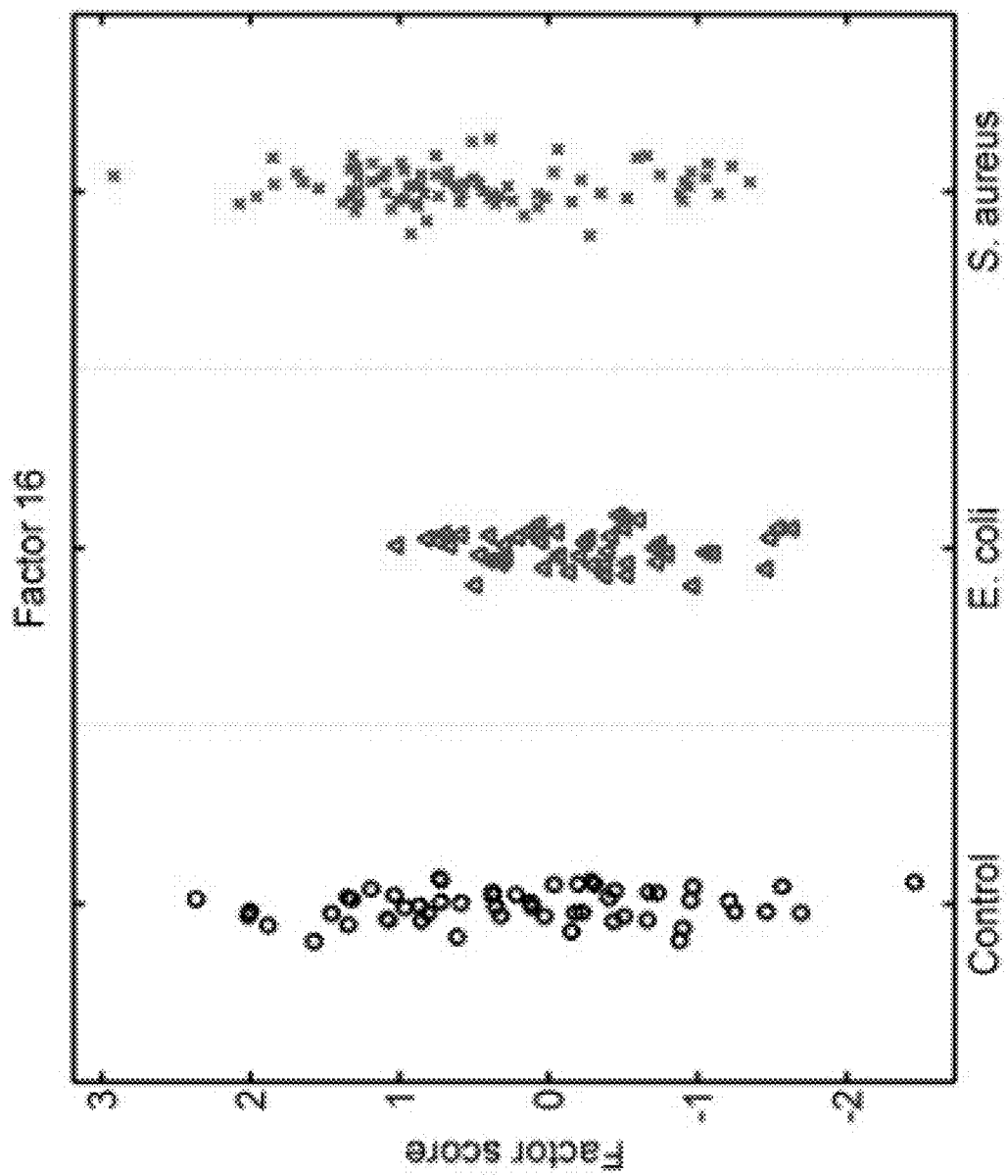
Figure 10J:
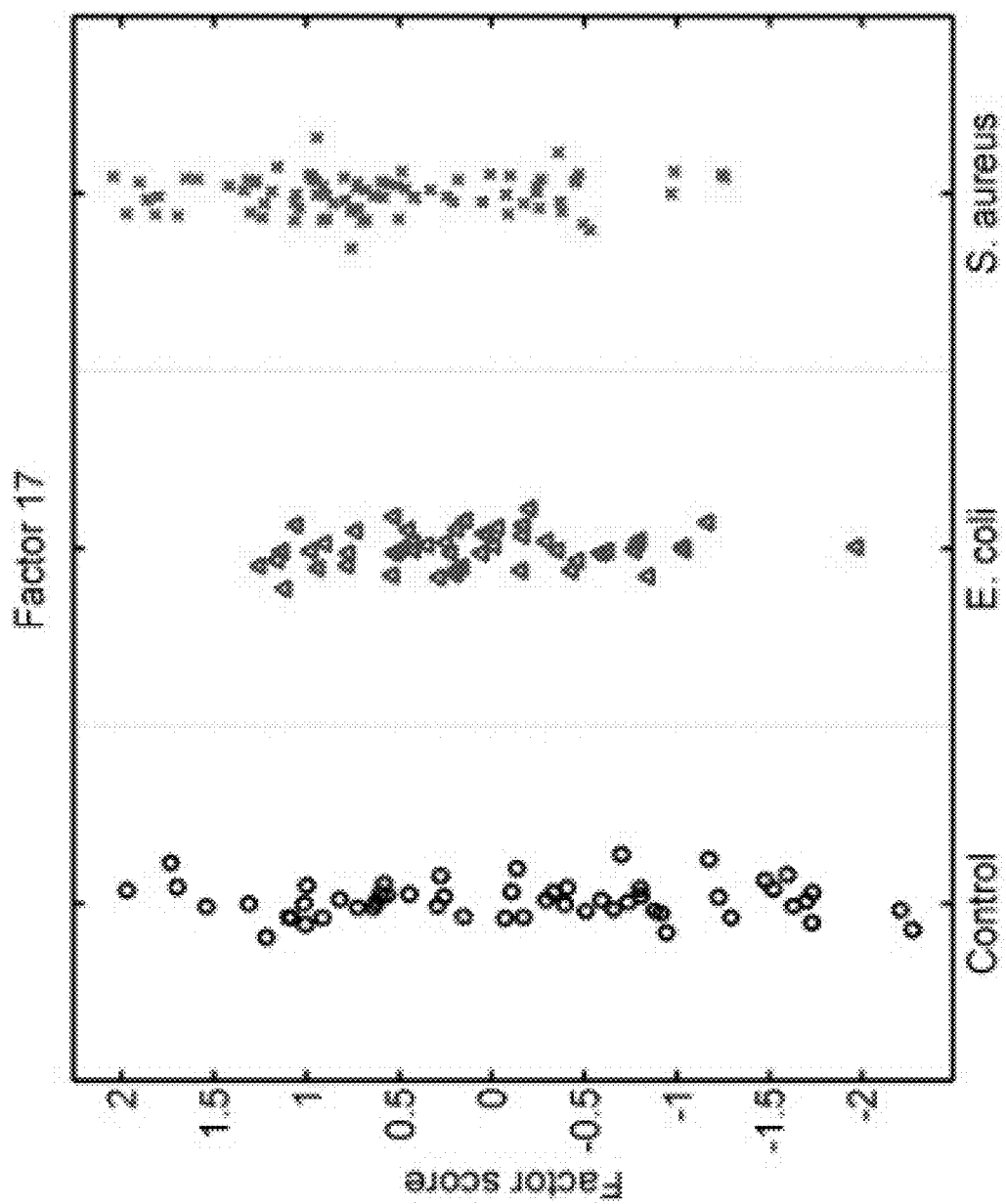
Figure 10K:
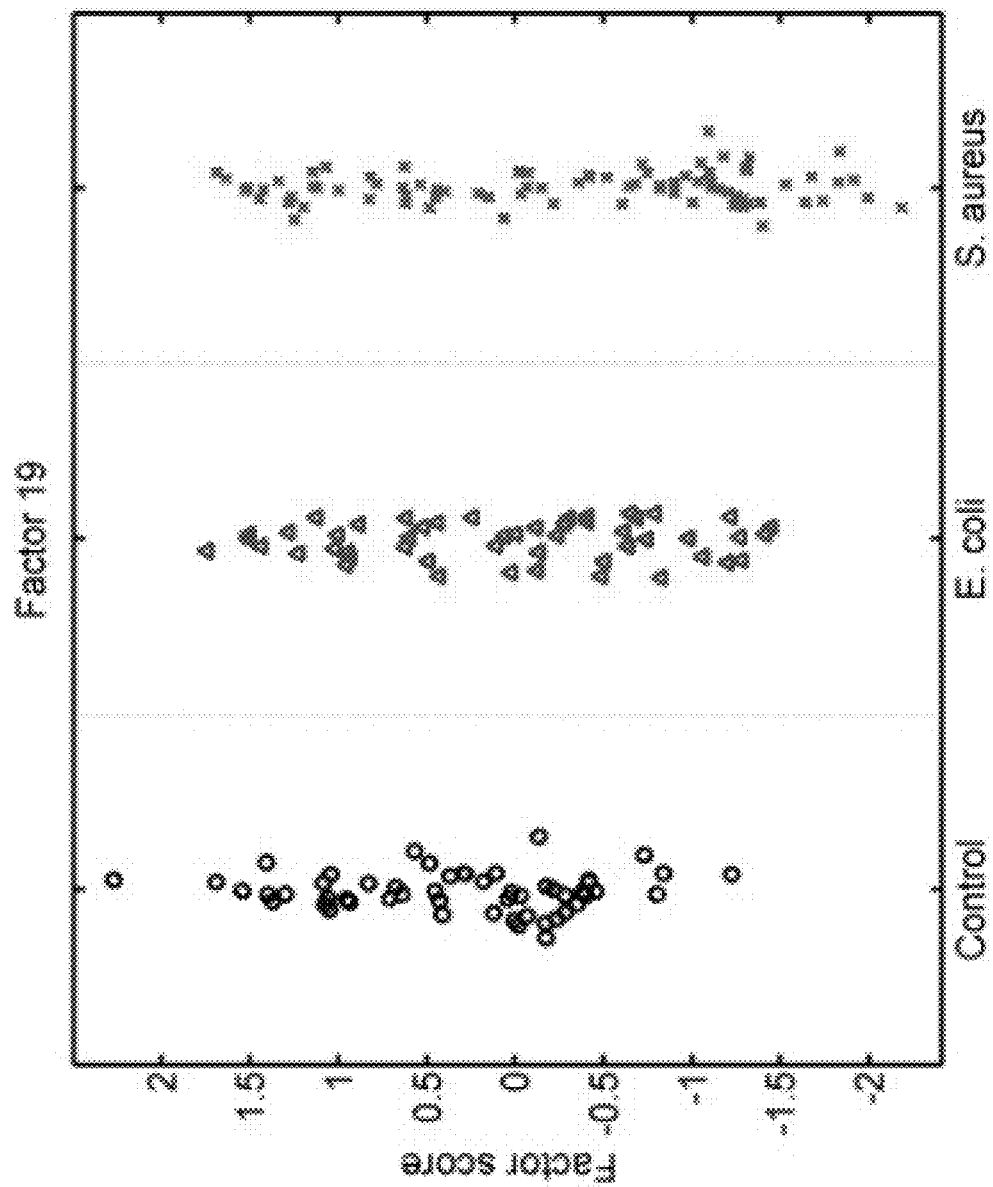
Figure 10L:
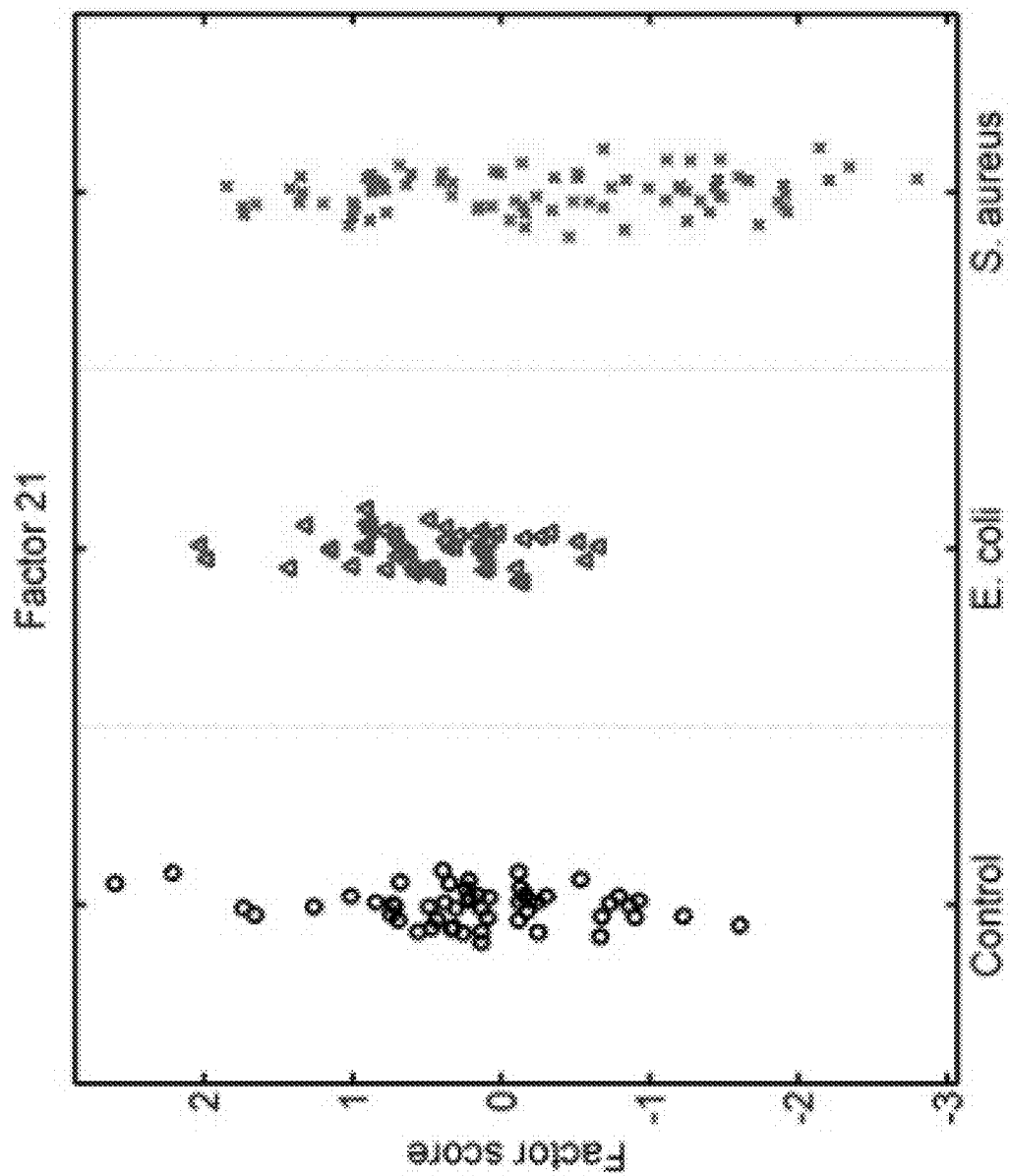
Figure 10M:
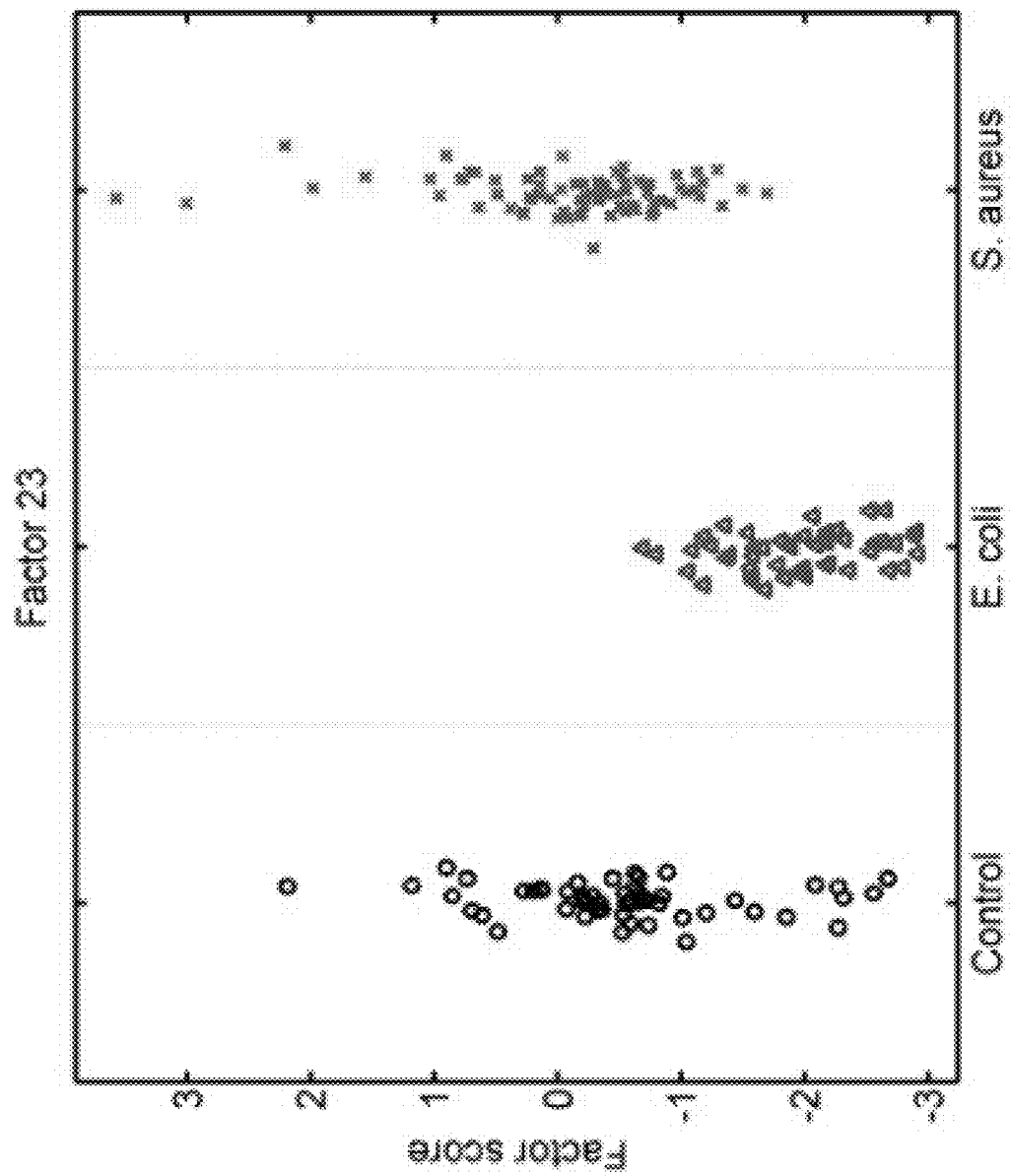
Figure 10N:
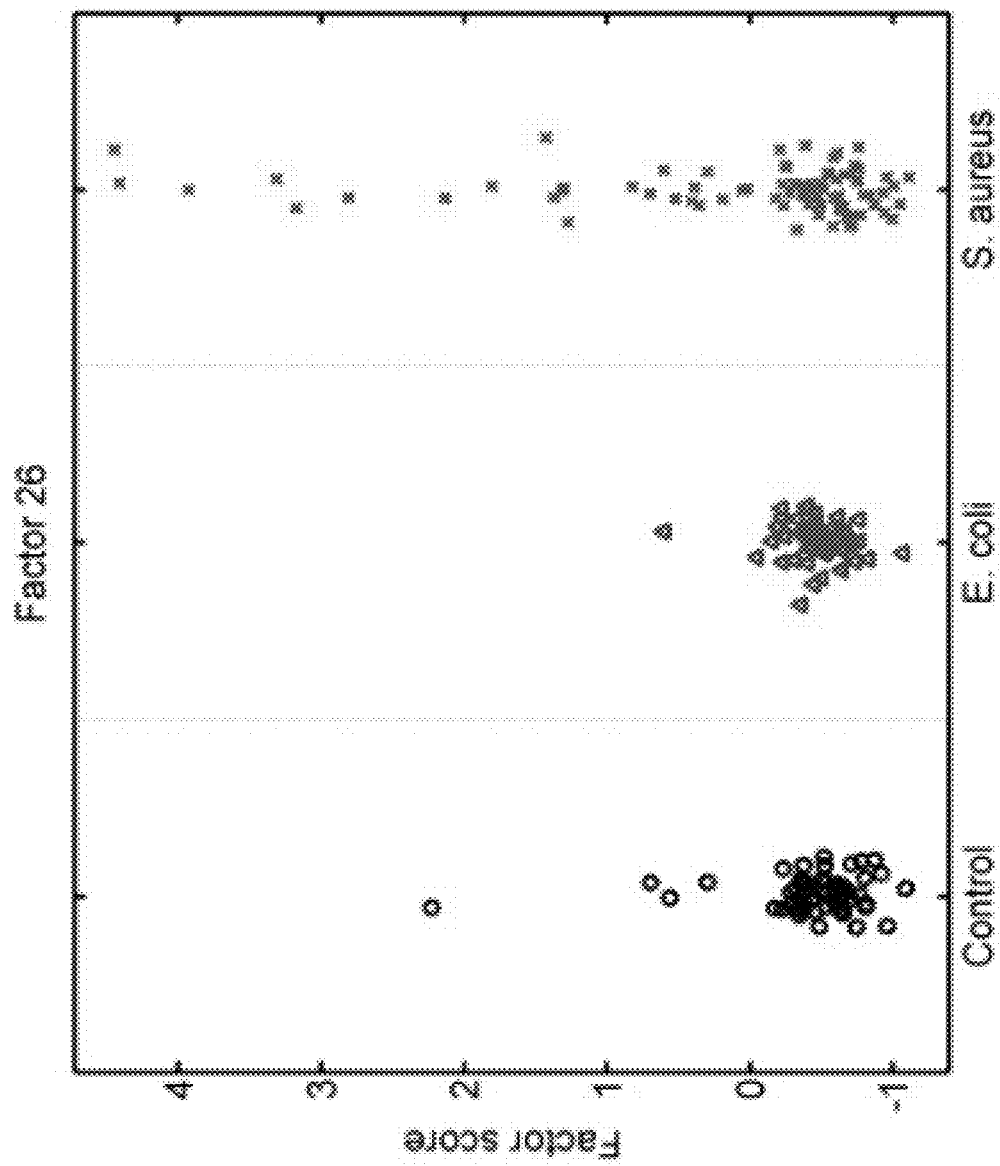
Figure 10O:
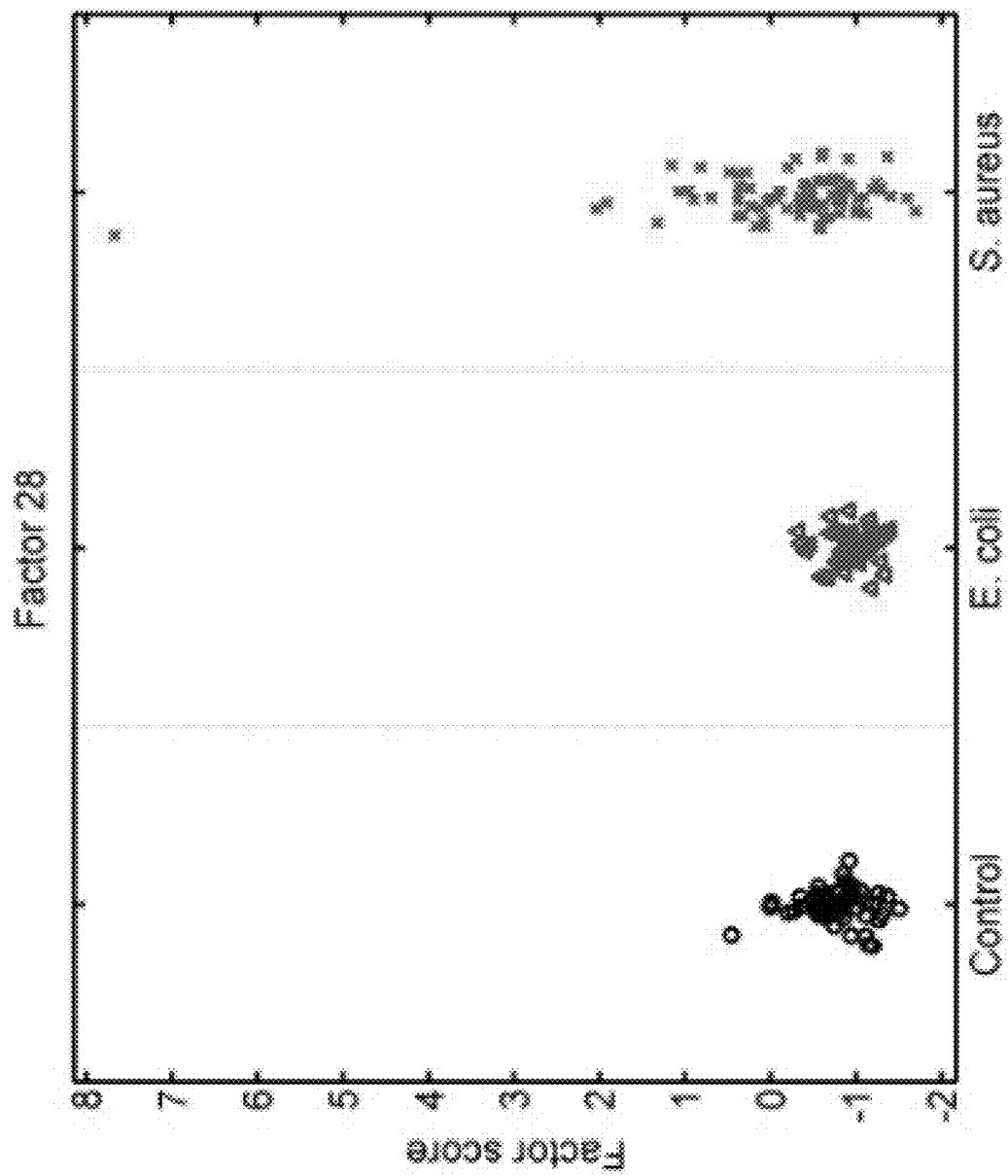
Figure 10P:
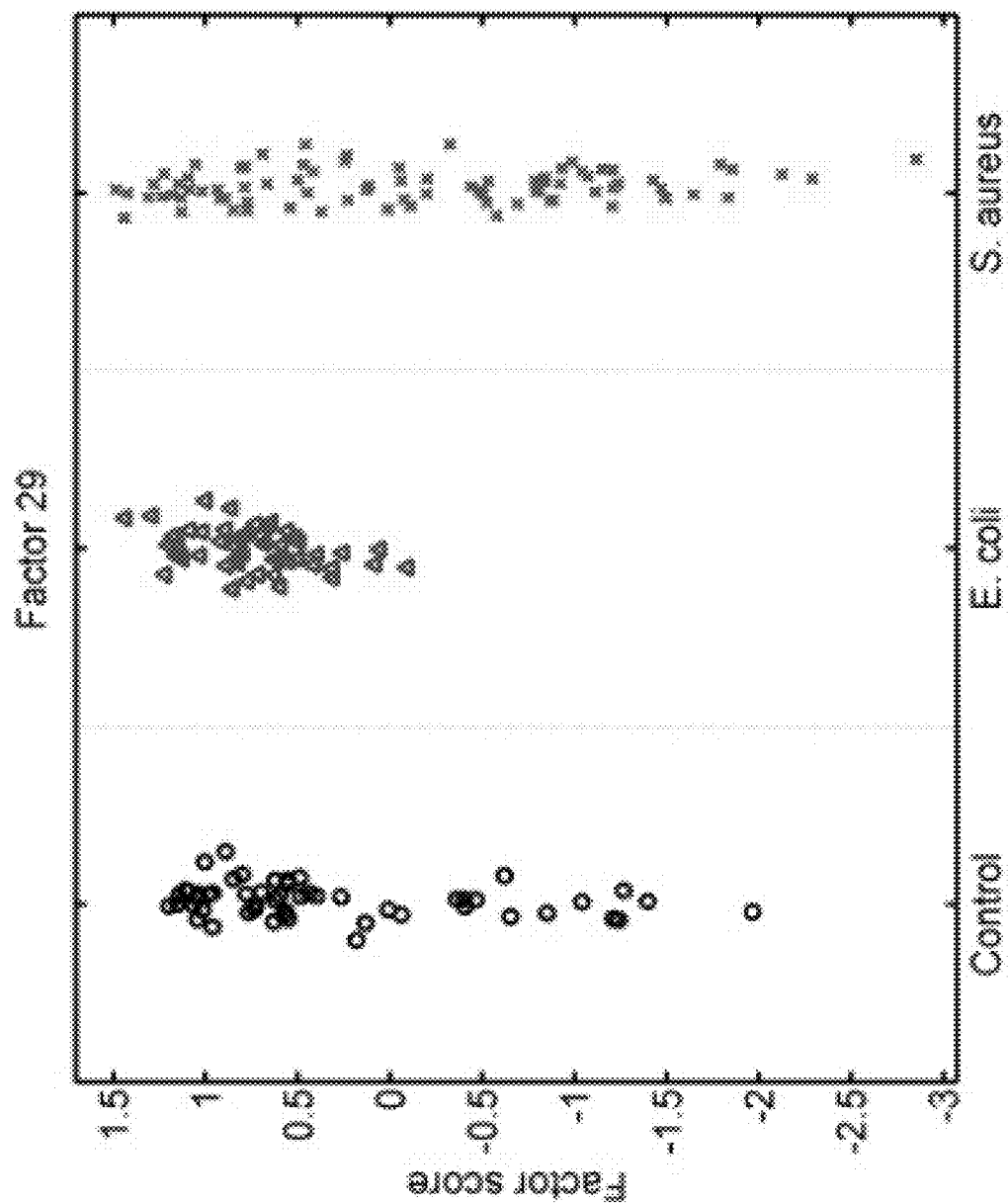

FIGS. 10A-10P show that sixteen murine factors independently associated with *S. aureus* infection projected onto healthy controls (left panel, black circles), animals with *E. coli* infection (middle panel, blue triangles), and animals with *S. aureus* infection (right panel, red "x"). The y-axis represents the factor score.

Figure 11:
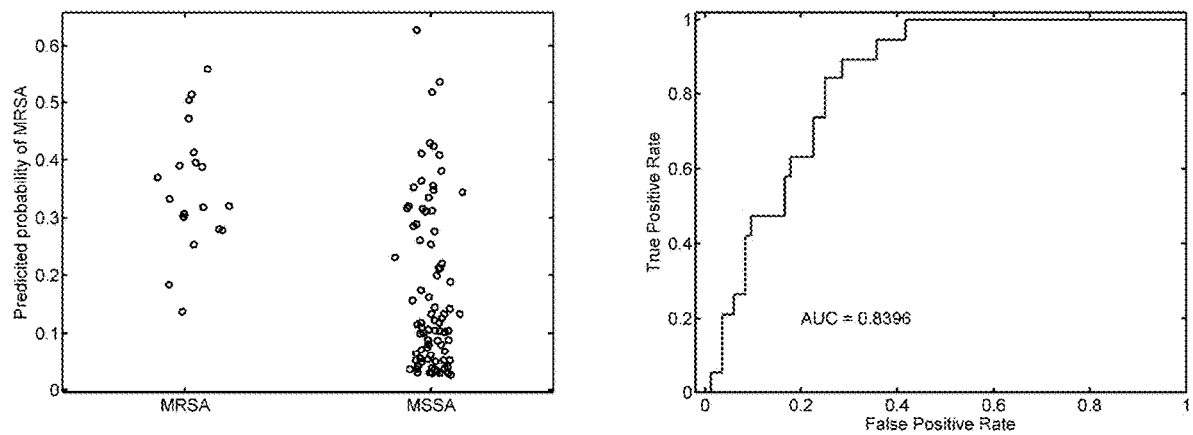

FIG. 11 shows that a factor-based classifier distinguishes MRSA from MSSA infection in mice. An ROC curve is shown for this classification.

Figure 12:
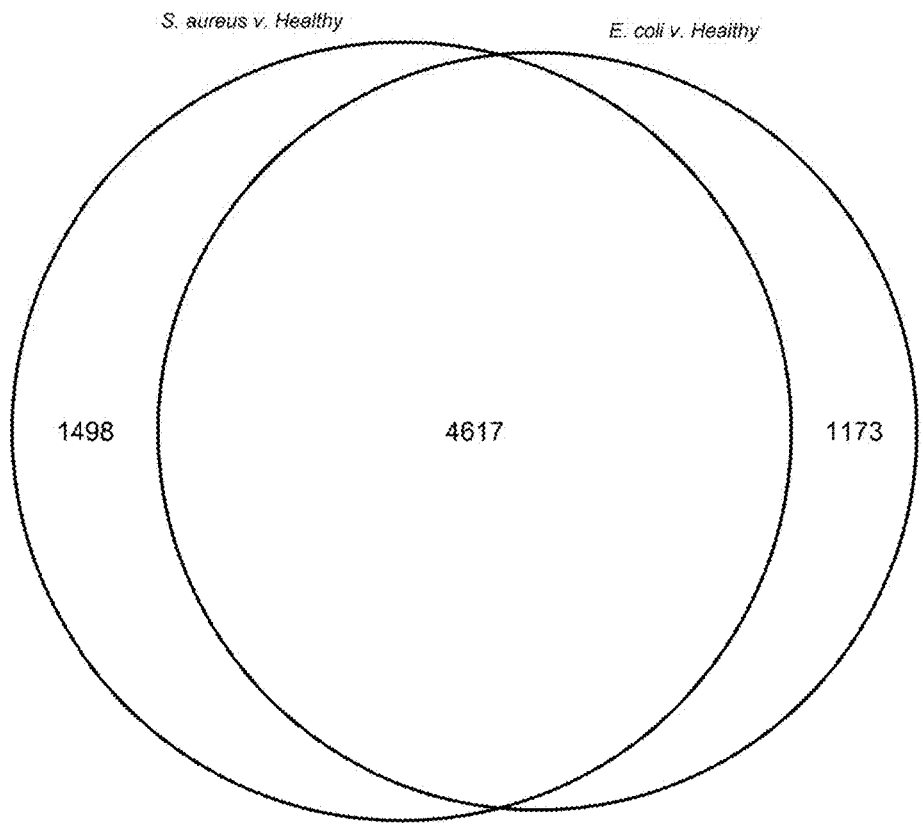

FIG. 12 shows Venn diagram demonstrating the number of overlapping probes in each human experimental group pairwise comparison. Probes were included that had significantly different levels of expression after Bonferroni correction. No probes met this cutoff for the *S. aureus* vs. *E. coli* comparison.

Figure 13A:
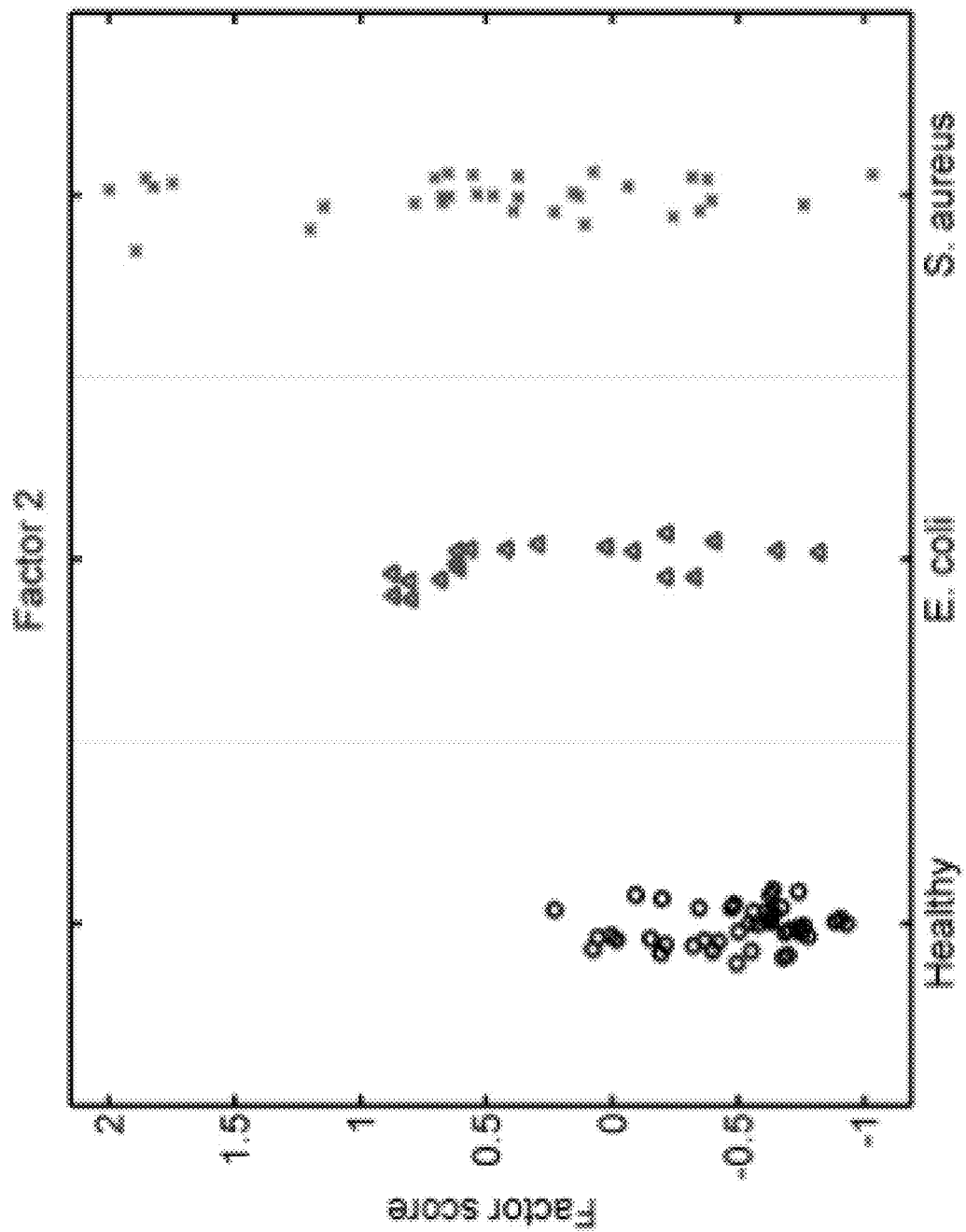
Figure 13B:
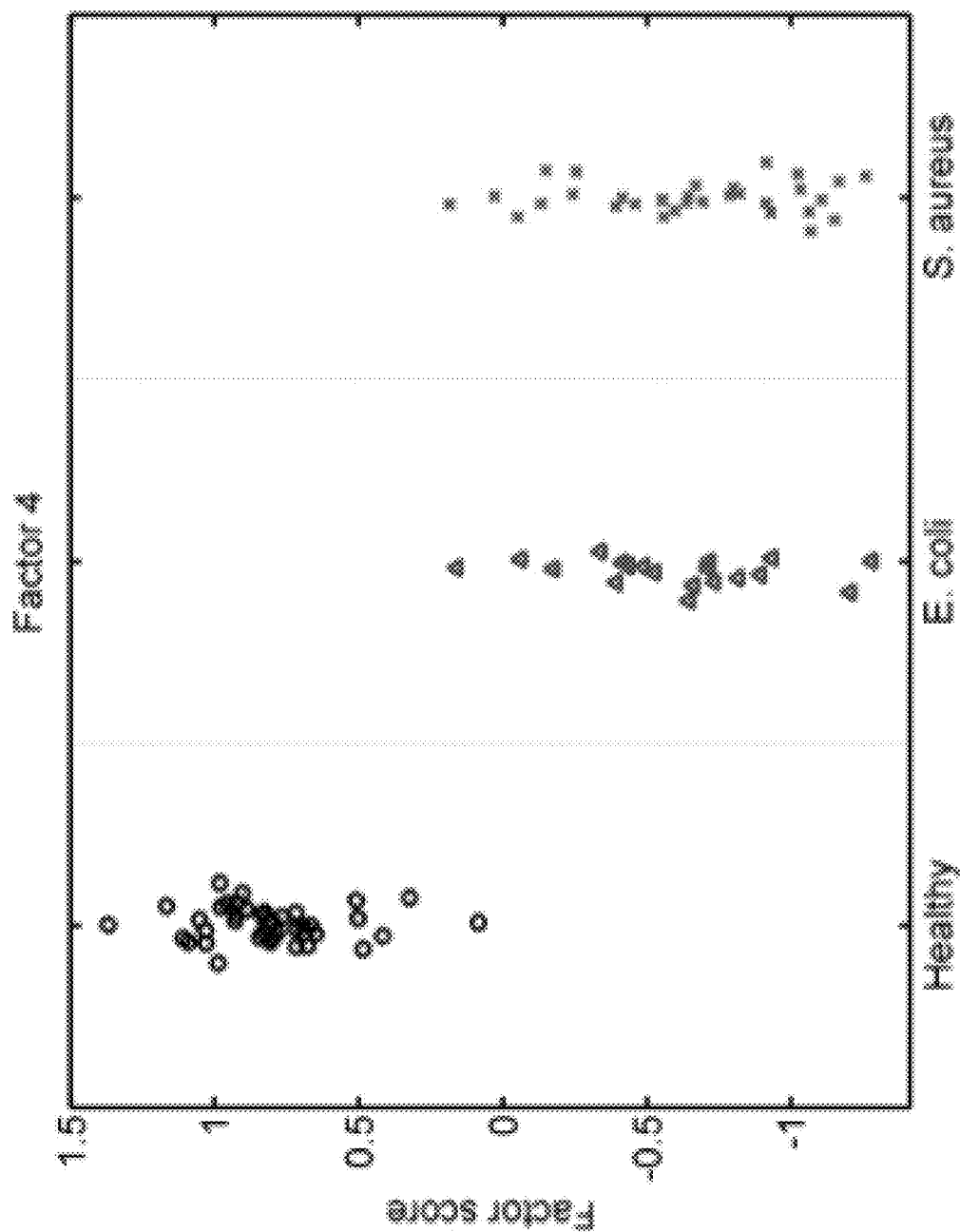
Figure 13C:
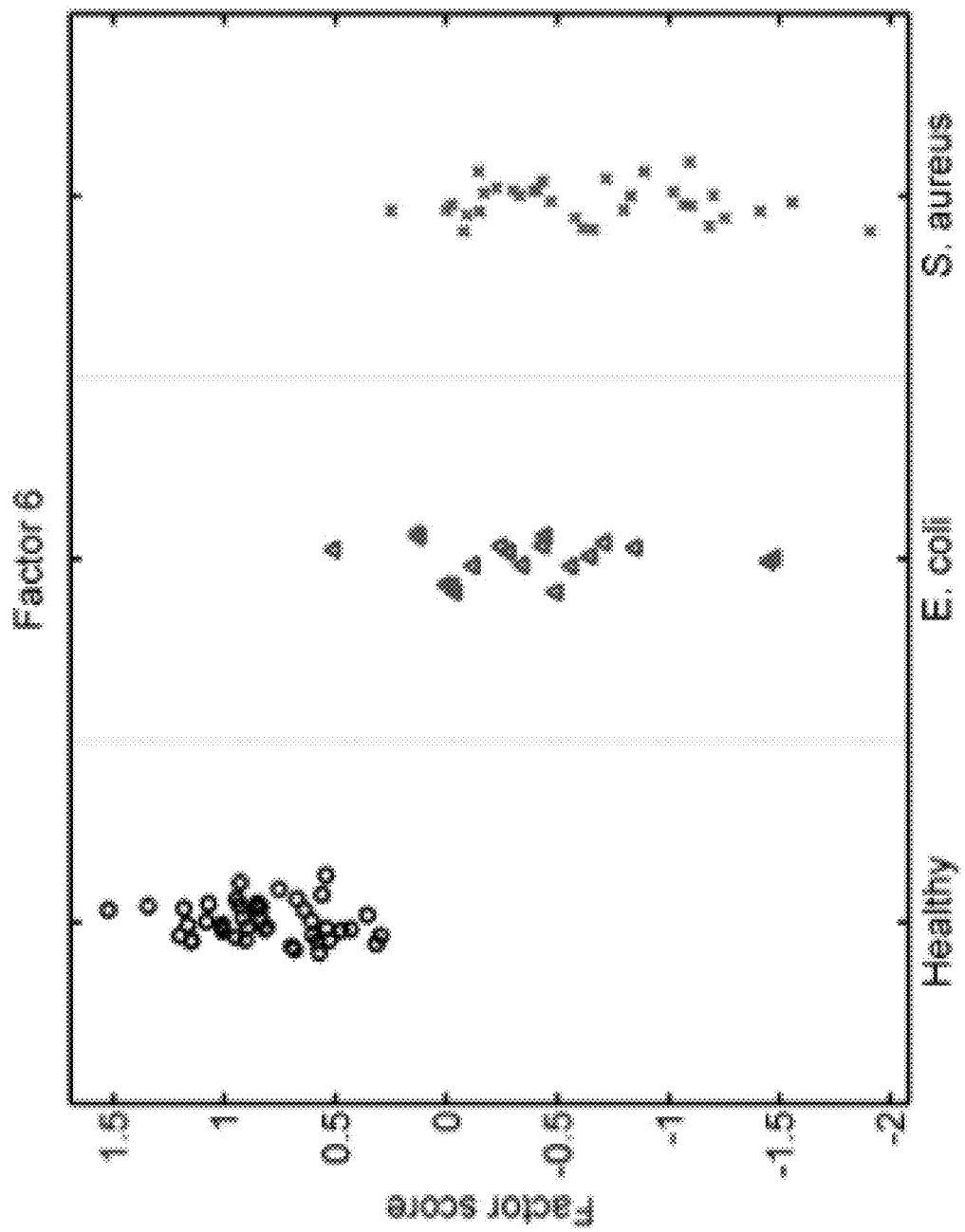
Figure 13D:
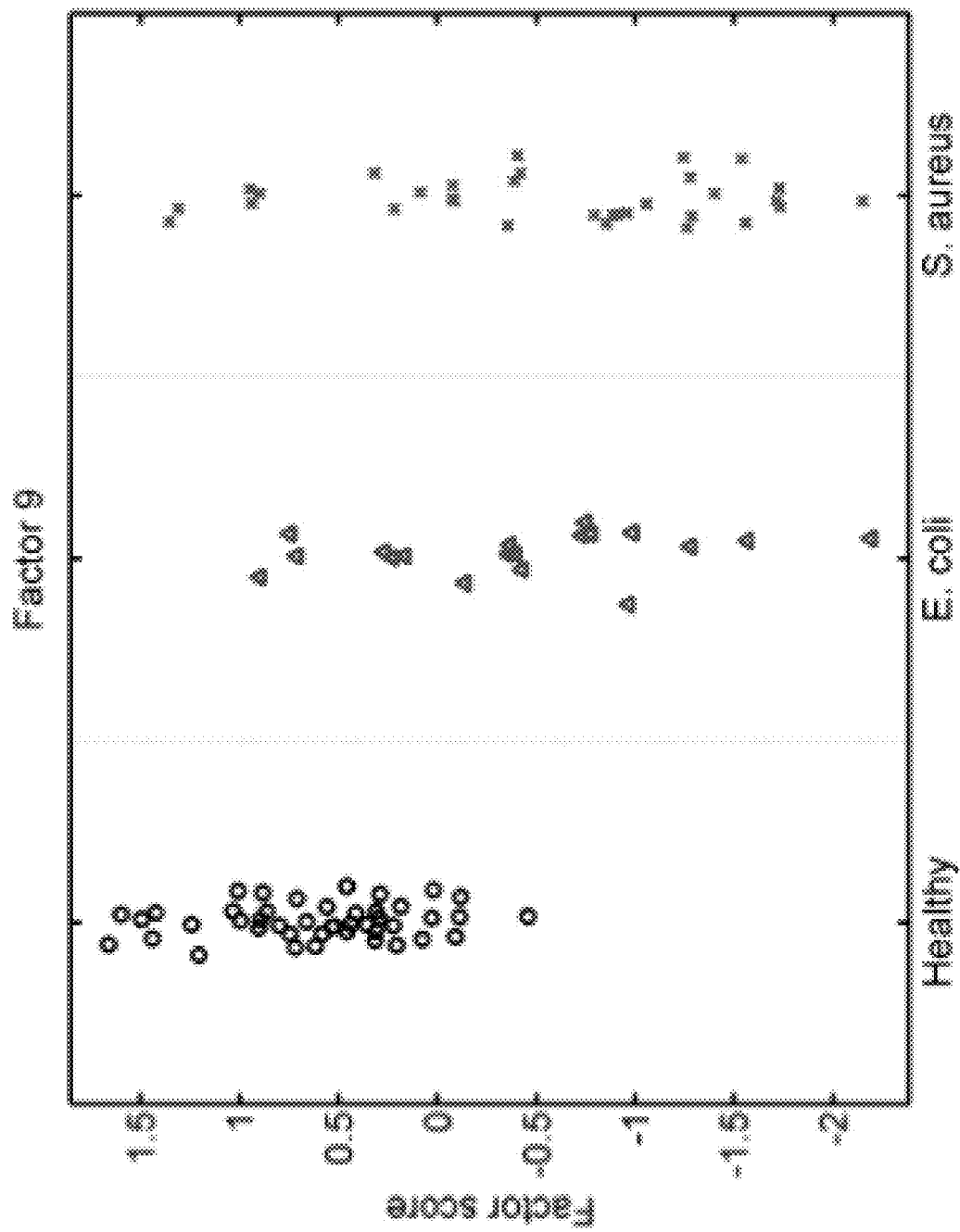
Figure 13E:
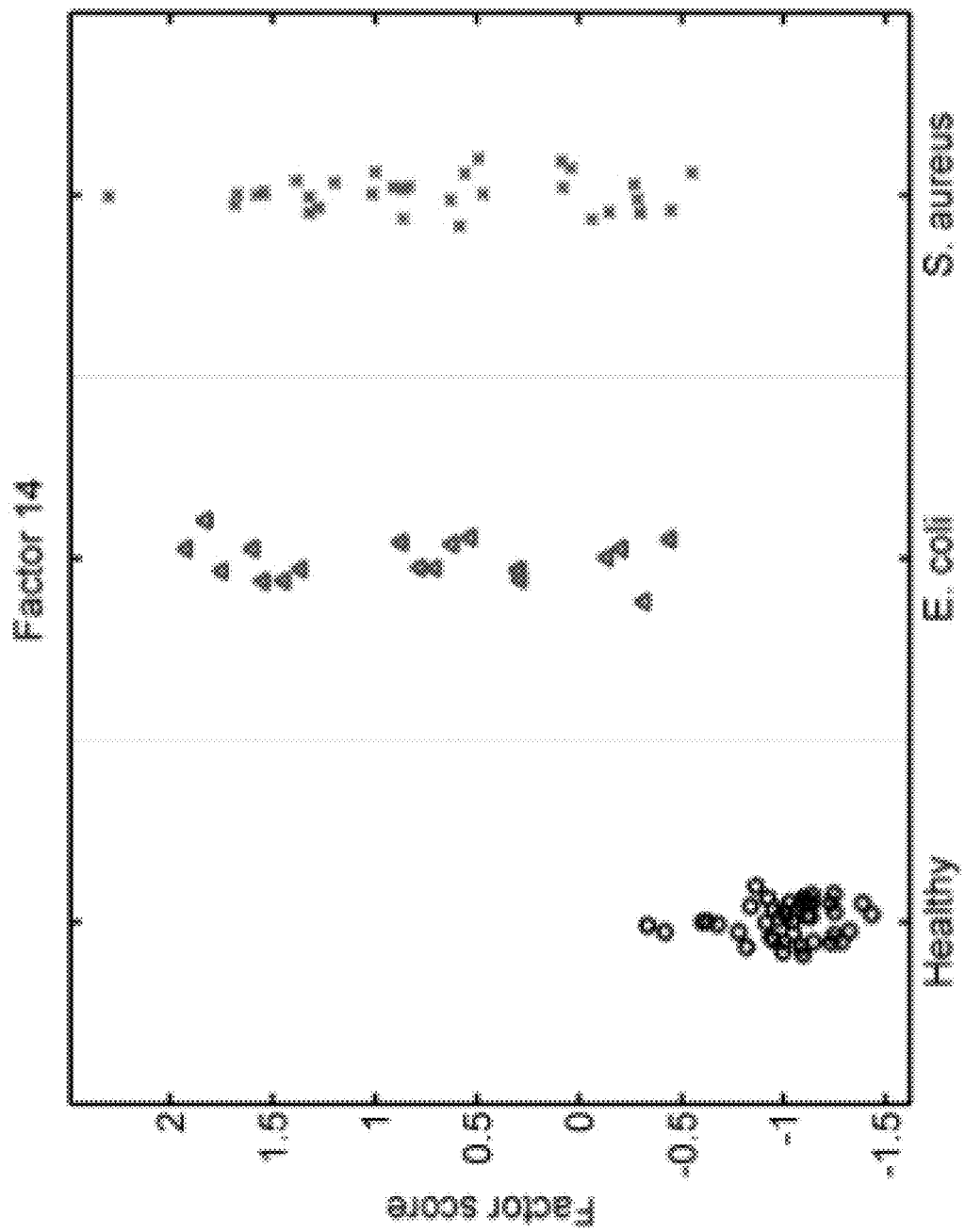
Figure 13F:
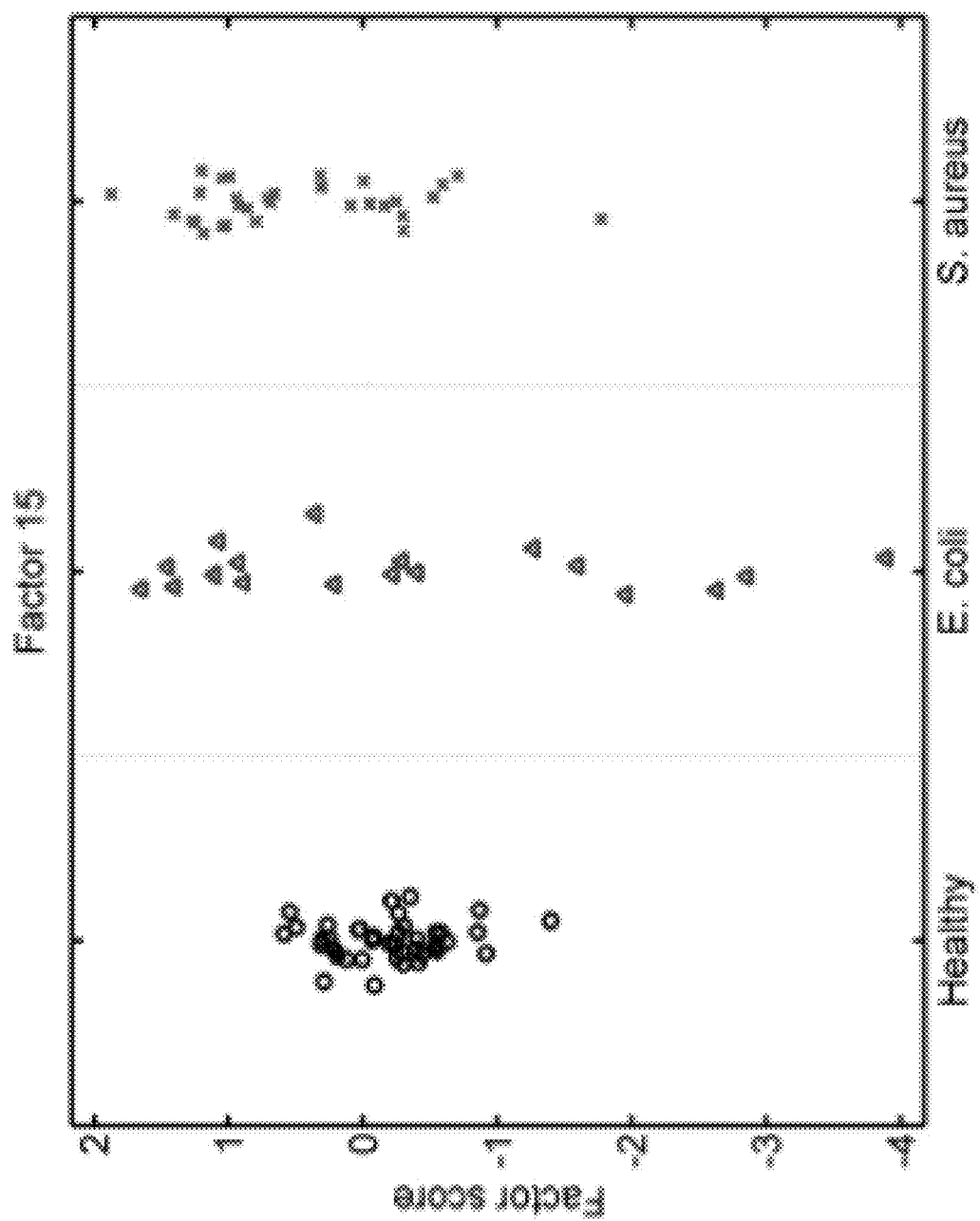
Figure 13G:
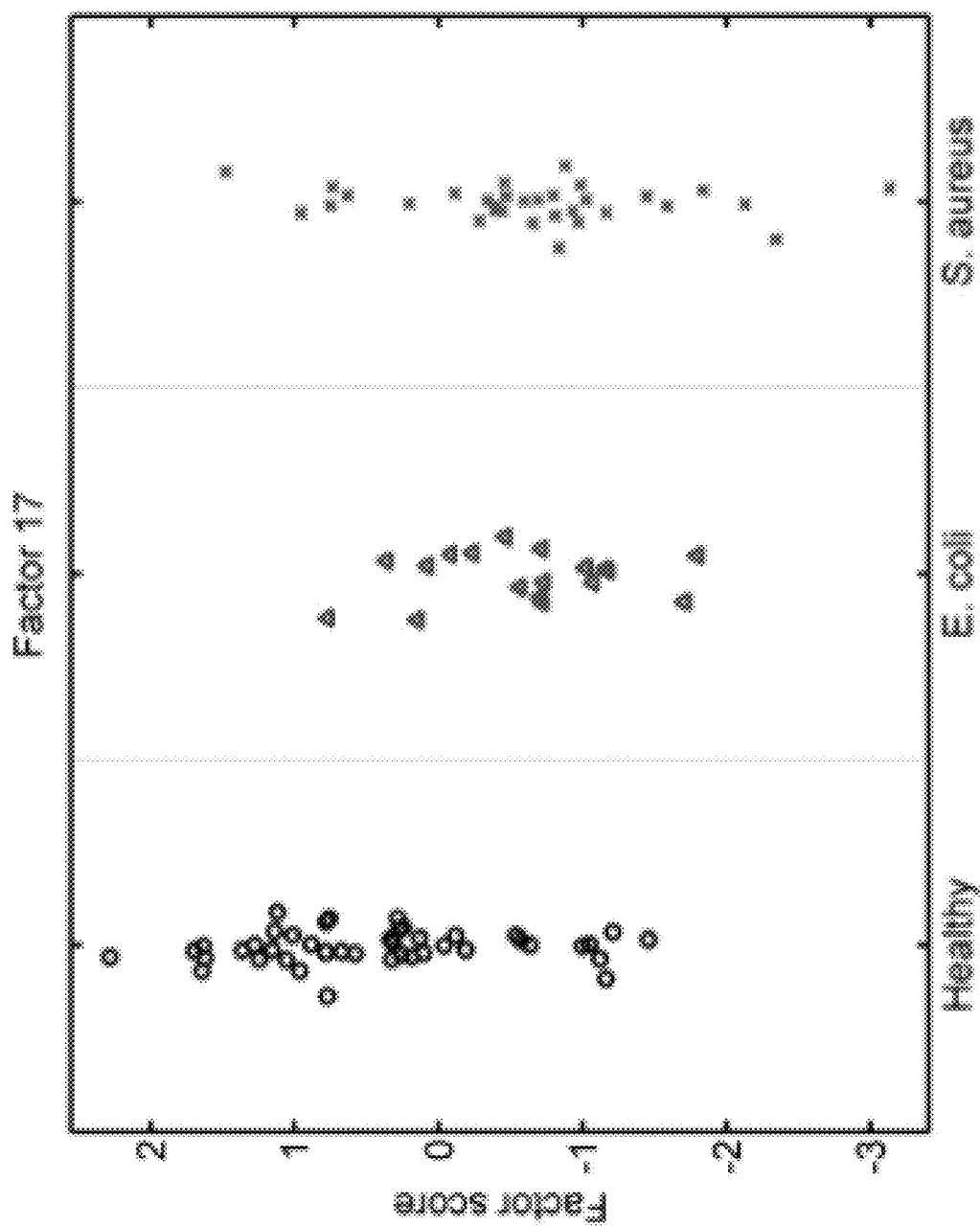
Figure 13H:
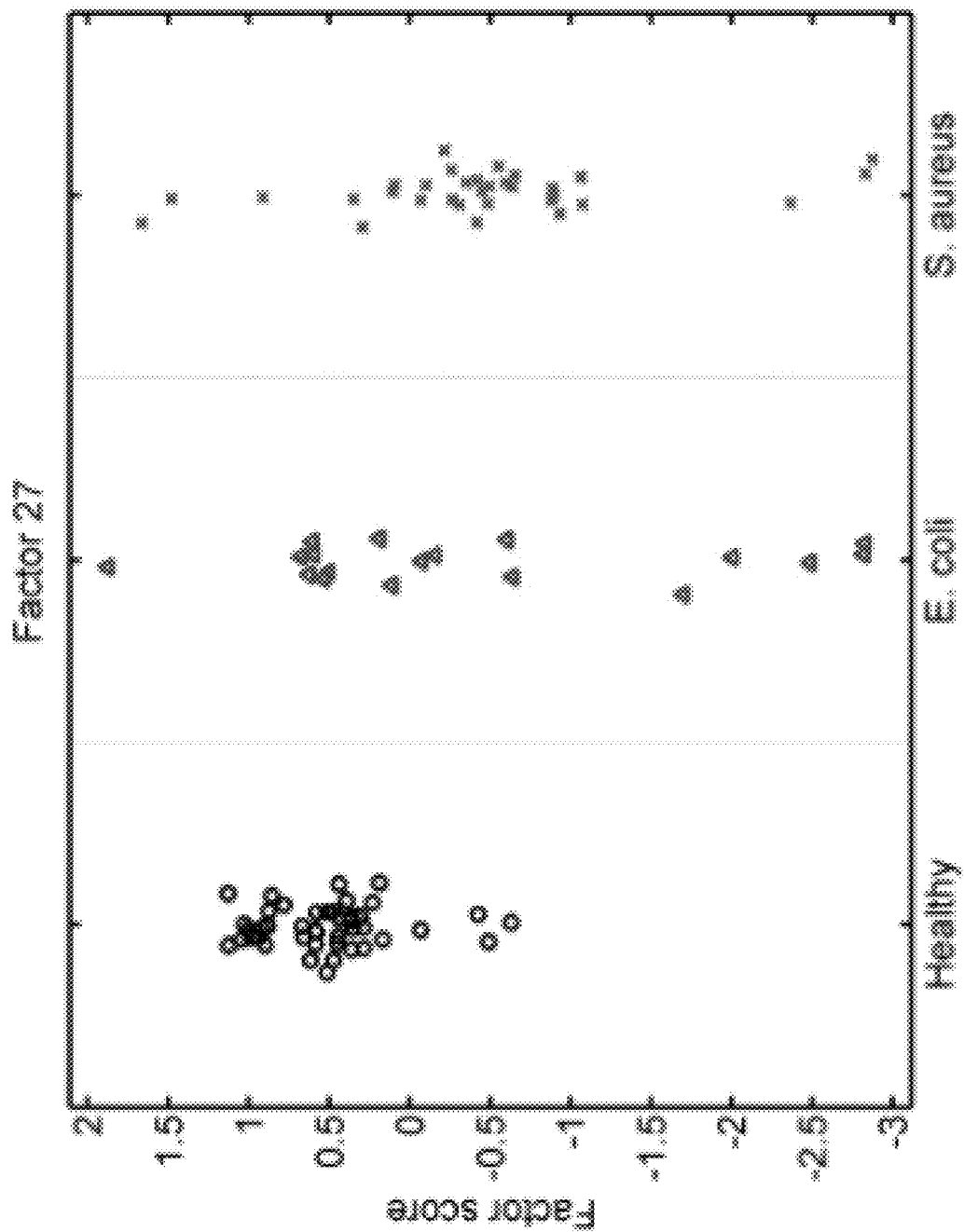
Figure 13I:
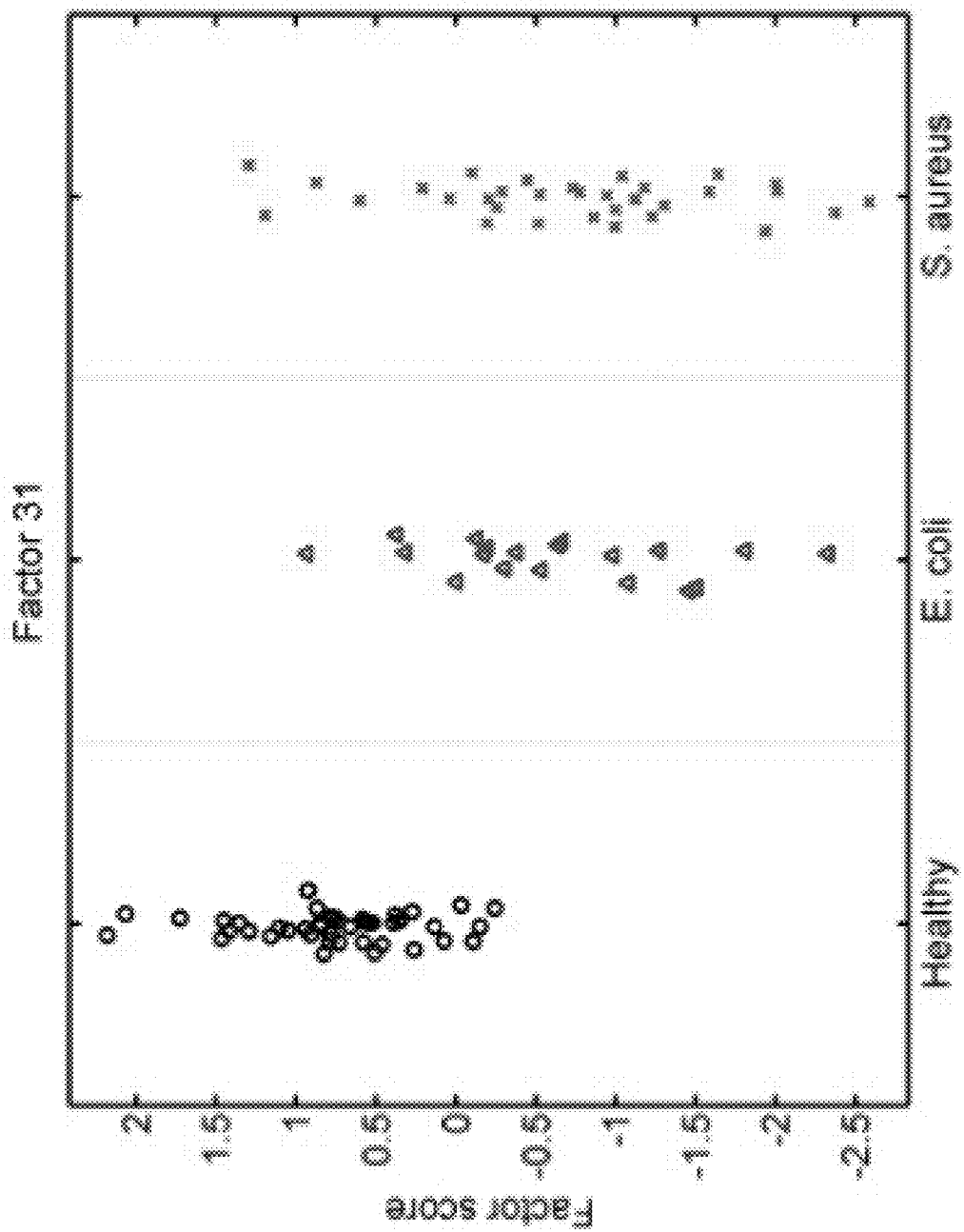
Figure 13J:
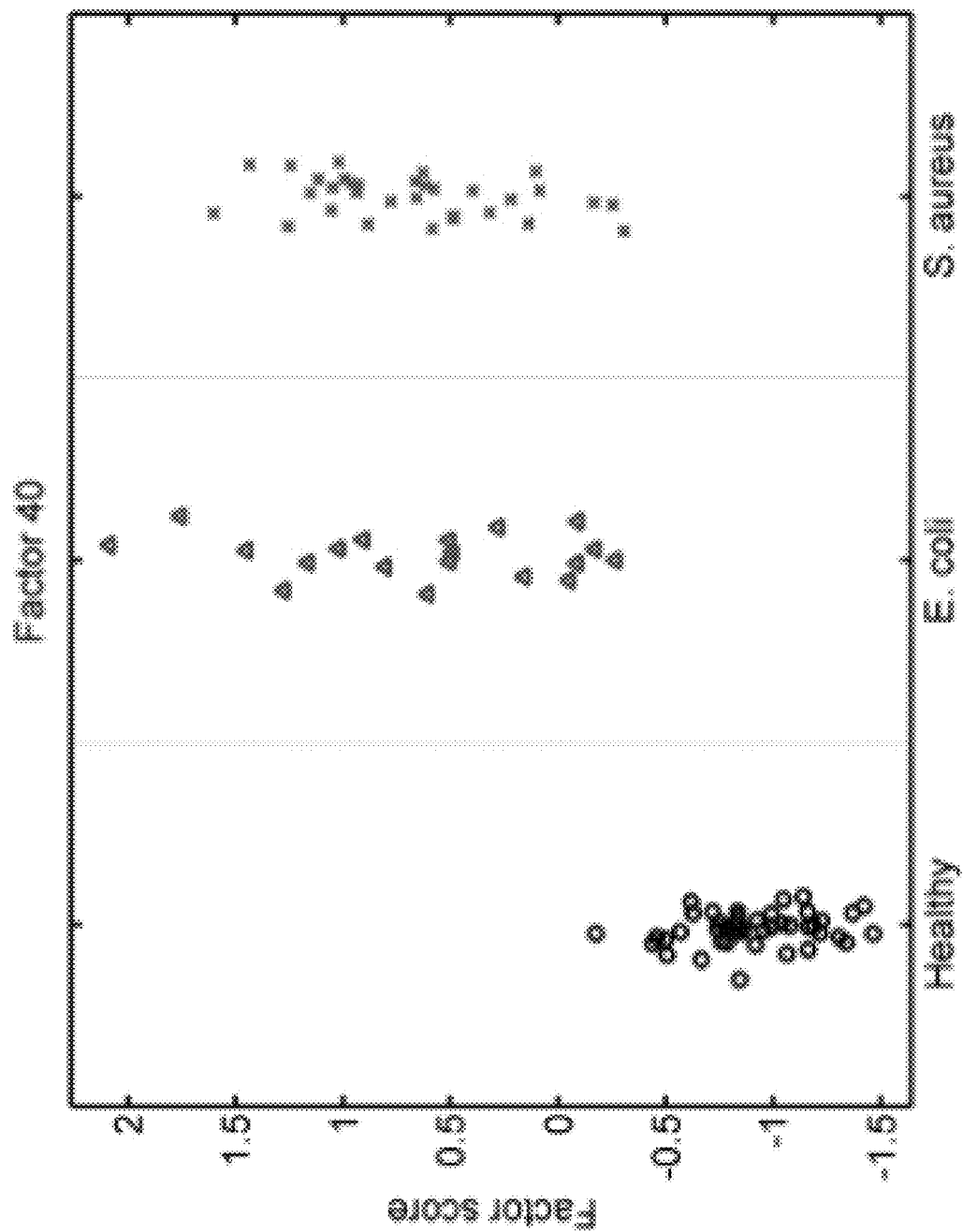
Figure 13K:
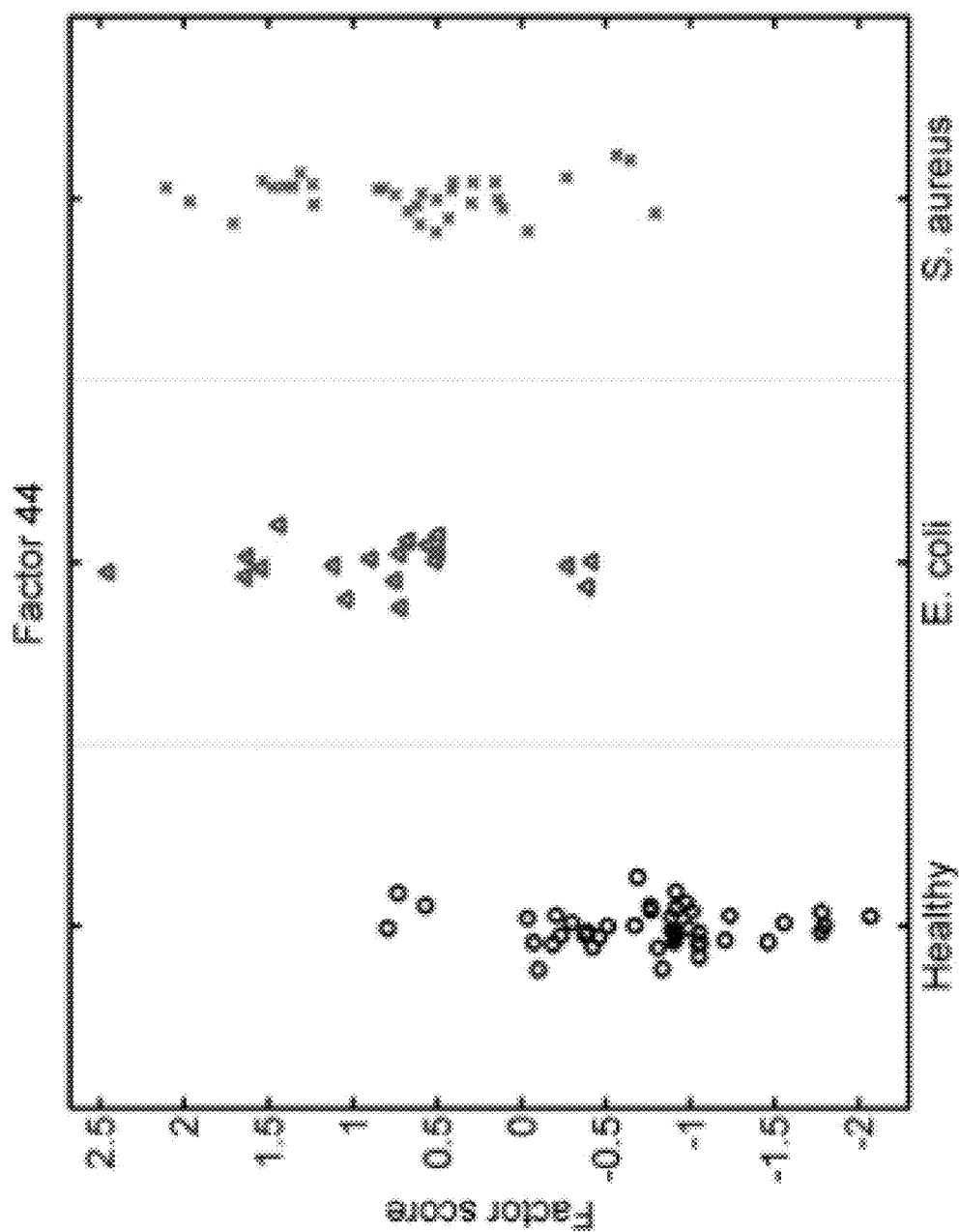
Figure 13L:
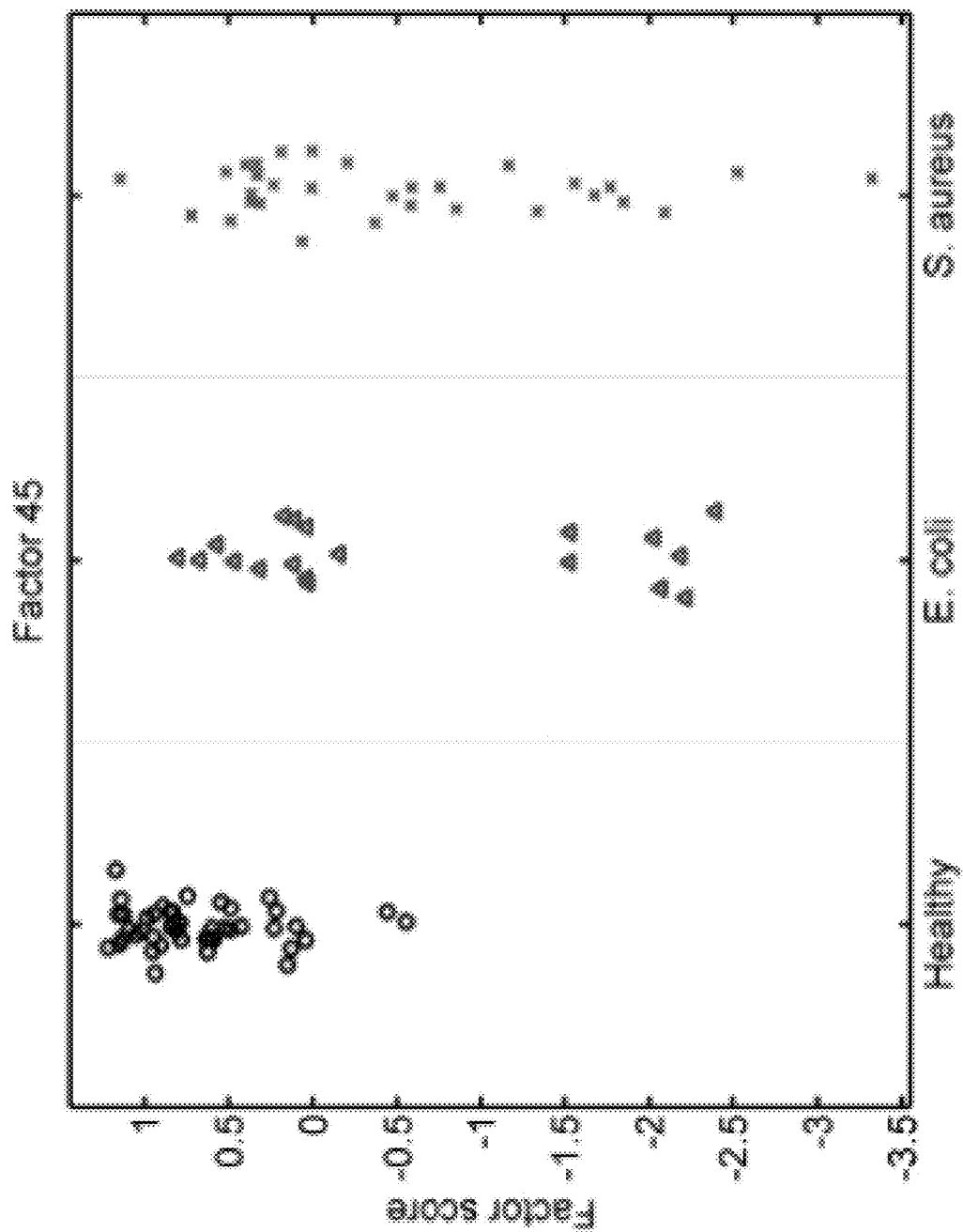
Figure 13M:
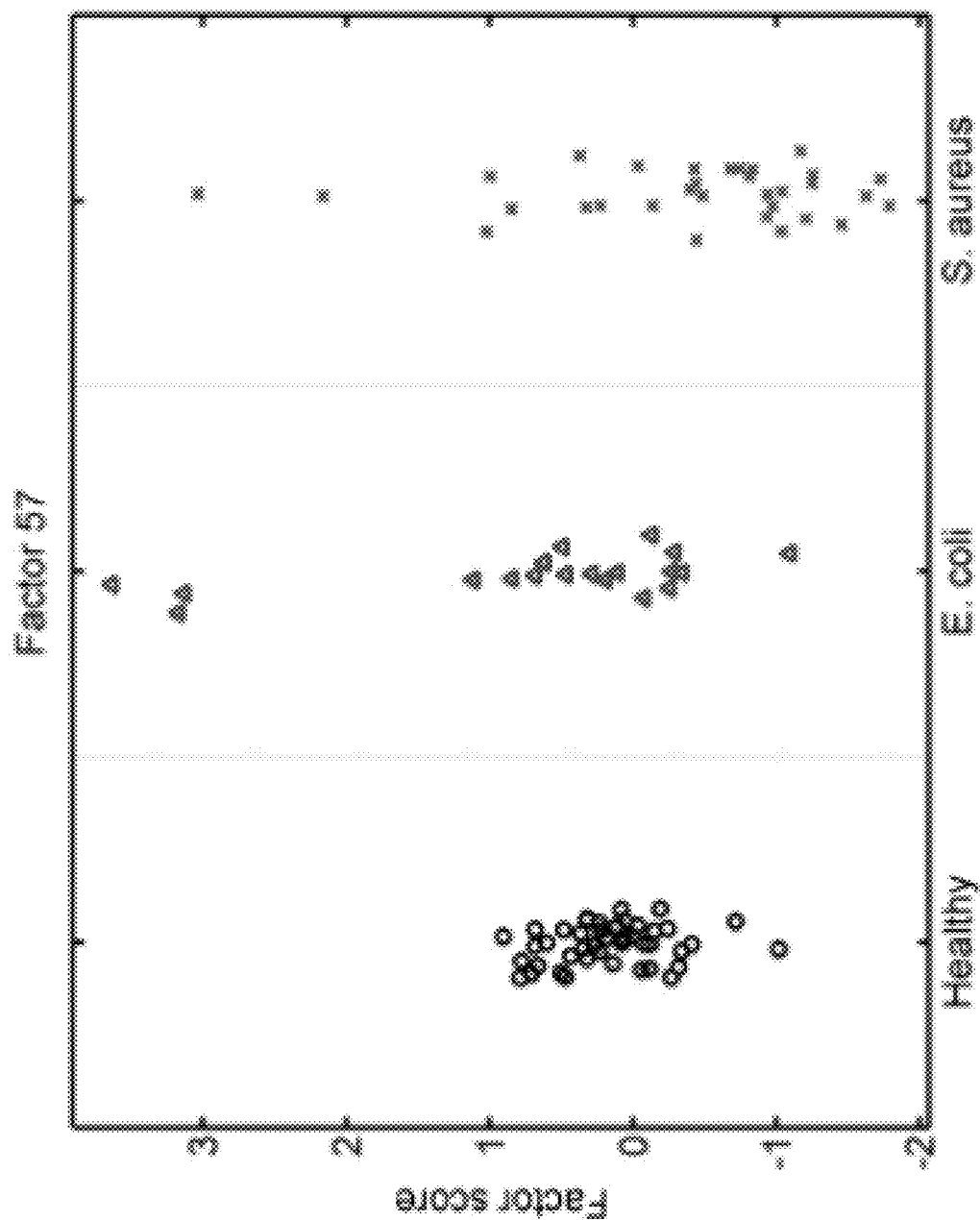
Figure 13N:
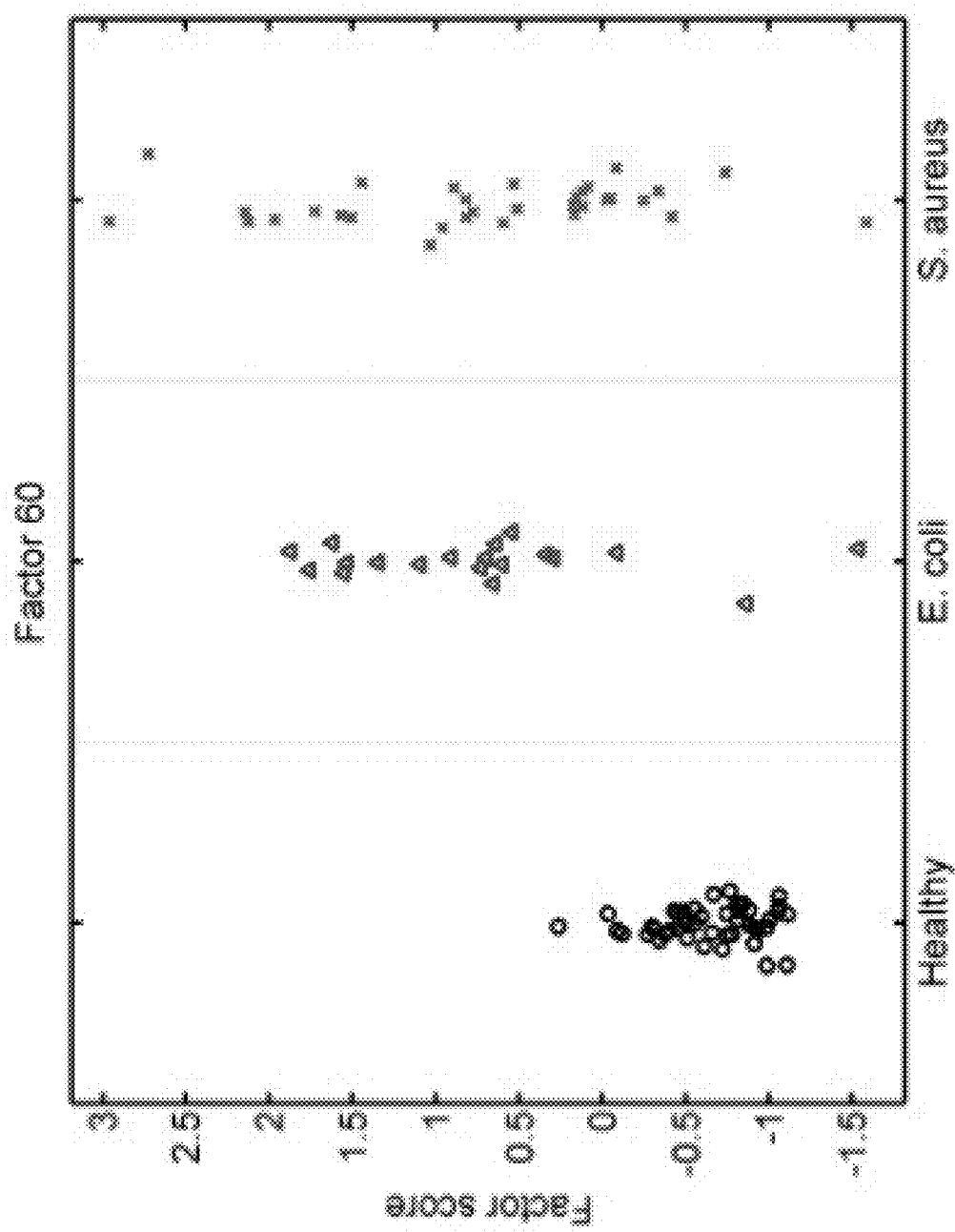
Figure 13O:
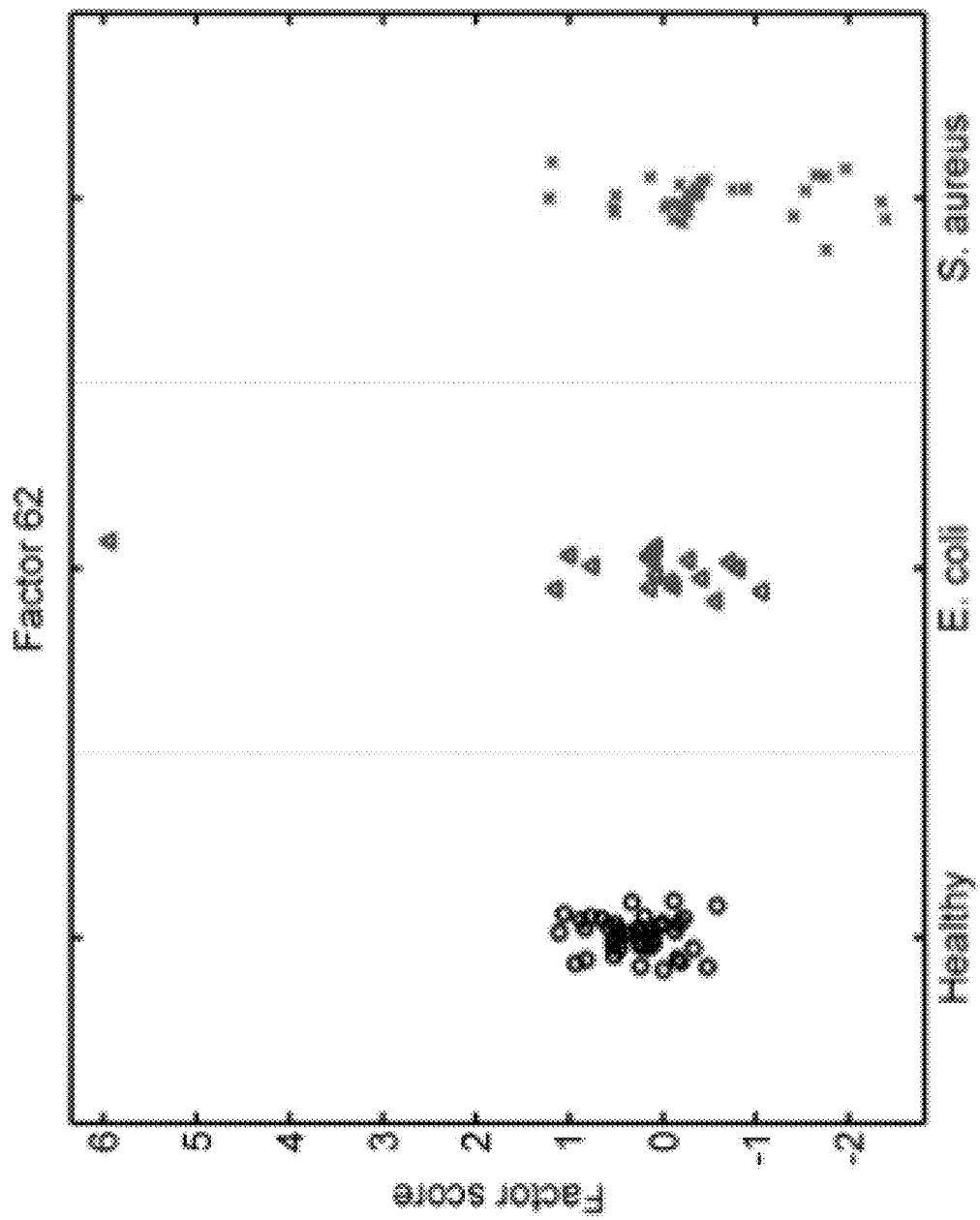
Figure 13P:
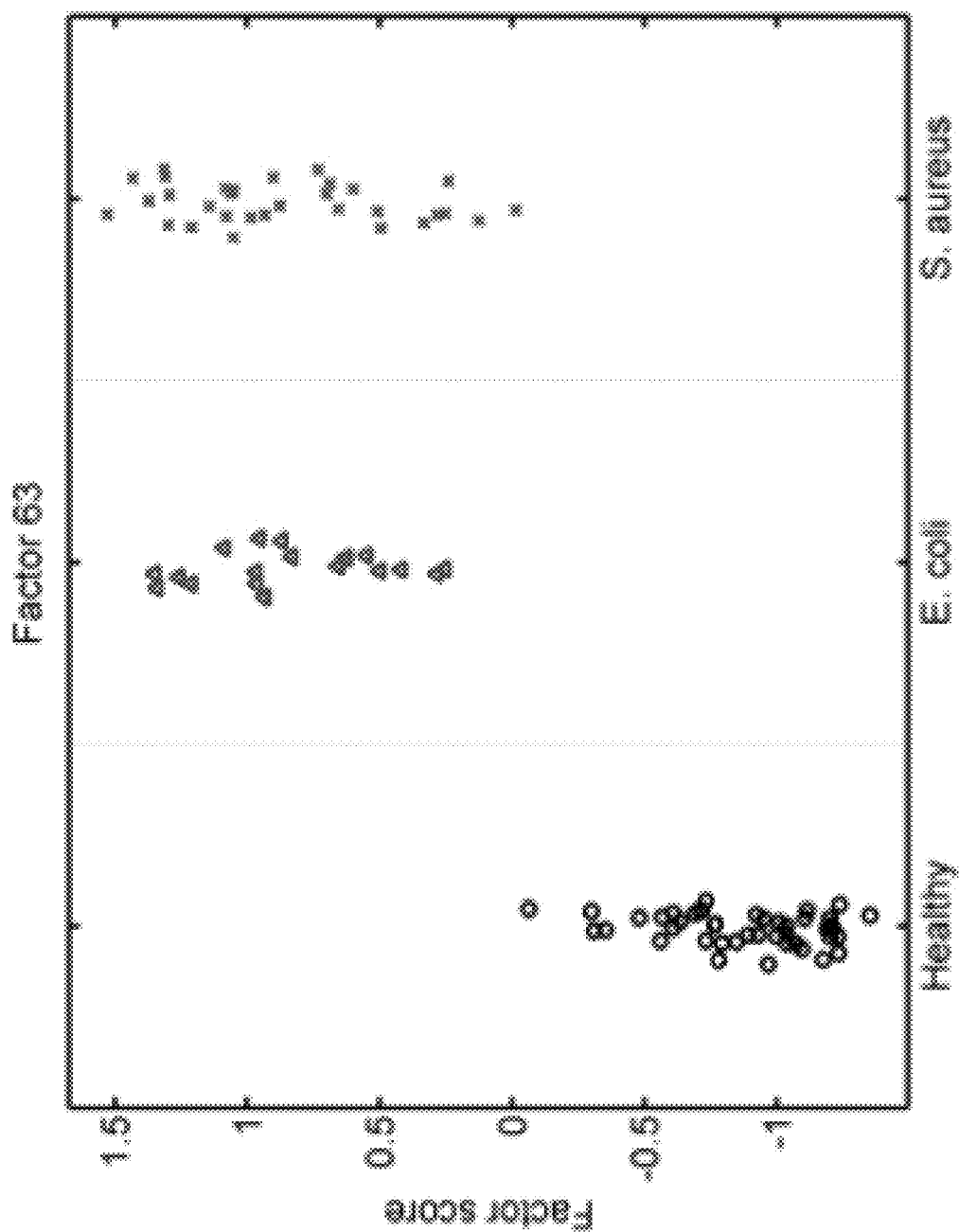
Figure 13Q:
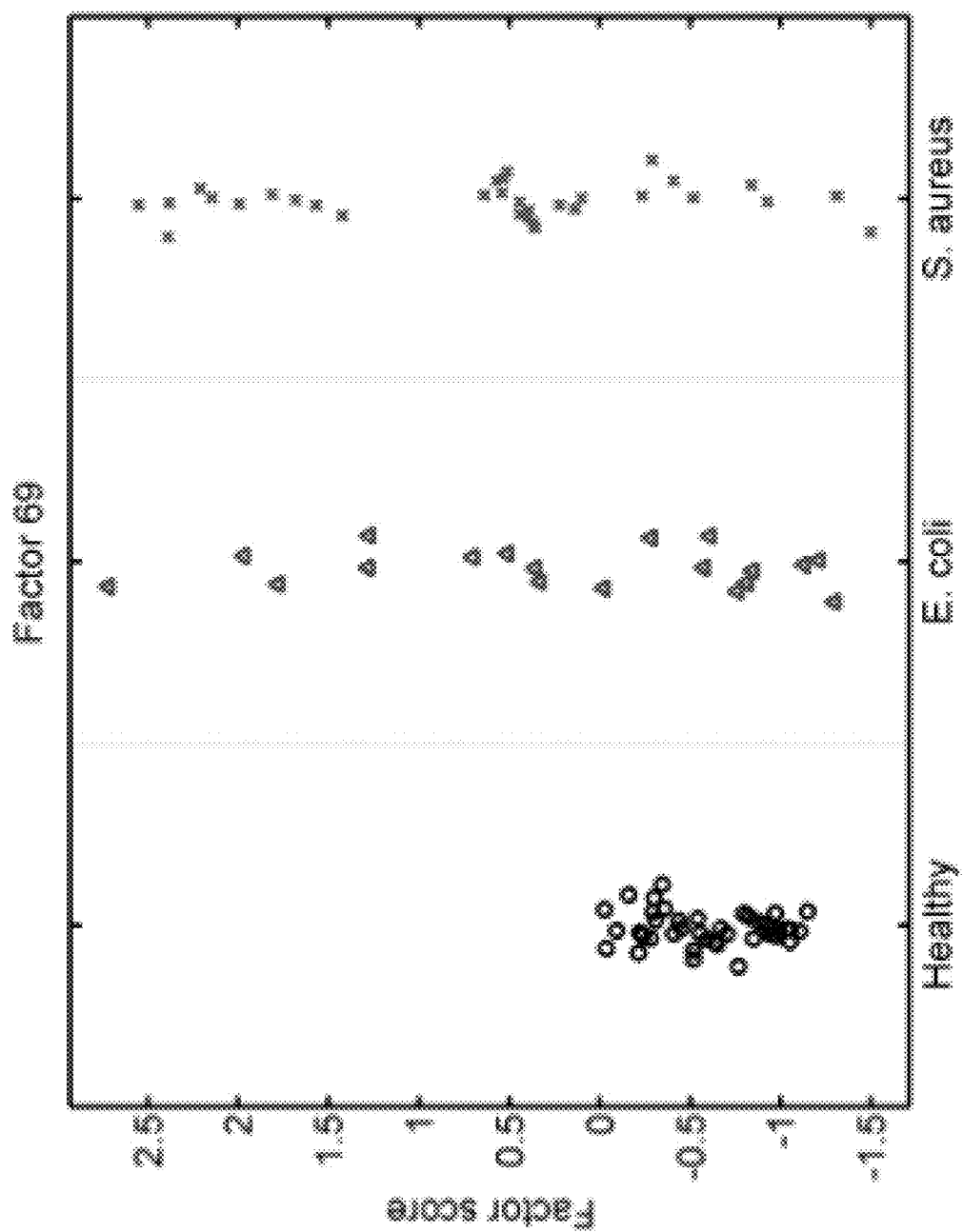
Figure 13R:
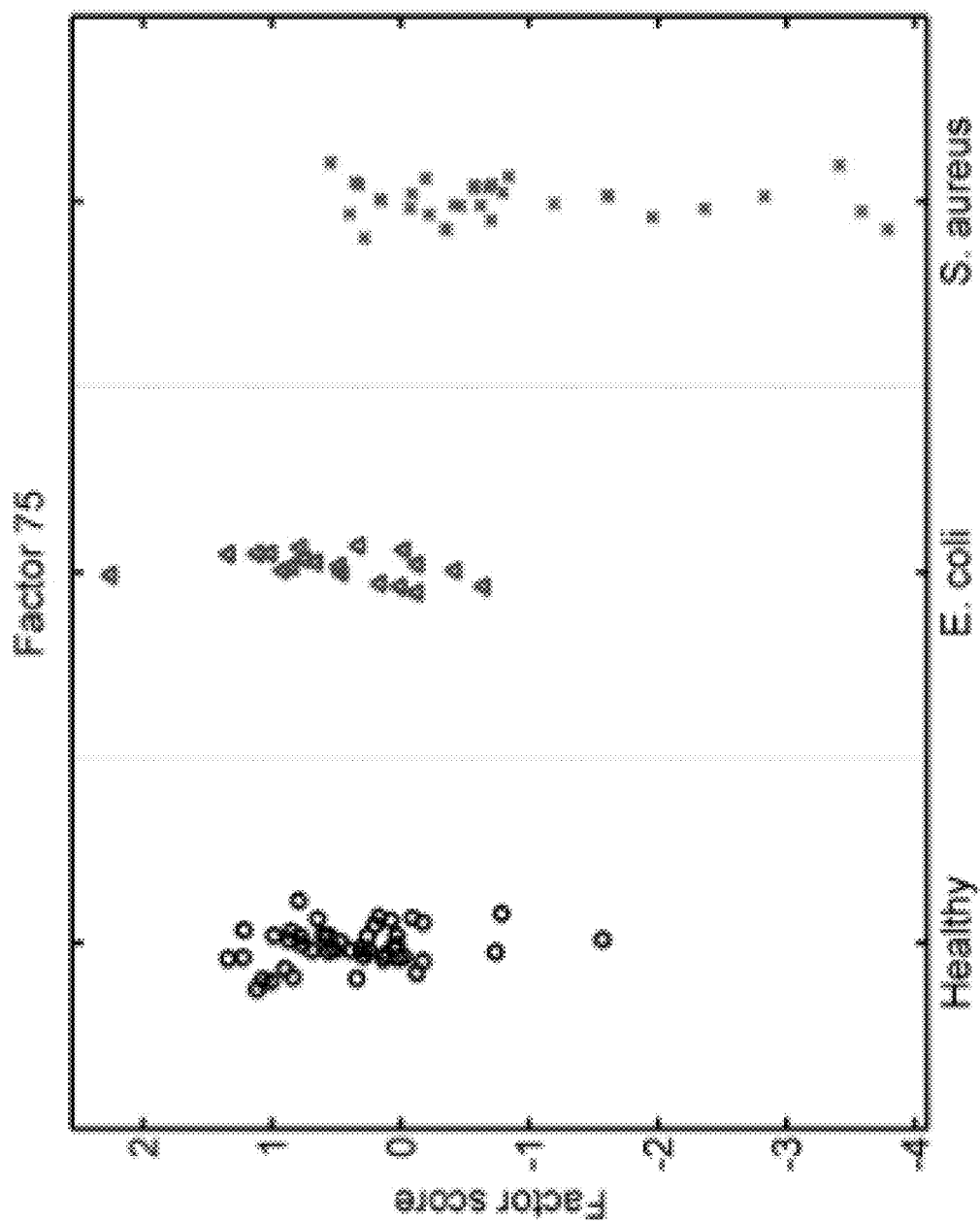
Figure 13S:
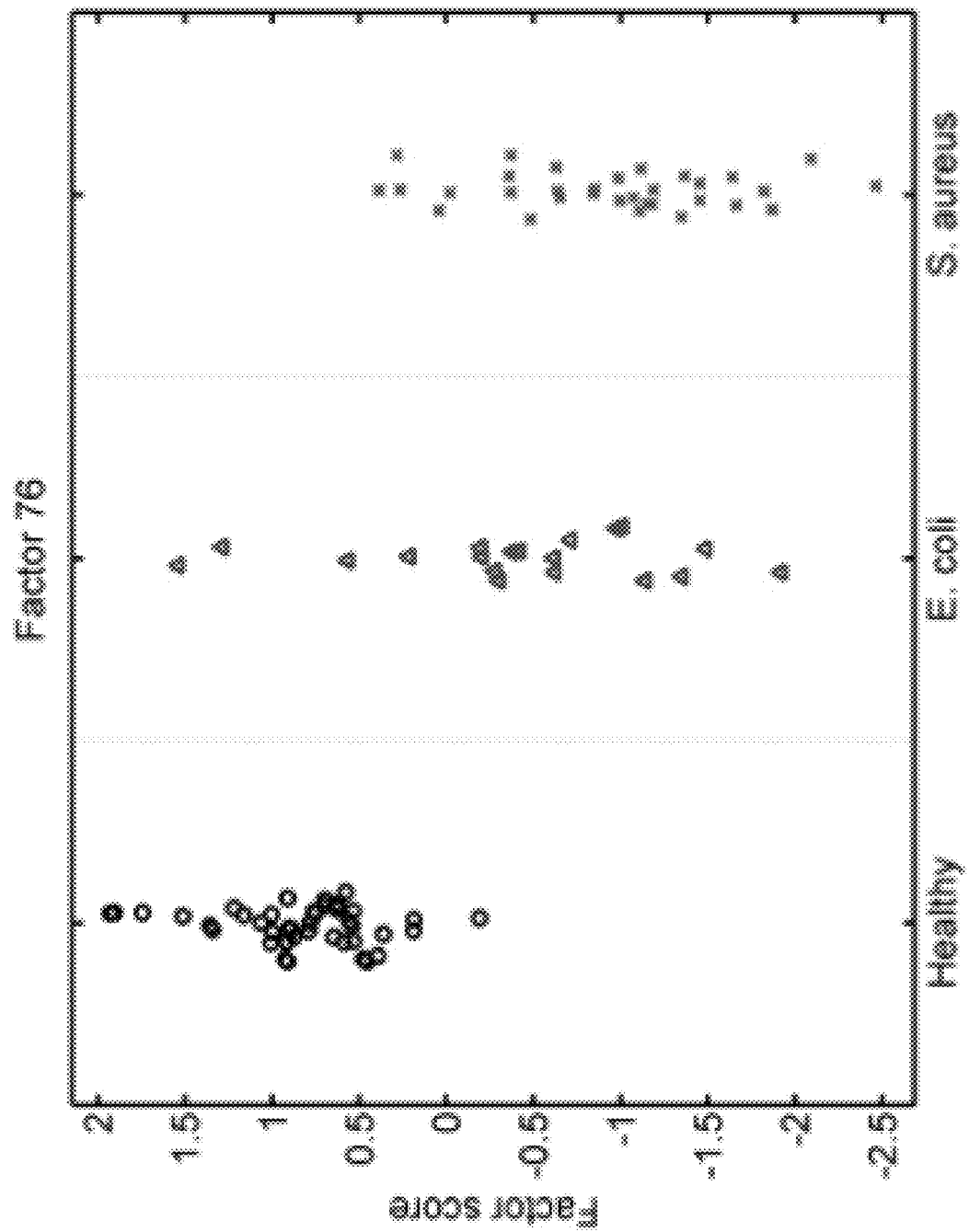

FIGS. 13A-13S show seventeen human factors independently associated with *S. aureus* BSI projected onto healthy controls (left panel, black circles), subjects with *E. coli* BSI (middle panel, blue triangles), and subjects with *S. aureus* BSI (right panel, red "x"). The y-axis represents the factor score.

Figure 14:
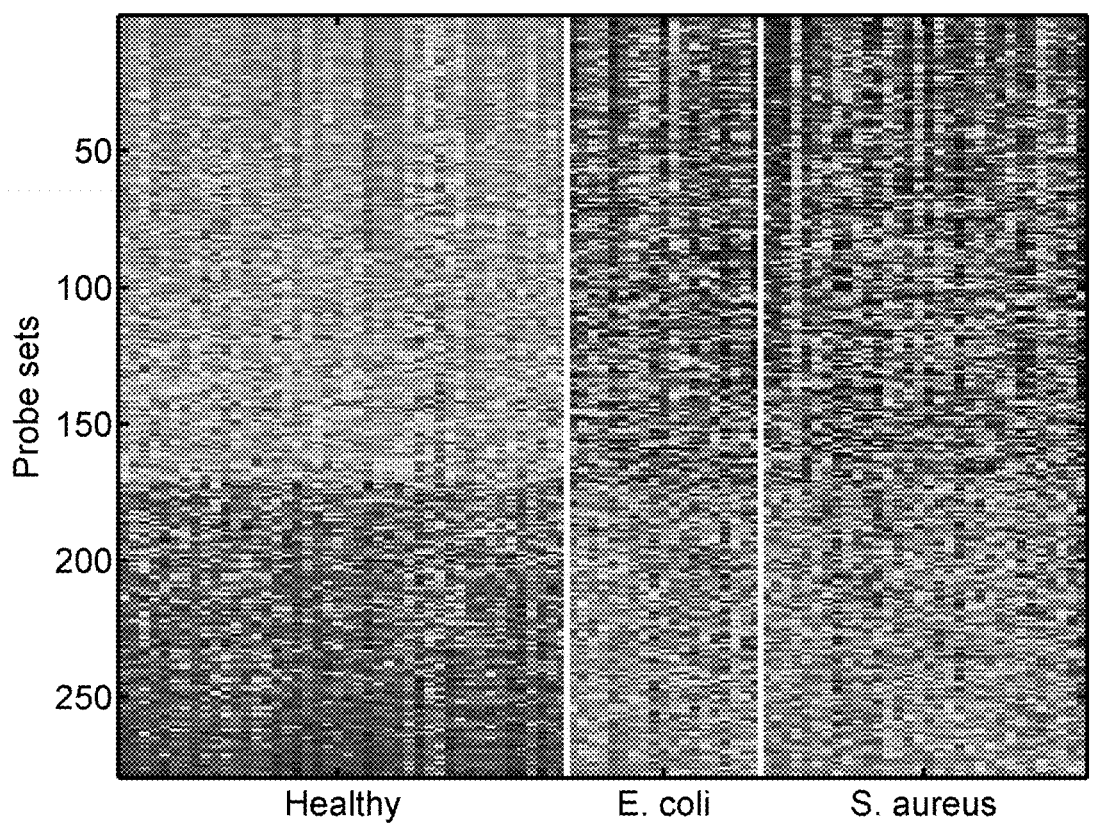

FIG. 14 shows heat map of genes contributing to the human *S. aureus* classifier. Genes within the top two factors contributing to the human *S. aureus* classifier were identified and ranked by p-value after Bonferroni correction. A subset of genes (86 after removing duplicates) is depicted here, stratified by pathogen.

DETAILED DESCRIPTION

The present disclosure provides biomarkers useful for identifying and/or classifying a bacterial infection a subject. *S. aureus* and *Escherichia coli* were used as prototypical Gram-positive and Gram-negative bacteria due to their prevalence and clinical relevance. Host gene expression was measured in mice with bacterial infection across multiple conditions. From these data, a molecular classifier was derived for *S. aureus* infection in inbred mice and validated in a cohort of outbred mice. Host gene expression data from a well-characterized cohort of septic human subjects was used to identify a molecular classifier that accurately distinguished *S. aureus* BSI from *E. coli* BSI or uninfected controls. Murine and human *S. aureus* classifiers exhibited significant similarity particularly in comparing *S. aureus* infection to the healthy state. Furthermore, both murine and human classifiers were validated in an independent human cohort. The present disclosure demonstrates that the in vivo host response to Gram-positive infections is conserved from mouse to human and can be harnessed as a novel diagnostic strategy in patients with bacterial sepsis.

This study takes significant steps forward on multiple levels in the ongoing effort to understand this pathogen; the host response to it; and identify new diagnostic and therapeutic avenues. A diagnostic modality capable of differentiating infection from health across species is described. Host gene expression classifiers can differentiate infection due to *S. aureus* from that of *E. coli* but this effect is less pronounced in the complex human host. The approach described here also affords great insight into the conserved and disparate pathways utilized by mice and humans in response to these infections. Evidence to support the paradigm shift in how diagnostics are thought about is provided as well as new areas for research into the pathways that subserve sepsis pathophysiology have been identified.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

Unless otherwise defined, all technical terms used herein have the same meaning as commonly understood by one of ordinary skill in the art to which this disclosure belongs.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

"About" is used to provide flexibility to a numerical range endpoint by providing that a given value may be "slightly above" or "slightly below" the endpoint without affecting the desired result.

The term "antibiotic" as used herein refers to an agent that either kills or inhibits the growth of a microorganism. Antibiotics may include beta-lactam antibiotics, such as penicillin, which are produced by fungi in the genus *Penicillium*, cephalosporins, carbapenems, aminoglycosides, sulfonamides, quinolones, oxazolidinones, fluoroquinolone, marcolide, ketolide, rifampin, chloramphenicol, glycopeptide, and trimethoprim. The antibiotics may be ciprofloxacin, levofloxacin, gatifloxacin, moxifloxacin, ofloxacin, norflaxacin, erythromycin, azithromycin, clarithromycin, telithromycin, rifamipin, tetracycline, minocycline, chloramphenicol, gentamicin, linezolid, penicillin, amoxicillin, ceftriaxone, imipenem, vancomycin, teicoplainin, sulfamethoxazole, isoniazid, ethambutol, para-aminosalicylic acid, mupicorin, or cycloserine.

The "area under curve" or "AUC" refers to area under a ROC curve. AUC under a ROC curve is a measure of accuracy. An area of 1 represents a perfect test, whereas an area of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

As used herein, the term "biomarker" refers to a naturally occurring biological molecule present in a subject at varying concentrations useful in identifying and/or classifying a disease or a condition, such as a bacterial infection. For example, the biomarker can be a gene that is upregulated or downregulated in a subject that has a disease, such as a bacterial infection. The biomarker can include genes, proteins, nucleic acids, ribonucleic acids, or a polypeptide used as an indicator or marker for bacterial infection. In some embodiments, the biomarker is a gene. In one embodiment where the bacterial infection comprises *S. aureus*, the biomarker is selected from the group consisting of the biomarkers provided in Tables 3-17, and combinations thereof. In another embodiment where the bacterial infection comprises *E. coli*, the biomarker is selected from the group consisting of the biomarkers provided in Tables 3-17, and combinations thereof.

As used herein, the term "bacterial infection" refers to those disease states characterized by the presence of a pathogenic bacteria. Such bacteria may be gram-positive or gram-negative. Examples of gram-positive bacteria include, but are not limited to, *S. aureus*. Examples of gram-negative bacteria include, but are not limited to, *E. coli*. A bacterial infection may be sepsis.

As used herein, the term "factor" refers to a group of co-expressed genes. A factor becomes a term in binary regression model to distinguish or predict subjects with and without infection, or distinguish the type of infection "Sample," "test sample," "specimen," "sample from a subject," and "patient sample" as used herein may be used interchangeable and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient that has a bacterial infection.

The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a blood sample (such as a plasma sample). A biological sample may be obtained directly from a subject (e.g., by blood or tissue sampling) or from a third party (e.g., received from an intermediary, such as a healthcare provider or lab technician).

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Sepsis" as used herein is a condition characterized by a whole-body inflammatory state that is triggered by either a proven (on the basis of sampling or radiology) or probable (considering the patient's clinical presentation, white cell count, CRP, radiology) infection. The infection may be caused by bacteria, virus or fungi. Triggers of sepsis include pneumonia, such as ventilator-associated pneumonia, abdominal infection, kidney infection, and bloodstream infection. The body may develop this inflammatory response by the immune system to microbes in the blood, urine, lungs, skin, or other tissues. A lay term for sepsis is blood poisoning, also used to describe septicaemia. Septicaemia is a related medical term referring to the presence of pathogenic organisms in the bloodstream, leading to sepsis.

Symptoms related to the provoking infection, sepsis is characterized by presence of acute inflammation present throughout the entire body, and is, therefore, frequently associated with fever and elevated white blood cell count (leukocytosis) or low white blood cell count (leukopenia) and lower-than-average temperature, and vomiting. The modern concept of sepsis is that the host's immune response to the infection causes most of the symptoms of sepsis, resulting in hemodynamic consequences and damage to organs. This immunological response causes widespread activation of acute-phase proteins, affecting the complement system and the coagulation pathways, which then cause damage to the vasculature as well as to the organs. Various neuroendocrine counter-regulatory systems are then activated as well, often compounding the problem. Even with immediate and aggressive treatment, this may progress to multiple organ dysfunction syndrome and eventually death.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. In certain embodiments, the treatment comprises anti-bacterial therapy, such as the administration of antibiotics.

The term "effective amount" or "therapeutically effective amount" refers to an amount sufficient to effect beneficial or desirable biological and/or clinical results.

2. Factors and Biomarkers for Bacterial Infection

One aspect of the present disclosure provides biomarkers useful for the identification and/or classification of a bacterial infection. In one embodiment, the present disclosure provides biomarkers that are differentially expressed, such as upregulated, down-regulated, or disregulated in a bacterial infection, as compared to normal populations who do not have the condition, such a bacterial infection.

In some embodiments, the bacterial infection comprises a gram-positive bacteria, such as *S. aureus*. In those embodiments where the bacterial infection comprises *S. aureus*, the biomarker is selected from the group consisting of the biomarkers provided in Tables 3-17, and combinations thereof. In other embodiments, the bacterial infection comprises a gram-negative bacteria, such as *E. coli*. In those embodiments where the bacterial infection comprises *E. coli*, the biomarker is selected from the group consisting of the biomarkers provided in Tables 3-17, and combinations thereof.

In some embodiments, the biomarkers are selected from one or more biomarkers that are up-regulated, down-regulated or over-expressed in a subject suffering from a bacterial infection.

In some specific embodiments, the biomarkers are selected from one or more biomarkers up-regulated, down-regulated or over-expressed more than 50-fold, 40-fold, 30-fold, 20-fold, 15-fold, 10-fold, 9-fold, 8-fold, 7-fold, 6-fold, 5-fold, 4-fold, 3-fold, 2-fold, or 1-fold in a subject suffering from a bacterial infection, when compared to a control. In some embodiments, the biomarker comprises one or more biomarkers found in Tables 3-17, wherein the up-regulation, down-regulating or over-expression of one or more of the biomarker in the subject's biological sample, when compared to a control, indicates that the subject is suffering from a bacterial infection comprising *S. aureus*. In other embodiments, the biomarker comprises one or more biomarkers found in Tables 3-17, wherein the up-regulation, down-regulation, or over-expression of one or more of the biomarkers indicates the subject is suffering from a bacterial infection comprising *E. coli*.

In some embodiments, at least about one of the differentially expressed biomarkers may have an increased expression level compared to the control. In some embodiments, at least about one of the differentially expressed biomarkers may have a decreased expression level compared to the control. In some embodiments, at least about one of the differentially expressed biomarkers may have an increased expression level compared to the control and at least about one of the differentially expressed biomarkers may have a decreased expression level compared to the control.

3. Methods Using Biomarkers of the Present Disclosure

The present disclosure describes how different hosts respond differently to *S. aureus* than to *E. coli* infection in a quantifiable way, providing a new diagnostic avenue. Bayesian sparse factor modeling and penalized binary regression were used to define peripheral blood gene-expression classifiers of murine and human *S. aureus* infection. The murine-derived classifier distinguished *S. aureus* infection from healthy controls and *Escherichia coli*-infected mice across a range of conditions (mouse and bacterial strain, time post infection) and was validated in outbred mice (AUC>0.97). A *S. aureus* classifier derived from a cohort of 94 human subjects distinguished *S. aureus* blood stream infection (BSI) from healthy subjects (AUC 0.99) and *E. coli* BSI (AUC 0.84). Murine and human responses to *S. aureus* infection share common biological pathways, allowing the murine model to classify *S. aureus* BSI in humans (AUC 0.84). Both murine and human *S. aureus* classifiers were validated in an independent human cohort (AUC 0.95 and 0.92, respectively). The approach described here lends insight into the conserved and disparate pathways utilized by mice and humans in response to these infections. Furthermore, this study advances the understanding of *S. aureus* infection; the host response to it; and identifies new diagnostic and therapeutic avenues.

A series of genes or biomarkers may be selected from Tables 3-17 and optimized for diagnosis. The number of genes may be at least 1 gene, at least 5 genes, at least 10 genes, at least 25 genes, at least 30 genes, at least 35 genes, at least 40 genes, at least 45 genes, at least 50 genes, at least 55 genes, at least 60 genes, at least 65 genes, at least 70 genes, at least 75 genes, at least 80 genes, at least 85 genes, at least 90 genes, at least 95 genes, at least 100 genes, at least 125 genes, at least 150 genes, at least 175 genes, at least 200 gene, or at least 250 genes selected from Tables 3-17. RNA probes may be developed for the selected genes. A patient sample may be obtained and examined. For example, RNA may be examined after extraction from the sample or directed from the sample without extraction. The RNA may be measured by PCR or another RNA detection platform. The RNA expression may be measure and compared to control level for these selected genes. An algorithm may be used to produce a probability or score. Cut-off values or scores may be established and used to make a definitive diagnosis. For example, if the patient's gene expression levels are above the cut-off value or score, the patient is diagnosed as having infection. After the diagnosis is made, the subject may be treated for the infection.

In one embodiment, the present disclosure provides a method for identifying and/or classifying a bacterial infection in a subject comprising, consisting of, or consisting essentially of:

(a) determining a biomarker expression profile (expression level) in a biological sample from the subject;

(b) characterizing the subject's biomarker profile; and (c) comparing the subject's biomarker profile with the biomarker profile of a control from subjects not suffering from a bacterial infection (e.g., a healthy subject); and (d) administering an appropriate ant-bacterial therapy if one or more of the biomarkers are upregulated, downregulated or overexpressed.

In one embodiment, the method further includes obtaining the biological sample from the subject. In one embodiment, the identification and/or classification of a condition such as a bacterial infection can be determined by comparing the subjects biomarker profile to a reference biomarker profile, such as one that corresponds to biological samples obtained from a normal population (e.g., healthy population) that do not have a condition such as a bacterial infection, or that corresponds to biological samples obtained from a population that have a condition such as a bacterial infection. Optionally, the reference profile comprises multiple biomarker expression profiles, with each corresponding to a type of a condition such as a bacterial infection with a gram-negative or gram-positive bacteria.

In some embodiments, the present disclosure provides methods for identifying and/or classifying a condition such as bacterial infection by characterizing a biomarker found in Tables 3-17.

4. Methods of Developing a Diagnostic Assay

The present invention is directed to a method of developing a diagnostic assay for identifying and/or classifying a bacterial infection in a subject. The method comprising determining the gene expression levels of at least about two biomarkers in a subject infected with bacterial infection, wherein the biomarkers are selected from one or more of the top 200 genes of mouse factors 7, 15, 23, and 26, human factors 4, 20, 40, and 74, as shown in Tables 3-10; genes discriminating infection due to MRSA or MSSA, as shown in Table 11, a gene from the 50 most significant biological pathways arising from the pairwise comparisons, as shown in Tables 12-16, or one of the genes in common between mice and humans, as shown in Table 17. The method comprises comparing the gene expression levels of the biomarkers in the subject with the gene expression levels of the biomarkers in a control; identifying factors, wherein each factor comprises differentially expressed biomarkers that have the greatest ability to differentiate between gene expression in the subject and the control; providing a weighted value for the differentially expressed biomarkers within the factor; and determining a relationship between the factor and the bacterial infection using the weighted values of the differentially expressed biomarkers with an algorithm, wherein a relationship between the factor and the bacterial infection is used to develop the diagnostic assay.

The diagnostic assay may distinguish a subject that has a *Staphylococcus aureus* blood stream infection from a healthy subject. The biomarkers may be selected from human factor 20 (56 genes) and/or human factor 74 (137 genes), which are shown in Tables 8 and 10, respectively. The factor may comprise about 1 to about 193 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, or at least about 193 of the biomarkers listed in Tables 8 and 10. The relationship may have an AUC value of about 0.9500 to about 0.9999. For example, the AUC value may be at least about 0.9500, at least about 0.9550, at least about 0.9600, at least about 0.9650, at least about 0.9750, at least about 0.9800, at least about 0.9850, at least about 0.9860, at least about 0.9870, at least about 0.9880, at least about 0.9885, at least about 0.9890, at least about 0.9898, at least about 0.9900, or at least about 0.9999. The relationship may have an AUC value of at least about 0.9898.

The diagnostic assay may distinguish a subject that has a *Staphylococcus aureus* blood stream infection from a subject that has an *Escherichia coli* blood stream infection. The biomarkers may be selected from human factor 20 (56 genes) and/or human factor 74 (137 genes), which are shown in Tables 8 and 10, respectively. The factor may comprise about 1 to about 193 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, or at least about 193 of the biomarkers listed in Tables 8 and 10. The relationship may have an AUC value of about 0.8100 to about 0.9999. For example, the AUC value may be at least about 0.8100, at least about 0.8150, at least about 0.8200, at least about 0.8250, at least about 0.8300, at least about 0.8350, at least about 0.8360, at least about 0.8370, at least about 0.8380, at least about 0.8400, at least about 0.8500, at least about 0.8550, at least about 0.8600, at least about 0.8650, at least about 0.8700, at least about 0.8750, at least about 0.8800, at least about 0.8850, at least about 0.8900, at least about 0.8950, at least about 0.9000, at least about 0.9100, at least about 0.9200, at least about 0.9300, at least about 0.9400, at least about 0.9500, at least about 0.9600, at least about 0.9700, at least about 0.9800, at least about 0.9900, or at least about 0.9999. The relationship may have an AUC value of at least 0.8372.

The diagnostic assay may distinguish a subject that has an *Escherichia coli* blood stream infection from a healthy subject. The biomarkers may be selected from human factor 20 (56 genes) and/or human factor 74 (137 genes), which are shown in Tables 8 and 10, respectively. The factor may comprise about 1 to about 193 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least bout 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, or at least about 193 of the biomarkers listed in Tables 8 and 10. The relationship may have an AUC value of about 0.9000 to about 0.9999. For example, the AUC value may be at least about 0.9000, at least about 0.9050, at least about 0.9100, at least about 0.9150, at least about 0.9200, at least about 0.9210, at least about 0.9220, at least about 0.9230, at least about 0.9240, at least about 0.9250, at least about 0.9260, at least about 0.9270, at least about 0.9280, at least about 0.9300, at least about 0.9350, at least about 0.9400, at least about 0.9500, at least about 0.9600, at least about 0.9700, at least about 0.9800, at least about 0.9900, or at least about 0.9999. The relationship may have an AUC value of at least about 0.9229.

The diagnostic assay may distinguish a subject that has a gram positive blood stream infection from a subject that has a gram negative blood stream infection. The biomarkers may be selected from human factor 40 (26 genes), as shown in Table 9. The factor may comprise about 1 to about 26 biomarkers. For example, the factor may comprise at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, or at least about 26 of the biomarkers listed in Table 9. The relationship may have an AUC value of about 0.8100 to about 0.9999. For example, the AUC value may be 0.8100, at least about 0.8150, at least about 0.8200, at least about 0.8250, at least about 0.8300, at least about 0.8350, at least about 0.8400, at least about 0.8450, at least about 0.8480, at least about 0.8490, at least about 0.8500, at least about 0.8510, at least about 0.8520, at least about 0.8550, at least about 0.8600, at least about 0.8650, at least about 0.8700, at least about 0.8750, at least about 0.8800, at least about 0.8850, at least about 0.8900, at least about 0.8950, at least about 0.9000, at least about 0.9100, at least about 0.9200, at least about 0.9300, at least about 0.9400, at least about 0.9500, at least about 0.9600, at least about 0.9700, at least about 0.9800, at least about 0.9900, or at least about 0.9999. The relationship may have an AUC value of at least about 0.8503.

The diagnostic assay may distinguish a subject that has a *Staphylococcus aureus* blood stream infection from a healthy subject. The biomarkers may be selected from human factor 4 (349 genes), as shown in Table 7. The factor may comprise about 1 to about 349 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, at least about 250, at least about 255, at least about 260, at least about 265, at least about 270, at least about 275, at least about 280, at least about 285, at least about 290, at least about 295, at least about 300, at least about 305, at least about 310, at least about 315, at least about 320, at least about 325, at least about 330, at least about 335, at least about 340, at least about 345, at least about 349 of the biomarkers listed in Table 7. The relationship may have an AUC value of about 0.9000 to about 0.9999. For example, the AUC value may be at least about 0.9000, at least about 0.9050, at least about 0.9100, at least about 0.9150, at least about 0.9200, at least about 0.9210, at least about 0.9215, at least about 0.9220, at least about 0.9230, at least about 0.9240, at least about 0.9250, at least about 0.9260, at least about 0.9270, at least about 0.9280, at least about 0.9300, at least about 0.9350, at least about 0.9400, at least about 0.9500, at least about 0.9600, at least about 0.9700, at least about 0.9800, at least about 0.9900, or at least about 0.9999. The relationship may have an AUC value of at least about 0.9217.

The diagnostic assay may distinguish a subject that has a *Staphylococcus aureus* blood stream infection from a healthy subject. The biomarkers may be selected from mouse factors 7, 15, and/or 26, of which the top 200 of each factor are shown in Tables 3, 4, and 6. The factor may comprise about 1 to about 250 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, or at least about 250 of the biomarkers listed in Tables 3, 4, and 6. The relationship may have an AUC value of about 0.9200 to about 0.9999. For example, the AUC value may be at least about 0.9200, at least about 0.9250, at least about 0.9300, at least about 0.9350, at least about 0.9400, at least about 0.9450, at least about 0.9500, at least about 0.9510, at least about 0.9520, at least about 0.9530, at least about 0.9540, at least about 0.9550, at least about 0.9600, at least about 0.9650, at least about 0.9700, at least about 0.9750, at least about 0.9800, at least about 0.9850, at least about 0.9900, at least about 0.9950, or at least about 0.9999. The relationship may have an AUC value of at least about 0.9522.

The diagnostic assay may distinguish a subject that has a Staphylococcus aureus blood stream infection from a healthy subject. The biomarkers may be selected from mouse factors 7, 15, 23, and/or 26, of which the top 200 of each factor are shown in Tables 3, 4, 5, and 6. The factor may comprise about 1 to about 250 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, or at least about 250 of the biomarkers listed in Tables 3, 4, 5, and 6. The relationship may have an AUC value of about 0.9500 to about 0.9999. For example, the AUC value may be at least about 0.9500, at least about 0.9550, at least about 0.9600, at least about 0.9650, at least about 0.9700, at least about 0.9750, at least about 0.9800, at least about 0.9850, at least about 0.9900, at least about 0.9910, at least about 0.9920, at least about 0.9930, at least about 0.9940, at least about 0.9950, at least about 0.9960, at least about 0.9970, at least about 0.9980, at least about 0.9990, or at least about 0.9999. The relationship may have an AUC value of at least about 0.9964.

The diagnostic assay may distinguish a subject that has a Staphylococcus aureus blood stream infection from a subject that has an Escherichia coli blood stream infection. The biomarkers may be selected from mouse factors 7, 15, 23, and/or 26, of which the top 200 of each factor are shown in Tables 3, 4, 5, and 6. The factor may comprise about 1 to about 250 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, or at least about 250 of the biomarkers listed in Tables 3, 4, 5, and 6. The relationship may have an AUC value of about 0.9500 to about 0.9999. For example, the AUC value may be at least about 0.9500, at least about 0.9550, at least about 0.9600, at least about 0.9650, at least about 0.9700, at least about 0.9750, at least about 0.9800, at least about 0.9850, at least about 0.9900, at least about 0.9910, at least about 0.9920, at least about 0.9930, at least about 0.9940, at least about 0.9950, at least about 0.9960, at least about 0.9970, at least about 0.9980, at least about 0.9990, or at least about 0.9999. The relationship may have an AUC value of at least about 0.9935.

The diagnostic assay may distinguish a subject that has an Escherichia coli blood stream infection from a healthy subject. The biomarkers may be selected from mouse factors 7, 15, 23, and/or 26, of which the top 200 of each factor are shown in Tables 3, 4, 5, and 6. The factor may comprise about 1 to about 250 biomarkers. For example, the factor may comprise at least about 1, at least about 2, at least about 3, at least about 4, at least about 5, at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 105, at least about 110, at least about 115, at least about 120, at least about 125, at least about 130, at least about 135, at least about 140, at least about 145, at least about 150, at least about 155, at least about 160, at least about 165, at least about 170, at least about 175, at least about 180, at least about 185, at least about 190, at least about 195, at least about 200, at least about 205, at least about 210, at least about 215, at least about 220, at least about 225, at least about 230, at least about 235, at least about 240, at least about 245, or at least about 250 of the biomarkers listed in Tables 3, 4, 5, and 6. The relationship may have an AUC value of about 0.9200 to about 0.9999. For example, the AUC value may be at least about 0.9200, at least about 0.9250, at least about 0.9300, at least about 0.9350, at least about 0.9400, at least about 0.9440, at least about 0.9450, at least about 0.9460, at least about 0.9470, at least about 0.9480, at least about 0.9490, at least about 0.9500, at least about 0.9510, at least about 0.9520, at least about 0.9530, at least about 0.9540, at least about 0.9550, at least about 0.9600, at least about 0.9650, at least about 0.9700, at least about 0.9750, at least about 0.9800, at least about 0.9850, at least about 0.9900, at least about 0.9950, or at least about 0.9999. The relationship may have an AUC value of at least about 0.9484.

5. Methods of Identifying and Treating a Bacterial Infection

The present invention is directed to method of identifying and treating a bacterial infection in a subject. The method comprises performing the diagnostic assay as developed by the methods, as described above, and administrating an antibacterial therapy to the subject diagnosed with a bacterial infection. The method further comprising quantifying the amount of at least about one biomarker present in a biological sample derived from the subject, wherein the biomarker may be associated with a factor.

The present invention is also directed towards a method of identifying and treating a subject suspected of having a bacterial blood stream infection (BSI). The method comprises determining gene expression levels of at least about two biomarkers in a peripheral blood cell sample of the subject, wherein the biomarkers are selected from any one of Tables 3-17; comparing the gene expression levels of the at least about two biomarkers to standard gene expression levels wherein the standard gene expression levels correspond to the gene expression levels for the biomarkers in a control; identifying the subject as having a bacterial BSI if the gene expression levels of the biomarkers are different than the standard gene expression levels; and administering an effective amount of antibiotic therapy to treat the subject identified as having a bacterial BSI. The bacterial BSI may be *Staphylococcus aureus* BSI or *Escherichia coli* BSI. The bacterial blood stream infection may be *S. aureus* BSI and the biomarkers may be selected from one of Tables 3-8 or 10.

The present invention is directed to method of distinguishing and treating *Staphylococcus aureus* blood stream infection (BSI) from *Escherichia coli* BSI in a subject suspected of having a bacterial infection. The method comprises determining gene expression levels of at least about two biomarkers in a peripheral blood cell sample of the subject, wherein the biomarkers are selected from any one of Tables 8 and 10 or Tables 3-6; comparing the gene expression levels of the at least about two biomarkers to standard gene expression levels wherein the standard gene expression levels correspond to the gene expression levels for the biomarkers in a control; identifying the subject as having a *S. aureus* BSI if the gene expression levels of the biomarkers are different than the standard gene expression levels and identifying the subject as having an *E. coli* BSI if the gene expression levels of the biomarkers are the same as the standard gene expression levels; and administering an effective amount of appropriate antibacterial therapy to treat the subject identified as having a *S. aureus* BSI or *E. coli*. The control may be a subject having an *E. coli* BSI. The present invention is directed to method of distinguishing and treating a gram positive bacterial infection from a gram negative bacterial infection in a subject suspected of having a bacterial infection. The method comprises determining gene expression levels of at least about two biomarkers in a peripheral blood cell sample of the subject, wherein the biomarkers are selected from Table 9; comparing the gene expression levels of the at least about two biomarkers to standard gene expression levels wherein the standard gene expression levels correspond to the gene expression levels for the biomarkers in a control; identifying the subject as having a gram positive bacterial infection if the gene expression levels of the biomarkers are different than the standard gene expression levels in a control; and administering an effective amount of appropriate antibacterial therapy to treat the subject identified as a gram positive bacterial infection. The gram positive bacterial infection may be *Staphylococcus aureus*. The control may be a subject having a gram negative bacterial infection. The gram negative bacterial infection may be *Escherichia coli*.

The present invention is directed method of identifying and treating a subject suspected of having a methicillin-resistant *Staphylococcus aureus* (MRSA) infection. The method comprises determining gene expression levels of at least about one biomarker in a peripheral blood cell sample of the subject wherein the biomarker is selected from Table 11; comparing the gene expression levels of the biomarker to a standard gene expression level of the biomarker, wherein the standard gene expression level corresponds to the gene expression level of the biomarker in a subject that has a methicillin-sensitive *Staphylococcus aureus* (MSSA) infection; identifying the subject as having MRSA if the gene expression levels of the biomarkers are different than the standard gene expression levels; and administering an effective amount of an antibiotic therapy to treat the subject identified as having MRSA. The antibiotic therapy may be mupirocine or vancomycin.

6. Methods of Determining Efficacy of Treatment Using Biomarkers

Another aspect of the present disclosure provides for methods for monitoring the treatment of conditions such as a bacterial infection. In one embodiment, the method comprises a method of determining the efficacy of treatment regime (e.g., anti-bacterial therapy) in a subject comprising, consisting of, or consisting essentially of: (a) determining a baseline value for the expression of one or more biomarkers associated with bacterial infection; (b) administering to the subject an anti-bacterial therapy regime; and (c) redetermining the expression levels of one or more biomarkers in the subject, wherein observed changes in one or more or the biomarker expression levels as compared to a control is correlated with the efficacy of the therapeutic regimen.

In instances where a change in the biomarker expression is not seen, a change in treatment may be warranted. Such a determination, and the different type of treatment to employ, can be made readily determined by one skilled in the art.

7. Probability and Threshold

A probability score could be produced using various methods, such as those methods using a ENet score as described in Chen et al., IEEE Transactions on Biomedical Engineering 58: 468-479 (2011). For example, one method of determining the probability score is the following: Let X be a p×n matrix of observed data in the real number domain, where each column corresponds to one of n samples, quantifying the associated gene-expression values for all p genes under investigation. To address the "large p, small n" problem in an unsupervised setting the data are assumed to satisfy X=AS+E, where A is a p×r matrix, S is r×n and E is p×n. The columns of A represent the factor "loadings" and each column of S represents factor "scores" for the associated sample (column of X); the rows of S are called factors. E is the usual error matrix.

Thresholds may be defined based on how the classifier performs using the final testing platform that would be implemented clinically. This will require a balance of sensitivity, specificity, and input from end-users. An alternative to a threshold is determining the probability that the patient in question has a *S. aureus* infection.

8. Treatment

Treatment may include being administered oxygen, either by a tube that is placed near the nose or through a clear plastic mask. Depending on the results of the tests, the physician may order medications. These medications may include antibiotics given intravenously (given directly into the vein). Initially, the antibiotics may be those that kill many different bacteria because the exact kind of infection the patient has is not known. Once the blood culture results show the identity of the bacteria, the doctor may select a different antibiotic that kills the specific organism responsible for the infection. The doctor may also order IV salt solution saline and medications to increase the blood pressure it is too low. The patient may be admitted to the hospital at least until the blood culture results are known. If the patient is very ill and with low blood pressure, the doctor may admit the patient to the intensive care unit (ICU) and may consult specialist doctors to help in the management of the illness. If results show an infection in the abdomen, either drainage of the infection by the placement of tubes or surgery may be necessary. The physician will administer anti-autoimmune drugs or biologics as well to modify the body's aggressive immune response to microbes, which leads to sepsis.

Treatment for sepsis or severe sepsis/septic shock may further include early goal directed therapy, antibiotic, a vasopressor, such as norepinephrine and dopamine, a steroid, such as corticosteroids, insulin, painkillers, sedatives, oxygen, cerebrospinal fluid, and intravenous fluid to the subject. For application of these therapies, a central venous catheter and an arterial catheter may be used. Other hemodynamic variables (such as cardiac output, mixed venous oxygen saturation, or stroke volume variation) may also be used.

Treatment of organ dysfunction may include hemodialysis in kidney failure, mechanical ventilation in pulmonary dysfunction, transfusion of blood products, and drug and fluid therapy for circulatory failure. Ensuring adequate nutrition may further be required by enteral feeding, but if necessary by parenteral nutrition during a prolonged illness.

a. *S. aureus*

*S. aureus* bacterial infection may be treated with an antibiotic, such as penicillin and penicillinase-resistant β-lactam antibiotics, such as methicillin, dicloxacillin, nafcillin, oxacillin, and flucloxacillin, cephalosporin, gentamicin, or combinations thereof. *S. aureus* infection may also be treated with a combination therapy of a penicillinase-resistant penicillin or cephalosporin (in case the organism is MSSA) and clindamycin or a quinolone. Other therapies include clindamycin, trimethoprim-sulfamethoxazole (TMP-SMX), rifampin, doxycycline, or a quinolone. Combination of TMP-SMX and rifampin may also be used i. MRSA In some embodiments, the subject has MRSA and is resistant to β-lactam antibiotic, such as methicillin. MRSA is also called oxacillin-resistant *S. aureus*. MRSA may be treated with mupirocine or vancomycin.

b. *E. coli*

*E. coli* bacterial infection may be treated with antibiotics.

9. Composition of Matter

Another aspect of the present disclosure provides a composition of matter comprising, consisting of, or consisting essentially of: (a) a probe array for determining a biomarker level in a sample, the array comprising of a plurality of probes that hybridizes to one or more biomarkers that are associated with bacterial infection; or (b) a kit for determining a biomarker level in a sample, comprising the probe array of (a) and instructions for carrying out the determination of biomarker expression level in the sample. In certain embodiments the probe array of (a) further comprises a solid support with the plurality of probes attached thereto.

10. Sample

The present disclosure provides a method of determining the identification and/or classification of a bacterial infection on at least one sample obtained from an individual. The individual may be any mammal, but is preferably a human.

The present disclosure may involve obtaining more than one sample, such as two samples, such as three samples, four samples or more from individuals, and preferably the same individual. This allows the relative comparison of expression both as in the presence or absence of at least one biomarker between the two samples. Alternatively, a single sample may be compared against a "standardized" sample, such a sample comprising material or data from several samples, preferably also from several individuals.

11. Sample Preparation

Before analyzing the sample, it will often be desirable to perform one or more sample preparation operations upon the sample. Typically, these sample preparation operations will include such manipulations as concentration, suspension, extraction of intracellular material, e.g., nucleic acids from tissue/whole cell samples and the like, amplification of nucleic acids, fragmentation, transcription, labeling and/or extension reactions.

Any method required for the processing of a sample prior to detection by any of the methods noted herein falls within the scope of the present disclosure. These methods are typically well known by a person skilled in the art.

12. Detection

It is within the general scope of the present disclosure to provide methods for the detection of gene expression as a biomarker. An aspect of the present disclosure relates to the detection of the gene expression as described in the plots and graphs of the figures contained herein. As used herein, the term "detect" or "determine the presence of" refers to the qualitative measurement of undetectable, low, normal, or high concentrations of one or more biomarkers such as, for example, nucleic acids, ribonucleic acids, or polypeptides and other biological molecules. Detection may include 1) detection in the sense of presence versus absence of one or more biomarkers as well as 2) the registration/quantification of the level or degree of expression of one or more biomarkers, depending on the method of detection employed. The term "quantify" or "quantification" may be used interchangeable, and refer to a process of determining the quantity or abundance of a substance in a sample (e., a biomarker), whether relative or absolute. For example, quantification may be determined by methods including but not limited to, micro-array analysis, qRT-PCR, band intensity on a Northern or Western blot, or by various other methods known in the art.

The detection of one or more biomarker molecules allows for the identification and/or classification of a condition such as a bacterial infection. The classification of such conditions is of relevance both medically and scientifically and may provide important information useful for the diagnosis, prognosis and treatment of the condition. The diagnosis of a condition such as a bacterial infection is the affirmation of the presence of the condition, as is the object of the present disclosure, on the expression of at least one biomarker herein. Prognosis is the estimate or prediction of the probable outcome of a condition such as a bacterial infection and the prognosis of such is greatly facilitated by increasing the amount of information on the particular condition. The method of detection is thus a central aspect of the present disclosure.

Any method of detection falls within the general scope of the present disclosure. The detection methods may be generic for the detection of gene expression, nucleic acids, polypeptides and the like. The detection methods may be directed towards the scoring of a presence or absence of one or more biomarker molecules or may be useful in the detection of expression levels.

The detection methods can be divided into two categories herein referred to as in situ methods or screening methods. The term in situ method refers to the detection of nucleic acid and/or protein molecules in a sample wherein the structure of the sample has been preserved. This may thus be a biopsy wherein the structure of the tissue is preserved. In situ methods are generally histological i.e. microscopic in nature and include but are not limited to methods such as: in situ hybridization techniques and in situ PCR methods.

Screening methods generally employ techniques of molecular biology and most often require the preparation of the sample material in order to access the nucleic acid and/or polypeptide molecules to be detected. Screening methods include, but are not limited to methods such as: Array systems, affinity matrices, Northern blotting and PCR techniques, such as real-time quantitative RT-PCR.

13. Probe

One aspect of the present disclosure is to provide a probe which can be used for the detection of a gene, a nucleic acid and/or polypeptide molecule as defined herein. A probe as defined herein is a specific sequence of a nucleic acid and/or polypeptide used to detect nucleic acids and/or polypeptides by hybridization. For example, a nucleic acid is also here any nucleic acid, natural or synthetic such as DNA, RNA, LNA or PNA. A probe may be labeled, tagged or immobilized or otherwise modified according to the requirements of the detection method chosen. A label or a tag is an entity making it possible to identify a compound to which it is associated. It is within the scope of the present disclosure to employ probes that are labeled or tagged by any means known in the art such as but not limited to: radioactive labeling, fluorescent labeling and enzymatic labeling. Furthermore the probe, labeled or not, may be immobilized to facilitate detection according to the detection method of choice and this may be accomplished according to the preferred method of the particular detection method.

14. Detection Methods

Another aspect of the present disclosure regards the detection of nucleic acid and/or polypeptide molecules by any method known in the art. In the following are given examples of various detection methods that can be employed for this purpose, and the present disclosure includes all the mentioned methods, but is not limited to any of these. In some embodiments, the RNA gene expression levels may be determined.

c. In Situ Hybridization

In situ hybridization (ISH) applies and extrapolates the technology of nucleic acid and/or polypeptide hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/across cells, such as the expression of miRNAs/nucleic acid molecules. Sample cells are treated to increase their permeability to allow the probe to enter the cells, the probe is added to the treated cells, allowed to hybridize at pertinent temperature, and then excess probe is washed away. A complementary probe is labeled with a radioactive, fluorescent or antigenic tag, so that the probe's location and quantity in the tissue can be determined using autoradiography, fluorescence microscopy or immunoassay, respectively. The sample may be any sample as herein described. The probe is likewise a probe according to any probe based upon the biomarkers mentioned herein.

An aspect of the present disclosure includes the method of detection by in situ hybridization as described herein.

d. In Situ PCR

In situ PCR is the PCR based amplification of the target nucleic acid sequences prior to ISH. For detection of RNA, an intracellular reverse transcription (RT) step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labeled nucleotides (e.g. digoxigenin-11-dUTP, fluorescein-dUTP, 3H-CTP or biotin-16-dUTP) which have been incorporated into the PCR products during thermal cycling.

An embodiment of the present disclosure concerns the method of in situ PCR as mentioned herein above for the detection of nucleic acid molecules as detailed herein.

e. Microarray

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used e.g. to measure the expression levels of large numbers of polypeptides/proteins/nucleic acids simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

An aspect of the present disclosure regards the use of microarrays for the expression profiling of biomarkers in conditions such as bacterial infection. For this purpose, and by way of example, RNA is extracted from a cell or tissue sample, the small RNAs (18-26-nucleotide RNAs) are size-selected from total RNA using denaturing polyacrylamide gel electrophoresis (PAGE). Then oligonucleotide linkers are attached to the 5' and 3' ends of the small RNAs and the resulting ligation products are used as templates for an RT-PCR reaction with 10 cycles of amplification. The sense strand PCR primer has a Cy3 fluorophore attached to its 5' end, thereby fluorescently labeling the sense strand of the PCR product. The PCR product is denatured and then hybridized to the microarray. A PCR product, referred to as the target nucleic acid that is complementary to the corresponding RNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular biomarker, using a number of positive and negative controls and array data normalization methods, which will result in assessment of the level of expression of a particular biomarker.

Several types of microarrays can be employed such as spotted oligonucleotide microarrays, pre-fabricated oligonucleotide microarrays or spotted long oligonucleotide arrays.

In spotted oligonucleotide microarrays the capture probes are oligonucleotides complementary to nucleic acid sequences. This type of array is typically hybridized with amplified.

PCR products of size-selected small RNAs from two samples to be compared that are labeled with two different fluorophores. Alternatively, total RNA containing the small RNA fraction is extracted from the abovementioned two samples and used directly without size-selection of small RNAs, and 3' end labeled using T4 RNA ligase and short RNA linkers labeled with two different fluorophores. The samples can be mixed and hybridized to one single microarray that is then scanned, allowing the visualization of up-regulated and down-regulated biomarker genes in one go. The downside of this is that the absolute levels of gene expression cannot be observed, but the cost of the experiment is reduced by half. Alternatively, a universal reference can be used, comprising of a large set of fluorophore-labelled oligonucleotides, complementary to the array capture probes.

In pre-fabricated oligonucleotide microarrays or single-channel microarrays, the probes are designed to match the sequences of known or predicted biomarkers. There are commercially available designs that cover complete genomes from companies such as Affymetrix, or Agilent. These microarrays give estimations of the absolute value of gene expression and therefore the comparison of two conditions requires the use of two separate microarrays.

Spotted long oligonucleotide arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

An embodiment of the present disclosure concerns the method of microarray use and analysis as described herein.

f. PCR

The terms "PCR reaction", "PCR amplification", "PCR", "pre-PCR", "Q-PCR", "real-time quantitative PCR" and "real-time quantitative RT-PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification and Q Beta Replicase systems. The products formed by said amplification reaction may or may not be monitored in real time or only after the reaction as an end-point measurement.

g. Real-Time Quantitative RT-PCR

Real-time quantitative RT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample. There are 3 methods which vary in difficulty and detail. Like other forms of polymerase chain reaction, the process is used to amplify DNA samples, using thermal cycling and a thermostable DNA polymerase.

The three commonly used methods of quantitative polymerase chain reaction are through agarose gel electrophoresis, the use of SYBR Green, a double stranded DNA dye, and the fluorescent reporter probe. The latter two of these three can be analysed in real-time, constituting real-time polymerase chain reaction method.

Agarose gel electrophoresis is the simplest method, but also often slow and less accurate then other methods, depending on the running of an agarose gel via electrophoresis. It cannot give results in real time. The unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown. This method is generally used as a simple measure of whether the probe target sequences are present or not, and rarely as 'true' Q-PCR.

Using SYBR Green dye is more accurate than the gel method, and gives results in real time. A DNA binding dye binds all newly synthesized double stranded (ds)DNA and an increase in fluorescence intensity is measured, thus allowing initial concentrations to be determined. However, SYBR Green will label all dsDNA including any unexpected PCR products as well as primer dimers, leading to potential complications and artifacts. The reaction is prepared as usual, with the addition of fluorescent dsDNA dye. The reaction is run, and the levels of fluorescence are monitored; the dye only fluoresces when bound to the dsDNA. With reference to a standard sample or a standard curve, the dsDNA concentration in the PCR can be determined.

The fluorescent reporter probe method is the most accurate and most reliable of the methods. It uses a sequence-specific nucleic acid based probe so as to only quantify the probe sequence and not all double stranded DNA. It is commonly carried out with DNA based probes with a fluorescent reporter and a quencher held in adjacent positions, so-called dual-labeled probes. The close proximity of the reporter to the quencher prevents its fluorescence; it is only on the breakdown of the probe that the fluorescence is detected. This process depends on the 5' to 3' exonuclease activity of the polymerase involved. The real-time quantitative PCR reaction is prepared with the addition of the dual-labeled probe. On denaturation of the double-stranded DNA template, the probe is able to bind to its complementary sequence in the region of interest of the template DNA (as the primers will too). When the PCR reaction mixture is heated to activate the polymerase, the polymerase starts synthesizing the complementary strand to the primed single stranded template DNA. As the polymerization continues it reaches the probe bound to its complementary sequence, which is then hydrolyzed due to the 5'-3' exonuclease activity of the polymerase thereby separating the fluorescent reporter and the quencher molecules. This results in an increase in fluorescence, which is detected. During thermal cycling of the real-time PCR reaction, the increase in fluorescence, as released from the hydrolyzed dual-labeled probe in each PCR cycle is monitored, which allows accurate determination of the final, and so initial, quantities of DNA.

Any method of PCR that can determine the expression of a nucleic acid molecule as defined herein falls within the scope of the present disclosure. A preferred embodiment of the present disclosure includes the real-time quantitative RT-PCR method, based on the use of either SYBR Green dye or a dual-labeled probe for the detection and quantification of nucleic acids according to the herein described.

h. Northern Blot Analysis

An aspect of the present disclosure includes the detection of the nucleic acid molecules herein disclosed by techniques such as Northern blot analysis. Many variations of the protocol exist.

The following examples are offered by way of illustration and not by way of limitation.

The present invention has multiple aspects, illustrated by the following non-limiting examples.

15. Examples

The foregoing may be better understood by reference to the following examples, which are presented for purposes of illustration and are not intended to limit the scope of the invention.

Example 1

Materials and Methods

Preparation of Bacterial Cells.

One methicillin-susceptible *S. aureus* (Sanger 476) and three methicillin-resistant *S. aureus* genetic backgrounds (USA100, USA300, and MW2) were used. Overnight *S. aureus* cultures were inoculated into fresh tryptic soy broth and incubated aerobically at 30° C. to log-phase growth (optical density 600 nm of ~1.0). Cells were harvested by centrifugation, rinsed, and resuspended in phosphate-buffered saline (PBS). *E. coli* O18:K1:H7 was grown at 30° C. overnight in Luria-Bertani broth. Cultures were then diluted with fresh medium and grown for an additional 1 to 2 hours. Upon reaching log phase, cells were treated as described for *S. aureus*.

Human Subjects.

Subjects were enrolled at Duke University Medical Center (DUMC; Durham, N.C.), Durham VAMC (Durham, N.C.), UNC Hospitals (Chapel Hill, N.C.), and Henry Ford Hospital (Detroit, Mich.) as part of a prospective, NIH-sponsored study to develop novel diagnostic tests for severe sepsis and community acquired pneumonia (ClinicalTrials-.gov NCT00258869). Enrolled patients had a known or suspected infection and exhibited two or more Systemic Inflammatory Response Syndrome criteria. Patients were excluded if they had an imminently terminal co-morbid condition, advanced AIDS (CD4 count, 50), were being appropriately treated with an antibiotic pre-enrollment, or were enrolled in another clinical trial. Blood was drawn for microarray analysis on the day of hospital presentation with the exception of two subjects (S19 and S29). In these latter two cases, blood was not available for microarray preparation from that time point. However, blood drawn 24 hours into the hospitalization was available and so was used. Subjects in the current report had culture-confirmed monomicrobial BSI due to *S. aureus* (n=32; median age 58 years; range 24-91) or *E. coli* (n=19; median age 58; range 25-91). Uninfected controls (n=43; median age 30 years; range 23-59) were enrolled at DUMC as part of a study on the effect of aspirin on platelet function among healthy volunteers. Subjects were recruited through advertisements posted on the Duke campus. Blood used to derive gene expression data in these healthy controls was drawn prior to aspirin challenge.

Murine Sepsis Experiments.

Except where noted, mice were purchased from The Jackson Laboratory (Bar Harbor, Me.) and allowed to acclimate for 7 days. All experiments were performed on 6-8 week old mice. For the murine *S. aureus* classifier, seven inbred mouse strains (3 mice/strain: 129S1/SvImJ, A/J, AKR/J, BALB/cByJ, C57BL/6J, C3H/HeJ, and NOD/LtJ) were IP inoculated with $10^7$ CFU/g of *S. aureus* Sanger476, euthanized at 2 h after injection, and bled. This was repeated using the four different *S. aureus* genetic backgrounds (USA100, USA300, MW2, and Sanger476) in A/J mice (n=3 per *S. aureus* background). For time series experiments, both A/J and C57BL/6J mouse strains were IP inoculated with *S. aureus* Sanger476 as above, and sacrificed at 2, 4, 6, and 12 h after injection (n=5 per mouse strain at each time point). For survival experiments, mice were monitored twice daily after injection and culled upon reaching a moribund state. Animal sacrifice was carried out by carbon dioxide inhalation. Blood was collected by intracardiac puncture and stored in RNAlater at −70° C. for microarray experiments.

The murine *E. coli* infection model was carried out as described above except a smaller inoculum ($6 \times 10^4$ CFU/g) was used. Furthermore, the time at which animals were sickest but still alive was 24 hours for *E. coli* inoculation, which is later than for *S. aureus*. Consequently, A/J and C57BL/6J mice inoculated with *E. coli* were sacrificed 24 h after challenge (n=5 per mouse strain). Control mice were not injected.

Outbred CD-1 mice were purchased from Charles River Laboratories (Wilmington, Mass.) to validate the murine *S. aureus* classifier. CD-1 mice were IP inoculated with $10^7$ CFU/g of *S. aureus* (USA300 and Sanger 476) and $6 \times 10^4$ CFU/g of *E. coli*. Animals including controls were sacrificed at 2 and 24 h postinfection (n=10 mice per pathogen at each time point). Blood was collected and stored as described for the derivation cohort.

Example 2

Microarray Preparation

Total RNA was extracted from mouse blood using the Mouse RiboPure Blood RNA kit (Ambion, Austin, Tex.) according to the manufacturer's instructions. Globin mRNA was removed from whole blood RNA using the Globinclear kit (Ambion, Austin, Tex.). All samples passed the quality criteria of the Agilent Bioanalyzer and were used for microarray analysis. Since the total RNA yield of many samples was low, one round of linear amplification was performed for all samples using the MessageAmp Premier kit (Ambion, Austin, Tex.). RNA integrity numbers were calculated for all samples and found to be within tolerance limits. Microarrays were normalized using Robust Multichip Average (RMA). Affymetrix GeneChip Mouse Genome 430 2.0 Arrays were used (Santa Clara, Calif.). Biotin-labeled cDNA was hybridized to the arrays for 16 hours at 45° C. according to the manufacturer's instructions. Arrays were then washed and labeled with streptavidin-phycoerythrin (strep-PE), and the signal was amplified using biotinylated antistreptavidin followed by another round of staining with strep-PE. These steps were performed on the Affymetrix fluidics station according to the recommended protocol. Amplification and microarray hybridization were performed at the Duke University Microarray Core. Labeled gene chips were scanned using an Affymetrix Genechip Scanner 7G (Santa Clara, Calif.). This array contains 45,101 probe sets to analyze the expression level of over 39,000 transcripts and variants from over 34,000 mouse genes.

Human microarrays were prepared by first extracting total RNA from human blood using the PAXgene Blood RNA Kit (Qiagen, Valencia, Calif.) according to the manufacturer's recommended protocol including DNase treatment. Following isolation, RNA quantity was determined via a Nanodrop UV-Vis Spectrophotometer (Thermo Fisher Scientific, Pittsburgh, Pa.) and quality via capillary electrophoresis using the Agilent 2100 Bioanalyzer (Agilent, Santa Clara, Calif.). RNA quantity and quality was assessed using the Agilent 2100 Bioanalyzer (Agilent, Santa Clara, Calif.). RNA integrity numbers were calculated for all samples and found to be within tolerance limits. Microarrays were normalized using RMA. Hybridization and microarray data collection was then performed at Expression Analysis (Durham, N.C.) using the GeneChip® Human Genome U 33A 2.0 Array (Affymetrix, Santa Clara, Calif.) according to the "Affymetrix Technical Manual."

Target was prepared and hybridized according to the "Affymetrix Technical Manual". A set of four peptide nucleic acid (PNA) oligomers (Applied Biosystems, Foster City, Calif.) with sequences complimentary to globin mRNA were added to 2.5 ug of total RNA to reduce globin RNA transcription, then converted into cDNA using Reverse Transcriptase (Invitrogen) and a modified oligo(dT)24 primer that contains T7 promoter sequences (GenSet). After first strand synthesis, residual RNA was degraded by the addition of RNaseH and a double-stranded cDNA molecule was generated using DNA Polymerase I and DNA Ligase. The cDNA was then purified and concentrated using a phenol:chloroform extraction followed by ethanol precipitation. The cDNA products were incubated with T7 RNA Polymerase and biotinylated ribonucleotides using an In vitroTranscription kit (Affymetrix). The resultant cRNA product was purified using an RNeasy column (Qiagen) and quantified with a spectrophotometer. The cRNA target (20 ug) was incubated at 94° C. for 35 minutes in fragmentation buffer (Tris, MgOAc, KOAc). The fragmented cRNA was diluted in hybridization buffer (MES, NaCl, EDTA, Tween 20, Herring Sperm DNA, Acetylated BSA) containing biotin-labeled OligoB2 and Eukaryotic Hybridization Controls (Affymetrix). The hybridization cocktail was denatured at 99° C. for 5 minutes, incubated at 45° C. for 5 minutes and then injected into a GeneChip cartridge. The GeneChip array was incubated at 42° C. for at least 16 hours in a rotating oven at 60 rpm. GeneChips were washed with a series of nonstringent (25° C.) and stringent (50° C.) solutions variable amounts of MES, Tween20 and SSPE. The microarrays were then stained with Streptavidin Phycoerythrin and the fluorescent signal was amplified using a biotinylated antibody solution. Fluorescent images were detected in a GeneChip® Scanner 3000 and expression data was extracted using the GeneChip Operating System v 1.1 (Affymetrix). All GeneChips were scaled to a median intensity setting of 500.

Fluorescent images were detected in a GeneChip Scanner 3000 and expression data was extracted using the GeneChip Operating System v 1.1 (Affymetrix). All Gene-Chips were scaled to a median intensity setting of 500. Murine and human microarray data have been deposited in the NCBI GEO (accession # GSE33341).

Example 3

Deriving the Murine and Human *S. aureus* Classifiers

Microarray data was analyzed in two steps following the analysis strategy previously outlined and utilized. First, a Bayesian sparse factor model was fit to the expression data without regard to phenotype. Second, factors were then used as independent variables to build a penalized binary regression with variable selection model trained to identify *S. aureus* infection. In order to minimize issues with overfitting, batch was not included in the regression models. A Bayesian penalized regression technique was used for variable selection which allows for weighted model averaging of the resultant models, such that weights are computed from model fit on the training data. The model averaging approach incorporates uncertainty in choice of model as well as regression coefficient. This has been shown to lead to out of sample predictive accuracies that are superior to penalized maximum likelihood approaches. Assumptions for this approach are typical of probit regression including a linear response surface between predictors and the transformed latent probability variable. Genes were filtered for analysis using nonspecific filtering for genes with high mean expression and high variance across samples. Samples with a high number of outlying genes were removed during the factor analysis. Mice were batched into discrete experiments with each experiment containing the relevant controls to avoid confounding. The development and application of this methodological approach has been previously described. Using the same murine experimental data, another classifier was derived to classify methicillin resistant vs. methicillin-sensitive S. aureus infection. The methodology was otherwise the same as that described above.

A factor model was fitted on the human data independently from the mouse data. The factor model was fit to 9,109 genes after nonspecific filtering to remove unexpressed and uniformly expressed genes. Z-scores were computed independently for each gene without regard to experimental design. Subjects with absolute zscores greater than 3 in more than 5% of the genes on the array were identified as outliers and were not used to fit the factor model. The factor model was trained on the 91 samples (after removal of three outliers) from three batches of expression data, and this resulted in 79 factors. These 79 factors were then projected onto the full data set (including the three subjects removed for validation) with the goal of distinguishing S. aureus BSI from healthy controls or E. coli BSI. Leave-one-out cross-validation was utilized in order to control for overfitting of the penalized binary regression model. In order to minimize issues with overfitting, batch was not included in the regression models. Matlab (Natick, Mass., USA) scripts to perform these operations are available. Nonparametric testing was used to evaluate model performance (Wilcoxon rank sum for 2-group comparisons or Kruskal-Wallis for 3 or more-group comparisons) unless otherwise indicated.

One limitation of this approach is that the marginal significance of genes within the factor-based classifier cannot be defined. Instead, gene lists were created to identify genes with differential expression between specified groups with respect to gene-level and factor-level analyses. For 3-group comparisons (S. aureus vs. E. coli vs. Healthy controls) one-way analysis of variance (ANOVA) was used. For pairwise comparisons, Student's t-test was used. Results were statistically significant at p<0.05 after Bonferroni correction for multiple testing. Spreadsheets of gene/factor lists are provided as supplemental material.

Example 4

Creating a Human Ortholog of the Murine S. aureus Classifier

Chip Comparer available from URL: chipcomparer.genome.duke.edu/) was used to identify human orthologs for all possible mouse genes. When there were multiple orthologs, the anti-sense target probes that shared the fewest probes with other genes as identified by the probe label. Chip Comparer identified 17,600 probe sets on the Affymetrix GeneChip Human Genome U133A 2.0 Array that have orthologs in the Affymetrix GeneChip Mouse Genome 430 2.0 Array. Factor scores from the mouse factor model were estimated using this set of 17,600 genes as follows: Given a matrix of expression values, X, and a factor model X=BF+e, missing values were first replaced by mean expression levels for those genes. Step 2: Inverse regression was utilized to compute F, to estimate the factor scores. Step 3: X was estimated by computing BF* and replaced missing values with the corresponding values from this matrix. Steps 2 and 3 were then repeated until the estimates for the missing values converged.

Example 5

External Validation in an Independent Cohort

To externally validate the murine and human S. aureus classifiers, publically available expression data from a pediatric cohort with S. aureus infection and healthy controls were used. Hospitalized children with invasive S. aureus infection were enrolled with sample collection occurring after microbiological confirmation. Healthy controls included children undergoing elective surgical procedures and at healthy outpatient clinic visits. This dataset includes multiple expression platforms. For the purposes of consistency, subjects with Affymetrix U133A data yielding 46 S. aureus-infected patients and 10 healthy controls were included. Given the absence of subjects with E. coli infection in the validation cohort, new murine and human S. aureus classifiers were derived that excluded animals or subjects with E. coli infection. These classifiers were derived and then projected onto the 56-sample validation cohort as described heretofore.

Example 6

Heat Map Generation

In order to generate heat maps of gene expression, the factors from the murine and human S. aureus classifiers were used. Probes from each factor were identified and tested for differential expression in a one-way ANOVA. Probes with significantly different levels of expression after Bonferroni correction were retained. For the murine data, there were thousands of probes (~1000-3000, typically) meeting these criteria. Consequently, the p-values were sorted in ascending order and the 100 most significant probes from each factor were retained. Duplicate probes across the factors were removed. The human expression heat map was created in the same manner except all significant probes are presented considering there were fewer factors and genes in the human S. aureus classifier as compared to the murine classifier. Heat maps were generated using Matlab (Natick, Mass., USA).

Example 7

Pathway Analysis

Pathway analysis for functional annotation of genes was performed with the MetaCore tool of the GeneGO package (GeneGo, Inc., St. Joseph, Mich., USA) available from URL: www.genego.com). P-values were assigned to pathways based on the number of genes mapping to a particular pathway relative to the total number of genes in that pathway. Statistically significant pathways were defined as a p-value <0.05 (False Discovery Rate [FDR]-adjusted) based on hypergeometric distributions.

Example 8

Murine Sepsis Due to S. aureus and E. coli

Clinically relevant S. aureus infections in humans typically arise from a primary focus with secondary dissemination. To mimic this process, mice were inoculated via the intraperitoneal (IP) route. Infection-susceptible and infection-resistant inbred mouse strains (A/J and C57BL/6J, respectively) were inoculated with S. aureus (Sanger476) or E. coli (O18:K1:H7) (n=5 per mouse strain and bacterial species). A survival analysis was carried out to determine the optimal duration of infection for subsequent experiments (FIG. 7A). Based on this data, A/J and C57BL/6J mice were infected with S. aureus (sacrificed at t=0, 2, 4, 6, and 12 hours post-infection; n=10 animals/time point) or E. coli (t=0, 2, 6, 12, and 24 hours post-infection; n=10 animals/ time point). The effect of infection status, bacterial pathogen, and duration of infection on global patterns of gene expression was assessed using principal component analysis (PCA) (Partek Genomics Suite) (FIG. 7B-D). Gene expression patterns clustered by infection status and by pathogen (S. aureus vs. E. coli). Animals infected with S. aureus demonstrated a time-dependent change in gene expression that first manifested at two hours, by which time bacteremia has occurred. This pattern remained stable through 12 hours, when most animals have succumbed to sepsis. E. coli-infected animals did not reveal this time-dependent progression based on the time points sampled, but had a distinctly different pattern of gene expression that was evident at 2 hours and persisted through 24 hours following infection. A heat map depicting the time-dependent nature of these gene expression changes is presented in FIG. 8.

Example 9

Peripheral Blood Gene Expression Signatures Classify S. aureus-Infected from Uninfected Mice To create a host gene expression-based classifier for S. aureus infection, mice from a variety of experimental conditions were utilized (n=187 total). Seven strains of inbred mice were challenged with 4 S. aureus genetic backgrounds via IP inoculation and sacrificed at various time points as described in Experimental Procedures. The comparator group for model derivation included 50 A/J or C57BL/6J mice inoculated with E. coli (O18:K1:H7) as well as 54 non-inoculated mice. Whole blood mRNA was used to generate microarray expression data. A list of differentially expressed genes is presented in Tables 3-17. FIG. 9 presents the number of overlapping genes in each pairwise comparison. Patterns of co-expressing genes were defined using sparse latent factor regression in an unsupervised manner (i.e. without knowledge of the source animal's infection status). Factor models are a well-known technique for describing correlation structure in high dimension, low sample size data sets. The sparse latent factor model works by collecting genes that are highly correlated into groups. Predictive models are then built from the latent factors— vectors that describe the aggregate behavior of the group. Subsequently, these factors served as independent variables in a variable selection, binary regression model to distinguish animals with and without S. aureus infection. This approach was taken in lieu of using individual gene expression changes for several reasons. A given gene with biological relevance may be differentially expressed in response to S. aureus infection but not to the degree that would meet statistical significance. Considering this altered gene expression exists amid a network of other such changes, the collective perturbations in that particular pathway would be more easily detected using factor analysis. Furthermore, changes across multiple biological pathways will be reflected across multiple factors. These can then be collectively harnessed for their diagnostic potential using a binary regression model.

Figure 1:
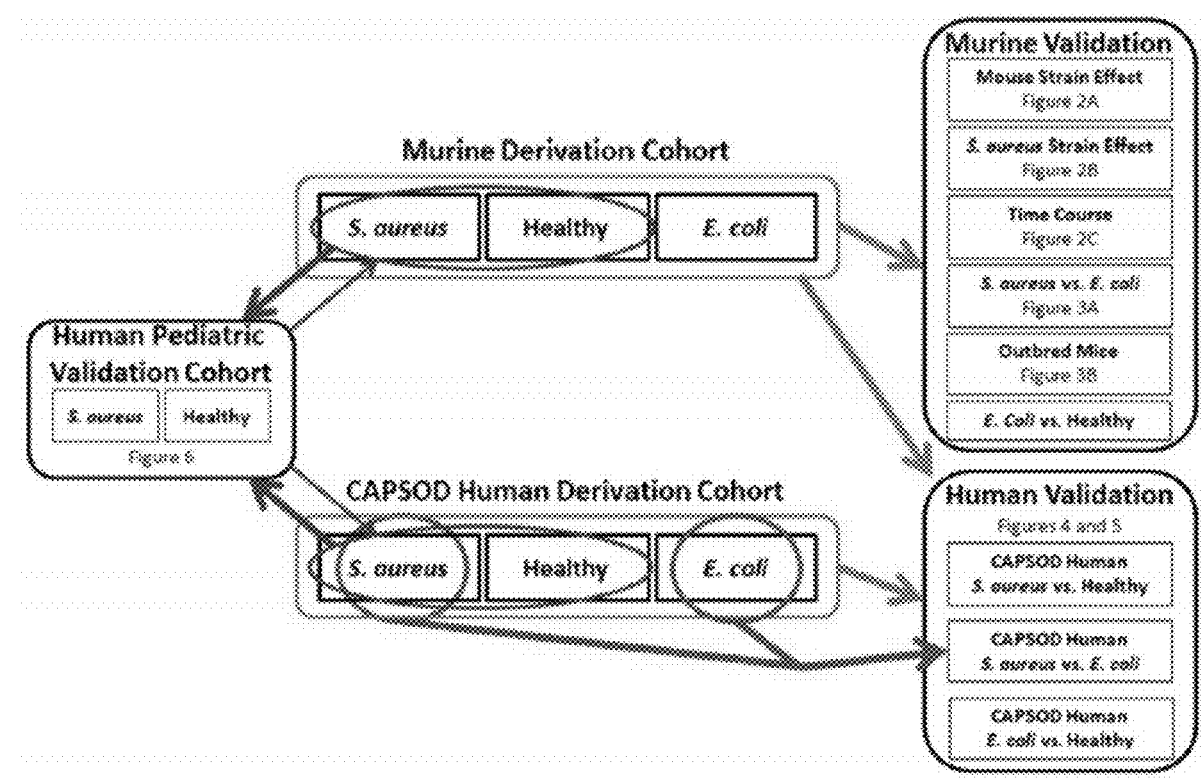
FIG. 1 shows a schematic of derivation and validation cohorts.

Thirty factors were identified, of which 16 demonstrated a pattern of expression significantly associated with infection status (mFactors 15, 7, 23, 13, 9, 29, 28, 2, 17, 16, 21, 1, 5, 4, 26, and 19 in order of greatest significance; ANOVA; p<0.0017 for S. aureus vs. control vs. E. coli after Bonferroni correction; FIG. 10). These 30 factors were fitted into a penalized binary regression model, termed the "murine S. aureus classifier". The best performing model, as defined by the model with the largest log likelihood value, included four factors (mFactors 7, 15, 23, and 26). Other models may be just as adequate, but this "top" model is referred to. Leave-one-out cross-validation was used to control overfitting and to estimate the model's performance in subgroups of experimental conditions as described below (mouse strain, S. aureus genetic background, duration of infection, and bacterial species [S. aureus vs. E. coli]). A schematic of the derivation and validation experiments is depicted in FIG. 1.

The Murine Derivation Cohort includes S. aureus infection (n=83), healthy control mice (n=54), and E. coli infection (n=50). It served as a validation cohort to assess Mouse Strain Effect, S. aureus Genetic Background Effect, Time Course, and to compare S. aureus vs. E. coli and E. coli vs. Healthy. The murine S. aureus classifier was externally validated in Outbred Mice (n=30) and the CAPSOD Human Cohort. The CAPSOD Human Cohort includes S. aureus BSI (n=32), healthy volunteers (n=43), and E. coli BSI (n=19). It served as a validation cohort to compare S. aureus vs. Healthy, S. aureus vs. E. coli, and E. coli vs. Healthy. Model derivation and validation using the entire cohort of animals or humans is depicted by the blue outline and arrows. An independent classifier was generated using only subjects with S. aureus or E. coli BSI (green outline). This classifier was validated using leave one out cross validation (green arrow). The Human Pediatric Cohort (n=46 S. aureus, 10 Healthy) used for external validation does not include patients with E. coli infection. Therefore, S. aureus classifiers were generated from the murine and CAPSOD cohorts that excluded E. coli data (red outline and thick red arrow). The Human Pediatric Cohort was used to derive a Human S. aureus vs. Healthy classifier which was validated in the S. aureus-infected and Healthy populations within the murine and CAPSOD human cohorts (thin red arrow).

Figure 2:
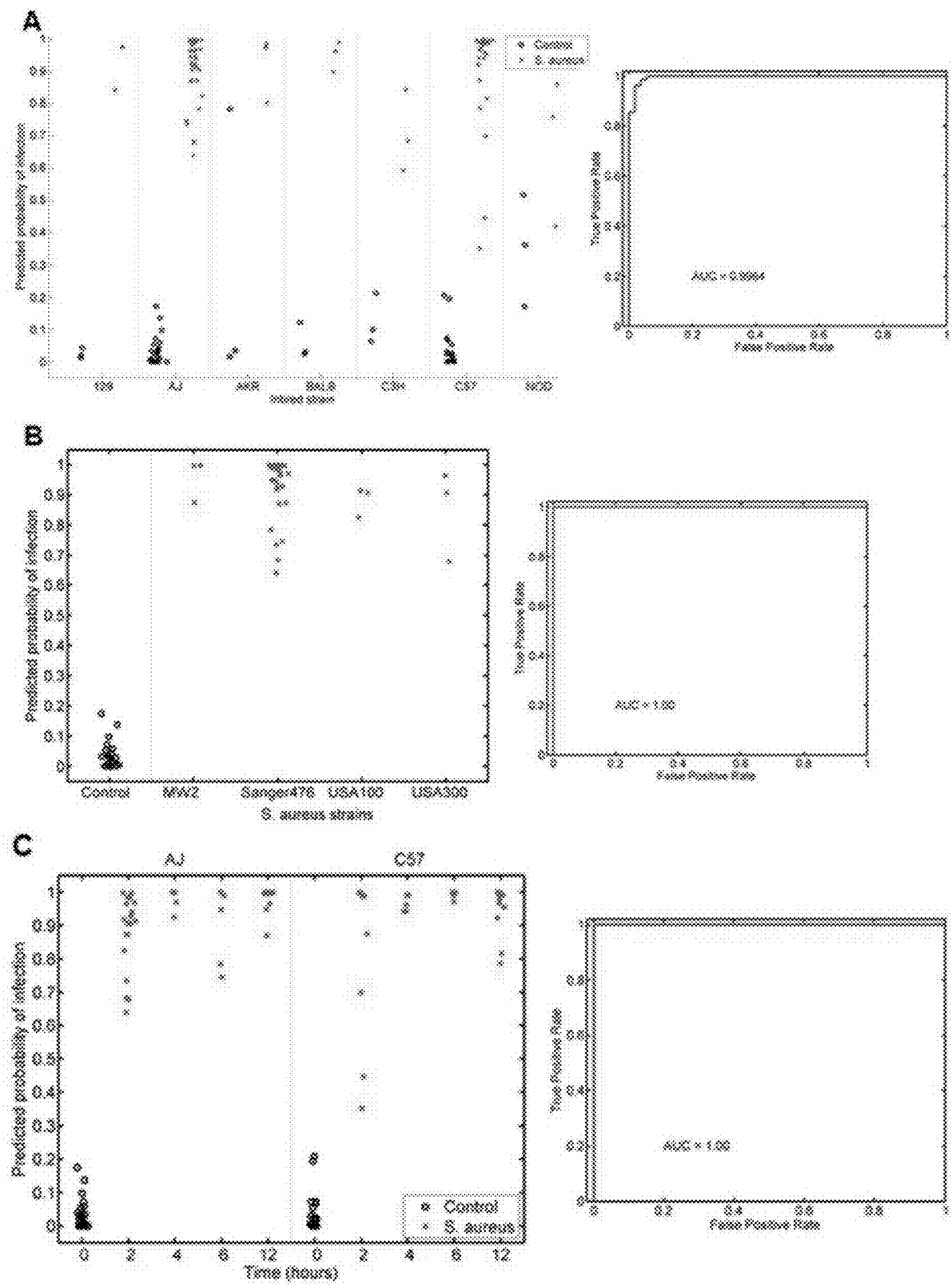
FIG. 2 shows that murine *S. aureus* classifier accurately identifies *S. aureus* infection under a variety of conditions.

The ability of the murine-derived host gene expression classifier to identify S. aureus infection was tested in 7 inbred mouse strains of varying infection susceptibilities. In all 7 strains, the murine S. aureus classifier accurately differentiated S. aureus-infected from control mice (p=4.89× $10^{-16}$; AUC=0.9964) (FIG. 2A). The ability to characterize S. aureus infection persisted when A/J mice (infection-susceptible) were challenged with four different S. aureus backgrounds: USA100 (the predominant US nosocomial methicillin resistant S. aureus [MRSA] genetic background); USA300 (the predominant US community-acquired MRSA genetic background); USA400 (MW2); and Sanger 476 (a methicillin susceptible genetic background) (p=1.92×$10^{-10}$ vs. control mice; AUC=1.00) (FIG. 2B). Furthermore, the murine S. aureus classifier consistently discriminated S. aureus infected mice from controls at 2, 4, 6, and 12 hours post-inoculation (p=4.41×$10^{-16}$ vs. uninfected mice; AUC 1.00) (FIG. 2C). This time interval was selected because two hours is the earliest time point at which S. aureus can be cultured from blood; while 12 hours was the point at which animals began to die of S. aureus sepsis (FIG. 7A). In summary, a classifier based on murine-derived host gene expression accurately identified the presence of S. aureus infection in mice under a variety of host, pathogen, and temporal conditions.

Example 10

Murine S. aureus Classifier Distinguishes S. aureus Infected from E. coli-Infected Mice Next, it was determined whether the murine S. aureus classifier could differentiate S. aureus from E. coli infection.

Both the infection-susceptible A/J and infection-resistant C57BL/6J strains were infected with either *S. aureus* (Sanger 476) or *E. coli* (O18:K1:H7). Animals were sacrificed at 2, 6, and 12 hours after inoculation. The murine *S. aureus* classifier correctly identified 50 of 53 (94.3%) animals as either infected with *S. aureus* or not at 2 hours (50/53), 100% of animals at 6 hours (n=20), and 96.7% of animals at 12 hours (29/30) (FIG. 3A). This corresponded to an overall p-value of $7.94 \times 10^{-26}$ by Kruskal-Wallis test (comparing *S. aureus* vs. *E. coli* vs. Healthy controls) with an AUC of 0.9935 across all time points. Next, the murine *S. aureus* classifier was independently validated in outbred CD-1 mice with *S. aureus* infection (Sanger 476 or USA300), *E. coli* infection (O18:K1:H7), or uninfected controls (10 animals per condition). The murine derived *S. aureus* model accurately classified 95% of all animals where the reference standard was the known experimental condition (38/40; $p=1.47 \times 10^{-6}$; 90% sensitivity and 100% specificity; AUC=0.9775) (FIG. 3B).

The murine *S. aureus* classifier was generated to identify *S. aureus* infection within a population including both healthy and *E. coli* infected animals. However, it is possible this classifier is primarily distinguishing "sick" from "not-sick" phenotypes. In such a case, it would be expected that the classifier would still differentiate animals with *E. coli* infection from uninfected controls. However, this was not observed (AUC 0.5089; p=0.8785) demonstrating the specificity of this classifier for *S. aureus* infection. Thus, a murine derived host gene expression classifier accurately distinguished *S. aureus*-infected from *E. coli*-infected or uninfected mice across multiple host strains, pathogens, post-infection time points, and was validated in outbred mice.

Given this ability to discriminate infection due to different bacterial species, the potential for a factor based classifier was further explored to distinguish infection due to methicillin-resistant (MRSA) or methicillin-sensitive *S. aureus* (MSSA), which have been shown to differ in their pathogenicity and virulence. The same 30 factors described above were fitted into a penalized binary regression model with the specific aim of differentiating MRSA from MSSA infection. Leave-one-out cross-validation was used to control overfitting and to estimate the model's performance in a population of 19 MRSA-infected and 84 MSSA-infected mice (FIG. 11). Despite some overlap, this classifier accurately differentiated infection due to MRSA or MSSA (AUC 0.8396; $p=4.14 \times 10^{-6}$). Genes discriminating infection due to MRSA or MSSA that remained significant after adjusting for multiple tests are presented in Table 11. Table 11 shows the probes and corresponding genes that were differentially expressed (after Bonferroni correction) in mice with MRSA vs. MSSA infection.

Example 11

Human *S. aureus* Classifier

It was determined whether peripheral blood gene expression in humans could yield a classifier for *S. aureus* BSI. Peripheral whole blood mRNA from 32 patients with *S. aureus* BSI, 19 patients with *E. coli* BSI, and 43 healthy control subjects were used to generate microarray data (Table 1). Also presented is the average probe expression in each comparator group and the fold-change within the pairwise comparison. A list of differentially expressed genes is presented in Tables 7-10. FIG. 12 presents the number of overlapping genes in each pairwise comparison. Seventy-nine factors were defined and fitted into a linear regression model trained to identify the presence of *S. aureus* BSI. Although 17 factors were independently associated with *S. aureus* BSI (FIG. 13), only two factors remained in the best performing model (hFactors 20 and 74). Similar to the murine *S. aureus* classifier, the human *S. aureus* classifier was generated blind to microbiological diagnosis in an unsupervised manner. Gender was controlled for in the model's derivation considering the predilection for female sex in *E. coli* BSI (Table 2). The model's performance in phenotypic subgroups was estimated using leave-one-out cross-validation. The classifier accurately differentiated those with *S. aureus* BSI from healthy controls (72/75 correctly classified; AUC=0.9898; $p=5.41 \times 10^{-13}$) (FIG. 4A). The human *S. aureus* classifier also correctly distinguished *S. aureus* from *E. coli* BSI in 82% (42/51) of cases (AUC=0.8372; $p=6.77 \times 10^{-4}$). When the human *S. aureus* classifier was applied to subjects with *E. coli* BSI vs. healthy controls, an intermediate level of discrimination (56/62 correctly classified; AUC 0.9229; $p=1.38 \times 10^{-7}$) was observed. This suggests that the human classifier is partially pathogen specific since *E. coli* BSI could also be distinguished from healthy controls but not with the same degree of accuracy as *S. aureus* BSI. A heat map depicting these gene expression changes is presented in FIG. 14.

In the human *S. aureus* classifier described above, it is the inclusion of healthy controls that drives the discrimination from *S. aureus* BSI. Considering the clinical importance of differentiating Gram-positive from Gram-negative infections, rather than sick vs. healthy, a penalized binary regression model was created with the specific aim of differentiating human *S. aureus* (n=32) from *E. coli* (n=19) BSI. In this cohort, 52 factors were identified (different from the 79 factors identified when Healthy was included) of which only hFactor 40 remained in the top performing model after controlling for gender. Using leave-one-out cross-validation (FIG. 4B), this model had a sensitivity of 62.5% (20/32 *S. aureus* BSIs correctly classified) but a specificity of 94.7% (18/19 *E. coli* BSIs correctly classified). This corresponds to an AUC of 0.8503 ($p=3.47 \times 10^{-5}$).

Example 11

A Murine *S. aureus* Classifier Identifies *S. aureus* Infection in Humans

It was determined whether the murine *S. aureus* classifier could identify *S. aureus* BSI in humans. To accomplish this, the murine *S. aureus* classifier was projected onto human gene expression data. Specifically, Chip Comparer (available from URL: chipcomparer.genome.duke.edu/) provided a modified representation of the Affymetrix Mouse Genome 430 2.0 Array that only included orthologs of transcripts represented on the Affymetrix Human Genome U133A 2.0 Array. This resulted in a murine *S. aureus* classifier consisting only of genes with human orthologs (68.6% of the total array representation). This classifier was evaluated in the human cohort. To account for potential species specific variation in gene expression, predicted probabilities were plotted on a log it rather than a probabilistic scale. Using this murine *S. aureus* classifier, human patients with *S. aureus* BSI were distinguished from healthy controls (AUC=0.9484; $p=4.00 \times 10^{-11}$) (FIG. 5). Thus, the host response to *S. aureus* infection was sufficiently conserved that a predictive model generated in one species (*Mus musculus*) identified *S. aureus* BSI in another (*Homo sapiens*). However, the murine-derived *S. aureus* classifier did not differentiate between *S. aureus* and *E. coli* BSI in humans (AUC=0.5905; p=0.2883).

Example 11

Validation of Murine and Human Classifiers in an Independent Pediatric Population The murine and human *S. aureus* classifiers were externally validated in an independent human cohort. This validation cohort consisted of pediatric patients hospitalized due to invasive *S. aureus* infection (n=46) and healthy controls (n=10) who had gene expression data generated on a compatible platform (U133A array) with that used in this study. This cohort did not enroll children with *E. coli* infections. For this reason, *E. coli* infection was excluded from both classifiers. New murine and human *S. aureus* classifiers were developed in the same manner described above but without *E. coli*-related expression data. This modified murine *S. aureus* classifier was comprised of mFactors 7, 15, and 26 but not mFactor23. The modified human *S. aureus* classifier only contained hFactor4. Both the murine and human *S. aureus* classifiers differentiated children with *S. aureus* infection from healthy controls in this validation cohort (murine classifier AUC=0.9522, p-value=$9.03 \times 10^{-6}$ (FIG. 6A); human classifier AUC 0.9217, p-value $3.48 \times 10^{-5}$ (FIG. 6B)). The converse was also true. A *S. aureus* classifier trained on this independent pediatric cohort accurately discriminated *S. aureus* infection from healthy controls in the CAPSOD human cohort (70/75 correctly classified; AUC=0.9775, p-value=2.03610212) and murine cohort (123/137 correctly classified; AUC=0.9255; p=$4.56 \times 10^{-17}$).

Example 11

*S. aureus* Infection Induces Similar Host Gene-Expression Responses in Mouse and Human Pairwise comparisons were performed to identify genes with significantly different levels of expression (after Bonferroni correction). Comparisons included *S. aureus* infection vs. Healthy, *E. coli* infection vs. Healthy, and *S. aureus* vs. *E. coli* infection in mice and humans. Genes from each pairing were entered into the GeneGo pathway map database. The 50 most significant biological pathways arising from the pairwise comparisons are presented in Tables 12-16, which show the pathway analysis for the genes from pairwise comparisons in the mouse and human study. The top 50 ranked pathways from GeneGo MetaCore pathway analysis based upon p-value are shown. Pathways marked with an asterisk (*) correspond to pathways that are present in both the mouse and human response to the specified pathogen. The genes represented within common pathways are presented in Table 17. Table 17 shows the genes in pathways common to murine and human responses to infection. Human genes are in the top row for each pathway. Murine genes are in the bottom row for each pathway.

A similar number of pathways overlapped between the murine and human responses to *S. aureus* (12 of the top 50) and *E. coli* (14 of the top 50) infection. Most of the overlapping pathways in the murine and human responses to both *S. aureus* and *E. coli* belonged to the broad category of immune response including CD28, ICOS, and the MEF2 pathway. Cytoskeletal remodeling (TGF and WNT) and apoptosis were also common to both infection types in mice and humans. Some pathways were highly significant in the *S. aureus* vs. Healthy comparison but not manifest in *E. coli* vs. Healthy such as NF-kB-associated pathways; the CD40 immune response pathway; and clathrin-coated vesicle transport. As expected, these pathways were also differentially manifest in the direct comparison of murine *S. aureus* and *E. coli* infection. No statistically significant probes were identified that distinguished human *S. aureus* from *E. coli* BSI. One probe, corresponding to the F2RL3 gene, nearly met this statistical cutoff (p-value $5.94 \times 10^{-6}$ with a cutoff of $2.24 \times 10^{-6}$). F2RL3 encodes proteinase-activated receptor 4. This molecule is a G-protein coupled receptor activated by thrombin and trypsin but has not previously been implicated in the sepsis or immune response. It is expressed in multiple tissues with high levels in the lung, pancreas, thyroid, testis, and small intestine but not peripheral blood or lymphoid tissues.

Example 12

Discussion of Examples 1-11

The current investigation contributes to this goal through three key findings. First, *S. aureus* infection induces conserved host gene expression responses in mice that can differentiate from *E. coli*-infected or uninfected mice. This discovery was consistent and robust across multiple inbred mouse strains, *S. aureus* genetic backgrounds, time points, and was validated in outbred mice. The validation step strengthens generalizability and is an important improvement over previous murine gene-expression based classifiers that were developed and tested in only a single inbred mouse strain including the fields of infectious diseases; cancer progression; and aging. Furthermore, this murine predictor was specific for *S. aureus* infection and not simply a marker of illness based on the observation that mice with *E. coli* sepsis could not be distinguished from healthy, uninfected animals. The murine *S. aureus* classifier performed equally well at multiple time points despite progression of illness lending additional support to the specificity of this classifier. Second, human-derived host gene expression signatures differentiated *S. aureus* BSI from *E. coli* BSI or uninfected controls. In contrast to the murine-based classifier, the human-based model was less pathogen specific but still provided a significant degree of differentiation between *S. aureus* and *E. coli* BSI. Finally, the responses to *S. aureus* infection were highly conserved at the transcriptional and pathway level. This conserved response allowed the validation of the murine- and human-derived *S. aureus* classifiers in an independent cohort of *S. aureus*-infected patients.

Previous efforts to identify a discriminatory host gene expression signature for Gram-positive versus Gram-negative infections have yielded inconsistent results. This is likely due to the observation that transcriptional data derived from complex phenotypes such as infection do not produce just one predictive gene set, but rather generate multiple gene sets associated with the phenotype in question. In the current investigation, well-established methodologies were utilized to derive predictors for *S. aureus* infection in both mice and humans from gene expression data. A key component of this methodology was a dimensional reduction step generating sets of co-expressed genes, termed "factors." Multiple, individual factors differentiated between various infection states were observed although none performed universally well. For example, mFactor15 was associated with the lowest overall p-value during model generation. The AUC was 0.9587 for *S. aureus* vs. uninfected control mice but only 0.7942 for *S. aureus* vs. *E. coli*. In contrast, mFactor23 had an AUC of 0.9800 for *S. aureus* vs. *E. coli* but an AUC of 0.5926 for *S. aureus* vs. uninfected control mice. In order to generate a more robust classifier, factors were used as independent variables to generate a binary regression model. Factor models are an excellent technique for estimating correlation structure in very high dimensional data sets. This comprised the second step in generating the *S. aureus* predictors. It was only by including all factors to build the classifier that the model could be validated in the broadest set of conditions including different bacterial pathogens. Although redundancy among the genes in a molecular classifier is expected and is a potential limitation, such redundancy can also improve robustness for a specific phenotype as is likely to be the case in discriminating *S. aureus* from *E. coli* infection in mice. Comparisons at the individual gene level, as with pairwise comparisons, are likely to reveal differences in relatively simple biological responses. In contrast, dimension reduction with factor modeling as utilized in this study incorporates differences across multiple pathways, allowing for the detection of changes in a more complex pathobiology. Additionally, the factor model construction does not incorporate known biological pathways. This leads to gene groupings that are sometimes difficult to interpret. The advantage of the approach is the extreme dimension reduction which allows for discovery and cross-validation on very small data sets. This is one possible explanation for why the human *S. aureus* classifier differentiated *S. aureus* from *E. coli* whereas no genes met the threshold for differential expression after Bonferroni correction in a pairwise comparison between these two patient populations. The strength of this approach is offset by the possibility that smaller or transient changes in gene expression might be missed. Furthermore, there are likely many combinations of genes and factors that would perform similarly to that described here. This study presents findings related to the best performing classifier using the described methodologies.

The murine model has been effectively used to gain insights into the pathophysiology of sepsis in general and *S. aureus* in particular. Murine-derived gene expression signatures have also been successfully translated to non-infectious human conditions such as radiation exposure and breast cancer. Here, the robust performance of a murine-derived *S. aureus* classifier in both mice and humans was described and also offer several lines of evidence supporting a partially conserved host response to *S. aureus* infection in both host species. First, the murine-based predictor could differentiate human *S. aureus* BSI from uninfected controls. Second, the genetic pathways were highly conserved. For example, most of the relevant murine pathways were also significantly associated with *S. aureus* BSI in humans. Finally, the murine-based predictor was highly accurate in classifying *S. aureus* infection in an independent human cohort.

The data presented here also indicates that the *S. aureus* classifiers are not being driven by lineage-specific transcript abundance. Specifically, the total leukocyte count and cell lineage distribution (based on routine automated differential measurements) were not different between patients with *S. aureus* infection and *E. coli* infection ($15.7 \times 10^9$/L with 86.2% neutrophils vs. $14.1 \times 10^9$/L with 85.8% neutrophils, respectively). However, the human *S. aureus* classifier was still able to differentiate infection due to the two pathogens. The murine *S. aureus* classifier was highly successful in differentiating *S. aureus* infection from healthy and from *E. coli* infection yet was unable to differentiate *E. coli* from healthy. This result would not be expected if transcript abundance was driving the derivation of the classifier.

The overlap observed in the gene expression response to *S. aureus* infection in mouse and human was also consistent with published studies. NF-kB signaling pathways have been identified as a critical component of the murine response to infection, which was mirrored in the murine and human data presented here. Similar gene expression-based analyses of the human response to bacterial infection have also revealed the importance of other biological pathways including MHC class I and II antigen presentation, immunological synapse formation, TGF-b receptor signaling, TGF and WNT-dependent cytoskeleton remodeling, and T-cell receptor signaling, all of which were significantly associated with *S. aureus* infection in this study. Hence, mice and humans utilize many of the same or overlapping pathways in response to bacterial sepsis supporting the potential utility of murine-based diagnostics for human disease.

Example 13

Gene Subsets for Diagnostic Assay

The mouse factors 7, 15, 23 and 26 together classify mice infected with *S. aureus* as distinct from healthy mice with an area-under-the-curve (AUC or classification accuracy) of 0.996 (where 1 is perfect). In another scenario, mouse factors 7, 15, and 26 translated to their human equivalent are sufficient to distinguish between humans infected with *S. aureus* and those who are healthy with an AUC of 0.9484.

In order to determine the subset of genes used in a diagnostic test, the relative contribution each gene makes to the factor's classification performance will be determined. Specifically, the number of genes required to achieve greater than 90%, 95%, 97%, and 99% of the factor's classification performance will be defined. Depending on the number of genes necessary to achieve these performance levels, a more limited gene set for diagnostic test development may be used.

An overview of the steps necessary for diagnostic test development is as follows: the optimal subset of genes will be identified from the presented factors that retains classification performance (as described above). As an example, the 200 top performing genes from each murine factor are presented. mRNA-specific probes will be generated for each. Patients with known diagnoses will be tested to verify the selected gene's mRNA can be detected by PCR or some other detection platform. Target gene expression will be measured relative to internal controls. Subsequently, an algorithm will produce a score or probability of *S. aureus* infection. Thresholds will be defined, above and below which a diagnosis will be made. This report would then be reported to the user.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the invention as defined by the scope of the claims.

TABLE 1

| Subject | Subject Category | Race | Age | Gender | Source of Infection | Positive Culture Sources | WBC | PMN % |
|---|---|---|---|---|---|---|---|---|
| S1 | S. aureus | White | 82 | Male | Endocarditis | Blood | 23.6 | 96.4 |
| S2 | S. aureus | White | 70 | Female | Skin | Blood, Wound, Operative cultures | 11.6 | N/A[a] |
| S3 | S. aureus | Black | 41 | Male | Catheter[b] | Blood | 14.8 | N/A |
| S4 | S. aureus | White | 81 | Male | Skin | Blood, Pleural fluid | 16.2 | N/A |
| S5 | S. aureus | White | 81 | Male | Bone | Blood | 17.3 | N/A |
| S6 | S. aureus | Black | 55 | Male | Catheter | Blood, Vascular catheter site | 14.3 | 89.8 |
| S7 | S. aureus | Black | 69 | Female | Catheter | Blood | 13 | N/A |
| S8 | S. aureus | Black | 44 | Female | Catheter | Blood | 13 | 90 |
| S9 | S. aureus | Black | 51 | Male | Skin | Blood | 6.9 | 73 |
| S10 | S. aureus | Black | 47 | Male | Skin | Blood | 12 | 87 |
| S11 | S. aureus | White | 36 | Female | Endocarditis | Blood | 22.7 | 85 |
| S12 | S. aureus | White | 54 | Male | Bone | Blood | 9.8 | 88 |
| S13 | S. aureus | Black | 55 | Male | Bone | Blood, Skin, Synovial fluid | 18.3 | 87 |
| S14 | S. aureus | Black | 42 | Male | Unknown | Blood, Urine, Sputum | 7.6 | 82 |
| S15 | S. aureus | Black | 52 | Male | Bone | Blood | 10.9 | 79 |
| S16 | S. aureus | Black | 55 | Male | Bone | Blood, Skin | 28.6 | 95 |
| S17 | S. aureus | White | 52 | Male | Skin | Blood, Skin | 17.9 | 84 |
| S18 | S. aureus | N/A | 51 | Female | Lung | Blood | 19.8 | 78 |
| S19[c] | S. aureus | Black | 40 | Male | Skin | Blood, Skin | 14.7 | 93 |
| S20 | S. aureus | White | 60 | Male | Skin | Blood | N/A | N/A |
| S21 | S. aureus | Black | 59 | Male | Catheter | Blood | 7.5 | 75.5 |
| S22 | S. aureus | Black | 58 | Male | Bone | Blood | 27.9 | N/A |
| S23 | S. aureus | Black | 77 | Male | Urinary tract | Blood, Urine, Skin | 9.8 | 80.3 |
| S24 | S. aureus | Black | 91 | Male | Bone | Blood | 15.1 | 93 |
| S25 | S. aureus | White | 75 | Female | Catheter | Blood | 6 | 92 |
| S26 | S. aureus | Black | 58 | Male | Catheter | Blood | 23.9 | 87 |
| S27 | S. aureus | Black | 24 | Male | Urinary tract | Blood, Urine, Sputum | 16 | 76.4 |
| S28 | S. aureus | White | 74 | Male | Skin | Blood, Abscess | 33.2 | 89 |
| S29[c] | S. aureus | Black | 70 | Male | Skin | Blood | 19.6 | 82 |
| S30 | S. aureus | White | 61 | Male | Bone/CNS[d] | Blood, Abscess | 10.4 | 86 |
| S31 | S. aureus | Black | 52 | Male | Lung | Blood (S. aureus); Antigen test (S. pneumoniae) | 6.1 | 93 |
| S32 | S. aureus | Black | 38 | Male | Endocarditis | Blood | 16.8 | 94 |
| E1 | E. coli | Black | 43 | Female | Urinary tract | Blood, Urine | 32.6 | 87.3 |
| E2 | E. coli | White | 49 | Female | Urinary tract | Blood | 14 | 92.4 |
| E3 | E. coli | Black | 44 | Female | Urinary tract | Blood, Urine | 15.7 | N/A |
| E4 | E. coli | White | 70 | Female | Urinary tract | Blood, Urine | 20.7 | 88 |
| E5 | E. coli | Black | 40 | Male | Urinary tract | Blood, Urine | 15 | 83 |
| E6 | E. coli | White | 91 | Female | Urinary tract | Blood, Urine | 5.6 | N/A |
| E7 | E. coli | Black | 25 | Female | Urinary tract | Blood, Urine | 11.1 | 88 |
| E8 | E. coli | White | 62 | Male | Urinary tract | Blood, Urine | 13.3 | N/A |
| E9 | E. coli | Black | 70 | Male | Urinary tract | Blood | 2.4 | 94 |
| E10 | E. coli | Black | 32 | Female | Urinary tract | Blood, Urine | 25.1 | N/A |
| E11 | E. coli | White | 54 | Female | Urinary tract | Blood, Urine | 10.8 | 90 |
| E12 | E. coli | White | 74 | Female | Urinary tract | Blood, Urine | 7.3 | 97 |
| E13 | E. coli | Black | 79 | Female | Lung | Blood | 16.9 | 77 |
| E14 | E. coli | Black | 41 | Male | Urinary tract | Blood, Urine | 14.3 | 77.6 |
| E15 | E. coli | White | 65 | Male | Urinary tract | Blood, Urine | 21.6 | 85 |
| E16 | E. coli | White | 63 | Female | Urinary tract | Blood, Urine | 8.5 | N/A |
| E17 | E. coli | White | 81 | Female | Urinary tract | Blood, Urine | 14.1 | 86.5 |
| E18 | E. coli | Black | 69 | Female | Urinary tract | Blood, Urine | 11.1 | 67.6 |
| E19 | E. coli | White | 55 | Female | Urinary tract | Blood, Urine | 7.2 | 87.5 |
| H1 | Healthy | Black | 27 | Male | | | | |
| H2 | Healthy | White | 24 | Female | | | | |
| H3 | Healthy | White | 29 | Female | | | | |
| H4 | Healthy | White | 26 | Male | | | | |
| H5 | Healthy | Asian | 30 | Male | | | | |
| H6 | Healthy | Black | 24 | Male | | | | |
| H7 | Healthy | White | N/A | Male | | | | |
| H8 | Healthy | Asian | 24 | Male | | | | |
| H9 | Healthy | Asian | 23 | Male | | | | |
| H10 | Healthy | White | 50 | Female | | | | |
| H11 | Healthy | White | 23 | Female | | | | |

TABLE 1-continued

| Subject | Subject Category | Race | Age | Gender | Source of Infection | Positive Culture Sources | WBC | PMN % |
|---|---|---|---|---|---|---|---|---|
| H12 | Healthy | White | 24 | Female | | | | |
| H13 | Healthy | White | 44 | Male | | | | |
| H14 | Healthy | White | 24 | Female | | | | |
| H15 | Healthy | White | 28 | Female | | | | |
| H16 | Healthy | White | 26 | Male | | | | |
| H17 | Healthy | Asian | 30 | Female | | | | |
| H18 | Healthy | Black | 26 | Male | | | | |
| H19 | Healthy | White | 25 | Male | | | | |
| H20 | Healthy | White | 24 | Male | | | | |
| H21 | Healthy | White | 24 | Male | | | | |
| H22 | Healthy | Asian | 25 | Female | | | | |
| H23 | Healthy | Black | 24 | Female | | | | |
| H24 | Healthy | White | 43 | Female | | | | |
| H25 | Healthy | White | 26 | Female | | | | |
| H26 | Healthy | Black | 59 | Male | | | | |
| H27 | Healthy | Black | 25 | Female | | | | |
| H28 | Healthy | White | 24 | Male | | | | |
| H29 | Healthy | White | 25 | Male | | | | |
| H30 | Healthy | White | 26 | Male | | | | |
| H31 | Healthy | White | 24 | Male | | | | |
| H32 | Healthy | White | 26 | Male | | | | |
| H33 | Healthy | N/A | 25 | Male | | | | |
| H34 | Healthy | White | 53 | Female | | | | |
| H35 | Healthy | Black | 45 | Female | | | | |
| H36 | Healthy | White | 23 | Male | | | | |
| H37 | Healthy | White | 26 | Female | | | | |
| H38 | Healthy | White | 27 | Male | | | | |
| H39 | Healthy | Asian | 43 | Female | | | | |
| H40 | Healthy | Black | 32 | Female | | | | |
| H41 | Healthy | N/A | 25 | Female | | | | |
| H42 | Healthy | Black | 43 | Female | | | | |
| H43 | Healthy | White | N/A | Female | | | | |

[a]N/A — Not available.
[b]Catheter refers to vascular catheters.
[c]Gene expression data for S19 and S29 was generated from blood drawn on the second hospital day. Blood drawn on the day of admission was otherwise used for all other infected subjects.
[d]This subject had vertebral osteomyelitis associated with an epidural abscess.

TABLE 2

Characteristics of human subjects used for S. aureus classifier derivation.

| | S. aureus (n = 32) | Gram-negative (n = 19) | Healthy (n = 43) |
|---|---|---|---|
| Age in years, mean (range) | 58 (24-91) | 58 (25-91) | 30 (23-59) |
| Gender, n (%) | | | |
| Female | 6 (19) | 14 (74) | 21 (49) |
| Male | 26 (81) | 5 (26) | 22 (51) |
| Race, n (%) | | | |
| Black | 20 (63) | 9 (47) | 9 (21) |
| White | 11 (34) | 10 (53) | 26 (60) |
| Asian | 0 | 0 | 6 (14) |
| Unknown | 1 (3) | 0 | 2 (5) |
| Dialysis, n (%) | 12 (38) | 0 | 0 |
| Diabetes, n (%) | 13 (41) | 3 (16) | 0 |
| Immunosuppression, n (%) | 2 (6) | 2 (11) | 0 |

TABLE 3

| Mouse Factor 7 | | |
|---|---|---|
| PROBE ID | SYMBOL | GENE NAME |
| 1415741_at | Tmem165 | transmembrane protein 165 |
| 1415856_at | Emb | embigin |
| 1415899_at | Junb | Jun-B oncogene |
| 1416010_a_at | Ehd1 | EH-domain containing 1 |
| 1416035_at | Hif1a | hypoxia inducible factor 1 alpha subunit |
| 1416119_at | Txn1 | thioredoxin 1 |
| 1416249_at | Nadk | NAD kinase |
| 1416281_at | Wdr45l | Wdr45 like |
| 1416360_at | Snx18 | sorting nexin 18 |
| 1416378_at | Pnkp | polynucleotide kinase 3'-phosphatase |
| 1416381_a_at | Prdx5 | peroxiredoxin 5 |

TABLE 3-continued

Mouse Factor 7

| PROBE ID | SYMBOL | GENE NAME |
|---|---|---|
| 1416440_at | Cd164 | CD164 antigen |
| 1416442_at | Ier2 | immediate early response 2 |
| 1416522_a_at | Grcc10 | gene rich cluster C10 gene |
| 1416527_at | Rab32 | RAB32 member RAS oncogene family |
| 1416654_at | Slc31a2 | solute carrier family 31 member 2 |
| 1416983_s_at | Foxo1 | forkhead box O1 |
| 1417068_a_at | Ptpn1 | protein tyrosine phosphatase non-receptor type 1 |
| 1417190_at | Nampt | nicotinamide phosphoribosyltransferase |
| 1417230_at | Ralgps2 | Ral GEF with PH domain and SH3 binding motif 2 |
| 1417408_at | F3 | coagulation factor III |
| 1417409_at | Jun | Jun oncogene |
| 1417478_a_at | Ppp2r3c | protein phosphatase 2 regulatory subunit B'' gamma |
| 1417564_at | Med7 | mediator complex subunit 7 |
| 1417730_at | Ext1 | exostoses (multiple) 1 |
| 1418154_at | N4bp1 | NEDD4 binding protein 1 |
| 1418300_a_at | Mknk2 | MAP kinase-interacting serine/threonine kinase 2 |
| 1418465_at | Ncf4 | neutrophil cytosolic factor 4 |
| 1418539_a_at | Ptpre | protein tyrosine phosphatase receptor type E |
| 1418797_at | Ms4a8a | membrane-spanning 4-domains subfamily A member 8A |
| 1418847_at | Arg2 | arginase type II |
| 1418992_at | F10 | coagulation factor X |
| 1418993_s_at | F10 | coagulation factor X |
| 1419004_s_at | NA | NA |
| 1419006_s_at | Peli2 | pellino 2 |
| 1419178_at | Cd3g | CD3 antigen gamma polypeptide |
| 1419180_at | Bcl9l | B-cell CLL/lymphoma 9-like |
| 1419208_at | Map3k8 | mitogen-activated protein kinase kinase kinase 8 |
| 1419627_s_at | Clec4n | C-type lectin domain family 4 member n |
| 1419691_at | Camp | cathelicidin antimicrobial peptide |
| 1419766_at | Sik1 | salt inducible kinase 1 |
| 1420012_at | Xbp1 | X-box binding protein 1 |
| 1420197_at | Gadd45b | growth arrest and DNA-damage-inducible 45 beta |
| 1420631_a_at | Blcap | bladder cancer associated protein homolog (human) |
| 1420867_at | Tmed2 | transmembrane emp24 domain trafficking protein 2 |
| 1420868_s_at | Tmed2 | transmembrane emp24 domain trafficking protein 2 |
| 1421235_s_at | Recql5 | RecQ protein-like 5 |
| 1421326_at | Csf2rb | colony stimulating factor 2 receptor beta low-affinity (granulocyte-macrophage) |
| 1421411_at | Pstpip2 | proline-serine-threonine phosphatase-interacting protein 2 |
| 1421547_at | Cd180 | CD180 antigen |
| 1422084_at | Bmx | BMX non-receptor tyrosine kinase |
| 1422506_a_at | Cstb | cystatin B |
| 1422508_at | Atp6v1a | ATPase H+ transporting lysosomal V1 subunit A |
| 1422791_at | Pafah1b2 | platelet-activating factor acetylhydrolase isoform 1b subunit 2 |
| 1423100_at | Fos | FBJ osteosarcoma oncogene |
| 1423135_at | Thy1 | thymus cell antigen 1 theta |
| 1423213_at | Plxnc1 | plexin C1 |
| 1423326_at | Entpd1 | ectonucleoside triphosphate diphosphohydrolase 1 |
| 1423346_at | Degs1 | degenerative spermatocyte homolog 1 (*Drosophila*) |
| 1423411_at | Rbm47 | RNA binding motif protein 47 |
| 1423722_at | Vmp1 | vacuole membrane protein 1 |
| 1423904_a_at | Pvr | poliovirus receptor |
| 1423996_a_at | Il4ra | interleukin 4 receptor alpha |
| 1424256_at | Rdh12 | retinol dehydrogenase 12 |
| 1424302_at | Lilrb3 | leukocyte immunoglobulin-like receptor subfamily B (with TM and ITIM domains) member 3 |
| 1424424_at | Slc39a1 | solute carrier family 39 (zinc transporter) member 1 |
| 1424444_a_at | 1600014C10Rik | RIKEN cDNA 1600014C10 gene |
| 1424509_at | Cd177 | CD177 antigen |
| 1424996_at | Cflar | CASP8 and FADD-like apoptosis regulator |
| 1425406_at | Clec4a2 | C-type lectin domain family 4 member a2 |
| 1425587_a_at | Ptprj | protein tyrosine phosphatase receptor type J |
| 1425674_a_at | Ssu72 | Ssu72 RNA polymerase II CTD phosphatase homolog (yeast) |
| 1425822_a_at | Dtx1 | deltex 1 homolog (*Drosophila*) |
| 1426227_s_at | Vps37c | vacuolar protein sorting 37C (yeast) |
| 1426370_at | Far1 | fatty acyl CoA reductase 1 |
| 1426440_at | Dhrs7 | dehydrogenase/reductase (SDR family) member 7 |
| 1426575_at | Sgms1 | sphingomyelin synthase 1 |
| 1426600_at | Slc2a1 | solute carrier family 2 (facilitated glucose transporter) member 1 |
| 1426680_at | Sepn1 | selenoprotein N1 |
| 1426786_s_at | Dhx38 | DEAH (Asp-Glu-Ala-His) box polypeptide 38 |
| 1426808_at | Lgals3 | lectin galactose binding soluble 3 |
| 1427164_at | Il13ra1 | interleukin 13 receptor alpha 1 |
| 1427327_at | Pilra | paired immunoglobin-like type 2 receptor alpha |

TABLE 3-continued

Mouse Factor 7

| PROBE ID | SYMBOL | GENE NAME |
|---|---|---|
| 1427683_at | Egr2 | early growth response 2 |
| 1428094_at | Lamp2 | lysosomal-associated membrane protein 2 |
| 1428191_s_at | Mettl17 | methyltransferase like 17 |
| 1428381_a_at | Ppdpf | pancreatic progenitor cell differentiation and proliferation factor homolog (zebrafish)RIKEN cDNA 2700038C09 gene |
| 1428466_at | Chd3 | chromodomain helicase DNA binding protein 3 |
| 1428579_at | Fmnl2 | formin-like 2 |
| 1428663_at | Sgms2 | sphingomyelin synthase 2 |
| 1428749_at | Dmxl2 | Dmx-like 2 |
| 1428750_at | Cdc42ep2 | CDC42 effector protein (Rho GTPase binding) 2 |
| 1428781_at | Dmkn | dermokine |
| 1428902_at | Chst11 | carbohydrate sulfotransferase 11 |
| 1428985_at | Ints12 | integrator complex subunit 12 |
| 1429352_at | Mocos | molybdenum cofactor sulfurase |
| 1429503_at | Fam69a | family with sequence similarity 69 member A |
| 1429527_a_at | Plscr1 | phospholipid scramblase 1 |
| 1429782_at | Grcc10 | gene rich cluster C10 gene |
| 1429889_at | Faim3 | Fas apoptotic inhibitory molecule 3 |
| 1430289_a_at | Wdr77 | WD repeat domain 77 |
| 1431339_a_at | Efhd2 | EF hand domain containing 2 |
| 1433634_at | Irf2bp2 | interferon regulatory factor 2 binding protein 2 |
| 1433699_at | Tnfaip3 | tumor necrosis factor alpha-induced protein 3 |
| 1433968_a_at | Megf9 | multiple EGF-like-domains 9 |
| 1434015_at | Slc2a6 | solute carrier family 2 (facilitated glucose transporter) member 6 |
| 1434025_at | NA | NA |
| 1434310_at | Bmpr2 | bone morphogenic protein receptor type II (serine/threonine kinase) |
| 1434334_at | Prkd2 | protein kinase D2 |
| 1434378_a_at | Mxd4 | Max dimerization protein 4 |
| 1434402_at | Samd8 | sterile alpha motif domain containing 8 |
| 1434418_at | Lass6 | LAG1 homolog ceramide synthase 6 |
| 1434758_at | Crispld2 | cysteine-rich secretory protein LCCL domain containing 2 |
| 1434774_at | Rhbdf2 | rhomboid 5 homolog 2 (Drosophila) |
| 1434920_a_at | Evl | Ena-vasodilator stimulated phosphoprotein |
| 1435260_at | Akt3 | thymoma viral proto-oncogene 3 |
| 1435477_s_at | Fcgr2b | Fc receptor IgG low affinity IIb |
| 1435546_a_at | 1810013L24Rik | RIKEN cDNA 1810013L24 gene |
| 1436499_at | Sgms1 | sphingomyelin synthase 1 |
| 1436590_at | Ppp1r3b | protein phosphatase 1 regulatory (inhibitor) subunit 3B |
| 1436819_at | SEPT6 | septin 6 |
| 1437152_at | Mex3b | mex3 homolog B (C. elegans) |
| 1437313_x_at | Hmgb2 | high mobility group box 2 |
| 1437421_at | 6330509M05Rik | RIKEN cDNA 6330509M05 gene |
| 1438796_at | Nr4a3 | nuclear receptor subfamily 4 group A member 3 |
| 1438855_x_at | Tnfaip2 | tumor necrosis factor alpha-induced protein 2 |
| 1439814_at | Atp8b4 | ATPase class I type 8B member 4 |
| 1440458_at | Cmah | cytidine monophospho-N-acetylneuraminic acid hydroxylase |
| 1442122_at | AI451458 | expressed sequence AI451458 |
| 1444122_at | Sycp2 | synaptonemal complex protein 2 |
| 1445687_at | Gm885 | predicted gene 885 |
| 1447685_x_at | Ets2 | E26 avian leukemia oncogene 2 3' domain |
| 1448123_s_at | Tgfbi | transforming growth factor beta induced |
| 1448213_at | Anxa1 | annexin A1 |
| 1448231_at | Fkbp5 | FK506 binding protein 5 |
| 1448297_a_at | Tnk2 | tyrosine kinase non-receptor2 |
| 1448333_at | Adprh | ADP-ribosylarginine hydrolase |
| 1448443_at | Serpini1 | serine (or cysteine) peptidase inhibitor clade I member 1 |
| 1448462_at | Tdg | thymine DNA glycosylase |
| 1448561_at | Ncf2 | neutrophil cytosolic factor 2 |
| 1448573_a_at | Ceacam10 | carcinoembryonic antigen-related cell adhesion molecule 10 |
| 1448618_at | Mvp | major vault protein |
| 1448700_at | G0s2 | G0/G1 switch gene 2 |
| 1448724_at | Cish | cytokine inducible SH2-containing protein |
| 1448993_at | Atg3 | autophagy-related 3 (yeast) |
| 1449028_at | Rhou | ras homolog gene family member U |
| 1449037_at | Crem | cAMP responsive element modulator |
| 1449184_at | Pglyrp1 | peptidoglycan recognition protein 1 |
| 1449310_at | Ptger2 | prostaglandin E receptor 2 (subtype EP2) |
| 1449317_at | Cflar | CASP8 and FADD-like apoptosis regulator |
| 1449336_a_at | Slk | STE20-like kinase (yeast) |
| 1449731_s_at | Nfkbia | nuclear factor of kappa light polypeptide gene enhancer in B-cells inhibitor alpha |
| 1450081_x_at | Gpi1 | glucose phosphate isomerase 1 |
| 1450214_at | Adora2b | adenosine A2b receptor |

TABLE 3-continued

Mouse Factor 7

| PROBE ID | SYMBOL | GENE NAME |
|---|---|---|
| 1450829_at | Tnfaip3 | tumor necrosis factor alpha-induced protein 3 |
| 1451037_at | Ptpn9 | protein tyrosine phosphatase non-receptor type 9 |
| 1451201_s_at | Rnh1 | ribonuclease/angiogenin inhibitor 1 |
| 1451335_at | Plac8 | placenta-specific 8 |
| 1451340_at | Arid5a | AT rich interactive domain 5A (MRF1-like) |
| 1451507_at | Mef2c | myocyte enhancer factor 2C |
| 1451537_at | CM3l1 | chitinase 3-like 1 |
| 1451775_s_at | Il13ra1 | interleukin 13 receptor alpha 1 |
| 1452197_at | Smc4 | structural maintenance of chromosomes 4 |
| 1452237_at | Agfg1 | ArfGAP with FG repeats 1 |
| 1452301_at | Aldh3b1 | aldehyde dehydrogenase 3 family member B1 |
| 1452732_at | Asprv1 | aspartic peptidase retroviral-like 1 |
| 1453009_at | Cpm | carboxypeptidase M |
| 1453851_a_at | Gadd45g | growth arrest and DNA-damage-inducible 45 gamma |
| 1454654_at | Dirc2 | disrupted in renal carcinoma 2 (human) |
| 1454713_s_at | Hdc | histidine decarboxylase |
| 1454799_at | Agpat9 | 1-acylglycerol-3-phosphate O-acyltransferase 9 |
| 1454897_at | 6330509M05Rik | RIKEN cDNA 6330509M05 gene |
| 1455009_at | Cpd | carboxypeptidase D |
| 1455081_at | Txnl4b | thioredoxin-like 4B |
| 1455170_at | 2810001G20Rik | RIKEN cDNA 2810001G20 gene |
| 1455197_at | Rnd1 | Rho family GTPase 1 |
| 1455229_x_at | Pgs1 | phosphatidylglycerophosphate synthase 1 |
| 1455332_x_at | Fcgr2b | Fc receptor IgG low affinity IIb |
| 1455353_at | Tmcc1 | transmembrane and coiled coil domains 1 |
| 1455405_at | Pstpip2 | proline-serine-threonine phosphatase-interacting protein 2 |
| 1455658_at | Cggbp1 | CGG triplet repeat binding protein 1 |
| 1455660_at | Csf2rb | colony stimulating factor 2 receptor beta low-affinity (granulocyte-macrophage) |
| 1455665_at | Lonrf1 | LON peptidase N-terminal domain and ring finger 1 |
| 1455860_at | Pigh | phosphatidylinositol glycan anchor biosynthesis class H |
| 1456028_x_at | Marcks | myristoylated alanine rich protein kinase C substrate |
| 1456055_x_at | Pold1 | polymerase (DNA directed) delta 1 catalytic subunit |
| 1457035_at | AI607873 | expressed sequence AI607873 |
| 1457708_at | Mbd4 | methyl-CpG binding domain protein 4 |
| 1457728_at | Fam129c | family with sequence similarity 129 member C |
| 1458206_at | NA | NA |
| 1458351_s_at | NA | NA |
| 1459522_s_at | Gyg | glycogenin |
| 1459903_at | Sema7a | sema domain immunoglobulin domain (Ig) and GPI membrane anchor (semaphorin) 7A |
| 1460006_at | Zfhx3 | zinc finger homeobox 3 |
| 1460116_s_at | Spred1 | sprouty protein with EVH-1 domain 1 related sequence |
| 1460227_at | Timp1 | tissue inhibitor of metalloproteinase 1 |
| 1460251_at | Fas | Fas (TNF receptor superfamily member 6) |
| 1460282_at | Trem1 | triggering receptor expressed on myeloid cells 1 |
| 1460329_at | B4galt6 | UDP-Gal: betaGlcNAc beta 14-galactosyltransferase polypeptide 6 |
| 1460335_at | Lysmd3 | LysM putative peptidoglycan-binding domain containing 3 |

TABLE 4

Mouse Factor 15

| PROBE ID | SYMBOL | GENE NAME |
|---|---|---|
| 1415741_at | Tmem165 | transmembrane protein 165 |
| 1415871_at | Tgfbi | transforming growth factor beta induced |
| 1415922_s_at | Marcksl1 | MARCKS-like 1 |
| 1416010_a_at | Ehd1 | EH-domain containing 1 |
| 1416298_at | Mmp9 | matrix metallopeptidase 9 |
| 1416359_at | Snx18 | sorting nexin 18 |
| 1416369_at | Hiatl1 | hippocampus abundant transcript-like 1 |
| 1416381_a_at | Prdx5 | peroxiredoxin 5 |
| 1416472_at | Syap1 | synapse associated protein 1 |
| 1416522_a_at | Grcc10 | gene rich cluster C10 gene |
| 1416576_at | Socs3 | suppressor of cytokine signaling 3 |
| 1416908_s_at | Tsn | translin |
| 1417191_at | Dnajb9 | DnaJ (Hsp40) homolog subfamily B |
| 1417250_at | Rlim | ring finger protein LIM domain interacting member 9 |
| 1417266_at | Ccl6 | chemokine (C-C motif) ligand 6 |
| 1417288_at | Plekha2 | pleckstrin homology domain-containing family A (phosphoinositide binding specific) member 2 |

TABLE 4-continued

Mouse Factor 15

| PROBE ID | SYMBOL | GENE NAME |
| --- | --- | --- |
| 1417291_at | Tnfrsf1a | tumor necrosis factor receptor superfamily member 1a |
| 1417297_at | Itpr3 | inositol 14 |
| 1417434_at | Gpd2 | glycerol phosphate dehydrogenase 2 mitochondrial5-triphosphate receptor 3 |
| 1417457_at | Cks2 | CDC28 protein kinase regulatory subunit 2 |
| 1417483_at | Nfkbiz | nuclear factor of kappa light polypeptide gene enhancer in B-cells inhibitor zeta |
| 1417508_at | Rnf19a | ring finger protein 19A |
| 1417542_at | Rps6ka2 | ribosomal protein S6 kinase polypeptide 2 |
| 1417544_a_at | Flot2 | flotillin 2 |
| 1417566_at | Abhd5 | abhydrolase domain containing 5 |
| 1417586_at | Timeless | timeless homolog (*Drosophila*) |
| 1417588_at | Galnt3 | UDP-N-acetyl-alpha-D-galactosamine: polypeptide N-acetylgalactosaminyltransferase 3 |
| 1417730_at | Ext1 | exostoses (multiple) 1 |
| 1418054_at | Neurod4 | neurogenic differentiation 4 |
| 1418133_at | Bcl3 | B-cell leukemia/lymphoma 3 |
| 1418154_at | N4bp1 | NEDD4 binding protein 1 |
| 1418300_a_at | Mknk2 | MAP kinase-interacting serine/threonine kinase 2 |
| 1418398_a_at | Tspan32 | tetraspanin 32 |
| 1418465_at | Ncf4 | neutrophil cytosolic factor 4 |
| 1418576_at | Yipf5 | Yip1 domain family member 5 |
| 1418578_at | Dgka | diacylglycerol kinase alpha |
| 1418992_at | F10 | coagulation factor X |
| 1418993_s_at | F10 | coagulation factor X |
| 1419208_at | Map3k8 | mitogen-activated protein kinase kinase kinase 8 |
| 1419406_a_at | Bcl11a | B-cell CLL/lymphoma 11A (zinc finger protein) |
| 1419432_at | Spam1 | sperm adhesion molecule 1 |
| 1419998_at | NA | NA |
| 1420197_at | Gadd45b | growth arrest and DNA-damage-inducible 45 beta |
| 1420394_s_at | NA | NA |
| 1420498_a_at | Dab2 | disabled homolog 2 (*Drosophila*) |
| 1420631_a_at | Blcap | bladder cancer associated protein homolog (human) |
| 1421065_at | Jak2 | Janus kinase 2 |
| 1421326_at | Csf2rb | colony stimulating factor 2 receptor beta |
| 1421479_at | Zfp318 | zinc finger protein 318 low-affinity (granulocyte-macrophage) |
| 1421895_at | NA | NA |
| 1422491_a_at | Bnip2 | BCL2/adenovirus E1B interacting protein 2 |
| 1422507_at | Cstb | cystatin B |
| 1422508_at | Atp6v1a | ATPase H+ transporting |
| 1422953_at | Fpr2 | formyl peptide receptor 2 lysosomal V1 subunit A |
| 1423053_at | Arf4 | ADP-ribosylation factor 4 |
| 1423326_at | Entpd1 | ectonucleoside triphosphate diphosphohydrolase 1 |
| 1423345_at | Degs1 | degenerative spermatocyte homolog 1 (*Drosophila*) |
| 1423558_at | Ifngr2 | interferon gamma receptor 2 |
| 1423588_at | Arpc4 | actin related protein 2/3 complex subunit 4 |
| 1423596_at | Nek6 | NIMA (never in mitosis gene a)-related expressed kinase 6 |
| 1423612_at | Clp1 | CLP1 cleavage and polyadenylation factor I subunit |
| 1423989_at | Tecpr1 | tectonin beta-propeller repeat containing 1 homolog (*S. cerevisiae*) |
| 1424141_at | Hectd1 | HECT domain containing 1 |
| 1424444_a_at | 1600014C10Rik | RIKEN cDNA 1600014C10 gene |
| 1424724_a_at | D16Ertd472e | DNA segment Chr 16 |
| 1424727_at | Ccr5 | chemokine (C-C motif) receptor 5 ERATO Doi 472 expressed |
| 1424779_at | Reep3 | receptor accessory protein 3 |
| 1424852_at | Mef2c | myocyte enhancer factor 2C |
| 1424990_at | Orai1 | ORAI calcium release-activated calcium modulator 1 |
| 1425289_a_at | Cr2 | complement receptor 2 |
| 1425485_at | Mtmr6 | myotubularin related protein 6 |
| 1425486_s_at | Mtmr6 | myotubularin related protein 6 |
| 1425493_at | Bmpr1a | bone morphogenetic protein receptor type 1A |
| 1425611_a_at | Cux1 | cut-like homeobox 1 |
| 1425706_a_at | Ddb2 | damage specific DNA binding protein 2 |
| 1426369_at | Far1 | fatty acyl CoA reductase 1 |
| 1426373_at | Ski | ski sarcoma viral oncogene homolog (avian) |
| 1426377_at | Zfp281 | zinc finger protein 281 |
| 1426390_a_at | Arf1 | ADP-ribosylation factor 1 |
| 1426473_at | Dnajc9 | DnaJ (Hsp40) homolog subfamily C |
| 1426550_at | Sidt1 | SID1 transmembrane family member 1 member 9 |
| 1426565_at | Igf1r | insulin-like growth factor I receptor |
| 1426818_at | Arrdc4 | arrestin domain containing 4 |
| 1426977_at | Usp47 | ubiquitin specific peptidase 47 |
| 1427164_at | Il13ra1 | interleukin 13 receptor alpha 1 |
| 1427532_at | Trat1 | T cell receptor associated transmembrane adaptor 1 |
| 1427689_a_at | Tnip1 | TNFAIP3 interacting protein 1 |

TABLE 4-continued

Mouse Factor 15

| PROBE ID | SYMBOL | GENE NAME |
| --- | --- | --- |
| 1428141_at | Gga2 | golgi associated gamma adaptin ear containing |
| 1428191_s_at | Mettl17 | methyltransferase like 17 ARF binding protein 2 |
| 1428207_at | Bcl7a | B-cell CLL/lymphoma 7A |
| 1428214_at | Tomm7 | translocase of outer mitochondrial membrane 7 homolog (yeast) |
| 1428381_a_at | Ppdpf | pancreatic progenitor cell differentiation and proliferation factor homolog (zebrafish)RIKEN cDNA 2700038C09 gene |
| 1428545_at | 0610007L01Rik | RIKEN cDNA 0610007L01 gene |
| 1428579_at | Fmnl2 | formin-like 2 |
| 1428669_at | Bmyc | brain expressed myelocytomatosis oncogene |
| 1429321_at | Rnf149 | ring finger protein 149 |
| 1429400_at | Clcn5 | chloride channel 5 |
| 1433864_at | Lrp12 | low density lipoprotein-related protein 12 |
| 1433939_at | Aff3 | AF4/FMR2 family member 3 |
| 1433943_at | NA | NA |
| 1434054_at | NA | NA |
| 1434123_at | Fut11 | fucosyltransferase 11 |
| 1434175_s_at | Tecpr1 | tectonin beta-propeller repeat containing 1 |
| 1434402_at | Samd8 | sterile alpha motif domain containing 8 |
| 1434521_at | Rfx7 | regulatory factor X7 |
| 1434547_at | Cpd | carboxypeptidase D |
| 1434573_at | Traf3ip3 | TRAF3 interacting protein 3 |
| 1434705_at | Ctbp2 | C-terminal binding protein 2 |
| 1435260_at | Akt3 | thymoma viral proto-oncogene 3 |
| 1435517_x_at | Ralb | v-ral simian leukemia viral oncogene homolog B (ras related) |
| 1435793_at | Aph1b | anterior pharynx defective 1b homolog (C. elegans) |
| 1436511_at | BC031781 | cDNA sequence BC031781 |
| 1436921_at | Atp7a | ATPase Cu++ transporting |
| 1436999_at | Pid1 | phosphotyrosine interaction domain containing 1 alpha polypeptide |
| 1437152_at | Mex3b | mex3 homolog B (C. elegans) |
| 1437270_a_at | Clcf1 | cardiotrophin-like cytokine factor 1 |
| 1437421_at | 6330509M05Rik | RIKEN cDNA 6330509M05 gene |
| 1437591_a_at | Wdr1 | WD repeat domain 1 |
| 1437870_at | Slco4c1 | solute carrier organic anion transporter family member 4C1 |
| 1437992_x_at | Gja1 | gap junction protein alpha 1 |
| 1438044_at | 1700047M11Rik | RIKEN cDNA 1700047M11 gene |
| 1438670_at | Ptpn1 | protein tyrosine phosphatase non-receptor type 1 |
| 1439160_at | Pramef8 | PRAME family member 8 |
| 1439443_x_at | Tkt | transketolase |
| 1439457_x_at | Atg12 | autophagy-related 12 (yeast) |
| 1439814_at | Atp8b4 | ATPase class I |
| 1440458_at | Cmah | cytidine monophospho-N-acetylneuraminic acid hydroxylase type 8B member 4 |
| 1443021_at | Mthfs | 5 10-methenyltetrahydrofolate synthetase |
| 1444459_at | NA | NA |
| 1448204_at | Sav1 | salvador homolog 1 (Drosophila) |
| 1448443_at | Serpini1 | serine (or cysteine) peptidase inhibitor clade I |
| 1448561_at | Ncf2 | neutrophil cytosolic factor 2 member 1 |
| 1448573_a_at | Ceacam10 | carcinoembryonic antigen-related cell adhesion molecule 10 |
| 1448617_at | Cd53 | CD53 antigen |
| 1448700_at | G0s2 | G0/G1 switch gene 2 |
| 1448742_at | Snai1 | snail homolog 1 (Drosophila) |
| 1448758_at | Nrbf2 | nuclear receptor binding factor 2 |
| 1448786_at | Plbd1 | phospholipase B domain containing 1 |
| 1449037_at | Crem | cAMP responsive element modulator |
| 1449324_at | Ero1l | ERO1-like (S. cerevisiae) |
| 1449336_a_at | Slk | STE20-like kinase (yeast) |
| 1449677_s_at | Tmem38b | transmembrane protein 38B |
| 1449947_s_at | Zfhx3 | zinc finger homeobox 3 |
| 1450116_at | Fam48a | family with sequence similarity 48 member A |
| 1450214_at | Adora2b | adenosine A2b receptor |
| 1450377_at | Thbs1 | thrombospondin 1 |
| 1450424_a_at | Il18bp | interleukin 18 binding protein |
| 1450459_at | 2010106G01Rik | RIKEN cDNA 2010106G01 gene |
| 1451079_at | Adpgk | ADP-dependent glucokinase |
| 1451486_at | Slc46a3 | solute carrier family 46 member 3 |
| 1451507_at | Mef2c | myocyte enhancer factor 2C |
| 1451767_at | Ncf1 | neutrophil cytosolic factor 1 |
| 1452093_at | Tmem185b | transmembrane protein 185B |
| 1452197_at | Smc4 | structural maintenance of chromosomes 4 |
| 1452205_x_at | NA | NA |
| 1452301_at | Aldh3b1 | aldehyde dehydrogenase 3 family member B1 |
| 1452316_at | Ints12 | integrator complex subunit 12 |

TABLE 4-continued

Mouse Factor 15

| PROBE ID | SYMBOL | GENE NAME |
| --- | --- | --- |
| 1452414_s_at | Ccdc86 | coiled-coil domain containing 86 |
| 1452922_at | Ppp1r3d | protein phosphatase 1 regulatory subunit 3D |
| 1453283_at | Pgm1 | phosphoglucomutase 1 |
| 1454976_at | Sod2 | superoxide dismutase 2 mitochondrial |
| 1454984_at | Lifr | leukemia inhibitory factor receptor |
| 1455019_x_at | Ckap4 | cytoskeleton-associated protein 4 |
| 1455089_at | Gng12 | guanine nucleotide binding protein (G protein) gamma 12 |
| 1455104_at | Mxd1 | MAX dimerization protein 1 |
| 1455133_s_at | AI848100 | expressed sequence AI848100 |
| 1455197_at | Rnd1 | Rho family GTPase 1 |
| 1455660_at | Csf2rb | colony stimulating factor 2 receptor beta |
| 1455729_at | Gnaq | guanine nucleotide binding protein alpha q polypeptide low-affinity (granulocyte-macrophage) |
| 1455899_x_at | Socs3 | suppressor of cytokine signaling 3 |
| 1456135_s_at | Pxn | paxillin |
| 1456545_at | Il18rap | interleukin 18 receptor accessory protein |
| 1456700_x_at | Marcks | myristoylated alanine rich protein kinase C substrate |
| 1457404_at | Nfkbiz | nuclear factor of kappa light polypeptide gene enhancer in B-cells inhibitor zeta |
| 1457579_at | D11Ertd717e | DNA segment Chr 11 |
| 1457644_s_at | Cxcl1 | chemokine (C-X-C motif) ligand 1 ERATO Doi 717 expressed |
| 1457753_at | Tlr13 | toll-like receptor 13 |
| 1457793_a_at | Whsc1l1 | Wolf-Hirschhorn syndrome candidate 1-like 1 (human) |
| 1457825_x_at | Tcn2 | transcobalamin 2 |
| 1457976_at | 2010002M12Rik | RIKEN cDNA 2010002M12 gene |
| 1458308_at | Sbno2 | strawberry notch homolog 2 (*Drosophila*) |
| 1458351_s_at | NA | NA |
| 1458518_at | Cpeb2 | cytoplasmic polyadenylation element binding protein 2 |
| 1458525_at | NA | NA |
| 1458668_at | Tpd52 | tumor protein D52 |
| 1458933_at | Slc22a15 | solute carrier family 22 (organic anion/cation transporter) member 15 |
| 1459522_s_at | Gyg | glycogenin |
| 1459718_x_at | Klf6 | Kruppel-like factor 6 |
| 1459961_a_at | Stat3 | signal transducer and activator of transcription 3 |
| 1460006_at | Zfhx3 | zinc finger homeobox 3 |
| 1460033_at | A330023F24Rik | RIKEN cDNA A330023F24 gene |
| 1460197_a_at | Steap4 | STEAP family member 4 |
| 1460227_at | Timp1 | tissue inhibitor of metalloproteinase 1 |
| 1460251_at | Fas | Fas (TNF receptor superfamily member 6) |
| 1460282_at | Trem1 | triggering receptor expressed on myeloid cells 1 |
| 1460338_a_at | Crlf3 | cytokine receptor-like factor 3 |
| 1460458_at | Crispld2 | cysteine-rich secretory protein LCCL domain containing 2 |
| 1460510_a_at | Coq10b | coenzyme Q10 homolog B (*S. cerevisiae*) |
| 1460573_at | AI848100 | expressed sequence AI848100 |
| 1460598_at | Il28ra | interleukin 28 receptor alpha |

TABLE 5

Mouse Factor 23

| PROBE ID | SYMBOL | GENE NAME |
| --- | --- | --- |
| 1415734_at | Rab7 | RAB7 member RAS oncogene family |
| 1415778_at | Morf4l2 | mortality factor 4 like 2 |
| 1415826_at | Atp6v1h | ATPase H+ transporting lysosomal V1 subunit H |
| 1415856_at | Emb | embigin |
| 1415871_at | Tgfbi | transforming growth factor beta induced |
| 1416011_x_at | Ehd1 | EH-domain containing 1 |
| 1416012_at | Ehd1 | EH-domain containing 1 |
| 1416067_at | Ifrd1 | interferon-related developmental regulator 1 |
| 1416082_at | Rab1 | RAB1 member RAS oncogene family |
| 1416459_at | Arf2 | ADP-ribosylation factor 2 |
| 1416466_at | Vapa | vesicle-associated membrane protein associated protein A |
| 1416467_at | Ddx3x | DEAD/H (Asp-Glu-Ala-Asp/His) box polypeptide 3 X-linked |
| 1416496_at | Mrfap1 | Morf4 family associated protein 1 |
| 1417218_at | Calhm2 | calcium homeostasis modulator 2 |
| 1417268_at | Cd14 | CD14 antigen |
| 1417291_at | Tnfrsf1a | tumor necrosis factor receptor superfamily member 1a |
| 1417392_a_at | Slc7a7 | solute carrier family 7 (cationic amino acid transporter y+ system) member 7 |

TABLE 5-continued

Mouse Factor 23

| PROBE ID | SYMBOL | GENE NAME |
|---|---|---|
| 1417478_a_at | Ppp2r3c | protein phosphatase 2 regulatory subunit B" gamma |
| 1417564_at | Med7 | mediator complex subunit 7 |
| 1417591_at | Ptges2 | prostaglandin E synthase 2 |
| 1417597_at | Cd28 | CD28 antigen |
| 1417730_at | Ext1 | exostoses (multiple) 1 |
| 1417741_at | Pygl | liver glycogen phosphorylase |
| 1418300_a_at | Mknk2 | MAP kinase-interacting serine/threonine kinase 2 |
| 1418465_at | Ncf4 | neutrophil cytosolic factor 4 |
| 1418468_at | Anxa11 | annexin A11 |
| 1418841_s_at | Cdk11b | cyclin-dependent kinase 11B |
| 1418992_at | F10 | coagulation factor X |
| 1418993_s_at | F10 | coagulation factor X |
| 1419091_a_at | Anxa2 | annexin A2 |
| 1419180_at | Bcl9l | B-cell CLL/lymphoma 9-like |
| 1419607_at | Tnf | tumor necrosis factor |
| 1419609_at | Ccr1 | chemokine (C-C motif) receptor 1 |
| 1419722_at | Klk8 | kallikrein related-peptidase 8 |
| 1420012_at | Xbp1 | X-box binding protein 1 |
| 1420361_at | Slc11a1 | solute carrier family 11 (proton-coupled divalent metal ion transporters) member 1 |
| 1420886_a_at | Xbp1 | X-box binding protein 1 |
| 1420997_a_at | Gpi1 | glucose phosphate isomerase 1 |
| 1421291_at | Il18rap | interleukin 18 receptor accessory protein |
| 1421463_at | Siglece | sialic acid binding Ig-like lectin E |
| 1421478_a_at | Zfp318 | zinc finger protein 318 |
| 1421855_at | Fgl2 | fibrinogen-like protein 2 |
| 1422002_at | Mxd1 | MAX dimerization protein 1 |
| 1422013_at | Clec4a2 | C-type lectin domain family 4 member a2 |
| 1422046_at | Itgam | integrin alpha M |
| 1422573_at | Ampd3 | adenosine monophosphate deaminase 3 |
| 1422631_at | Ahr | aryl-hydrocarbon receptor |
| 1422791_at | Pafah1b2 | platelet-activating factor acetylhydrolase isoform 1b subunit 2 |
| 1422879_at | Sypl | synaptophysin-like protein |
| 1422880_at | Sypl | synaptophysin-like protein |
| 1422887_a_at | Ctbp2 | C-terminal binding protein 2 |
| 1422931_at | Fosl2 | fos-like antigen 2 |
| 1423053_at | Arf4 | ADP-ribosylation factor 4 |
| 1423100_at | Fos | FBJ osteosarcoma oncogene |
| 1423112_at | Ube2d3 | ubiquitin-conjugating enzyme E2D 3 (UBC4/5 homolog yeast) |
| 1423135_at | Thy1 | thymus cell antigen 1 theta |
| 1423170_at | Taf7 | TAF7 RNA polymerase II TATA box binding protein (TBP)-associated factor |
| 1423326_at | Entpd1 | ectonucleoside triphosphate diphosphohydrolase 1 |
| 1423361_at | Ymel1l | YME1-like 1 (S. cerevisiae) |
| 1423383_a_at | Osbpl9 | oxysterol binding protein-like 9 |
| 1423466_at | Ccr7 | chemokine (C-C motif) receptor 7 |
| 1423558_at | Ifngr2 | interferon gamma receptor 2 |
| 1423596_at | Nek6 | NIMA (never in mitosis gene a)-related expressed kinase 6 |
| 1423706_a_at | Pgd | phosphogluconate dehydrogenase |
| 1423854_a_at | Rasl11b | RAS-like family 11 member B |
| 1423903_at | Pvr | poliovirus receptor |
| 1424027_at | Pxn | paxillin |
| 1424441_at | Slc27a4 | solute carrier family 27 (fatty acid transporter) member 4 |
| 1424942_a_at | Myc | myelocytomatosis oncogene |
| 1425128_at | B3gnt8 | UDP-GlcNAc: betaGal beta-13-N-acetylglucosaminyltransferase 8 |
| 1425346_at | Zfp318 | zinc finger protein 318 |
| 1425347_a_at | Zfp318 | zinc finger protein 318 |
| 1425485_at | Mtmr6 | myotubularin related protein 6 |
| 1425486_s_at | Mtmr6 | myotubularin related protein 6 |
| 1425663_at | Il1rn | interleukin 1 receptor antagonist |
| 1425674_a_at | Ssu72 | Ssu72 RNA polymerase II CTD phosphatase homolog (yeast) |
| 1426112_a_at | Cd72 | CD72 antigen |
| 1426227_s_at | Vps37c | vacuolar protein sorting 37C (yeast) |
| 1426299_at | Snx20 | sorting nexin 20 |
| 1426312_at | Bre | brain and reproductive organ-expressed protein |
| 1426377_at | Zfp281 | zinc finger protein 281 |
| 1426396_at | Cd247 | CD247 antigen |
| 1426473_at | Dnajc9 | DnaJ (Hsp40) homolog subfamily C member 9 |
| 1426501_a_at | Tifa | TRAF-interacting protein with forkhead-associated domain |
| 1426554_a_at | Pgam1 | phosphoglycerate mutase 1 |
| 1426565_at | Igf1r | insulin-like growth factor I receptor |
| 1426648_at | Mapkapk2 | MAP kinase-activated protein kinase 2 |
| 1426722_at | Slc38a2 | solute carrier family 38 member 2 |

TABLE 5-continued

Mouse Factor 23

| PROBE ID | SYMBOL | GENE NAME |
|---|---|---|
| 1426755_at | Ckap4 | cytoskeleton-associated protein 4 |
| 1426798_a_at | Ppp1r15b | protein phosphatase 1 regulatory (inhibitor) subunit 15b |
| 1426808_at | Lgals3 | lectin galactose binding soluble 3 |
| 1426988_at | Klhdc5 | kelch domain containing 5 |
| 1427102_at | Slfn4 | schlafen 4 |
| 1427227_at | Gabrg1 | gamma-aminobutyric acid (GABA) A receptor subunit gamma 1 |
| 1427314_at | Tmed7 | transmembrane emp24 protein transport domain containing 7 |
| 1427747_a_at | Lcn2 | lipocalin 2 |
| 1427899_at | Rnf6 | ring finger protein (C3H2C3 type) 6 |
| 1428141_at | Gga2 | golgi associated gamma adaptin ear containing ARF binding protein 2 |
| 1428192_at | Kbtbd7 | kelch repeat and BTB (POZ) domain containing 7 |
| 1428243_at | 1700021K19Rik | RIKEN cDNA 1700021K19 gene |
| 1428720_s_at | NA | NA |
| 1428875_at | Golim4 | golgi integral membrane protein 4 |
| 1428942_at | Mt2 | metallothionein 2 |
| 1429413_at | Cpm | carboxypeptidase M |
| 1429527_a_at | Plscr1 | phospholipid scramblase 1 |
| 1429693_at | Dab2 | disabled homolog 2 (*Drosophila*) |
| 1430443_at | Anxa10 | annexin A10 |
| 1431339_a_at | Efhd2 | EF hand domain containing 2 |
| 1431774_a_at | Lyrm1 | LYR motif containing 1 |
| 1433508_at | Klf6 | Kruppel-like factor 6 |
| 1433939_at | Aff3 | AF4/FMR2 family member 3 |
| 1433943_at | NA | NA |
| 1434402_at | Samd8 | sterile alpha motif domain containing 8 |
| 1434418_at | Lass6 | LAG1 homolog ceramide synthase 6 |
| 1434432_at | Rffl | ring finger and FYVE like domain containing protein |
| 1434502_x_at | Slc4a1 | solute carrier family 4 (anion exchanger) member 1 |
| 1434556_at | Tmem170b | transmembrane protein 170B |
| 1435176_a_at | Id2 | inhibitor of DNA binding 2 |
| 1435260_at | Akt3 | thymoma viral proto-oncogene 3 |
| 1435449_at | Bcl2l11 | BCL2-like 11 (apoptosis facilitator) |
| 1435517_x_at | Ralb | v-ral simian leukemia viral oncogene homolog B (ras related) |
| 1435644_at | Sh3pxd2b | SH3 and PX domains 2B |
| 1436333_a_at | Synj1 | synaptojanin 1 |
| 1436590_at | Ppp1r3b | protein phosphatase 1 regulatory (inhibitor) subunit 3B |
| 1436763_a_at | Klf9 | Kruppel-like factor 9 |
| 1436921_at | Atp7a | ATPase Cu++ transporting alpha polypeptide |
| 1436986_at | Sntb2 | syntrophin basic 2 |
| 1436999_at | Pid1 | phosphotyrosine interaction domain containing 1 |
| 1437152_at | Mex3b | mex3 homolog B (*C. elegans*) |
| 1437270_a_at | Clcf1 | cardiotrophin-like cytokine factor 1 |
| 1437271_at | Clcf1 | cardiotrophin-like cytokine factor 1 |
| 1437313_x_at | Hmgb2 | high mobility group box 2 |
| 1437363_at | Homer1 | homer homolog 1 (*Drosophila*) |
| 1437870_at | Slco4c1 | solute carrier organic anion transporter family member 4C1 |
| 1438021_at | Rbm47 | RNA binding motif protein 47 |
| 1438044_at | 1700047M11Rik | RIKEN cDNA 1700047M11 gene |
| 1438627_x_at | Pgd | phosphogluconate dehydrogenase |
| 1438650_x_at | Gja1 | gap junction protein alpha 1 |
| 1438657_x_at | NA | NA |
| 1440458_at | Cmah | cytidine monophospho-N-acetylneuraminic acid hydroxylase |
| 1441843_s_at | NA | NA |
| 1444402_at | Zc3h12c | zinc finger CCCH type containing 12C |
| 1445687_at | Gm885 | predicted gene 885 |
| 1448165_at | Casp2 | caspase 2 |
| 1448190_at | Mrpl33 | mitochondrial ribosomal protein L33 |
| 1448199_at | Ankrd10 | ankyrin repeat domain 10 |
| 1448210_at | Rab1 | RAB1 member RAS oncogene family |
| 1448231_at | Fkbp5 | FK506 binding protein 5 |
| 1448291_at | Mmp9 | matrix metallopeptidase 9 |
| 1448318_at | Plin2 | perilipin 2 |
| 1448377_at | Slpi | secretory leukocyte peptidase inhibitor |
| 1448511_at | Ptprcap | protein tyrosine phosphatase receptor type C polypeptide-associated protein |
| 1448617_at | Cd53 | CD53 antigen |
| 1448648_at | Fam114a1 | family with sequence similarity 114 member A1 |
| 1448728_a_at | Nfkbiz | nuclear factor of kappa light polypeptide gene enhancer in B-cells inhibitor zeta |
| 1448795_a_at | NA | NA |
| 1448861_at | Traf5 | TNF receptor-associated factor 5 |
| 1448898_at | Ccl9 | chemokine (C-C motif) ligand 9 |

TABLE 5-continued

Mouse Factor 23

| PROBE ID | SYMBOL | GENE NAME |
| --- | --- | --- |
| 1449303_at | Sesn3 | sestrin 3 |
| 1449310_at | Ptger2 | prostaglandin E receptor 2 (subtype EP2) |
| 1449336_a_at | Slk | STE20-like kinase (yeast) |
| 1449342_at | Ptplb | protein tyrosine phosphatase-like (proline instead of catalytic arginine) member b |
| 1450513_at | Cd33 | CD33 antigen |
| 1450654_a_at | Dhdds | dehydrodolichyl diphosphate synthase |
| 1450858_a_at | Ube2d3 | ubiquitin-conjugating enzyme E2D 3 (UBC4/5 homolog yeast) |
| 1451097_at | Vasp | vasodilator-stimulated phosphoprotein |
| 1452045_at | Zfp281 | zinc finger protein 281 |
| 1452163_at | Ets1 | E26 avian leukemia oncogene 1 5' domain |
| 1452181_at | Ckap4 | cytoskeleton-associated protein 4 |
| 1452443_s_at | Helz | helicase with zinc finger domain |
| 1452922_at | Ppp1r3d | protein phosphatase 1 regulatory subunit 3D |
| 1453985_at | 0610007P08Rik | RIKEN cDNA 0610007P08 gene |
| 1454064_a_at | Rnf138 | ring finger protein 138 |
| 1454699_at | Sesn1 | sestrin 1 |
| 1454762_at | Xkrx | X Kell blood group precursor related X linked |
| 1454896_at | Rbpj | recombination signal binding protein for immunoglobulin kappa J region |
| 1454976_at | Sod2 | superoxide dismutase 2 mitochondrial |
| 1454984_at | Lifr | leukemia inhibitory factor receptor |
| 1455229_x_at | Pgs1 | phosphatidylglycerophosphate synthase 1 |
| 1455353_at | Tmcc1 | transmembrane and coiled coil domains 1 |
| 1455729_at | Gnaq | guanine nucleotide binding protein alpha q polypeptide |
| 1456037_x_at | Preb | prolactin regulatory element binding |
| 1456307_s_at | Adcy7 | adenylate cyclase 7 |
| 1456388_at | Atp11a | ATPase class VI type 11A |
| 1456545_at | Il18rap | interleukin 18 receptor accessory protein |
| 1457035_at | AI607873 | expressed sequence AI607873 |
| 1457645_at | C130079G13Rik | RIKEN cDNA C130079G13 gene |
| 1457917_at | Lck | lymphocyte protein tyrosine kinase |
| 1458067_at | Fam179b | family with sequence similarity 179 member B |
| 1458518_at | Cpeb2 | cytoplasmic polyadenylation element binding protein 2 |
| 1458668_at | Tpd52 | tumor protein D52 |
| 1460197_a_at | Steap4 | STEAP family member 4 |
| 1460227_at | Timp1 | tissue inhibitor of metalloproteinase 1 |
| 1460271_at | Trem3 | triggering receptor expressed on myeloid cells 3 |
| 1460329_at | B4galt6 | UDP-Gal: betaGlcNAc beta 14-galactosyltransferase polypeptide 6 |
| 1460335_at | Lysmd3 | LysM putative peptidoglycan-binding domain containing 3 |
| 1460408_at | Gabrg1 | gamma-aminobutyric acid (GABA) A receptor subunit gamma 1 |
| 1460510_a_at | Coq10b | coenzyme Q10 homolog B (*S. cerevisiae*) |
| 1460573_at | AI848100 | expressed sequence AI848100 |
| 1460735_at | Svil | supervillin |

TABLE 6

Mouse Factor 26

| PROBE ID | SYMBOL | GENE NAME |
| --- | --- | --- |
| 1415686_at | Rab14 | RAB14 member RAS oncogene family |
| 1415800_at | Gja1 | gap junction proteinalpha 1 |
| 1415830_at | Orc5 | origin recognition complex subunit 5 |
| 1415871_at | Tgfbi | transforming growth factor beta induced |
| 1416019_at | Dr1 | down-regulator of transcription 1 |
| 1416234_at | Lrrc59 | leucine rich repeat containing 59 |
| 1416360_at | Snx18 | sorting nexin 18 |
| 1416369_at | Hiatl1 | hippocampus abundant transcript-like 1 |
| 1416435_at | Ltbr | lymphotoxin B receptor |
| 1416502_a_at | Preb | prolactin regulatory element binding |
| 1416522_a_at | Grcc10 | gene rich cluster C10 gene |
| 1416527_at | Rab32 | RAB32 member RAS oncogene family |
| 1416543_at | Nfe2l2 | nuclear factor erythroid derived 2 like 2 |
| 1416573_at | Pofut2 | protein O-fucosyltransferase 2 |
| 1416576_at | Socs3 | suppressor of cytokine signaling 3 |
| 1416700_at | Rnd3 | Rho family GTPase 3 |
| 1416881_at | Mcl1 | myeloid cell leukemia sequence 1 |
| 1416981_at | Foxo1 | forkhead box O1 |
| 1416983_s_at | Foxo1 | forkhead box O1 |

TABLE 6-continued

Mouse Factor 26

| PROBE ID | SYMBOL | GENE NAME |
|---|---|---|
| 1417297_at | Itpr3 | inositol 145-triphosphate receptor 3 |
| 1417392_a_at | Slc7a7 | solute carrier family 7 (cationic amino acid transporter y+ system) member 7 |
| 1417446_at | Slc12a4 | solute carrier family 12 member 4 |
| 1417460_at | Ifitm2 | interferon induced transmembrane protein 2 |
| 1417509_at | Rnf19a | ring finger protein 19A |
| 1417566_at | Abhd5 | abhydrolase domain containing 5 |
| 1417661_at | Rdm1 | RAD52 motif 1 |
| 1417696_at | Soat1 | sterol O-acyltransferase 1 |
| 1417744_a_at | Ralb | v-ral simian leukemia viral oncogene homolog B (ras related) |
| 1417859_at | Gas7 | growth arrest specific 7 |
| 1417890_at | Pdxp | pyridoxal (pyridoxine vitamin B6) phosphatase |
| 1417985_at | Nrarp | Notch-regulated ankyrin repeat protein |
| 1418133_at | Bcl3 | B-cell leukemia/lymphoma 3 |
| 1418468_at | Anxa11 | annexin A11 |
| 1418574_a_at | Shfm1 | split hand/foot malformation (ectrodactyly) type 1 |
| 1418612_at | Slfn1 | schlafen 1 |
| 1418798_s_at | Srpk3 | serine/arginine-rich protein specific kinase 3 |
| 1418901_at | Cebpb | CCAAT/enhancer binding protein (C/EBP) beta |
| 1418930_at | Cxcl10 | chemokine (C-X-C motif) ligand 10 |
| 1419006_s_at | Peli2 | pellino 2 |
| 1419178_at | Cd3g | CD3 antigen gamma polypeptide |
| 1419508_at | Ripk1 | receptor (TNFRSF)-interacting serine-threonine kinase 1 |
| 1419641_at | Purb | purine rich element binding protein B |
| 1419709_at | Stfa3 | stefin A3 |
| 1419721_at | Niacr1 | niacin receptor 1 |
| 1419722_at | Klk8 | kallikrein related-peptidase 8 |
| 1420369_a_at | Csn2 | casein beta |
| 1420394_s_at | NA | NA |
| 1420591_at | Gpr84 | G protein-coupled receptor 84 |
| 1420873_at | Twf1 | twinfilin actin-binding protein homolog 1 (*Drosophila*) |
| 1421366_at | Clec5a | C-type lectin domain family 5 member a |
| 1421547_at | Cd180 | CD180 antigen |
| 1421863_at | Vamp1 | vesicle-associated membrane protein 1 |
| 1422013_at | Clec4a2 | C-type lectin domain family 4 member a2 |
| 1422506_a_at | Cstb | cystatin B |
| 1422519_at | Cask | calcium/calmodulin-dependent serine protein kinase (MAGUK family) |
| 1422557_s_at | Mt1 | metallothionein 1 |
| 1423167_at | Mobkl3 | MOB1 Mps One Binder kinase activator-like 3 (yeast) |
| 1423313_at | Pde7a | phosphodiesterase 7A |
| 1423383_a_at | Osbpl9 | oxysterol binding protein-like 9 |
| 1423632_at | Gpr146 | G protein-coupled receptor 146 |
| 1423670_a_at | Srpr | signal recognition particle receptor ('docking protein') |
| 1423743_at | Arcn1 | archain 1 |
| 1423754_at | Ifitm3 | interferon induced transmembrane protein 3 |
| 1423838_s_at | 2400003C14Rik | RIKEN cDNA 2400003C14 gene |
| 1423989_at | Tecpr1 | tectonin beta-propeller repeat containing 1 |
| 1424032_at | Hvcn1 | hydrogen voltage-gated channel 1 |
| 1424254_at | Ifitm1 | interferon induced transmembrane protein 1 |
| 1424256_at | Rdh12 | retinol dehydrogenase 12 |
| 1424564_at | 2410001C21Rik | RIKEN cDNA 2410001C21 gene |
| 1424573_at | Tmed5 | transmembrane emp24 protein transport domain containing 5 |
| 1424906_at | Pqlc3 | PQ loop repeat containing |
| 1425128_at | B3gnt8 | UDP-GlcNAc: betaGal beta-13-N-acetylglucosaminyltransferase 8 |
| 1425407_s_at | NA | NA |
| 1425492_at | Bmpr1a | bone morphogenetic protein receptor type 1A |
| 1425587_a_at | Ptprj | protein tyrosine phosphatase receptor type J |
| 1425933_a_at | Nt5c2 | 5'-nucleotidase cytosolic II |
| 1425977_a_at | Slk | STE20-like kinase (yeast) |
| 1426063_a_at | Gem | GTP binding protein (gene overexpressed in skeletal muscle) |
| 1426368_at | Rin2 | Ras and Rab interactor 2 |
| 1426369_at | Far1 | fatty acyl CoA reductase 1 |
| 1426708_at | Antxr2 | anthrax toxin receptor 2 |
| 1426865_a_at | Ncam1 | neural cell adhesion molecule 1 |
| 1426899_at | Tbc1d23 | TBC1 domain family member 23 |
| 1426978_at | NA | NA |
| 1427243_at | Rell1 | RELT-like 1 |
| 1428141_at | Gga2 | golgi associated gamma adaptin ear containing ARF binding protein 2 |
| 1428214_at | Tomm7 | translocase of outer mitochondrial membrane 7 homolog (yeast) |
| 1428231_at | Cpsf6 | cleavage and polyadenylation specific factor 6 |
| 1428357_at | 2610019F03Rik | RIKEN cDNA 2610019F03 gene |
| 1428702_at | Ddx28 | DEAD (Asp-Glu-Ala-Asp) box polypeptide 28 |

TABLE 6-continued

Mouse Factor 26

| PROBE ID | SYMBOL | GENE NAME |
|---|---|---|
| 1428719_at | NA | NA |
| 1428985_at | Ints12 | integrator complex subunit 12 |
| 1429115_at | NA | NA |
| 1429321_at | Rnf149 | ring finger protein 149 |
| 1429466_s_at | NA | NA |
| 1429527_a_at | Plscr1 | phospholipid scramblase 1 |
| 1429775_a_at | NA | NA |
| 1433454_at | Abtb2 | ankyrin repeat and BTB (POZ) domain containing 2 |
| 1433815_at | Jakmip1 | janus kinase and microtubule interacting protein 1 |
| 1434025_at | NA | NA |
| 1434054_at | NA | NA |
| 1434070_at | Jag1 | jagged 1 |
| 1434126_at | 4930402H24Rik | RIKEN cDNA 4930402H24 gene |
| 1434310_at | Bmpr2 | bone morphogenic protein receptor type II (serine/threonine kinase) |
| 1434311_at | Cnot6l | CCR4-NOT transcription complex subunit 6-like |
| 1434431_x_at | Adora2b | adenosine A2b receptor |
| 1434484_at | 1100001G20Rik | RIKEN cDNA 1100001G20 gene |
| 1434487_at | Mef2d | myocyte enhancer factor 2D |
| 1434773_a_at | Slc2a1 | solute carrier family 2 (facilitated glucose transporter) member 1 |
| 1434814_x_at | Gpi1 | glucose phosphate isomerase 1 |
| 1435077_at | Asxl1 | additional sex combs like 1 (*Drosophila*) |
| 1435176_a_at | Id2 | inhibitor of DNA binding 2 |
| 1435231_at | Coq4 | coenzyme Q4 homolog (yeast) |
| 1435458_at | Pim1 | proviral integration site 1 |
| 1435996_at | Card11 | caspase recruitment domain family member 11 |
| 1436077_a_at | Fcho1 | FCH domain only 1 |
| 1436103_at | Rab3ip | RAB3A interacting protein |
| 1436666_at | NA | NA |
| 1437111_at | Zc3h12c | zinc finger CCCH type containing 12C |
| 1437225_x_at | Gnai3 | guanine nucleotide binding protein (G protein) alpha inhibiting 3 |
| 1437270_a_at | Clcf1 | cardiotrophin-like cytokine factor 1 |
| 1437313_x_at | Hmgb2 | high mobility group box 2 |
| 1438031_at | Rasgrp3 | RAS guanyl releasing protein 3 |
| 1438627_x_at | Pgd | phosphogluconate dehydrogenase |
| 1439443_x_at | Tkt | transketolase |
| 1439662_at | Homer1 | homer homolog 1 (*Drosophila*) |
| 1439799_at | NA | NA |
| 1441079_at | Mbd4 | methyl-CpG binding domain protein 4 |
| 1441962_at | Alox5 | arachidonate 5-lipoxygenase |
| 1442122_at | AI451458 | expressed sequence AI451458 |
| 1444090_at | Pram1 | PML-RAR alpha-regulated adaptor molecule 1 |
| 1444985_at | NA | NA |
| 1447918_x_at | Iglv1 | immunoglobulin lambda variable 1 |
| 1448159_at | Rab7 | RAB7 member RAS oncogene family |
| 1448306_at | Nfkbia | nuclear factor of kappa light polypeptide gene enhancer in B-cells inhibitor alpha |
| 1448333_at | Adprh | ADP-ribosylarginine hydrolase |
| 1448377_at | Slpi | secretory leukocyte peptidase inhibitor |
| 1448543_at | Slmo2 | slowmo homolog 2 (*Drosophila*) |
| 1448559_at | Flot1 | flotillin 1 |
| 1448604_at | Uck2 | uridine-cytidine kinase 2 |
| 1448856_a_at | Msra | methionine sulfoxide reductase A |
| 1448948_at | Slc50a1 | solute carrier family 50 (sugar transporter) member 1 |
| 1448957_at | Rbpj | recombination signal binding protein for immunoglobulin kappa J region |
| 1449028_at | Rhou | ras homolog gene family member U |
| 1449455_at | Hck | hemopoietic cell kinase |
| 1449591_at | Casp4 | caspase 4 apoptosis-related cysteine peptidase |
| 1449712_s_at | Atp6v1e1 | ATPase H+ transporting lysosomal V1 subunit E1 |
| 1449829_at | Itgb2l | integrin beta 2-like |
| 1449858_at | Cd86 | CD86 antigen |
| 1450295_s_at | Pvr | poliovirus receptor |
| 1450459_at | 2010106G01Rik | RIKEN cDNA 2010106G01 gene |
| 1450742_at | Bysl | bystin-like |
| 1450786_x_at | Pdlim5 | PDZ and LIM domain 5 |
| 1450882_s_at | NA | NA |
| 1450913_at | B4galt6 | UDP-Gal: betaGlcNAc beta 14-galactosyltransferase polypeptide 6 |
| 1450937_at | Lin7c | lin-7 homolog C (*C. elegans*) |
| 1450971_at | Gadd45b | growth arrest and DNA-damage-inducible 45 beta |
| 1451015_at | Tkt | transketolase |
| 1451037_at | Ptpn9 | protein tyrosine phosphatase non-receptor type 9 |
| 1451079_at | Adpgk | ADP-dependent glucokinase |

TABLE 6-continued

Mouse Factor 26

| PROBE ID | SYMBOL | GENE NAME |
| --- | --- | --- |
| 1451171_at | 2310008H04Rik | RIKEN cDNA 2310008H04 gene |
| 1451275_at | Uhrf1bp1l | UHRF1 (ICBP90) binding protein 1-like |
| 1451317_at | Ythdf2 | YTH domain family 2 |
| 1451387_s_at | Cuta | cutA divalent cation tolerance homolog (E. coli) |
| 1451436_at | Sbno1 | sno strawberry notch homolog 1 (Drosophila) |
| 1451458_at | Tmem2 | transmembrane protein 2 |
| 1451537_at | Chi3l1 | chitinase 3-like 1 |
| 1451713_a_at | Fcer2a | Fc receptor IgE low affinity II alpha polypeptide |
| 1451767_at | Ncf1 | neutrophil cytosolic factor 1 |
| 1452024_a_at | Ldb1 | LIM domain binding 1 |
| 1452118_at | Rrp1b | ribosomal RNA processing 1 homolog B (S. cerevisiae) |
| 1452162_at | Wdr48 | WD repeat domain 48 |
| 1452163_at | Ets1 | E26 avian leukemia oncogene 1 5' domain |
| 1452306_at | Zfyve26 | zinc finger FYVE domain containing 26 |
| 1452408_at | NA | NA |
| 1452483_a_at | Cd44 | CD44 antigen |
| 1452732_at | Asprv1 | aspartic peptidase retroviral-like 1 |
| 1453009_at | Cpm | carboxypeptidase M |
| 1454197_a_at | Ccdc86 | coiled-coil domain containing 86 |
| 1454654_at | Dirc2 | disrupted in renal carcinoma 2 (human) |
| 1454711_at | Trio | triple functional domain (PTPRF interacting) |
| 1454880_s_at | Bmf | BCL2 modifying factor |
| 1454979_at | Diap1 | diaphanous homolog 1 (Drosophila) |
| 1455000_at | Gpr68 | G protein-coupled receptor 68 |
| 1455002_at | Ptp4a1 | protein tyrosine phosphatase 4a1 |
| 1455032_at | Ccnyl1 | cyclin Y-like 1 |
| 1455300_at | Tet2 | tet oncogene family member 2 |
| 1455332_x_at | Fcgr2b | Fc receptor IgG low affinity IIb |
| 1456037_x_at | Preb | prolactin regulatory element binding |
| 1456341_a_at | Klf9 | Kruppel-like factor 9 |
| 1456875_at | Gm19906 | predicted gene19906 |
| 1457376_at | NA | NA |
| 1457753_at | Tlr13 | toll-like receptor 13 |
| 1457825_x_at | Tcn2 | transcobalamin 2 |
| 1459903_at | Sema7a | sema domain immunoglobulin domain (Ig) and GPI membrane anchor (semaphorin) 7A |
| 1459916_at | Gm19980 | predicted gene 19980 |
| 1460257_a_at | NA | NA |
| 1460282_at | Trem1 | triggering receptor expressed on myeloid cells 1 |
| 1460287_at | Timp2 | tissue inhibitor of metalloproteinase 2 |
| 1460351_at | S100a11 | S100 calcium binding protein A11 (calgizzarin) |

TABLE 7

Human Factor 4

| PROBE ID | SYMBOL | GENE NAME |
| --- | --- | --- |
| 200060_s_at | RNPS1 | RNA binding protein S1 serine-rich domain |
| 200633_at | UBB | ubiquitin B |
| 200675_at | CD81 | CD81 molecule |
| 200693_at | YWHAQ | tyrosine 3-monooxygenase/tryptophan 5-monooxygenase activation protein theta polypeptide |
| 200702_s_at | DDX24 | DEAD (Asp-Glu-Ala-Asp) box polypeptide 24 |
| 200717_x_at | RPL7 | ribosomal protein L7 |
| 200739_s_at | SUMO3 | SMT3 suppressor of mif two 3 homolog 3 (S. cerevisiae) |
| 200741_s_at | RPS27 | ribosomal protein S27 |
| 200743_s_at | TPP1 | tripeptidyl peptidase I |
| 200764_s_at | CTNNA1 | catenin (cadherin-associated protein) alpha 1 102 kDa |
| 200766_at | CTSD | cathepsin D |
| 200767_s_at | FAM120A | family with sequence similarity 120A |
| 200874_s_at | NOP56 | NOP56 ribonucleoprotein homolog (yeast) |
| 200875_s_at | NOP56 | NOP56 ribonucleoprotein homolog (yeast) |
| 200881_s_at | DNAJA1 | DnaJ (Hsp40) homolog subfamily A member 1 |
| 200886_s_at | PGAM1 | phosphoglycerate mutase 1 (brain) |
| 200947_s_at | GLUD1 | glutamate dehydrogenase 1 |
| 200951_s_at | CCND2 | cyclin D2 |
| 200954_at | ATP6V0C | ATPase H+ transporting lysosomal 16 kDa V0 subunit c |
| 200955_at | IMMT | inner membrane protein mitochondrial |
| 200968_s_at | PPIB | peptidylprolyl isomerase B (cyclophilin B) |
| 200969_at | SERP1 | stress-associated endoplasmic reticulum protein 1 |
| 200984_s_at | CD59 | CD59 molecule complement regulatory protein |
| 200985_s_at | CD59 | CD59 molecule complement regulatory protein |

TABLE 7-continued

Human Factor 4

| PROBE ID | SYMBOL | GENE NAME |
| --- | --- | --- |
| 200998_s_at | CKAP4 | cytoskeleton-associated protein 4 |
| 201015_s_at | JUP | junction plakoglobin |
| 201055_s_at | HNRNPA0 | heterogeneous nuclear ribonucleoprotein A0 |
| 201087_at | PXN | paxillin |
| 201243_s_at | ATP1B1 | ATPase Na+/K+ transporting beta 1 polypeptide |
| 201260_s_at | SYPL1 | synaptophysin-like 1 |
| 201332_s_at | STAT6 | signal transducer and activator of transcription 6 |
| 201353_s_at | BAZ2A | bromodomain adjacent to zinc finger domain 2A |
| 201369_s_at | ZFP36L2 | zinc finger protein 36 C3H type-like 2 |
| 201395_at | RBM5 | RNA binding motif protein 5 |
| 201396_s_at | SGTA | small glutamine-rich tetratricopeptide repeat (TPR)-containing alpha |
| 201449_at | TIA1 | TIA1 cytotoxic granule-associated RNA binding protein |
| 201525_at | APOD | apolipoprotein D |
| 201530_x_at | EIF4A1 | eukaryotic translation initiation factor 4A1 |
| 201532_at | PSMA3 | proteasome (prosome macropain) subunit alpha type 3 |
| 201556_s_at | VAMP2 | vesicle-associated membrane protein 2 (synaptobrevin 2) |
| 201601_x_at | IFITM1 | interferon induced transmembrane protein 1 (9-27) |
| 201602_s_at | PPP1R12A | protein phosphatase 1 regulatory (inhibitor) subunit 12A |
| 201614_s_at | RUVBL1 | RuvB-like 1 (*E. coli*) |
| 201650_at | KRT19 | keratin 19 |
| 201699_at | PSMC6 | proteasome (prosome macropain) 26S subunit ATPase 6 |
| 201700_at | CCND3 | cyclin D3 |
| 201701_s_at | PGRMC2 | progesterone receptor membrane component 2 |
| 201737_s_at | 6-Mar | membrane-associated ring finger (C3HC4) 6 |
| 201751_at | JOSD1 | Josephin domain containing 1 |
| 201840_at | NEDD8 | neural precursor cell expressed developmentally down-regulated 8 |
| 201881_s_at | ARIH1 | ariadne homolog ubiquitin-conjugating enzyme E2 binding protein 1 (*Drosophila*) |
| 201903_at | UQCRC1 | ubiquinol-cytochrome c reductase core protein I |
| 201960_s_at | MYCBP2 | MYC binding protein 2 |
| 201984_s_at | EGFR | epidermal growth factor receptor |
| 202007_at | NID1 | nidogen 1 |
| 202008_s_at | NID1 | nidogen 1 |
| 202054_s_at | ALDH3A2 | aldehyde dehydrogenase 3 family member A2 |
| 202056_at | KPNA1 | karyopherin alpha 1 (importin alpha 5) |
| 202057_at | KPNA1 | karyopherin alpha 1 (importin alpha 5) |
| 202162_s_at | CNOT8 | CCR4-NOT transcription complex subunit 8 |
| 202234_s_at | SLC16A1 | solute carrier family 16 member 1 (monocarboxylic acid transporter 1) |
| 202240_at | PLK1 | polo-like kinase 1 |
| 202273_at | PDGFRB | platelet-derived growth factor receptor beta polypeptide |
| 202329_at | CSK | c-src tyrosine kinase |
| 202360_at | MAML1 | mastermind-like 1 (*Drosophila*) |
| 202368_s_at | TRAM2 | translocation associated membrane protein 2 |
| 202382_s_at | GNPDA1 | glucosamine-6-phosphate deaminase 1 |
| 202426_s_at | RXRA | retinoid X receptor alpha |
| 202508_s_at | SNAP25 | synaptosomal-associated protein 25 kDa |
| 202548_s_at | ARHGEF7 | Rho guanine nucleotide exchange factor (GEF) 7 |
| 202566_s_at | SVIL | supervillin |
| 202623_at | EAPP | E2F-associated phosphoprotein |
| 202624_s_at | CABIN1 | calcineurin binding protein 1 |
| 202636_at | RNF103 | ring finger protein 103 |
| 202693_s_at | STK17A | serine/threonine kinase 17a |
| 202694_at | STK17A | serine/threonine kinase 17a |
| 202709_at | FMOD | fibromodulin |
| 202750_s_at | TFIP11 | tuftelin interacting protein 11 |
| 202756_s_at | GPC1 | glypican 1 |
| 202787_s_at | MAPKAPK3 | mitogen-activated protein kinase-activated protein kinase 3 |
| 202795_x_at | TRIOBP | TRIO and F-actin binding protein |
| 202796_at | SYNPO | synaptopodin |
| 202830_s_at | SLC37A4 | solute carrier family 37 (glucose-6-phosphate transporter) member 4 |
| 202859_x_at | IL8 | interleukin 8 |
| 202972_s_at | FAM13A | family with sequence similarity 13 member A |
| 202973_x_at | FAM13A | family with sequence similarity 13 member A |
| 202985_s_at | BAG5 | BCL2-associated athanogene 5 |
| 203023_at | NOP16 | NOP16 nucleolar protein homolog (yeast) |
| 203199_s_at | MTRR | 5-methyltetrahydrofolate-homocysteine methyltransferase reductase |
| 203236_s_at | LGALS9 | lectin galactoside-binding soluble 9 |
| 203376_at | CDC40 | cell division cycle 40 homolog (*S. cerevisiae*) |
| 203460_s_at | PSEN1 | presenilin 1 |
| 203610_s_at | TRIM38 | tripartite motif containing 38 |
| 203693_s_at | E2F3 | E2F transcription factor 3 |
| 203718_at | PNPLA6 | patatin-like phospholipase domain containing 6 |

TABLE 7-continued

Human Factor 4

| PROBE ID | SYMBOL | GENE NAME |
|---|---|---|
| 203764_at | DLGAP5 | discs large (*Drosophila*) homolog-associated protein 5 |
| 203794_at | CDC42BPA | CDC42 binding protein kinase alpha (DMPK-like) |
| 203863_at | ACTN2 | actinin alpha 2 |
| 203864_s_at | ACTN2 | actinin alpha 2 |
| 204217_s_at | RTN2 | reticulon 2 |
| 204218_at | C11orf51 | chromosome 11 open reading frame 51 |
| 204237_at | GULP1 | GULP engulfment adaptor PTB domain containing 1 |
| 204238_s_at | C6orf108 | chromosome 6 open reading frame 108 |
| 204242_s_at | ACOX3 | acyl-CoA oxidase 3 pristanoyl |
| 204249_s_at | LMO2 | LIM domain only 2 (rhombotin-like 1) |
| 204250_s_at | CEP164 | centrosomal protein 164 kDa |
| 204287_at | SYNGR1 | synaptogyrin 1 |
| 204447_at | ProSAPiP1 | ProSAPiP1 protein |
| 204464_s_at | EDNRA | endothelin receptor type A |
| 204491_at | PDE4D | phosphodiesterase 4D cAMP-specific |
| 204496_at | STRN3 | striatin calmodulin binding protein 3 |
| 204497_at | ADCY9 | adenylate cyclase 9 |
| 204597_x_at | STC1 | stanniocalcin 1 |
| 204697_s_at | CHGA | chromogranin A (parathyroid secretory protein 1) |
| 205053_at | PRIM1 | primase DNA polypeptide 1 (49 kDa) |
| 205064_at | SPRR1B | small proline-rich protein 1B |
| 205067_at | IL1B | interleukin 1 beta |
| 205144_at | NA | NA |
| 205151_s_at | TRIL | TLR4 interactor with leucine-rich repeats |
| 205182_s_at | ZNF324 | zinc finger protein 324 |
| 205225_at | ESR1 | estrogen receptor 1 |
| 205243_at | SLC13A3 | solute carrier family 13 (sodium-dependent dicarboxylate transporter) member 3 |
| 205296_at | RBL1 | retinoblastoma-like 1 (p107) |
| 205340_at | ZBTB24 | zinc finger and BTB domain containing 24 |
| 205364_at | ACOX2 | acyl-CoA oxidase 2 branched chain |
| 205396_at | SMAD3 | SMAD family member 3 |
| 205483_s_at | ISG15 | ISG15 ubiquitin-like modifier |
| 205590_at | RASGRP1 | RAS guanyl releasing protein 1 (calcium and DAG-regulated) |
| 205680_at | MMP10 | matrix metallopeptidase 10 (stromelysin 2) |
| 205734_s_at | AFF3 | AF4/FMR2 family member 3 |
| 205887_x_at | MSH3 | mutS homolog 3 (*E. coli*) |
| 206099_at | PRKCH | protein kinase C eta |
| 206147_x_at | SCML2 | sex comb on midleg-like 2 (*Drosophila*) |
| 206266_at | GPLD1 | glycosylphosphatidylinositol specific phospholipase D1 |
| 206421_s_at | SERPINB7 | serpin peptidase inhibitor clade B (ovalbumin) member 7 |
| 206614_at | GDF5 | growth differentiation factor 5 |
| 206653_at | POLR3G | polymerase (RNA) III (DNA directed) polypeptide G (32 kD) |
| 206931_at | ZNF141 | zinc finger protein 141 |
| 206932_at | CH25H | cholesterol 25-hydroxylase |
| 207022_s_at | LDHC | lactate dehydrogenase C |
| 207076_s_at | ASS1 | argininosuccinate synthase 1 |
| 207086_x_at | NA | NA |
| 207160_at | IL12A | interleukin 12A (natural killer cell stimulatory factor 1 cytotoxic lymphocyte maturation factor 1 p35) |
| 207174_at | GPC5 | glypican 5 |
| 207385_at | TFDP3 | transcription factor Dp family member 3 |
| 207588_at | NA | NA |
| 207759_s_at | NA | NA |
| 207908_at | KRT2 | keratin 2 |
| 208043_at | NA | NA |
| 208113_x_at | PABPC3 | poly(A) binding protein cytoplasmic 3 |
| 208114_s_at | ISG20L2 | interferon stimulated exonuclease gene 20 kDa-like 2 |
| 208334_at | NDST4 | N-deacetylase/N-sulfotransferase (heparan glucosaminyl) 4 |
| 208340_at | NA | NA |
| 208381_s_at | SGPL1 | sphingosine-1-phosphate lyase 1 |
| 208556_at | GPR31 | G protein-coupled receptor 31 |
| 208683_at | CAPN2 | calpain 2 (m/II) large subunit |
| 208709_s_at | NRD1 | nardilysin (N-arginine dibasic convertase) |
| 208710_s_at | AP3D1 | adaptor-related protein complex 3 delta 1 subunit |
| 208729_x_at | HLA-B | major histocompatibility complex class I B |
| 208738_x_at | SUMO2 | SMT3 suppressor of mif two 3 homolog 2 (*S. cerevisiae*) |
| 208748_s_at | FLOT1 | flotillin 1 |
| 208750_s_at | ARF1 | ADP-ribosylation factor 1 |
| 208765_s_at | HNRNPR | heterogeneous nuclear ribonucleoprotein R |
| 208786_s_at | MAP1LC3B | microtubule-associated protein 1 light chain 3 beta |
| 208800_at | SRP72 | signal recognition particle 72 kDa |
| 208817_at | COMT | catechol-O-methyltransferase |
| 208820_at | PTK2 | PTK2 protein tyrosine kinase 2 |
| 208852_s_at | CANX | calnexin |
| 208853_s_at | CANX | calnexin |

TABLE 7-continued

Human Factor 4

| PROBE ID | SYMBOL | GENE NAME |
|---|---|---|
| 208856_x_at | RPLP0 | ribosomal protein large P0 |
| 208857_s_at | PCMT1 | protein-L-isoaspartate (D-aspartate) O-methyltransferase |
| 208875_s_at | PAK2 | p21 protein (Cdc42/Rac)-activated kinase 2 |
| 209021_x_at | ATG13 | ATG13 autophagy related 13 homolog (S. cerevisiae) |
| 209047_at | AQP1 | aquaporin 1 (Colton blood group) |
| 209055_s_at | CDC5L | CDC5 cell division cycle 5-like (S. pombe) |
| 209087_x_at | MCAM | melanoma cell adhesion molecule |
| 209088_s_at | UBN1 | ubinuclein 1 |
| 209169_at | GPM6B | glycoprotein M6B |
| 209170_s_at | GPM6B | glycoprotein M6B |
| 209197_at | SYT11 | synaptotagmin XI |
| 209225_x_at | TNPO1 | transportin 1 |
| 209253_at | SORBS3 | sorbin and SH3 domain containing 3 |
| 209352_s_at | SIN3B | SIN3 homolog B transcription regulator (yeast) |
| 209393_s_at | EIF4E2 | eukaryotic translation initiation factor 4E family member 2 |
| 209479_at | CCDC28A | coiled-coil domain containing 28A |
| 209556_at | NCDN | neurochondrin |
| 209623_at | MCCC2 | methylcrotonoyl-CoA carboxylase 2 (beta) |
| 209666_s_at | CHUK | conserved helix-loop-helix ubiquitous kinase |
| 209689_at | CCDC93 | coiled-coil domain containing 93 |
| 209726_at | CA11 | carbonic anhydrase XI |
| 209822_s_at | VLDLR | very low density lipoprotein receptor |
| 209865_at | SLC35A3 | solute carrier family 35 (UDP-N-acetylglucosamine (UDP-GlcNAc) transporter) member A3 |
| 209866_s_at | LPHN3 | latrophilin 3 |
| 209972_s_at | AIMP2 | aminoacyl tRNA synthetase complex-interacting multifunctional protein 2 |
| 209973_at | NFKBIL1 | nuclear factor of kappa light polypeptide gene enhancer in B-cells inhibitor-like 1 |
| 210158_at | ERCC4 | excision repair cross-complementing rodent repair deficiency complementation group 4 |
| 210163_at | CXCL11 | chemokine (C-X-C motif) ligand 11 |
| 210251_s_at | RUFY3 | RUN and FYVE domain containing 3 |
| 210344_at | OSBPL7 | oxysterol binding protein-like 7 |
| 210346_s_at | CLK4 | CDC-like kinase 4 |
| 210377_at | ACSM3 | acyl-CoA synthetase medium-chain family member 3 |
| 210470_x_at | NONO | non-POU domain containing octamer-binding |
| 210613_s_at | SYNGR1 | synaptogyrin 1 |
| 210627_s_at | MOGS | mannosyl-oligosaccharide glucosidase |
| 210677_at | SOAT2 | sterol O-acyltransferase 2 |
| 210731_s_at | LGALS8 | lectin galactoside-binding soluble 8 |
| 210732_s_at | LGALS8 | lectin galactoside-binding soluble 8 |
| 210823_s_at | PTPRS | protein tyrosine phosphatase receptor type S |
| 210919_at | PHLPP1 | PH domain and leucine rich repeat protein phosphatase 1 |
| 211054_at | INVS | inversin |
| 211055_s_at | INVS | inversin |
| 211070_x_at | DBI | diazepam binding inhibitor (GABA receptor modulator acyl-CoA binding protein) |
| 211165_x_at | EPHB2 | EPH receptor B2 |
| 211190_x_at | CD84 | CD84 molecule |
| 211224_s_at | ABCB11 | ATP-binding cassette sub-family B (MDR/TAP) member 11 |
| 211334_at | MRE11A | MRE11 meiotic recombination 11 homolog A (S. cerevisiae) |
| 211375_s_at | ILF3 | interleukin enhancer binding factor 3 90 kDa |
| 211380_s_at | PRKG1 | protein kinase cGMP-dependent type I |
| 211413_at | PADI4 | peptidyl arginine deiminase type IV |
| 211555_s_at | GUCY1B3 | guanylate cyclase 1 soluble beta 3 |
| 211775_x_at | MGC13053 | hypothetical MGC13053 |
| 211794_at | FYB | FYN binding protein |
| 211833_s_at | BAX | BCL2-associated X protein |
| 211954_s_at | IPO5 | importin 5 |
| 211964_at | COL4A2 | collagen type IV alpha 2 |
| 211995_x_at | ACTG1 | actin gamma 1 |
| 211996_s_at | NA | NA |
| 212037_at | PNN | pinin desmosome associated protein |
| 212075_s_at | CSNK2A1 | casein kinase 2 alpha 1 polypeptide |
| 212152_x_at | ARID1A | AT rich interactive domain 1A (SWI-like) |
| 212154_at | SDC2 | syndecan 2 |
| 212274_at | LPIN1 | lipin 1 |
| 212282_at | TMEM97 | transmembrane protein 97 |
| 212307_s_at | OGT | O-linked N-acetylglucosamine (GlcNAc) transferase (UDP-N-acetylglucosamine: polypeptide-N-acetylglucosaminyl transferase) |
| 212328_at | LIMCH1 | LIM and calponin homology domains 1 |
| 212387_at | TCF4 | transcription factor 4 |
| 212439_at | IP6K1 | inositol hexakisphosphate kinase 1 |
| 212440_at | SNRNP27 | small nuclear ribonucleoprotein 27 kDa (U4/U6.U5) |
| 212738_at | ARHGAP19 | Rho GTPase activating protein 19 |

TABLE 7-continued

Human Factor 4

| PROBE ID | SYMBOL | GENE NAME |
|---|---|---|
| 212854_x_at | NA | NA |
| 212938_at | COL6A1 | collagen type VI alpha 1 |
| 212951_at | GPR116 | G protein-coupled receptor 116 |
| 212966_at | HIC2 | hypermethylated in cancer 2 |
| 213022_s_at | UTRN | utrophin |
| 213039_at | ARHGEF18 | Rho/Rac guanine nucleotide exchange factor (GEF) 18 |
| 213067_at | MYH10 | myosin heavy chain 10 non-muscle |
| 213073_at | ZFYVE26 | zinc finger FYVE domain containing 26 |
| 213135_at | TIAM1 | T-cell lymphoma invasion and metastasis 1 |
| 213168_at | SP3 | Sp3 transcription factor |
| 213185_at | KIAA0556 | KIAA0556 |
| 213188_s_at | MINA | MYC induced nuclear antigen |
| 213334_x_at | HAUS7 | HAUS augmin-like complex subunit 7 |
| 213351_s_at | TMCC1 | transmembrane and coiled-coil domain family 1 |
| 213395_at | MLC1 | megalencephalic leukoencephalopathy with subcortical cysts 1 |
| 213397_x_at | NA | NA |
| 213436_at | CNR1 | cannabinoid receptor 1 (brain) |
| 213439_x_at | RUNDC3A | RUN domain containing 3A |
| 213659_at | ZNF75D | zinc finger protein 75D |
| 213687_s_at | RPL35A | ribosomal protein L35a |
| 213816_s_at | MET | met proto-oncogene (hepatocyte growth factor receptor) |
| 213874_at | SERPINA4 | serpin peptidase inhibitor clade A (alpha-1 antiproteinase antitrypsin) member 4 |
| 214319_at | FRY | furry homolog (*Drosophila*) |
| 214349_at | NA | NA |
| 214380_at | PRPF31 | PRP31 pre-mRNA processing factor 31 homolog (*S. cerevisiae*) |
| 214387_x_at | SFTPC | surfactant protein C |
| 214565_s_at | NA | NA |
| 214727_at | BRCA2 | breast cancer 2 early onset |
| 214915_at | ZNF362 | zinc finger protein 362 |
| 214952_at | NCAM1 | neural cell adhesion molecule 1 |
| 215067_x_at | PRDX2 | peroxiredoxin 2 |
| 215240_at | ITGB3 | integrin beta 3 (platelet glycoprotein IIIa antigen CD61) |
| 215254_at | RCAN1 | regulator of calcineurin 1 |
| 215510_at | ETV2 | ets variant 2 |
| 215727_x_at | NA | NA |
| 215974_at | HCG4B | HLA complex group 4B (non-protein coding) |
| 216048_s_at | RHOBTB3 | Rho-related BTB domain containing 3 |
| 216752_at | PIK3R4 | phosphoinositide-3-kinase regulatory subunit 4 |
| 216971_s_at | PLEC | plectin |
| 217455_s_at | SSTR2 | somatostatin receptor 2 |
| 217544_at | NA | NA |
| 217640_x_at | SKA1 | spindle and kinetochore associated complex subunit 1 |
| 217641_at | GPR135 | G protein-coupled receptor 135 |
| 217740_x_at | RPL7A | ribosomal protein L7a |
| 217799_x_at | UBE2H | ubiquitin-conjugating enzyme E2H |
| 217889_s_at | CYBRD1 | cytochrome b reductase 1 |
| 217903_at | STRN4 | striatin calmodulin binding protein 4 |
| 217924_at | C6orf106 | chromosome 6 open reading frame 106 |
| 217928_s_at | PPP6R3 | protein phosphatase 6 regulatory subunit 3 |
| 217941_s_at | ERBB2IP | erbb2 interacting protein |
| 217992_s_at | EFHD2 | EF-hand domain family member D2 |
| 217996_at | PHLDA1 | pleckstrin homology-like domain family A member 1 |
| 218006_s_at | ZNF22 | zinc finger protein 22 (KOX 15) |
| 218028_at | ELOVL1 | ELOVL fatty acid elongase 1 |
| 218048_at | COMMD3 | COMM domain containing 3 |
| 218049_s_at | MRPL13 | mitochondrial ribosomal protein L13 |
| 218358_at | CRELD2 | cysteine-rich with EGF-like domains 2 |
| 218380_at | NA | NA |
| 218390_s_at | FAM204A | family with sequence similarity 204 member A |
| 218541_s_at | C8orf4 | chromosome 8 open reading frame 4 |
| 218580_x_at | AURKAIP1 | aurora kinase A interacting protein 1 |
| 218625_at | NRN1 | neuritin 1 |
| 218694_at | ARMCX1 | armadillo repeat containing X-linked 1 |
| 218710_at | TTC27 | tetratricopeptide repeat domain 27 |
| 218771_at | PANK4 | pantothenate kinase 4 |
| 218920_at | FAM193B | family with sequence similarity 193 member B |
| 219051_x_at | METRN | meteorin glial cell differentiation regulator |
| 219058_x_at | TINAGL1 | tubulointerstitial nephritis antigen-like 1 |
| 219388_at | GRHL2 | grainyhead-like 2 (*Drosophila*) |
| 219485_s_at | PSMD10 | proteasome (prosome macropain) 26S subunit non-ATPase 10 |
| 219495_s_at | ZNF180 | zinc finger protein 180 |
| 219528_s_at | BCL11B | B-cell CLL/lymphoma 11B (zinc finger protein) |
| 219829_at | ITGB1BP2 | integrin beta 1 binding protein (melusin) 2 |
| 219975_x_at | OLAH | oleoyl-ACP hydrolase |
| 219988_s_at | RNF220 | ring finger protein 220 |

TABLE 7-continued

Human Factor 4

| PROBE ID | SYMBOL | GENE NAME |
| --- | --- | --- |
| 220156_at | EFCAB1 | EF-hand calcium binding domain 1 |
| 220243_at | ZBTB44 | zinc finger and BTB domain containing 44 |
| 220357_s_at | SGK2 | serum/glucocorticoid regulated kinase 2 |
| 220403_s_at | TP53AIP1 | tumor protein p53 regulated apoptosis inducing protein 1 |
| 220650_s_at | SLC9A5 | solute carrier family 9 (sodium/hydrogen exchanger) member 5 |
| 220663_at | IL1RAPL1 | interleukin 1 receptor accessory protein-like 1 |
| 220750_s_at | LEPRE1 | leucine proline-enriched proteoglycan (leprecan) 1 |
| 220769_s_at | WDR78 | WD repeat domain 78 |
| 220991_s_at | RNF32 | ring finger protein 32 |
| 221036_s_at | APR1B | anterior pharynx defective 1 homolog B (*C. elegans*) |
| 221066_at | RXFP3 | relaxin/insulin-like family peptide receptor 3 |
| 221080_s_at | DENND1C | DENN/MADD domain containing 1C |
| 221102_s_at | TRPM6 | transient receptor potential cation channel subfamily M member 6 |
| 221280_s_at | PARD3 | par-3 partitioning defective 3 homolog (*C. elegans*) |
| 221296_at | TECTA | tectorin alpha |
| 221510_s_at | GLS | glutaminase |
| 221625_at | ZNF506 | zinc finger protein 506 |
| 221888_at | CC2D1A | coiled-coil and C2 domain containing 1A |
| 221896_s_at | HIGD1A | HIG1 hypoxia inducible domain family member 1A |
| 222014_x_at | MTO1 | mitochondrial translation optimization 1 homolog (*S. cerevisiae*) |
| 222015_at | CSNK1E | casein kinase 1 epsilon |
| 222062_at | IL27RA | interleukin 27 receptor alpha |
| 222144_at | KIF17 | kinesin family member 17 |
| 222158_s_at | PPPDE1 | PPPDE peptidase domain containing 1 |
| 222165_x_at | C9orf16 | chromosome 9 open reading frame 16 |
| 222226_at | SAA3P | serum amyloid A3 pseudogene |
| 31845_at | ELF4 | E74-like factor 4 (ets domain transcription factor) |
| 34063_at | RECQL5 | RecQ protein-like 5 |
| 35160_at | LDB1 | LIM domain binding 1 |
| 37943_at | ZFYVE26 | zinc finger FYVE domain containing 26 |
| 38398_at | MADD | MAP-kinase activating death domain |
| 40359_at | RASSF7 | Ras association (RalGDS/AF-6) domain family (N-terminal) member 7 |
| 41512_at | BRAP | BRCA1 associated protein |
| 54632_at | THADA | thyroid adenoma associated |
| 65635_at | ENGASE | endo-beta-N-acetylglucosaminidase |

TABLE 8

Human Factor 20

| PROBE ID | SYMBOL | GENE NAME |
| --- | --- | --- |
| 200992_at | IPO7 | importin 7 |
| 201034_at | ADD3 | adducin 3 (gamma) |
| 201149_s_at | TIMP3 | TIMP metallopeptidase inhibitor 3 |
| 201412_at | LRP10 | low density lipoprotein receptor-related protein 10 |
| 201565_s_at | ID2 | inhibitor of DNA binding 2 dominant negative helix-loop-helix protein |
| 201651_s_at | PACSIN2 | protein kinase C and casein kinase substrate in neurons 2 |
| 201662_s_at | ACSL3 | acyl-CoA synthetase long-chain family member 3 |
| 201721_s_at | LAPTM5 | lysosomal protein transmembrane 5 |
| 201761_at | MTHFD2 | methylenetetrahydrofolate dehydrogenase (NADP+ dependent) 2 methenyltetrahydrofolate cyclohydrolase |
| 202350_s_at | MATN2 | matrilin 2 |
| 202628_s_at | SERPINE1 | serpin peptidase inhibitor clade E (nexin plasminogen activator inhibitor type 1) member 1 |
| 203191_at | ABCB6 | ATP-binding cassette sub-family B (MDR/TAP) member 6 |
| 203216_s_at | MYO6 | myosin VI |
| 203229_s_at | CLK2 | CDC-like kinase 2 |
| 203879_at | PIK3CD | phosphoinositide-3-kinase catalytic delta polypeptide |
| 203884_s_at | RAB11FIP2 | RAB11 family interacting protein 2 (class I) |
| 203950_s_at | CLCN6 | chloride channel 6 |
| 204025_s_at | PDCD2 | programmed cell death 2 |
| 204060_s_at | NA | NA |
| 204215_at | C7orf23 | chromosome 7 open reading frame 23 |
| 204316_at | RGS10 | regulator of G-protein signaling 10 |
| 204387_x_at | MRP63 | mitochondrial ribosomal protein 63 |
| 206541_at | KLKB1 | kallikrein B plasma (Fletcher factor) 1 |
| 208461_at | HIC1 | hypermethylated in cancer 1 |
| 208742_s_at | SAP18 | Sin3A-associated protein 18 kDa |
| 209043_at | PAPSS1 | 3'-phosphoadenosine 5'-phosphosulfate synthase 1 |
| 209115_at | UBA3 | ubiquitin-like modifier activating enzyme 3 |

TABLE 8-continued

Human Factor 20

| PROBE ID | SYMBOL | GENE NAME |
|---|---|---|
| 209146_at | MSMO1 | methylsterol monooxygenase 1 |
| 209227_at | TUSC3 | tumor suppressor candidate 3 |
| 209743_s_at | ITCH | itchy E3 ubiquitin protein ligase homolog (mouse) |
| 210545_at | ITSN2 | intersectin 2 |
| 212027_at | RBM25 | RNA binding motif protein 25 |
| 212668_at | SMURF1 | SMAD specific E3 ubiquitin protein ligase 1 |
| 212871_at | MAPKAPK5 | mitogen-activated protein kinase-activated protein kinase 5 |
| 212969_x_at | EML3 | echinoderm microtubule associated protein like 3 |
| 212983_at | HRAS | v-Ha-ras Harvey rat sarcoma viral oncogene homolog |
| 213336_at | BAZ1B | bromodomain adjacent to zinc finger domain 1B |
| 214140_at | SLC25A16 | solute carrier family 25 (mitochondrial carrier; Graves disease autoantigen) member 16 |
| 214355_x_at | NA | NA |
| 215169_at | NA | NA |
| 215420_at | IHH | Indian hedgehog |
| 216975_x_at | NPAS1 | neuronal PAS domain protein 1 |
| 217837_s_at | VPS24 | vacuolar protein sorting 24 homolog (*S. cerevisiae*) |
| 217891_at | C16orf58 | chromosome 16 open reading frame 58 |
| 217994_x_at | CPSF3L | cleavage and polyadenylation specific factor 3-like |
| 218136_s_at | SLC25A37 | solute carrier family 25 member 37 |
| 218478_s_at | ZCCHC8 | zinc finger CCHC domain containing 8 |
| 218675_at | SLC22A17 | solute carrier family 22 member 17 |
| 218756_s_at | DHRS11 | dehydrogenase/reductase (SDR family) member 11 |
| 218882_s_at | WDR3 | WD repeat domain 3 |
| 221087_s_at | APOL3 | apolipoprotein L3 |
| 221778_at | JHDM1D | jumonji C domain containing histone demethylase 1 homolog D (*S. cerevisiae*) |
| 221823_at | C5orf30 | chromosome 5 open reading frame 30 |
| 222255_at | PRX | periaxin |
| 40472_at | LPCAT4 | lysophosphatidylcholine acyltransferase 4 |
| 44617_at | OGFOD2 | 2-oxoglutarate and iron-dependent oxygenase domain containing 2 |

TABLE 9

Human Factor 40

| PROBE ID | SYMBOL | GENE NAME |
|---|---|---|
| 200989_at | HIF1A | hypoxia inducible factor 1 alpha subunit (basic helix-loop-helix transcription factor) |
| 201772_at | AZIN1 | antizyme inhibitor 1 |
| 202116_at | DPF2 | D4 zinc and double PHD fingers family 2 |
| 202552_s_at | CRIM1 | cysteine rich transmembrane BMP regulator 1 (chordin-like) |
| 203607_at | INPP5F | inositol polyphosphate-5-phosphatase F |
| 203643_at | ERF | Ets2 repressor factor |
| 204161_s_at | ENPP4 | ectonucleotide pyrophosphatase/phosphodiesterase 4 (putative) |
| 204284_at | PPP1R3C | protein phosphatase 1 regulatory (inhibitor) subunit 3C |
| 204452_s_at | FZD1 | frizzled family receptor 1 |
| 207583_at | ABCD2 | ATP-binding cassette sub-family D (ALD) member 2 |
| 208701_at | APLP2 | amyloid beta (A4) precursor-like protein 2 |
| 209054_s_at | WHSC1 | Wolf-Hirschhorn syndrome candidate 1 |
| 209593_s_at | TOR1B | torsin family 1 member B (torsin B) |
| 209840_s_at | LRRN3 | leucine rich repeat neuronal 3 |
| 210736_x_at | DTNA | dystrobrevin alpha |
| 213611_at | AQP5 | aquaporin 5 |
| 214062_x_at | NFKBIB | nuclear factor of kappa light polypeptide gene enhancer in B-cells inhibitor beta |
| 214952_at | NCAM1 | neural cell adhesion molecule 1 |
| 216222_s_at | MYO10 | myosin X |
| 216869_at | PDE1C | phosphodiesterase 1C calmodulin-dependent 70 kDa |
| 220585_at | HKDC1 | hexokinase domain containing 1 |
| 221402_at | OR1F1 | olfactory receptor family 1 subfamily F member 1 |
| 221651_x_at | NA | NA |
| 221708_s_at | UNC45A | unc-45 homolog A (*C. elegans*) |
| 222296_at | NA | NA |
| 222316_at | NA | NA |

TABLE 10

Human Factor 74

| PROBE ID | SYMBOL | GENE NAME |
| --- | --- | --- |
| 1487_at | ESRRA | estrogen-related receptor alpha |
| 201045_s_at | RAB6A | RAB6A member RAS oncogene family |
| 201046_s_at | RAD23A | RAD23 homolog A (*S. cerevisiae*) |
| 201751_at | JOSD1 | Josephin domain containing 1 |
| 201752_s_at | ADD3 | adducin 3 (gamma) |
| 201753_s_at | ADD3 | adducin 3 (gamma) |
| 201951_at | ALCAM | activated leukocyte cell adhesion molecule |
| 202058_s_at | KPNA1 | karyopherin alpha 1 (importin alpha 5) |
| 202579_x_at | HMGN4 | high mobility group nucleosomal binding domain 4 |
| 202786_at | STK39 | serine threonine kinase 39 |
| 202813_at | TARBP1 | TAR (HIV-1) RNA binding protein 1 |
| 202814_s_at | HEXIM1 | hexamethylene bis-acetamide inducible 1 |
| 202954_at | UBE2C | ubiquitin-conjugating enzyme E2C |
| 203092_at | TIMM44 | translocase of inner mitochondrial membrane 44 homolog (yeast) |
| 203100_s_at | CDYL | chromodomain protein Y-like |
| 203276_at | LMNB1 | lamin B1 |
| 203694_s_at | DHX16 | DEAH (Asp-Glu-Ala-His) box polypeptide 16 |
| 203763_at | DYNC2LI1 | dynein cytoplasmic 2 light intermediate chain 1 |
| 203806_s_at | FANCA | Fanconi anemia complementation group A |
| 203848_at | AKAP8 | A kinase (PRKA) anchor protein 8 |
| 203984_at | CASP9 | caspase 9 apoptosis-related cysteine peptidase |
| 203991_s_at | KDM6A | lysine (K)-specific demethylase 6A |
| 204056_s_at | MVK | mevalonate kinase |
| 204109_s_at | NFYA | nuclear transcription factor Y alpha |
| 204244_s_at | DBF4 | DBF4 homolog (*S. cerevisiae*) |
| 204403_x_at | FAM115A | family with sequence similarity 115 member A |
| 204535_s_at | REST | RE1-silencing transcription factor |
| 204632_at | RPS6KA4 | ribosomal protein S6 kinase 90 kDa polypeptide 4 |
| 205000_at | DDX3Y | DEAD (Asp-Glu-Ala-Asp) box polypeptide 3 Y-linked |
| 205098_at | CCR1 | chemokine (C-C motif) receptor 1 |
| 205150_s_at | TRIL | TLR4 interactor with leucine-rich repeats |
| 205315_s_at | SNTB2 | syntrophin beta 2 (dystrophin-associated protein A1 59 kDa basic component 2) |
| 205345_at | BARD1 | BRCA1 associated RING domain 1 |
| 205513_at | TCN1 | transcobalamin I (vitamin B12 binding protein R binder family) |
| 205591_at | OLFM1 | olfactomedin 1 |
| 205718_at | ITGB7 | integrin beta 7 |
| 205848_at | GAS2 | growth arrest-specific 2 |
| 205908_s_at | OMD | osteomodulin |
| 205948_at | PTPRT | protein tyrosine phosphatase receptor type T |
| 205980_s_at | NA | NA |
| 206045_s_at | NOL4 | nucleolar protein 4 |
| 206173_x_at | GABPB1 | GA binding protein transcription factor beta subunit 1 |
| 206253_at | DLG2 | discs large homolog 2 (*Drosophila*) |
| 206302_s_at | NA | NA |
| 206445_s_at | PRMT1 | protein arginine methyltransferase 1 |
| 206525_at | GABRR1 | gamma-aminobutyric acid (GABA) receptor rho 1 |
| 206805_at | SEMA3A | sema domain immunoglobulin domain (Ig) short basic domain secreted (semaphorin) 3A |
| 206806_at | DGKI | diacylglycerol kinase iota |
| 207029_at | KITLG | KIT ligand |
| 207700_s_at | NCOA3 | nuclear receptor coactivator 3 |
| 207864_at | SCN7A | sodium channel voltage-gated type VII alpha |
| 207871_s_at | ST7 | suppression of tumorigenicity 7 |
| 208017_s_at | MCF2 | MCF.2 cell line derived transforming sequence |
| 208311_at | GPR50 | G protein-coupled receptor 50 |
| 208955_at | DUT | deoxyuridine triphosphatase |
| 209192_x_at | KAT5 | K(lysine) acetyltransferase 5 |
| 209346_s_at | PI4K2A | phosphatidylinositol 4-kinase type 2 alpha |
| 209412_at | TRAPPC10 | trafficking protein particle complex 10 |
| 209598_at | PNMA2 | paraneoplastic antigen MA2 |
| 209620_s_at | ABCB7 | ATP-binding cassette sub-family B (MDR/TAP) member 7 |
| 209621_s_at | PDLIM3 | PDZ and LIM domain 3 |
| 209658_at | CDC16 | cell division cycle 16 homolog (*S. cerevisiae*) |
| 209829_at | FAM65B | family with sequence similarity 65 member B |
| 210033_s_at | SPAG6 | sperm associated antigen 6 |
| 210034_s_at | RPL5 | ribosomal protein L5 |
| 210078_s_at | KCNAB1 | potassium voltage-gated channel shaker-related subfamily beta member 1 |
| 210386_s_at | MTX1 | metaxin 1 |
| 210394_x_at | NA | NA |
| 210470_x_at | NONO | non-POU domain containing octamer-binding |
| 210491_at | NA | NA |
| 210493_s_at | MFAP3L | microfibrillar-associated protein 3-like |
| 210697_at | ZNF257 | zinc finger protein 257 |
| 211238_at | ADAM7 | ADAM metallopeptidase domain 7 |

TABLE 10-continued

Human Factor 74

| PROBE ID | SYMBOL | GENE NAME |
| --- | --- | --- |
| 211691_x_at | NA | NA |
| 212125_at | RANGAP1 | Ran GTPase activating protein 1 |
| 212338_at | MYO1D | myosin ID |
| 212340_at | YIPF6 | Yip1 domain family member 6 |
| 212408_at | TOR1AIP1 | torsin A interacting protein 1 |
| 212412_at | PDLIM5 | PDZ and LIM domain 5 |
| 212413_at | 6-Sep | septin 6 |
| 212614_at | ARID5B | AT rich interactive domain 5B (MRF1-like) |
| 212615_at | CHD9 | chromodomain helicase DNA binding protein 9 |
| 212696_s_at | RNF4 | ring finger protein 4 |
| 212739_s_at | NME4 | non-metastatic cells 4 protein expressed in |
| 212774_at | ZNF238 | zinc finger protein 238 |
| 212849_at | AXIN1 | axin 1 |
| 213370_s_at | SFMBT1 | Scm-like with four mbt domains 1 |
| 213621_s_at | GUK1 | guanylate kinase 1 |
| 213793_s_at | HOMER1 | homer homolog 1 (*Drosophila*) |
| 213912_at | TBC1D30 | TBC1 domain family member 30 |
| 214937_x_at | PCM1 | pericentriolar material 1 |
| 215367_at | KIAA1614 | KIAA1614 |
| 215927_at | ARFGEF2 | ADP-ribosylation factor guanine nucleotide-exchange factor 2 (brefeldin A-inhibited) |
| 215945_s_at | TRIM2 | tripartite motif containing 2 |
| 216064_s_at | AGA | aspartylglucosaminidase |
| 216718_at | LINC00302 | long intergenic non-protein coding RNA 302 |
| 216753_at | NA | NA |
| 217436_x_at | NA | NA |
| 217440_at | NA | NA |
| 217496_s_at | IDE | insulin-degrading enzyme |
| 217892_s_at | LIMA1 | LIM domain and actin binding 1 |
| 217996_at | PHLDA1 | pleckstrin homology-like domain family A member 1 |
| 218111_s_at | CMAS | cytidine monophosphate N-acetylneuraminic acid synthetase |
| 218962_s_at | TMEM168 | transmembrane protein 168 |
| 218987_at | ATF7IP | activating transcription factor 7 interacting protein |
| 219045_at | RHOF | ras homolog gene family member F (in filopodia) |
| 219086_at | ZNF839 | zinc finger protein 839 |
| 219136_s_at | LMF1 | lipase maturation factor 1 |
| 219507_at | RSRC1 | arginine/serine-rich coiled-coil 1 |
| 219508_at | GCNT3 | glucosaminyl (N-acetyl) transferase 3 mucin type |
| 219569_s_at | TMEM22 | transmembrane protein 22 |
| 219677_at | SPSB1 | splA/ryanodine receptor domain and SOCS box containing 1 |
| 219680_at | NLRX1 | NLR family member X1 |
| 219744_at | FN3K | fructosamine 3 kinase |
| 219747_at | NDNF | neuron-derived neurotrophic factor |
| 220068_at | VPREB3 | pre-B lymphocyte 3 |
| 220077_at | CCDC134 | coiled-coil domain containing 134 |
| 220385_at | JPH2 | junctophilin 2 |
| 221240_s_at | B3GNT4 | UDP-GlcNAc: betaGal beta-13-N-acetylglucosaminyltransferase 4 |
| 221245_s_at | FZD5 | frizzled family receptor 5 |
| 221428_s_at | TBL1XR1 | transducin (beta)-like 1 X-linked receptor 1 |
| 221592_at | NA | NA |
| 221607_x_at | ACTG1 | actin gamma 1 |
| 221608_at | WNT6 | wingless-type MMTV integration site family member 6 |
| 221630_s_at | DDX4 | DEAD (Asp-Glu-Ala-Asp) box polypeptide 4 |
| 222150_s_at | PION | pigeon homolog (*Drosophila*) |
| 222285_at | NA | NA |
| 222288_at | NA | NA |
| 222289_at | KCNC2 | potassium voltage-gated channel Shaw-related subfamily member 2 |
| 35201_at | HNRNPL | heterogeneous nuclear ribonucleoprotein L |
| 38487_at | STAB1 | stabilin 1 |
| 38703_at | DNPEP | aspartyl aminopeptidase |
| 39549_at | NPAS2 | neuronal PAS domain protein 2 |
| 41657_at | STK11 | serine/threonine kinase 11 |
| 41858_at | PGAP2 | post-GPI attachment to proteins 2 |
| 52255_s_at | COL5A3 | collagen type V alpha 3 |
| 74694_s_at | RABEP2 | rabaptin RAB GTPase binding effector protein 2 |

TABLE 11

MRSA v. MSSA

| Probe Set ID | Gene Symbol | Gene Title | Entrez Gene ID | p-value |
|---|---|---|---|---|
| 1420021_s_at | Suz12 | suppressor of zeste 12 homolog (*Drosophila*) | 52615 | 5.54E−07 |
| 1422842_at | Xrn2 | 5'-3' exoribonuclease 2 | 24128 | 9.49E−07 |
| 1429432_at | Bat2l2 | HLA-B associated transcript 2-like 2 | 226562 | 7.86E−07 |
| 1434391_at | AI503316 | expressed sequence AI503316 | 105860 | 1.02E−06 |
| 1439247_at | Dock10 | dedicator of cytokinesis 10 | 210293 | 1.02E−06 |
| 1444279_at | Huwe1 | HECT, UBA and WWE domain containing 1 | 59026 | 3.22E−07 |
| 1446384_at | — | (Unannotated) | — | 1.33E−07 |
| 1446512_at | Zc3h15 | zinc finger CCCH-type containing 15 | 69082 | 2.34E−07 |
| 1449578_at | Supt16h | suppressor of Ty 16 homolog (*S. cerevisiae*) | 114741 | 2.91E−07 |
| 1450051_at | Atrx | alpha thalassemia/mental retardation syndrome X-linked homolog (human) | 22589 | 6.07E−07 |
| 1451685_at | Mllt6 | myeloid/lymphoid or mixed-lineage leukemia (trithorax homolog, *Drosophila*); translocated to, 6 | 246198 | 8.09E−07 |
| 1452470_at | Cep350 | centrosomal protein 350 | 74081 | 1.03E−06 |
| 1456112_at | Tpr | translocated promoter region | 108989 | 8.10E−07 |
| 1457731_at | Snapc3 | small nuclear RNA activating complex, polypeptide 3 | 77634 | 3.80E−07 |
| 1459398_at | Peli1 | Pellino 1 | 67245 | 7.47E−07 |

TABLE 12

Pathway analysis for the genes from pairwise comparisons in the mouse and human study. Pathways marked with an asterisk (*) correspond to pathways that are present in both the mouse and human response to specified pathogen.

MOUSE *S. aureus* VS. HEALTHY CONTROLS

| # | Pathway | p-value |
|---|---|---|
| 1 | Immune response_HMGB1/RAGE signaling pathway | 1.58E−14 |
| 2 | Immune response_T cell receptor signaling pathway | 7.40E−14 |
| 3 | Immune response_CD28 signaling | 2.75E−13 |
| 4 | Transcription_NF-kB signaling pathway | 5.45E−13 |
| 5 | Immune response_Oncostatin M signaling via MAPK in human cells | 1.24E−12 |
| 6 | Transport_Clathrin-coated vesicle cycle | 1.29E−12 |
| 7 | Signal transduction_JNK pathway | 5.29E−12 |
| 8 | Apoptosis and survival_APRIL and BAFF signaling | 5.95E−12 |
| 9 | Immune response_Regulation of T cell function by CTLA-4 | 6.32E−12 |
| 10 | Immune response_ICOS pathway in T-helper cell | 8.69E−12 |
| 11 | Immune response_TCR and CD28 co-stimulation in activation of NF-kB | 1.24E−11 |
| 12 | Immune response_IL-3 activation and signaling pathway | 1.38E−11 |
| 13 | Development_Flt3 signaling | 2.06E−11 |
| 14 | Immune response_IL-1 signaling pathway | 2.06E−11 |
| 15 | Immune response_CD137 signaling in immune cell | 3.03E−11 |
| 16 | Immune response_Oncostatin M signaling via MAPK in mouse cells | 3.18E−11 |
| 17 | G-protein signaling_Regulation of p38 and JNK signaling mediated by G-proteins | 5.86E−11 |
| 18 | Immune response_IL-17 signaling pathways | 5.88E−11 |
| 19 | Reproduction_GnRH signaling | 7.27E−11 |
| 20 | Immune response_CD40 signaling | 1.05E−10 |
| 21 | Development_TGF-beta-dependent induction of EMT via MAPK | 1.30E−10 |
| 22 | Development_Prolactin receptor signaling | 1.39E−10 |
| 23 | Apoptosis and survival_Lymphotoxin-beta receptor signaling | 4.08E−10 |
| 24 | Immune response_Gastrin in inflammatory response | 6.02E−10 |
| 25 | Development_GM-CSF signaling | 6.76E−10 |
| 26 | Immune response_Function of MEF2 in T lymphocytes | 6.76E−10 |
| 27 | Immune response_IL-22 signaling pathway | 7.58E−10 |
| 28 | Immune response_CCR5 signaling in macrophages and T lymphocytes | 8.59E−10 |
| 29 | Immune response_MIF in innate immunity response | 9.71E−10 |
| 30 | Immune response_Fc epsilon RI pathway | 1.27E−09 |
| 31 | Immune response_Immunological synapse formation | 1.36E−09 |
| 32 | Immune response_CXCR4 signaling via second messenger | 1.52E−09 |
| 33 | Chemotaxis_CXCR4 signaling pathway | 1.52E−09 |
| 34 | Immune response_MIF-mediated glucocorticoid regulation | 1.68E−09 |
| 35 | Cytoskeleton remodeling_TGF, WNT and cytoskeletal remodeling | 1.68E−09 |
| 36 | Apoptosis and survival_Anti-apoptotic TNFs/NF-kB/Bcl-2 pathway | 1.76E−09 |
| 37 | Immune response_IL-15 signaling | 2.14E−09 |
| 38 | Immune response_CD16 signaling in NK cells | 3.12E−09 |
| 39 | Cell adhesion_Chemokines and adhesion | 3.81E−09 |
| 40 | Cytokine production by Th17 cells in CF | 4.20E−09 |
| 41 | Mucin expression in CF via TLRs, EGFR signaling pathways | 4.38E−09 |
| 42 | G-protein signaling_Ras family GTPases in kinase cascades (scheme) | 4.44E−09 |

TABLE 12-continued

Pathway analysis for the genes from pairwise comparisons in the mouse and human study. Pathways marked with an asterisk (*) correspond to pathways that are present in both the mouse and human response to specified pathogen.
MOUSE *S. aureus* VS. HEALTHY CONTROLS

| # | Pathway | p-value |
|---|---|---|
| 43 | Immune response_HMGB1/TLR signaling pathway | 5.51E−09 |
| 44 | Chemotaxis_Leukocyte chemotaxis | 6.15E−09 |
| 45 | Apoptosis and survival_Regulation of Apoptosis by Mitochondrial Proteins | 6.98E−09 |
| 46 | G-protein signaling_N-RAS regulation pathway | 6.98E−09 |
| 47 | Immune response_NFAT in immune response | 7.06E−09 |
| 48 | Immune response_TREM1 signaling pathway | 7.58E−09 |
| 49 | Immune response_IL-27 signaling pathway | 1.01E−08 |
| 50 | Development_NOTCH1-mediated pathway for NF-KB activity modulation | 1.31E−08 |

TABLE 13

Pathway analysis for the genes from pairwise comparisons in the mouse and human study. Pathways marked with an asterisk (*) correspond to pathways that are present in both the mouse and human response to specified pathogen.
HUMAN *S. aureus* VS. HEALTHY CONTROLS

| # | Pathway | p-value |
|---|---|---|
| 1 | Cytoskeleton remodeling_TGF, WNT and cytoskeletal remodeling | 5.45E−11 |
| 2 | Immune response_NFAT in immune response | 1.13E−10 |
| 3 | Cytoskeleton remodeling_Cytoskeleton remodeling | 1.45E−09 |
| 4 | Protein folding and maturation_POMC processing | 1.79E−09 |
| 5 | Immune response_IL-4 signaling pathway | 1.43E−08 |
| 6 | Oxidative phosphorylation | 1.47E−08 |
| 7 | Immune response_CD28 signaling | 2.13E−08 |
| 8 | Immune response_T cell receptor signaling pathway | 3.90E−08 |
| 9 | Immune response_ICOS pathway in T-helper cell | 4.51E−08 |
| 10 | Immune response_TCR and CD28 co-stimulation in activation of NF-kB | 4.70E−08 |
| 11 | Immune response_Function of MEF2 in T lymphocytes | 7.12E−08 |
| 12 | Transcription_Role of heterochromatin protein 1 (HP1) family in transcriptional silencing | 1.31E−07 |
| 13 | Signal transduction_Activation of PKC via G-Protein coupled receptor | 1.90E−07 |
| 14 | Signal transduction_AKT signaling | 2.59E−07 |
| 15 | Development_TGF-beta receptor signaling | 3.47E−07 |
| 16 | Development_Role of HDAC and calcium/calmodulin-dependentkinase (CaMK) in control of skeletal myogenesis | 4.73E−07 |
| 17 | Immune response_BCR pathway | 4.73E−07 |
| 18 | Some pathways of EMT in cancer cells | 5.51E−07 |
| 19 | Regulation of degradation of deltaF508 CFTR in CF | 8.47E−07 |
| 20 | Apoptosis and survival_Granzyme A signaling | 9.21E−07 |
| 21 | Immune response_NF-AT signaling and leukocyte interactions | 1.16E−06 |
| 22 | Apoptosis and survival_Endoplasmic reticulum stress response pathway | 1.32E−06 |
| 23 | Development_WNT signaling pathway. Part 2 | 1.32E−06 |
| 24 | Immune response_Antigen presentation by MHC class I | 1.67E−06 |
| 25 | Development_PIP3 signaling in cardiac myocytes | 1.83E−06 |
| 26 | Immune response_CD40 signaling | 2.34E−06 |
| 27 | Cytoskeleton remodeling_Regulation of actin cytoskeleton by Rho GTPases | 2.68E−06 |
| 28 | Immune response_IL-10 signaling pathway | 3.01E−06 |
| 29 | Development_PDGF signaling via STATs and NF-kB | 3.09E−06 |
| 30 | Immune response_Immunological synapse formation | 3.58E−06 |
| 31 | Immune response_IL-2 activation and signaling pathway | 4.34E−06 |
| 32 | Translation_Regulation of EIF4F activity | 5.37E−06 |
| 33 | Immune response_IL-27 signaling pathway | 5.44E−06 |
| 34 | Immune response_Bacterial infections in normal airways | 6.52E−06 |
| 35 | Immune response_Th1 and Th2 cell differentiation | 7.07E−06 |
| 36 | Development_Leptin signaling via PI3K-dependent pathway | 7.86E−06 |
| 38 | Development_NOTCH1-mediated pathway for NF-KB activity modulation | 9.05E−06 |
| 37 | Immune response_CXCR4 signaling via second messenger | 9.05E−06 |
| 39 | CFTR folding and maturation (norm and CF) | 9.76E−06 |
| 40 | Immune response _CCR3 signaling in eosinophils | 1.02E−05 |
| 41 | PGE2 pathways in cancer | 1.14E−05 |
| 42 | Development_IGF-1 receptor signaling | 1.41E−05 |
| 43 | Immune response_Antigen presentation by MHC class II | 1.51E−05 |
| 44 | Transport_Clathrin-coated vesicle cycle | 1.67E−05 |
| 45 | Translation_Insulin regulation of translation | 1.71E−05 |
| 46 | Signal transduction_IP3 signaling | 1.73E−05 |
| 47 | Apoptosis and survival_nAChR in apoptosis inhibition and cell cycle progression | 1.82E−05 |

TABLE 13-continued

Pathway analysis for the genes from pairwise comparisons in the mouse and human study. Pathways marked with an asterisk (*) correspond to pathways that are present in both the mouse and human response to specified pathogen.
HUMAN *S. aureus* VS. HEALTHY CONTROLS

| # | Pathway | p-value |
|---|---------|---------|
| 48 | Transcription_NF-kB signaling pathway | 2.03E−05 |
| 49 | G-protein signaling_Regulation of RAC1 activity | 2.37E−05 |
| 50 | Development_GM-CSP signaling | 2.52E−05 |

TABLE 14

Pathway analysis for the genes from pairwise comparisons in the mouse and human study. Pathways marked with an asterisk (*) correspond to pathways that are present in both the mouse and human response to specified pathogen.
MOUSE *E. coli* VS. HEALTHY CONTROLS

| # | Pathway | p-value |
|---|---------|---------|
| 1 | Development_VEGF signaling via VEGFR2 - generic cascades | 5.51E−14 |
| 2 | Immune response_CCR5 signaling in macrophages and T lymphocytes | 4.40E−13 |
| 3 | Immune response_CD28 signaling | 6.16E−12 |
| 4 | Development_A2A receptor signaling | 3.10E−11 |
| 5 | Cytoskeleton remodeling_Role of PKA in cytoskeleton reorganisation | 7.11E−11 |
| 6 | Apoptosis and survival_Granzyme B signaling | 1.13E−10 |
| 7 | Immune response_Gastrin in inflammatory response | 2.52E−10 |
| 8 | Development_Prolactin receptor signaling | 2.63E−10 |
| 9 | Immune response_HMGB1/RAGE signaling pathway | 2.97E−10 |
| 10 | Apoptosis and survival_BAD phosphorylation | 1.82E−09 |
| 11 | Immune response_TREM1 signaling pathway | 2.69E−09 |
| 12 | Apoptosis and survival_Anti-apoptotic action of Gastrin | 2.81E−09 |
| 13 | Cytoskeleton remodeling_TGF, WNT and cytoskeletal remodeling | 3.96E−09 |
| 14 | Immune response_IL-1 signaling pathway | 4.27E−09 |
| 15 | Development_GM-CSF signaling | 5.64E−09 |
| 16 | Immune response_Function of MEF2 in T lymphocytes | 5.64E−09 |
| 17 | Development_Growth hormone signaling via STATs and PLC/IP3 | 6.47E−09 |
| 18 | Cytoskeleton remodeling_Reverse signaling by ephrin B | 9.11E−09 |
| 19 | Immune response_HMGB1 release from the cell | 1.04E−08 |
| 20 | Immune response_HMGB1/TLR signaling pathway | 1.04E−08 |
| 21 | Immune response_Inhibitory action of Lipoxins on pro-inflammatory TNF-alpha signaling | 1.38E−08 |
| 22 | Blood coagulation_GPCRs in platelet aggregation | 1.73E−08 |
| 23 | Immune response_Histamine H1 receptor signaling in immune response | 2.00E−08 |
| 24 | Immune response _IFN gamma signaling pathway | 2.29E−08 |
| 25 | Immune response_IL-22 signaling pathway | 2.45E−08 |
| 26 | Signal transduction_cAMP signaling | 2.51E−08 |
| 27 | Cell adhesion_Chemokines and adhesion | 3.31E−08 |
| 28 | Development_Flt3 signaling | 3.40E−08 |
| 29 | Signal transduction_Erk Interactions: Inhibition of Erk | 3.89E−08 |
| 30 | G-protein signaling_G-Protein alpha-q signaling cascades | 3.89E−08 |
| 31 | Development_Gastrin in cell growth and proliferation | 4.41E−08 |
| 32 | Chemotaxis_Leukocyte chemotaxis | 5.03E−08 |
| 33 | Development_EGFR signaling pathway | 5.89E−08 |
| 34 | Chemotaxis_Lipoxin inhibitory action on fMLP-induced neutrophil chemotaxis | 7.04E−08 |
| 35 | Immune response_ICOS pathway in T-helper cell | 7.04E−08 |
| 36 | Immune response_IL-15 signaling | 7.81E−08 |
| 37 | Signal transduction_Activation of PKC via G-Protein coupled receptor | 7.83E−08 |
| 38 | Regulation of CFTR activity (norm and CF) | 8.05E−08 |
| 39 | Immune response_Fc gamma R-mediated phagocytosis in macrophages | 9.96E−08 |
| 40 | G-protein signaling_G-Protein alpha-12 signaling pathway | 1.39E−07 |
| 41 | Cell adhesion_Role of tetraspanins in the integrin-mediated cell adhesion | 1.39E−07 |
| 42 | Apoptosis and survival_HTR1A signaling | 2.65E−07 |
| 43 | Immune response_Bacterial infections in normal airways | 2.65E−07 |
| 44 | HIV-1 signaling via CCR5 in macrophages and T lymphocytes | 2.99E−07 |
| 45 | Transcription_NF-kB signaling pathway | 2.99E−07 |
| 46 | Immune response_CXCR4 signaling via second messenger | 3.39E−07 |
| 47 | Cell adhesion_Ephrin signaling | 3.44E−07 |
| 48 | Cell adhesion_Histamine H1 receptor signaling in the interruption of cell barrier integrity | 3.44E−07 |
| 49 | Immune response_NFAT in immune response | 3.60E−07 |
| 50 | Some pathways of EMT in cancer cells | 3.60E−07 |

TABLE 15

Pathway analysis for the genes from pairwise comparisons in the mouse and human study. Pathways marked with an asterisk (*) correspond to pathways that are present in both the mouse and human response to specified pathogen.
HUMAN *E. coli* VS. HEALTHY CONTROLS

| # | Pathway | p-value |
|---|---|---|
| 1 | Cytoskeleton remodeling_TGF, WNT and cytoskeletal remodeling | 2.76E−10 |
| 2 | Immune response_HMGB1/RAGE signaling pathway | 1.15E−09 |
| 3 | Development_EPO-induced Jak-STAT pathway | 6.64E−09 |
| 4 | Immune response_Oncostatin M signaling via MAPK in mouse cells | 6.64E−09 |
| 5 | Cytoskeleton remodeling_Cytoskeleton remodeling | 7.59E−09 |
| 6 | Protein folding and maturation_POMC processing | 9.88E−09 |
| 7 | Development_Prolactin receptor signaling | 1.59E−08 |
| 8 | Immune response_IL-2 activation and signaling pathway | 2.29E−08 |
| 9 | Immune response_ICOS pathway in T-helper cell | 2.48E−08 |
| 10 | Immune response_Immunological synapse formation | 2.56E−08 |
| 11 | Immune response_Oncostatin M signaling via MAPK in human cells | 2.64E−08 |
| 12 | Immune response_NFAT in immune response | 6.40E−08 |
| 13 | Transcription_Role of heterochromatin protein 1 (HP1) family in transcriptional silencing | 8.70E−08 |
| 14 | Immune response_T cell receptor signaling pathway | 1.04E−07 |
| 15 | Immune response_Function of MEF2 in T lymphocytes | 1.95E−07 |
| 16 | Immune response_IL-4 signaling pathway | 2.55E−07 |
| 18 | Immune response _IFN gamma signaling pathway | 2.63E−07 |
| 19 | Immune response_BCR pathway | 2.63E−07 |
| 17 | Immune response_CD28 signaling | 2.63E−07 |
| 20 | Immune response_Histamine H1 receptor signaling in immune response | 3.65E−07 |
| 21 | Immune response_CD16 signaling in NK cells | 3.87E−07 |
| 22 | PGE2 pathways in cancer | 4.07E−07 |
| 23 | Development_VEGF signaling via VEGFR2 - generic cascades | 4.14E−07 |
| 24 | Development_Thrombopoietin-regulated cell processes | 4.21E−07 |
| 25 | Immune response_IL-4 - antiapoptotic action | 5.94E−07 |
| 26 | Normal and pathological TGF-beta-mediated regulation of cell proliferation | 5.96E−07 |
| 27 | Immune response_Th1 and Th2 cell differentiation | 8.97E−07 |
| 28 | Development_TGF-beta receptor signaling | 9.11E−07 |
| 29 | Chemotaxis_CXCR4 signaling pathway | 1.07E−06 |
| 30 | Development_PIP3 signaling in cardiac myocytes | 1.09E−06 |
| 31 | Development_Role of HDAC and calcium/calmodulin-dependent kinase (CaMK) in control of skeletal myogenesis | 1.15E−06 |
| 32 | Immune response_Gastrin in inflammatory response | 1.44E−06 |
| 33 | Cell adhesion_Chemokines and adhesion | 1.52E−06 |
| 34 | Transcription_Role of AP-1 in regulation of cellular metabolism | 1.69E−06 |
| 35 | Transcription_Sin3 and NuRD in transcription regulation | 1.69E−06 |
| 37 | Development_Growth hormone signaling via PI3K/AKT and MAPK cascades | 2.40E−06 |
| 36 | Translation_Insulin regulation of translation | 2.40E−06 |
| 38 | Signal transduction_IP3 signaling | 2.61E−06 |
| 39 | Translation _Regulation of EIF2 activity | 2.78E−06 |
| 40 | Immune response_NF-AT signaling and leukocyte interactions | 3.16E−06 |
| 43 | Immune response_IL-12-induced IFN-gamma production | 3.17E−06 |
| 42 | Immune response_IL-9 signaling pathway | 3.17E−06 |
| 41 | Immune response_Regulation of T cell function by CTLA-4 | 3.17E−06 |
| 44 | Translation _Regulation of EIF4F activity | 3.18E−06 |
| 45 | Immune response_IL-15 signaling | 3.32E−06 |
| 47 | G-protein signaling_N-RAS regulation pathway | 3.52E−06 |
| 46 | Immune response_IL-22 signaling pathway | 3.52E−06 |
| 48 | Immune response_IL-27 signaling pathway | 3.77E−06 |
| 49 | Apoptosis and survival_Granzyme A signaling | 3.78E−06 |
| 50 | Immune response_Signaling pathway mediated by IL-6 and IL-1 | 3.78E−06 |

TABLE 16

Pathway analysis for the genes from pairwise comparisons in the mouse and human study.
MOUSE *S. aureus* VS. *E. coli*

| # | Pathway | p-value |
|---|---|---|
| 1 | Cytoskeleton remodeling_TGF, WNT and cytoskeletal remodeling | 4.98E−13 |
| 2 | Development_IGF-1 receptor signaling | 1.17E−12 |
| 3 | Transport_Clathrin-coated vesicle cycle | 1.27E−12 |
| 4 | Development_PIP3 signaling in cardiac myocytes | 2.24E−12 |
| 5 | Immune response_HMGB1/RAGE signaling pathway | 2.32E−12 |
| 6 | Immune response_IL-15 signaling | 6.07E−12 |
| 7 | Immune response_IL-2 activation and signaling pathway | 9.24E−12 |
| 8 | Development_GM-CSF signaling | 1.80E−11 |
| 9 | Immune response_HMGB1/TLR signaling pathway | 2.74E−11 |

TABLE 16-continued

Pathway analysis for the genes from pairwise comparisons in the mouse and human study.
MOUSE *S. aureus* VS. *E. coli*

| # | Pathway | p-value |
|---|---------|---------|
| 10 | Apoptosis and survival_APRIL and BAFF signaling | 3.22E-11 |
| 11 | Immune response_IL-3 activation and signaling pathway | 3.84E-11 |
| 12 | Cell adhesion_Chemokines and adhesion | 4.55E-11 |
| 13 | Immune response_CD40 signaling | 6.24E-11 |
| 14 | Signal transduction_AKT signaling | 7.25E-11 |
| 15 | Immune response_Gastrin in inflammatory response | 8.44E-11 |
| 16 | Cytoskeleton remodeling_Cytoskeleton remodeling | 3.97E-10 |
| 17 | Development_NOTCH1-mediated pathway for NF-KB activity modulation | 5.11E-10 |
| 18 | Cell cycle_Influence of Ras and Rho proteins on G1/S Transition | 7.37E-10 |
| 19 | Apoptosis and survival_HTR1A signaling | 8.53E-10 |
| 20 | Immune response_IL-1 signaling pathway | 1.06E-09 |
| 21 | Transcription_NF-kB signaling pathway | 2.25E-09 |
| 22 | Immune response_Regulation of T cell function by CTLA-4 | 2.27E-09 |
| 23 | Immune response_IL-17 signaling pathways | 4.61E-09 |
| 24 | Immune response_Bacterial infections in normal airways | 5.21E-09 |
| 25 | Mucin expression in CF via TLRs, EGFR signaling pathways | 5.21E-09 |
| 26 | Development_TGF-beta-dependent induction of EMT via MAPK | 6.16E-09 |
| 27 | Apoptosis and survival_Anti-apoptotic TNFs/NF-kB/Bcl-2 pathway | 7.98E-09 |
| 28 | Development_EPO-induced Jak-STAT pathway | 9.02E-09 |
| 29 | Development_VEGF signaling via VEGFR2 - generic cascades | 1.01E-08 |
| 30 | Immune response_Histamine H1 receptor signaling in immune response | 1.06E-08 |
| 31 | Apoptosis and survival_Regulation of Apoptosis by Mitochondrial Proteins | 1.80E-08 |
| 32 | Apoptosis and survival_Endoplasmic reticulum stress response pathway | 2.37E-08 |
| 33 | Immune response_Oncostatin M signaling via MAPK in human cells | 3.27E-08 |
| 34 | Development_Role of HDAC and calcium/calmodulin-dependent kinase (CaMK) in control of skeletal myogenesis | 3.79E-08 |
| 35 | Development_FGFR signaling pathway | 3.79E-08 |
| 36 | Immune response_BCR pathway | 3.79E-08 |
| 37 | Development_Flt3 signaling | 4.37E-08 |
| 38 | Immune response_CCR5 signaling in macrophages and T lymphocytes | 4.62E-08 |
| 39 | Apoptosis and survival_Granzyme B signaling | 7.07E-08 |
| 40 | NGF activation of NF-kB | 7.15E-08 |
| 41 | Development_Thrombopoietin-regulated cell processes | 7.35E-08 |
| 42 | Apoptosis and survival_Lymphotoxin-beta receptor signaling | 8.88E-08 |
| 43 | Development_Growth hormone signaling via PI3K/AKT and MAPK cascades | 8.88E-08 |
| 44 | Development_PEDF signaling | 9.68E-08 |
| 45 | Development_A3 receptor signaling | 9.68E-08 |
| 46 | Transcription_Receptor-mediated HIF regulation | 1.05E-07 |
| 47 | IL-1 beta-dependent CFTR expression | 1.19E-07 |
| 48 | Translation _Regulation of EIF4F activity | 1.20E-07 |
| 49 | Immune response_ICOS pathway in T-helper cell | 1.21E-07 |
| 50 | Proteolysis_Role of Parkin in the Ubiquitin-Proteasomal Pathway | 1.31E-07 |

TABLE 17

Genes in pathways common to murine and human responses to infection.
Human genes are in the top row for each pathway. Murine genes are in the bottom row for each pathway.

| Pairwise comparison | Pathway | Genes |
|---|---|---|
| *S. aureus* vs. Healthy | Cytoskeleton remodeling_TGF, WNT and cytoskeletal remodeling | AKT1 AKT3 ACTG1 ACTR3 ACTR3B ARPC1A ARPC2 AXIN1 CRK CSNK2A1 CSNK2B COL4A2 COL4A3 DSTN DVL1 DVL2 DVL3 PTK2 FZD3 FZD5 FZD7 GSK3B CHUK LIMK2 LAMA1 LAMC1 MYL6 MYL6B PPP1CB PPP1R12A MMP13 MKNK1 MYL12A MYL12B RPS6KA5 NCL PIK3CB PIK3R1 PIK3R3 PLAUR PPARD RHEB ROCK2 SMAD3 SOS2 TAB1 TCF7L2 TGFB1 TGFBR1 TLN2 LEF1 TCF7 TSC2 VAV1 VEGFA VCL MYC SRC MTOR CDKN2B MAPK13 MAPK14 tP53 Akt1 Akt3 Acta2 Actb Actg1 Actn4 Actr2 Actr3 Arpc1b Arpc4 Arpc5 Axin2 Ctnnb1 Cdc42 Crk Col4a2 Dstn Dvl2 Mapk1 Fzd1 Fzd7 Grb2 Mdm2 Ppp1r12a Map3k11 Rps6ka5 Nlk Serpine1 Pak1 Plaur Ppard Pxn Rheb Rhoa Sos1 Sos2 Map3k7 Tgfbr2 Lef1 Tcf7 Vav1 Jun Myc Raf1 Eif4e Cdkn1a Mapk11 Mapk13 |
| | Immune response_NFAT in immune response | AKT1 AKT3 BLNK CD28 CD247 CD3D CD3E CD3G CD79A CD79B PPP3CC CALM1 CALM3 FCER1A FCER1G GSK3B NFKBIA CHUK IKBKB ITPR1 ITPR3 ITK IGHV3-23 IGKC IGK@ IGL@ IGHM LAT LCK LYN |

TABLE 17-continued

Genes in pathways common to murine and human responses to infection.
Human genes are in the top row for each pathway. Murine genes are in the bottom row for each pathway.

| Pairwise comparison | Pathway | Genes |
|---|---|---|
| | | HLA-DMA HLA-DMB HLA-DOA HLA-DOB HLA-DPA1 HLA-DPB1 HLA-DQA1 HLA-DQA2 HLA-DQB1 HLA-DRA HLA-DRB1 HLA-DRB3 HLA-DRB4 HLA-DRB5 NFAT5 NFATC1 NFATC3 REL RELA PIK3CB PIK3R1 PIK3R3 PRKCQ PLCG1 TRAC TRA@ TRAT1 VAV1 ZAP70 |
| | | Akt1 Akt3 Blnk Cd28 Cd247 Cd3d Cd3e Cd3g Cd79a Cd79b Cd80 Cd86 Fcer1g Ms4a2 Nfkbia Nfkbib Nfkbie Ikbkb Itpr2 Itpr3 Itk Igk Lat Lck H2-Eb2 Nfatc2 Nfatc3 Relb Nfkb2 Rel Rela Prkcq Plcg1 Lcp2 Tcrb-J Trat1 Vav1 Zap70 |
| | Immune response_CD28 signaling | AKT1 AKT3 BAD BCL2L1 CD28 CD247 CD3D CD3E CD3G PPP3CC CALM1 CALM3 FYN GRAP2 GSK3B NFKBIA CHUK IKBKB ITPR1 ITPR3 ITK LAT LCK NFAT5 NFATC1 NFATC3 REL RELA PIK3CB PIK3R1 PIK3R3 PRKCQ PLCG1 TRAC TRA@ VAV1 ZAP70 |
| | | Akt1 Akt3 Bad Bc2al1 Cd28 Cd247 Cd3d Cd3e Cd3g Cd80 Cd86 Fyn Grap2 Grb2 Nfkbia Nfkbib Nfkbie Ikbkb Itpr2 Itpr3 Itk Mapk8 Lat Lck Map2k4 Map2k7 Nfatc2 Nfatc3 Relb Nfkb2 Rel Rela Pak1 Prkcq Plcg1 Lcp2 Tcrb-J Vav1 Zap70 Jun |
| | Immune response_T cell receptor signaling pathway | CD247 CD3D CD3E CD3G CD4 RASGRP1 PPP3CC CALM1 CALM3 ELK1 FYN NFKBIA CHUK IKBKB ITPR1 ITPR3 ITK LAT LCK MALT1 HLA-DMA HLA-DMB HLA-DOA HLA-DOB HLA-DPA1 HLA-DPB1 HLA-DQA1 HLA-DQA2 HLA-DQB1 HLA-DRA HLA-DRB1 HLA-DRB3 HLA-DRB4 HLA-DRB5 NFATC1 NFATC3 REL RELA PRKCQ PLCG1 SOS2 TRAC TRA@ TRAT1 VAV1 ZAP70 |
| | | Bcl10 Card11 Cd247 Cd3d Cd3e Cd3g Cd4 Rasgrp1 Mapk1 Elk1 Fyn Grb2 Nfkbia Nfkbib Nfkbie Ikbkb Itpr2 Itpr3 Itk Lat Lck H2-Eb2 Ube2v2 Nfatc2 Nfatc3 Relb Nfkb2 Rel Rela Prkcq Plcg1 Sos1 Sos2 Lcp2 Tcrb-J Trat1 Vav1 Zap70 Fos Raf1 |
| | Immune response_ICOS pathway in T-helper cell | AKT1 AKT3 BAD CD28 CD247 CD3D CD3E CD3G PPP3CC CALM1 CALM3 GNA15 GNB5 GNB1 GNG10 GNG3 GNG5 NFKBIA ICOS IKBKB ITPR1 ITPR3 ITK LAT LCK HLA-DMA HLA-DMB HLA-DOA HLA-DOB HLA-DPA1 HLA-DPB1 HLA-DQAI HLA-DQA2 HLA-DQB1 HLA-DRA HLA-DRB1 HLA-DRB3 HLA-DRB4 HLA-DRB5 REL RELA PIK3CB PIK3R1 PIK3R3 PRKCQ PLCG1 TRAC TRA@ TRAT1 VAV1 ZAP70 |
| | | Akt1 Akt3 Bad Cd28 Cd247 Cd3d Cd3e Cd3g Cd80 Cd86 Cdc42 Gnb1 Gnb2 Gng12 Gng2 Gab2 Grb2 Nflcbia Nfkbib Nfkbie Ikbkb Itpr2 Itpr3 Itk Lat Lck H2-Eb2 Nfatc2 Relb Nfkb2 Rel Rela Pik3r5 Prkcq Plcg1 Lcp2 Tcrb-J Trat1 Vav1 Zap70 |
| | Immune response_TCR and CD28 co-stimulation in activation of NF-kB | AKT1 AKT3 CD28 CD247 CD3D CD3E CD3G CD4 GRAP2 NFKBIA CHUK IKBKB ITK LAT LCK MALT1 HLA-DMA HLA-DMB HLA-DOA HLA-DOB HLA-DPA1 HLA-DPB1 HLA-DQA1 HLA-DQA2 HLA-DQB1 HLA-DRA HLA-DRB1 HLA-DRB3 HLA-DRB4 HLA-DRB5 REL RELA PIK3CB PIK3R1 PIK3R3 PRKCQ PLCG1 TRAC TRA@ VAV1 ZAP70 |
| | | Akt1 Akt3 Bcl10 Card11 Cd28 Cd247 Cd3d Cd3e Cd3g Cd4 Cd80 Cd86 Grap2 Grb2 Nfkbia Nfkbib Nfkbie Ikbkb Itk Lat Lck H2-Eb2 Ube2v2 Relb Nfkb2 Rel Rela Prkcq Plcg1 Lcp2 Tcrb-J Vav1 Zap70 |
| | Immune response_Function of MEF2 in T lymphocytes | CABIN1 CALM1 CALM3 CAMK4 CAMKK2 CARM1 CD247 CD3D CD3E CD3G HDAC1 HDAC4 HDAC5 HDAC9 ITPR1 ITPR3 LAT LCK MAP2K5 MAP2K6 MAPK14 MEF2A MEF2B MEF2C NCOA2 PLCG1 PPP3CC PRKCA PRKCG PRK CH PRKCQ PRKCZ PRKD3 TRA@ TRAC YWHAQ ZAP70 |
| | | Cabin1 Camk4 Camkk1 Cd247 Cd3d Cd3e Cd3g Hdac4 Hdac7 IL2 Itpr2 Itpr3 Jun Lat Lck Map2k6 Map3k3 Mapk11 Mef2c Mef2d Ncoa2 Nfatc2 Nr4a1 Plcg1 Prkcd Prkce Prkcq Prkd2 Prkd3 Tcrb-J Ywhab Ywhae Ywhag Zap70 |
| | Immune response_CD40 signaling | AKT1 AKT3 BCL2L1 CCND2 CD40LG CFLAR CHUK FAS FASLG FCER2 ICAM1 IKBKB JAK2 JAK3 LTA LYN MAP3K14 MAPK13 MAPK14 NFKBIA PIK3CB PIK3R1 REL RELA TNFAIP3 TP53 TRAF1 TRAF3IP2 TRAF5 |

TABLE 17-continued

Genes in pathways common to murine and human responses to infection.
Human genes are in the top row for each pathway. Murine genes are in the bottom row for each pathway.

| Pairwise comparison | Pathway | Genes |
|---|---|---|
| | Immune response_Immunological synapse formation | Akt1 Akt3 Bcl2l1 Cbl Ccl12 Cd80 Cd86 Cflar Fas Fcer2a Icam1 Ikbkb Il6 Irf1 Jak2 Jun Map2k4 Map3k14 Map3k7 Mapk11 Mapk13 Mapk8 Nfkb2 Nfkbia Nfkbib Nfkbie Ptgs2 Rel Rela Relb Smpd1 Stat3 Tnfaip3 Traf1 Traf5 Traf6 ACTG1 ACTR3 ACTR3B ARF6 ARPC1A ARPC2 CD2 CD247 CD28 CD3D CD3E CD3G CD4 CD58 CRKL CXCR4 CYTH1 DOCK2 FYN GNB1 GNB5 GNG10 GNG3 GNG5 HLA-DMA HLA-DMB HLA-DOA HLA-DOB HLA-DPA1 HLA-DPB1 HLA-DQA1 HLA-DQA2 HLA-DQB1 HLA-DRA HLA-DRB1 HLA-DRB3 HLA-DRB4 HLA-DRB5 ICAM1 ICAM2 ITPR1 ITPR3 PIK3CB PIK3R1 PIK3R3 PLCG1 RASGRP2 SKAP1 TLN2 TRA@ TRAC VAV1 VCL<br>Actb Actg1 Actn4 Actr2 Actr3 Arf6 Arpc1b Arpc4 Arpc5 Cbl Cd2 Cd247 Cd28 Cd3d Cd3e Cd3g Cd4 Cd80 Cd86 Cdc42 Cxcr4 Fyn Gnb1 Gnb2 Gng12 Gng2 Grb2 H2-Eb2 Icam1 Icam2 Itgb2 Itpr2 Itpr3 Lcp2 Pik3r5 Plcg1 Rac2 Rasgrp2 Skap1 Tcrb-J Vav1 |
| | Immune response_IL-27 signaling pathway | CD28 ICAM1 IFNGR1 IL10 IL12RB2 EB13 IL27RA IL6ST JAK1 JAK2 REL RELA SOCS3 STAT1 TBX21 MYC<br>Cd28 Icam1 Ifng Ifngr2 Il10 Il2 Ebi3 Il27ra Il6st Jak2 Relb Nfkb2 Rel Rela Pim1 Socs3 Stat1 Stat3 Itgb2 Myc |
| | Development_NOTCH1-mediated pathway for NF-KB activity modulation | ADAM17 HDAC1 RBBP4 RBBP7 H3F3A H3F3B HIST1H4B HIST1H4D HIST1H4E HIST1H4F HIST1H4H HIST1H4J HIST1H4K HIST2H4A HIST2H4B NFKBIA CHUK IKBKB IL1A IL1R1 JAG1 NCOR1 REL RELA MAP3K14 RBPJ SAP30 NCOR2 APH1B PSEN1 PSENEN Adam17 Rbbp4 H3f3b Hist1 h4j Nfkbia Nfkbib Nfkbie Ikbkb Il1a Irak2 Jag1 Ncor1 Relb Nfkb2 Rel Rela Map3k14 Notch1 Rbpj Sap30 Traf6 Aph1a Aph1b Aph1c Ncstn Psen1 |
| | Immune response_CXCR4 signaling via second messenger | AKT1 AKT3 CXCR4 FYN GNAI3 GNAZ GNB5 GNB1 GNG10 GNG3 GNG5 NFKBIA CHUK IKBKB ITPR1 ITPR3 ITK LAT LCK REL RELA PRKCQ PLCG1 ZAP70 Akt1 Akt3 Cxcr4 Fyn Gnai1 Gnai2 Gnai3 Gnb1 Gnb2 Gng12 Gng2 Nfkbia Nfkbib Nfkbie Ikbkb Itpr2 Itpr3 Itk Lat Lck Relb Nfkb2 Rel Rela Pik3r5 Prkcq Plcb3 Plcg1 Ptk2b Lcp2 Zap70 |
| | Transport_Clathrin-coated vesicle cycle | AP1G1 AP1S1 AP2M1 ACTG1 BIN1 SAR1A SAR1B SEC24A SEC24C SEC24D SEC31A SEC31B CLTC COPA COPB1 COPZ1 SH3GLB1 EPN1 HIP1R MYO1E NSF PIK3C3 PIK3R4 RABGEF1 RAB11A RAB4A RAB7A RAB11FIP1 STX12 STX16 STX7 STX8 PLIN3 VAMP2 VAMP4 VAMP7 YKT<br>Ap1b1 Ap1g1 Ap1g2 Ap2a2 Ap2b1 Arf1 Acta2 Actb Actg1 Bin1 Sar1a Sec23b Sec24b Sec24d Cltc Cltb Arcn1 Copb1 Dab2 Eeal Gosr1 Hip1 Hip1r Nsf Picalm Pikfyve Preb Rabgef1 Rab4b Rab5a Rab7 Rab8a Rab11 fip1 Stx12 Stx16 Stx6 Stx7 Vamp2 Vamp4 Vamp8 Vti1a Vti1b Ykt6 |
| | Transcription_NF-kB signaling pathway | AKT1 AKT3 CD28 NFKBIA IKBKAP CHUK IKBKB IL1A IL1R1 IRAK3 LY96 MYD88 REL RELA MAP3K14 PRKCQ TRAC TRA@ TNFRSF1B LTA TRADD Akt1 Akt3 Cd14 Cd28 Nfkbia Nfkbib Nfkbie Ikbkb Il1a Il1rap Irak2 Irak3 Lbp Ltbr Ly96 Myd88 Relb Nfkb2 Rel Rela Map3k14 Prkcq Ripk2 Tcrb-J Tlr4 Tnfrsf1a Tnfrsf1b Tnf Traf6 |
| | Development_GM-CSF signaling | AKT1 AKT3 BAD BCL2 BCL2L1 CSF2RA CASP3 ELK1 HCK NFKBIA CHUK IKBKB JAK2 LYN REL RELA PIK3CB PIK3R1 GNB2L1 SOS2 STAT5B MYC Akt1 Akt3 Bad Bcl2 Bcl2l1 Ccl12 Cish Csf2ra Csf2rb Egr1 Mapk1 Elk1 Grb2 Hck Nfkbia Nfkbib Nfkbie Ikbkb Jak2 Mcl1 Relb Nfkb2 Rel Rela Pim1 Sos1 Sos2 Stat3 Fos Myc |
| E. coli vs. Healthy | Cytoskeleton remodeling_TGF, WNT and cytoskeletal remodeling | AKT1 AKT3 ACTG1 ARPC1A ARPC2 SERPING1 CRK CSNK2A1 CCND1 DVL2 DVL3 MAPK1 PTK2 FZD5 GRB2 GSK3B LIMK2 LAMA1 MYL6 MYL6B PPP1R12A MMP13 MKNK1 MYL12A MYL12B RPS6KA5 NCL PIK3CB PIK3R1 PIK3R3 PLAUR PPARD SMAD2 SMAD3 SOS2 SHC1 TCF7L2 TGFB1 TGFBR1 LEF1 TCF7 TSC2 VAV1 VCL WNT11 WNT8B XIAP JUN MYC SRC MTOR CDKN2B MAPK13 MAPK14 TP53 Akt1 Akt2 Akt3 Acta2 Actb Actg1 Actr2 Arpc4 Ctnnb1 Cdc42 Crk Csnk2a1 Csnk2a2 Cfl2 Col4a2 Dock1 Dstn Dvl3 Ptk2 Foxo3 Fn1 Fzd1 Fzd3 Grb2 Chuk Limk2 Lamc1 Mdm2 Ppp1cb Ppp1r12a Map3k11 Mknk1 My12 Rps6ka5 Ncl |

TABLE 17-continued

Genes in pathways common to murine and human responses to infection.
Human genes are in the top row for each pathway. Murine genes are in the bottom row for each pathway.

| Pairwise comparison | Pathway | Genes |
|---|---|---|
| | | Serpine1 Pik3r3 Plaur Pxn Rheb Rock1 Rock2 Smad2 Sos1 Sos2 Shc1 Map3k7 Tgfbr1 Vcl Wnt8b Wnt16 Wnt5a Jun Myc Raf1 Eif4e Mtor Cdkn1a Mapk13 Mapk14 |
| | Immune response_HMGB1/RAGE signaling pathway | AKT1 AKT3 DIAPH1 MAPK1 PTK2 HMGB1 NFKBIA NFKBIB ICAM1 IL1A IL1B IL1RN MAPK9 KRAS MEF2A MEF2C MAP2K6 MYOG RELB PIK3CB PIK3R1 AGER TLR2 TNF JUN SRC NOS2 MAPK13 MAPK14 Akt1 Akt2 Akt3 Cdc42 Diap1 Ptk2 Nfkbia Nfkbib Icam1 Il1a Il1b Il6 Il1rn Kras Mef2a Mef2c Map2k6 Ccl4 Relb Nfkb2 Rel Rela Serpine1 Pxn Scg2 Tlr2 Tlr4 Tnf F3 Vcam1 Jun Raf1 Mapk13 Mapk14 Rps6ka3 |
| | Development_Prolactin receptor signaling | AKT1 AKT3 BCL2 CEBPB CREBBP CCND1 MAPK1 FYN GRB2 IRS1 JAK2 NEK3 NMI PIK3CB PIK3R1 PLCG1 PRL PTPN11 SOCS1 SOCS3 SOS2 STAT1 STAT5B SHC1 VAV1 CBL JUN MYC SRC Akt1 Akt2 Akt3 Bcl2 Bcl2l1 Csn2 Cebpb Nr3c1 Grb2 Jak2 Rela Socs1 Socs3 Sos1 Sos2 Stat3 Stat5a Shc1 Vav2 Cb1 Jun Myc Raf1 |
| | Immune response_ICOS pathway in T-helper cell | AKT1 AKT3 BAD CD28 CD247 CD3D CD3E CD3G PPP3CC CALM1 GNA15 GNB5 GNB1 GNG10 GNG5 GRB2 NFKBIA NFKBIB ICOS IKBKB ITPR1 ITPR2 ITPR3 ITK LAT LCK HLA-DMA HLA-DMB HLA-DOB HLA-DPA1 HLA-DPB1 HLA-DQA1 HLA-DQA2 HLA-DQB1 HLA-DRA HLA-DRB1 HLA-DRB3 HLA-DRB4 HLA-DRB5 RELB PIK3CB PIK3CG PIK3R1 PIK3R3 PRKCQ PLCG1 TRAC TRA@ VAV1 ZAP70 Akt1 Akt2 Akt3 Cd247 Cd3g Cd80 Cd86 Cdc42 Ppp3ca Ppp3cb Gnb1 Gnb5 Gng10 Gng12 Gng13 Gngt1 Gngt2 Gab2 Grb2 Nfkbia Nfkbib Icosl Ikbkb Itpr3 Lat Lck H2-Eb2 Nfatc2 Relb Nfkb2 Rel Rela Pdpk1 Pik3r3 Pik3r5 Lcp2 Tcrb-J Trat1 Zap70 |
| | Immune response_NFAT in immune response | AKT1 AKT3 BLNK CD28 CD247 CD3D CD3E CD3G CD79A CD79B PPP3CC CALM1 FCER1A FCER1G GSK3B NFKBIA NFKBIB IKBKB ITPR1 ITPR2 ITPR3 ITK IGHV3-23 1GKC IGK@ IGL@ IGHM LAT LCK LYN HLA-DMA HLA-DMB HLA-DOB HLA-DPA1 HLA-DPB1 HLA-DQA1 HLA-DQA2 HLA-DQB1 HLA-DRA HLA-DRB1 HLA-DRB3 HLA-DRB4 HLA-DRB5 NFAT5 NFATC1 NFATC3 RELB PIK3CB P1K3R1 PIK3R3 PRKCQ PLCG1 TRAC TRA@ VAV1 ZAP70 Akt1 Akt2 Akt3 Cd247 Cd3g Cd79a Cd79b Cd80 Cd86 Ppp3ca Ppp3cb Ms4a2 Nfkbia Nfkbib Chuk Ikbkb Itpr3 Igk Lat Lck Lyn H2-Eb2 Nfat5 Nfatc2 Relb Nfkb2 Rel Rela Pik3r3 Lcp2 Syk Tcrb-J Trat1 Zap70 |
| | Immune response_Function of MEF2 in T lymphocytes | CABIN1 CALM1 CAMK4 CAMKK2 CD247 CD3D CD3E CD3G HDAC1 HDAC4 HDAC9 ITPR1 ITPR2 ITPR3 JUN LAT LCK MAP2K5 MAP2K6 MAPK14 MEF2A MEF2B MEF2C NCOA2 PLCG1 PPP3CC PRKCA PRKCH PRKCQ PRICD3 TRA@ TRAC YWHAQ ZAP70 Cd247 Cd3g Hdac2 Hdac7 Itpr3 Jun Kat2b Lat Lck Map2k5 Map2k6 Mapk14 Mapk7 Mef2a Mef2c Mef2d Ncoa2 Nfatc2 Ppp3ca Ppp3cb Prkci Prkd2 Tcrb-J Ywhab Ywhae Ywhag Ywhaq Ywhaz Zap70 |
| | Immune response _IFN gamma signaling pathway | AKT1 AKT3 CALM1 CAMK2G CBL CEBPB CREBBP CRKL ICAM1 IFNGR1 IFNGR2 ITPR1 ITPR2 ITPR3 JAK1 JAK2 MAP2K6 MAP3K4 MAPK1 MAPK13 MAPK14 MCM5 MYC PIK3CB PIK3R1 PIK3R3 PRKCA PTPN11 SMAD7 SOCS1 SRC STAT1 STAT2 Afap1 Akt1 Akt2 Akt3 Cebpb Crkl Icam1 Itpr3 Stat2 Jak2 Mcm5 Map2k6 Map3k4 Pdpk1 Pik3r3 Ptk2b Smad7 Socs1 Cbl Myc Cdkn1a Mapk13 Mapk14 |
| | Immune response_CD28 signaling | AKT1 AKT3 BAD CALM1 CD247 CD28 CD3D CD3E CD3G FYN GRB2 GSK3B IKBKB ITK ITPR1 ITPR2 ITPR3 JUN LAT LCK MAPK9 NFAT5 NFATC1 NFATC3 NFKBIA NFKBIB PIK3CB PIK3R1 PIK3R3 PLCG1 PPP3CC PRKCQ RELB TRA@ TRAC VAV1 ZAP70 Akt1 Akt2 Akt3 Bcl2l1 Cd247 Cd3g Cd80 Cd86 Chuk Grap2 Grb2 Ikbkb Itpr3 Jun Lat Lck Lcp2 Map2k4 Nfat5 Nfatc2 Nfkb2 Nfkbia Nfkbib Pik3r3 Pip5k1a Ppp3ca Ppp3cb Rel Rela Relb Tcrb-J Zap70 |

TABLE 17-continued

Genes in pathways common to murine and human responses to infection.
Human genes are in the top row for each pathway. Murine genes are in the bottom row for each pathway.

| Pairwise comparison | Pathway | Genes |
|---|---|---|
| | Immune response_Histamine H1 receptor signaling in immune response | CALM1 GNA11 GNB1 GNB5 GNG10 GNG5 ICAM1 IKBKB ITPR1 ITPR2 ITPR3 JUN MAPK1 MAPK13 MAPK14 MAPK9 MMP1 MMP13 MMP3 MMP9 NFATC1 NFKBIA NFKBIB NOS2 PLA2G4A PLCB2 PPP3CC PRKCA TNF<br>Chuk F3 Fos Gnaq Gnb1 Gnb5 Gng10 Gng12 Gng13 Gngt1 Gngt2 Icam1 Ikbkb Il6 Itpr3 Jun Mapk13 Mapk14 Mmp1a Nfkbia Nfkbib Nos3 Pla2g4a Pla2g4c Plcb1 Plcb4 Ppp3ca Ppp3cb Ppp3r1 Raf1 Rela Tnf Vcam1 |
| | Development_VEGF signaling via VEGFR2 - generic cascades | ACTG1 AKT1 AKT3 FYN GRB2 GSK3B HSP90AA1 HSPB1 IKBKB ITPR1 ITPR2 ITPR3 JUN MAPK1 MAPK13 MAPK14 MAPKAPK2 NF1 NFATC1 NFKBIA NFKBIB NOS2 PIK3CB PIK3R1 PIK3R3 PLAUR PLCG1 PPP3CC PRKCA PRKCH PRKCQ PRKD3 PTGS1 PTK2 SH2D2A SHC1 SOS2 SRC TCF7L2 TRAP1 VCL<br>Actb Actg1 Akt1 Akt2 Akt3 Cdc42 Chuk Ctnnb1 Fos Grb2 Hsp90aa1 Hsp90b1 Hspb1 Ikbkb Itpr3 Jun Mapk13 Mapk14 Mapkapk2 Nck1 Nfl Nfkbia Nfkbib Nos3 Pak2 Pdpk1 Pik3r3 Plaur Ppp3ca Ppp3cb Prkci Prkd2 Ptgs2 Ptk2 Pxn Raf1 Rela Rock1 Shc1 Sos1 Sos2 Sphk1 Vcl |
| | Immune response_Gastrin in inflammatory response | AKT1 AKT3 ELAVL1 GNA11 GRB2 IKBKB IRS1 ITPR1 ITPR2 ITPR3 JUN MAP2K5 MAP2K6 MAP3K14 MAPK1 MAPK14 MAPK9 MEF2A MEF2B MEF2C MMP3 NFKBIA NFKBIB PIK3CB PIK3R1 PLCG1 PRKCA PTK2 SERPINB2 SHC1 SOS2 SRC<br>Akt1 Akt2 Akt3 Chuk Cxcl1 Elavl1 Elk1 Fos Gnaq Grb2 Hbegf Ikbkb Itpr3 Jun Map2k4 Map2k5 Map2k6 Map3k14 Map3k7 Mapk14 Mapk7 Mef2a Mef2c Mef2d Nfkbia Nfkbib Pdpk1 Ptgs2 Ptk2 Raf1 Rela Serpinb2 Shc1 Sos1 Sos2 Traf6 |
| | Cell adhesion_Chemokines and adhesion | ACTG1 AKT1 AKT3 ARPC1A ARPC2 CAV2 CCR1 CD44 CD47 CRK FLNA FLOT2 GNAI3 GNB1 GNB5 GNG10 GNG5 GRB2 GSK3B ITGA6 ITGB1 JUN LAMA1 LEF1 LIMK2 MAPK1 MMP1 MMP13 MSN MYC PIK3CB PIK3CG PIK3R1 PIK3R3 PLAUR PTEN PTK2 RAP1GAP RELB SDC2 SHC1 SOS2 SRC TCF7 TCF7L2 TRIO VAV1 VCL<br>Acta2 Actb Actg1 Actr2 Akt1 Akt2 Akt3 Arpc4 Braf Cav2 Ccr1 Cd44 Cd47 Cdc42 Cfl2 Col1a2 Col4a2 Crk Ctnnb1 Cxcl3 Cxcl5 Dock1 Flot2 Fn1 Gnai1 Gnai2 Gnai3 Gnb1 Gnb5 Gng10 Gng12 Gng13 Gngt1 Gngt2 Grb2 Itgb1 Jun Lamc1 Limk2 Mmp1a Msn Myc Nfkb2 Pik3r3 Pik3r5 Plaur Pten Ptk2 Pxn Raf1 Rap1gap Rel Rela Relb Rock1 Rock2 Serpine1 Shc1 Sos1 Sos2 Thbs1 Trio Vcl |
| | Immune response _IL-15 signaling | ADAM17 AKT1 AKT3 BCL2 FKBP1A GRB2 IKBKB IL15RA IL2RB LCK MAP2K6 MAP3K14 MAPK1 MAPK13 MAPK14 MKNK1 MTOR MYB MYC NFKBIA NFKBIB PIK3CB PIK3R1 PLCG1 PTK2 SHC1 SOS2<br>Adam17 Akt1 Akt2 Akt3 Bcl2 Bcl2l1 Chuk Eif4e Ets1 Fkbp1a Fos Gab2 Grb2 Ikbkb Il15ra Il6 Lck Map2k4 Map2k6 Map3k14 Mapk13 Mapk14 Mcl1 Mknk1 Mtor Myc Nfkbia Nfkbib Pdpk1 Plcb1 Ptk2 Raf1 Rela Rps6kbl Shc1 Sos1 Sos2 Syk |
| | Immune response_IL-22 signaling pathway | BCL2 CD28 CD4 HLA-DMA HLA-DMB HLA-DOB HLA-DPA1 HLA-DPB1 HLA-DQA1 HLA-DQA2 HLA-DQB1 HLA-DRA HLA-DRB1 HLA-DRB3 HLA-DRB4 HLA-DRB5 IL10RB IL12RB2 IL2RA IL2RB JAK1 JAK2 JAK3 JUN MAPK1 MAPK13 MAPK14 MAPK9 MYC SOCS3 STAT1 STAT4 STAT5B TRA@ TRAC<br>Bcl2 Bcl2l1 Cd86 Fos H2-Eb2 Il10rb Il2ra Jak2 Jak3 Jun Mapk13 Mapk14 Mcl1 Myc Socs3 Stat3 Stat5a Tcrb-J |

What is claimed is:

1. A method of developing a diagnostic assay for identifying and/or classifying a bacterial infection in a subject and treating the subject, the method comprising:

(a) determining the gene expression levels of biomarkers in a blood sample from the subject using microarray analysis, or PCR, or a combination thereof, wherein the biomarkers comprise the biomarkers of Factor 20 and Factor 74 listed in Table 8 and Table 10, and wherein the gene expression levels in the subject are up-regulated or down-regulated more than 1-fold compared to a control population with known bacterial infection status, with a regression model based on weighted gene expression levels that provides a classification accuracy or an area under the curve (AUC) value of about 0.8100 to about 0.9999 compared to a probability of infection in the control population;
(b) identifying the subject as having a bacterial infection based on the gene expression levels in the subject determined in step (a); and
(c) administering an effective amount of antibiotic therapy to the subject identified as having a bacterial infection in step (b).

2. The method of claim 1, wherein the subject has a *Staphylococcus aureus* blood stream infection and the control is healthy, the subject has a *Staphylococcus aureus* blood stream infection and the control has an *Escherichia coli* blood stream infection, or the subject has an *Escherichia coli* blood stream infection and the control is healthy.

3. The method of claim 1, wherein the subject has a gram positive blood stream infection and the control has a gram negative blood stream infection, or the subject has a gram negative blood stream infection and the control has a gram positive blood stream infection.

4. The method of claim 1, wherein the subject has a *Staphylococcus aureus* blood stream infection and the control is healthy.

5. The method of claim 1, wherein the subject is a mammal.

6. A method of using a diagnostic assay with a subject suspected of having a bacterial infection and treating the subject, the method comprising:
(a) determining in the assay the gene expression levels of biomarkers in a blood sample from the subject suspected of having a bacterial infection using microarray analysis, or PCR, or a combination thereof, wherein the biomarkers comprise the biomarkers of Factor 20 and Factor 74 listed in Table 8 and Table 10, and wherein the gene expression levels of the biomarkers in the subject are up-regulated or down-regulated more than 1-fold compared to a control population with known bacterial infection status, using combined weighted values of the gene expression levels in a regression model with a classification accuracy or an area under the curve (AUC) value of about 0.8100 to about 0.9999;
(b) diagnosing the subject as having a bacterial infection based on the gene expression levels of the biomarkers in the subject determined in step (a); and
(c) administering an effective amount of antibiotic therapy to the subject diagnosed as having a bacterial infection in step (b).

7. The method of claim 6, wherein the subject has a *Staphylococcus aureus* blood stream infection and the control is healthy the subject has a *Staphylococcus aureus* blood stream infection and the control has an *Escherichia coli* blood stream infection, or the subject has an *Escherichia coli* blood stream infection and the control is healthy.

8. The method of claim 6, wherein the subject has a gram positive blood stream infection and the control has a gram negative blood stream infection, or the subject has a gram negative blood stream infection and the control has a gram positive blood stream infection.

9. The method of claim 6, wherein the subject has a *Staphylococcus aureus* blood stream infection and the control is healthy.

10. A method of diagnosing and treating a bacterial infection in a subject, the method comprising:
(a) determining the gene expression levels of biomarkers in a blood sample from the subject using microarray analysis, or PCR, or a combination thereof, wherein the biomarkers comprise the biomarkers of Factor 20 and Factor 74 listed in Table 8 and Table 10, wherein the gene expression levels in the subject are up-regulated or down-regulated more than 1-fold compared to a control population with known bacterial infection status, with a regression model based on weighted gene expression levels that provides a classification accuracy or an area under the curve (AUC) value of about 0.8100 to about 0.9999;
(b) diagnosing the subject as having a bacterial infection based on the gene expression levels in the subject determined in step (a); and
(c) administering an effective amount of antibiotic therapy to the subject diagnosed as having a bacterial infection in step (b).

11. The method of claim 10, wherein the subject has a *Staphylococcus aureus* blood stream infection and the control is healthy, the subject has a *Staphylococcus aureus* blood stream infection and the control has an *Escherichia coli* blood stream infection, or the subject has an *Escherichia coli* blood stream infection and the control is healthy.

12. The method of claim 10, wherein the subject has a gram positive blood stream infection and the control has a gram negative blood stream infection, or the subject has a gram negative blood stream infection and the control has a gram positive blood stream infection.

13. The method of claim 10, wherein the subject has a *Staphylococcus aureus* blood stream infection and the control is healthy.

* * * * *